US010689693B2

United States Patent
Menschikowski et al.

(10) Patent No.: US 10,689,693 B2
(45) Date of Patent: Jun. 23, 2020

(54) METHOD AND MEANS FOR DIAGNOSING TUMORS

(71) Applicant: TECHNISCHE UNIVERSITÄT DRESDEN, Dresden (DE)

(72) Inventors: Mario Menschikowski, Radeberg (DE); Albert Hagelgans, Dresden (DE); Gabriele Siegert, Dresden (DE)

(73) Assignee: TECHNISCHE UNIVERSITÄT DRESDEN, Dresden (DE)

( * ) Notice: Subject to any disclaimer, the term of this patent is extended or adjusted under 35 U.S.C. 154(b) by 0 days.

(21) Appl. No.: 16/067,319

(22) PCT Filed: Dec. 22, 2016

(86) PCT No.: PCT/EP2016/082414
§ 371 (c)(1),
(2) Date: Jun. 29, 2018

(87) PCT Pub. No.: WO2017/114754
PCT Pub. Date: Jul. 6, 2017

(65) Prior Publication Data
US 2019/0010541 A1    Jan. 10, 2019

(30) Foreign Application Priority Data

Dec. 30, 2015  (DE) .......................... 10 2015 226 843
Aug. 31, 2016  (DE) .......................... 10 2016 216 438

(51) Int. Cl.
C12Q 1/68      (2018.01)
C12Q 1/6858    (2018.01)
C12Q 1/6851    (2018.01)
C12Q 1/6886    (2018.01)

(52) U.S. Cl.
CPC ......... C12Q 1/6858 (2013.01); C12Q 1/6851 (2013.01); C12Q 1/6886 (2013.01); *C12Q 2600/154* (2013.01)

(58) Field of Classification Search
None
See application file for complete search history.

(56) References Cited

U.S. PATENT DOCUMENTS

| | | | | |
|---|---|---|---|---|
| 5,541,308 A * | 7/1996 | Hogan | .................. | C12Q 1/6811 536/23.1 |
| 7,972,784 B2 * | 7/2011 | Model | .................. | C12Q 1/6858 435/6.11 |
| 2009/0155791 A1 * | 6/2009 | Wojdacz | .............. | C12Q 1/6827 435/6.12 |
| 2010/0233707 A1 | 9/2010 | Buckingham | | |
| 2011/0301050 A1 | 12/2011 | Pfeifer et al. | | |
| 2013/0022974 A1 * | 1/2013 | Chinnaiyan | .......... | C12Q 1/6886 435/6.11 |
| 2013/0295568 A1 * | 11/2013 | Link | ....................... | C12Q 1/686 435/6.11 |

FOREIGN PATENT DOCUMENTS

| | | |
|---|---|---|
| WO | 2012007462 A1 | 1/2012 |
| WO | 2012092259 A1 | 7/2012 |
| WO | 2013033714 A1 | 3/2013 |
| WO | 2013041731 A1 | 3/2013 |
| WO | 2013064163 A1 | 5/2013 |
| WO | 2013192351 A1 | 12/2013 |

OTHER PUBLICATIONS

Cottrell (Clinical Biochemistry 2004 vol. 37 p. 595) (Year: 2004).*
Yates et al. (Oncogene 2006 vol. 25 p. 1984) (Year: 2006).*
Bizouarn F. (2014) Introduction to Digital PCR. In: Biassoni R., Raso A. (eds) Quantitative Real-Time PCR. Methods in Molecular Biology (Methods and Protocols), vol. 1160. Humana Press, New York, NY (Year: 2014).*
International Search Report (and English Translation) and Written Opinion of the International Searching Authority for PCT/EP2016/082414, dated Mar. 20, 2017.
Redshaw, N., et al., "Quantification of epigenetic biomarkers: an evaluation of established and emerging methods for DNA methylation analysis", BMC Genomics, vol. 15, No. 1, pp. 1174 (2014).
Wojdacz, T.K., et al., "A new approach to primer design for the control of PCR bias in methylation studies", BMC Research Notes, vol. 1, No. 1, p. 54 (2008).
Wojdacz, T.K., et al., "Reversal of PCR bias for improved sensitivity of the DNA methylation melting curve assay", BioTechniques Rapid Dispatches, vol. 41, No. 3, pp. 274-278 (2006).
Wojdacz, T.K., et al., "Primer design versus PCR bias in metylation independent PCR amplifications", Epigenetics, vol. 4, No. 4, pp. 231-234 (2009).

(Continued)

*Primary Examiner* — Katherine D Salmon
(74) *Attorney, Agent, or Firm* — Heslin Rothenberg Farley & Mesiti P.C.

(57) ABSTRACT

The invention relates to a method and means for diagnosing tumors, in particular for an early diagnosis (prevention) and for differentiating between benign and malignant tumors using a PCR, in particular in bodily fluids. The method according to the invention is characterized by a combination of a pre-amplification process using a PCR, wherein methylated DNA sequences are amplified more strongly than non-methylated DNA sequences, and a subsequent quantification process using a special digital PCR, in which significantly more DNA is used than normally in the prior art. As comparison data indicates, the invention advantageously allows a clear reliable conclusion as to whether a malignant tumor disease is present or not. The invention is suitable for screening (prevention), monitoring the progress of a tumor disease, in particular to order to exclude a minimal residual disease (MRD), and for a differential diagnosis between malignant carcinoma and benign tumors.

20 Claims, 66 Drawing Sheets

Specification includes a Sequence Listing.

(56) References Cited

OTHER PUBLICATIONS

Okino, S.T., et al., "Chromatin changes on the CSTP1 promoter associated with its inactivation in prostate cancer", Molecular Carcinogenesis, vol. 46, No. 10, pp. 839-846 (2007).
Menschikowski, M., et al., "Aberrant methylation of the M-type phospholipase A2 receptor gene in leukemic cells", BMC Cancer, vol. 12, No. 1 pp. 576 (2012).
Database Geneseq [Online] "PCR primer amplifies promotor CpG islands of cancer related genes Seq86," XP55353581, retrieved from EBI accession No. GSN: ADQ77404, Database accession No. ADQ77404 (2004).
Database Geneseq [Online] "Methylation detecting PCR primer, SEQ ID 122", XP55353586, retrieved from EBI accession No. GSN: AXB24985, Database accession No. AXB24985 (2009).
Database Geneseq [Online] "Human RASSF1A gene specific probe/ RASS P2, SEQ ID 23", XP55353608, retrieved from EBI accession No. GSN:BCM21583, Database accession No. BCM21583 (2015).
Database Geneseq [Online] "Human RASSF1A gene specific probe/ RASS P1, SEQ ID 22", XP55353595, retrieved from EBI accession No. GSN:BCM21582, Database accession No. BCM21582 (2016).

\* cited by examiner

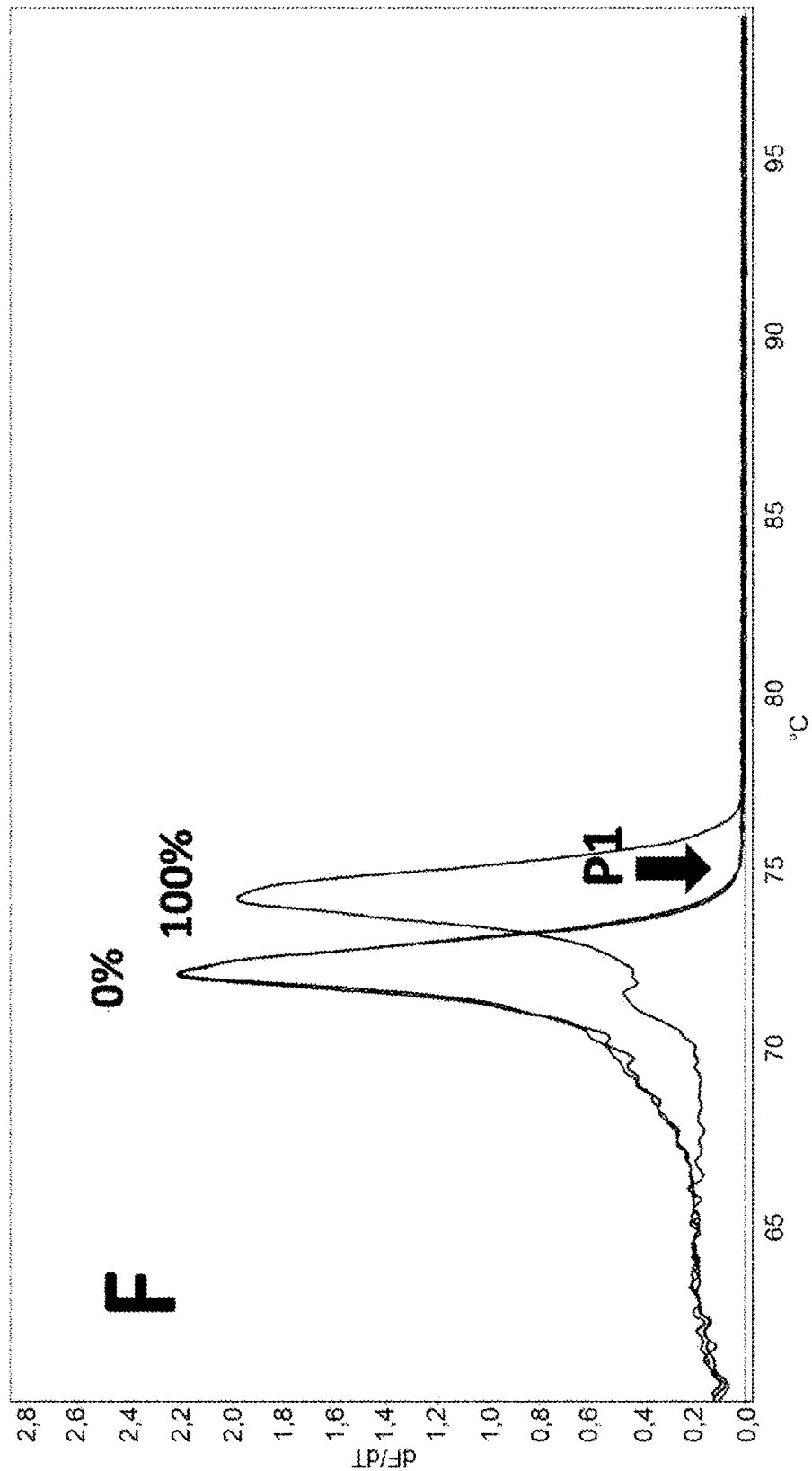

METHOD AND MEANS FOR DIAGNOSING TUMORS

CROSS REFERENCE TO RELATED APPLICATIONS

This application is the National Phase filing under 35 U.S.C. § 371 of International Application No. PCT/EP2016/082414, filed on Dec. 22, 2016, and published on Jul. 6, 2017, as WO 2017/114754 A1, and claims priority to German Application No. 102016216438.4, filed on Aug. 31, 2016 and German Application No. 102015226843.8, filed on Dec. 30, 2015. The entire disclosures of each of the prior applications are hereby incorporated herein by reference in their entirety.

FIELD OF THE INVENTION

The invention relates to a method and to means for diagnosing tumours, in particular for early diagnosis (precautionary examinations) and to distinguish between benign and malignant tumours by means of PCR, in particular in bodily fluids.

BRIEF SUMMARY OF THE INVENTION

The prognosis of cancer diseases such as prostate and breast cancer and other solid tumours goes hand in hand with the time of diagnosis. For example, the 5 to 10-year survival rates are highly dependent on the stage the tumour is at when the disease is discovered. Where a tumour disease is diagnosed too late, this is often associated with metastases having already occurred. Therefore, timely diagnosis of malignant tumours requires biomarkers that give early indications of such degeneration to a high degree of diagnostic sensitivity and specificity. Previously, the tumour markers known hitherto and used in clinical-chemical diagnosis have only proven useful for monitoring the progress of tumour patients following therapeutic interventions, but the large majority of them do not allow for use in early diagnosis (screening or precautionary examinations) of tumour diseases. The diagnostic sensitivities and specificities in this regard are still insufficient for using said biomarkers to reliably distinguish between healthy patients and those with tumours, in particular in the early stages of tumour development.

BACKGROUND ART

In addition to sequence-dependent changes to the DNA, tumour cells also differ on account of sequence-independent epigenetic DNA alterations, including hypermethylation. These tumour-specific changes in the DNA methylation can be used as new cancer markers (e.g. WO2012007462A1, WO2013064163A1, US20130022974, US20110301050).

However, these altered methylation patterns in selective DNA portions can currently only be detected in blood, urine or other human bodily fluids or smears and histological preparations to an insufficient level of analytical sensitivity. Currently, the methylation level in various targets of interest is mainly determined using PCR-based methods, which are carried out following bisulphite pre-treatment of genomic DNA, apart from in the case of methylation-sensitive restriction enzyme analysis (MSRE-PCR). The detection limits differ between the various methods for detecting methylated DNA. Direct BSP (Sanger sequencing) has a sensitivity of from 10-20%, whereas pyrosequencing and MALDI-TOF mass spectrometry-based methods achieve sensitivities of around 5% [1, 2]. MSP (methylation specific PCR), MethyLight, SMART-MSP (sensitive melting analysis after real time-methylation specific PCR) and MS-HRM (methylation-sensitive high-resolution melting) have a detection sensitivity of between 0.1-1.0% [3-6]. PCR bias is discussed as being a significant drawback of current PCR-based methods; this is a phenomenon whereby methylated and unmethylated DNA strands are copied at different levels of efficiency [3, 4].

Another problem associated with current DNA methylation detection methods is that of false positives, which may occur due to incomplete bisulphite conversion and non-specific primer annealing, in particular when methyl-specific primers are used [4]. In addition, none of the aforementioned methods involves a sensitive and above all quantitative detection of heterogeneously methylated DNA fragments, known as "epialleles". Digital PCR is a new technique in which no PCR bias occurs since each DNA molecule is copied in a separate reaction compartment [7, 8]. Regardless of the amount of DNA available and the assay design, sensitivities of up to 0.001% are described for dPCR [9]. Another advantage of this technique is that absolute values are obtained even when no calibrators are used.

Previously, a commercial test based on detecting cellular epigenetic changes such as DNA methylation as an early and typical feature of malignant changes was only available for diagnosing colorectal cancer by identifying the methylated SEPT9 [10], diagnosing gliomas by means of MGMT, and diagnosing lung cancer by detecting SHOX2 [11]. The SEPT9 test (Epigenomics AG, Berlin, Del.) has a diagnostic sensitivity of 72% and a diagnostic specificity of 90% for detecting colon cancer, i.e. 10% of the individuals tested are given pathological results despite there being no colon cancer [10]. For the GSTP1 gene, the LightMix Kit GSTP1 (Epigenomics, Berlin, Del.) is commercially available, although insufficiently high analytical sensitivity has meant this test has yet to be widely used in conjunction with PSA determination in the clinical-chemical diagnosis of prostate cancer. The ConfirmMDx test marketed by MDxHealth for detecting or ruling out prostate cancer in prostate tissue biopsy samples has a diagnostic sensitivity of 68% and a diagnostic specificity of 64% for detecting prostate tumour cells in the tissues tested, i.e. for 36% of the tissue samples tested, pathological findings are issued despite there being no prostate cancer [12].

The importance of establishing new biomarkers and providing corresponding commercial test kits, e.g. for diagnosing prostate cancer (PCa) can be seen in the high number (more than 150,000) of prostate biopsies carried out annually in Germany alone that were indicated on the basis of PSA determinations and in which tumours were only detected in around 25% of the cases studied [13, 14]. Prostate needle biopsies are an invasive diagnostic method associated with side effects requiring treatment such as bleeds and inflammation in around 5% of biopsies [13, 14]. In addition, not all PCa are detected with a single tissue biopsy, meaning that repeat tests are necessary; a negative result does not reliably rule out the possibility of PCa being present either [13, 14].

The object of the invention is to specify an improved method for diagnosing tumours and a kit for carrying out said method that are suitable in particular for early diagnosis (screening) and for distinguishing between benign and malignant tumours by means of PCR, in particular in bodily fluids.

The object is achieved by a method for diagnosing a tumour disease in an isolated sample, comprising the steps of:
a) bisulphite conversion of the DNA in the sample (conversion of unmethylated cytosine into uracil),
b) (pre-)amplification of methylated and unmethylated DNA sequences by means of PCR, the methylated DNA sequences (where these are tumour-specific) preferably being amplified to a greater extent than the unmethylated DNA sequences or alternatively the unmethylated DNA sequences (where these are tumour-specific) being amplified over the methylated DNA sequences, and then
c) quantifying the pre-amplified methylated and unmethylated DNA by means of digital PCR (dPCR), the number of pre-amplified DNA copies used in the dPCR preferably being above the normal Poisson distribution.

Step b) includes pre-amplifying genomic DNA by means of optimised bias-based PCR, the bias preferably being in favour of the methylated sequences or alternatively in favour of the unmethylated sequences (depending on the specificity for tumour DNA). Therefore, this step will also be referred to as bias-based PCR amplification (BBPA) below. In this step, genomic DNA sequences (referred to in the following as targets of interest or target sequences) that are known to be methylated in malignant tumours are each amplified by means of specific primer pairs such that corresponding unmethylated sequences (DNA from healthy cells) are also amplified. It was surprisingly found that, in the method according to the invention, the number of false positives is significantly reduced as a result compared with a (conventional) methyl-specific PCR (MS-PCR) using methyl-specific primers (MSP). To this end, for each primer pair the bias is first determined according to the $MgCl_2$ concentration, annealing temperature and number of cycles. In this way, considerably higher diagnostic specificities are achieved for distinguishing between healthy patients and those with tumours, without reducing the analytical sensitivity. A high diagnostic specificity, i.e. a low rate of false positives, is critical in deciding whether a test procedure can be used for screening for tumour diseases or precautionary examinations. In the method according to the invention, partially methylated DNA (known as heterogeneously methylated epialleles) are also advantageously amplified. In step b) (pre-amplification), the reaction conditions, such as $MgCl_2$ concentration and annealing temperature, are preferably selected such that the majority of the methylated sequences are copied regardless of how many unmethylated sequences there are in the sample being tested, and only unmethylated sequences are copied when there are no methylated DNA sequences present.

The term "target of interest" or target sequence also includes regulatory sequences outside of an open reading frame (ORF)

Advantageously, it has been found that, in the method according to the invention, the preferred pre-amplification of methylated sequences is also possible in samples in which there are high levels of background DNA (unmethylated DNA). In the method according to the invention, this DNA does not pose a problem. As a result, the method according to the invention is also suitable for analysing tumour DNA in bodily fluids, smears or tissue samples ("circulating free tumour DNA", cf-tumour DNA).

Generally, methylated DNA sequences are tumour-specific and are thus amplified to a greater extent in step b) than the unmethylated DNA sequences. This is the case, for example, in the targets of interest PLA2R1, RASSF1A, GSTP1, AOX1, SERPINE-1 and thrombomodulin prefer-ably studied in the following. However, there are also cases, e.g. the MGMT gene in glioblastoma [15], in which the unmethylated DNA sequences are tumour-specific and the methylated DNA sequences are found in the healthy tissue. In these cases, the unmethylated DNA sequences are preferably amplified to a greater extent in step b) than the methylated DNA sequences.

In step c), quantification is carried out by means of digital PCR (also referred to as dPCR below). In the known digital PCR methods, the DNA used undergoes limiting dilution in such a way that no DNA molecules or precisely one DNA molecule is present in as many compartments as possible (Poisson distribution). The inventors have now surprisingly discovered that increasing the amount of DNA used in the dPCR beyond the Poisson distribution (e.g. with 10,000 compartments, more than 80,000 DNA copies are analysed in the dPCR, i.e. at a copy per compartment (CPC) rate of >8) significantly improves the specificity and the distinction between healthy samples and malignant tumour diseases. According to the prior art, a Poisson distribution is present for the dPCR when the CPC is <8 since otherwise there are no compartments without DNA copies available to form the basis for the calculations [9].

The combination of steps b) and c) (also referred to as BBPA-dPCR in the following) advantageously achieves considerably higher analytical and diagnostic sensitivities, and the method according to the invention also surprisingly makes it possible to draw much more reliable conclusions as to whether or not there is a malignant tumour. As a result, the method is suitable for early detection screening (precautionary examinations). A further advantage of the method according to the invention is that it makes it possible to distinguish between benign and malignant tumours and to detect a minimal residual disease (MRD), thereby allowing the treatment and disease progression to be monitored. The principle of the method according to the invention is summarised in FIG. 1 on the basis of embodiments.

The inventors' preliminary studies surprisingly showed that, when an optimum annealing temperature was selected in the BBPA, the methylation level in the targets of interest studied in samples from healthy subjects (as determined in the subsequent dPCR) approached 0% as the number of PCR BBPA cycles increased, and that, at an appropriate annealing temperature, the methylation level in samples from female breast cancer patients and prostate cancer patients approached 100% when a suitable $MgCl_2$ concentration and number of cycles were selected in the BBPA (FIGS. 2-4, 7 and 8, Tables 2-5). This unexpected phenomenon is not yet fully understood, but it can be used to significantly improve the distinction between healthy samples, i.e. with no fc-tumour DNA, and diseased samples, i.e. with fcT-DNA detected accordingly. In principle, such a clear-cut distinction makes it possible to give a yes/no answer to the question of whether or not there is tumour-specific DNA and therefore a tumour disease present. In principle, this method makes it possible to specifically detect just one single tumour DNA molecule against a large background of normal DNA.

The greater the proportion of methylated sequences, the greater the likelihood of there being a malignant tumour disease, in particular in the advanced stage.

According to the prior art, digital PCR alone and the previously known PCR-based techniques alone (MS-qPCR or PCR followed by melting curve analysis (MS-HRM)) are not able to reliably distinguish between patients with tumours and healthy patients (with no tumours) using bodily fluid samples (liquid biopsy tests). For example, in the event of results that are very close to one another, i.e. in terms of the proportion of fcT-DNA compared with the proportion of normal wild type DNA, and no reliable distinction can be drawn between healthy patients and those with tumours, no further distinctions can be made by means of MS-HRM or dPCR alone unless additional DNA is added to the tests. However, this is often not possible when liquid biopsy materials, e.g. serum, plasma, urine, cerebrospinal fluid or smears, are used. By contrast, increasing the number of BBPA cycles in the BBPA-dPCR technique according to the invention makes it easier to clearly distinguish between healthy and diseased samples. This is particularly significant when distinguishing between benign hyperplasia, e.g. benign prostatic hyperplasia (BPH), and malignant diseases such as prostate cancer, as demonstrated in the embodiments on the basis of cell cultures and serum samples from prostate cancer patients.

In step b), the methylated and unmethylated DNA sequences of the targets of interest are preferably copied using a correspondingly high number of PCR cycles (preferably from 10 to 50 cycles), and are then quantified in the dPCR (step c)) either directly or after the amplified material has been slightly pre-diluted if the number of BBPA cycles is high.

Next, the individual steps of the method and preferred embodiments will be explained in more detail:

Prior to step a), DNA is preferably isolated (step a')) using known methods. A person skilled in the art also knows to carry out bisulphite conversion. The person skilled in the art can use commercially available kits for both steps.

In principle, the isolated sample can be a tissue sample. Advantageously, however, the method according to the invention is also suitable for detecting methylated tumour DNA in bodily fluids (liquid biopsy), e.g. full blood, serum, plasma, urine, cerebrospinal fluid, sputum, bronchial washing, semen, nipple discharge, vaginal secretion (smear) or lymph, particularly preferably serum, plasma or urine.

In step b) (BBPA), methylated and corresponding unmethylated DNA sequences of the same gene portion are copied by means of PCR such that the methylated DNA sequences (when specific for tumours) or unmethylated DNA sequences (when specific for tumours) are amplified to a greater extent.

Unlike the prior art, in which it is recommended to use primer pairs having at most two CpG sites, in some cases three CpG sites, that are all as close as possible to the 5' end but preferably not located at the 3' end of the primer sequences [4, 16-19], primers that together contain up to seven CpG sites in their sequences can be used according to the invention, in particular in combination with suitable $MgCl_2$ concentrations and annealing temperatures. In the process, the CpG sites can be distributed over the entire primer sequence, preferably so close to the 3' end that a cytosine of a CpG dinucleotide sequence is located directly at the 3' end. In this way, tumour DNA can be detected in a significantly more sensitive and at the same time more specific manner, i.e. without an increase in false-positive signals, even when there is a high proportion of normal DNA (wild-type DNA) in the sample being tested, which is often the case in human bodily fluids, smears or tissue samples. In addition, primers can also be designed for testing CpG-rich gene sequences that would otherwise not have been able to be tested.

Since the primers and in particular also the reaction conditions (annealing temperature always at $MgCl_2$ concentrations optimised accordingly in the reaction buffer) are selected such that they amplify both methylated and unmethylated DNA sequences, i.e. they are methylation-independent primers (MIP), when optimised reaction conditions are selected, the primers enter into competition reactions for methylated and unmethylated DNA molecules, thereby preventing false-positive signals, unlike when methylation-specific primers (MSP) are used. As well as higher specificity, methylated DNA copies can thus be identified in a considerably more sensitive and specific manner against a large background of unmethylated DNA copies. In addition, heterogeneously methylated DNA fragments (epialleles) are also quantified as well as homogeneously methylated fragments, thereby allowing for a more clear-cut differentiation between tumour diseases and healthy samples.

Preferably, the PCR conditions (in particular primer sequences, magnesium concentration, annealing temperature and in particular also the number of cycles) are set such that the bias is optimised in favour of the unmethylated DNA sequences, while unmethylated DNA sequences are also amplified at the same time.

In step b), magnesium concentrations (final concentrations) of from 0.5 to 15 mmol/l, preferably from 1 to 10 mmol/l, particularly preferably from 2 to 5 mmol/l, in particular from 2 to 4 mmol/l, particularly preferably from 2.5 to 3.5 mmol/l are preferably selected for the PCR.

The inventors have discovered that the bias can be shifted in favour of the methylated DNA sequences by a high annealing temperature and high 5'-CG-3' content. When the annealing temperature, $MgCl_2$ concentration, number of cycles and primer design are adapted to one another appropriately, the specificity and sensitivity of the method can advantageously be increased such that a liquid biopsy can be used for early tumour screening (precautionary examinations) and to detect a minimal residual disease (MRD). If methylated sequences are to be preferably pre-amplified over unmethylated sequences, high annealing temperatures and lower $MgCl_2$ concentrations (though only so low as to ensure unmethylated DNA sequences are still pre-amplified to a minor extent, thus preventing false-positive signals) are preferably selected in addition to the 5'-CG-3'-containing primer sequences. If unmethylated sequences are to be preferably pre-amplified over methylated sequences, in addition to the primer design (no 5'-CG-3'-containing sequence as far as possible, or at most two such sequences) the annealing temperature and $MgCl_2$ concentration can be adjusted accordingly in line with preliminary tests described below.

The primers are preferably selected in step b) such that they contain from zero to seven 5'-CG-3' dinucleotide sequences per primer pair, preferably from two to six, preferably from three to five, particularly preferably from one to at most three, more preferably either one or two 5'-CG-3' dinucleotide sequences per primer pair.

It has surprisingly also been found that the diagnostic sensitivity of the method can be increased further, i.e. a greater number of pathological results where there is actually a tumour disease, when, per target of interest, two or more (different) primer pairs that preferably all include the sequences detected by the probes in dPCR are used separately or simultaneously in the pre-amplification.

The annealing temperatures are preferably above 40° C., in particular above 45° C., and are preferably between 50 and 72° C., preferably between 53 and 70° C., particularly preferably up to 63° C. Like the $MgCl_2$ concentrations and the optimum number of cycles, the optimum annealing temperatures are preferably determined empirically for each primer pair.

The bias is optimised in favour of the methylated DNA sequences preferably by empirically adjusting the primer sequences and annealing temperatures, preferably together with the $MgCl_2$ concentrations, following the aforementioned selection rules. For each target of interest or each gene sequence, the PCR conditions (in particular primer selection and annealing temperature, together with the $MgCl_2$ concentration and number of cycles) are preferably determined using a sample having a known ratio of methylated DNA to unmethylated DNA (FIGS. 34-37 and Tables 21 and 22). If no bias is achieved using primers without 5'-CG-3' dinucleotide sequences, or the bias is only achieved at high annealing temperatures (e.g. above 70° C.), one 5'-CG-3' dinucleotide sequence is added; if this is insufficient, at most two, three or four 5'-CG-3' dinucleotide sequences are added (i.e. either one 5'-CG-3' dinucleotide sequence added to the forward and reverse primer sequence or from two to four 5'-CG-3' dinucleotide sequences added to the forward or reverse primer sequence). At low $MgCl_2$ concentrations (e.g. below 1.0 mmol/l), three 5'-CG-3' dinucleotide sequences are preferably added; if this is insufficient, at most eight, preferably at most seven 5'-CG-3' dinucleotide sequences are added per primer pair. In this case, it is irrelevant whether the 5'-CG-3' dinucleotide sequences are found at the 5' end, as is recommended in previous literature [4, 16-19]. On the contrary, the sensitivity of tests on samples containing a high background of normal wild-type DNA can be increased using primers in which the 5'-CG-3' dinucleotide sequences are located particularly close or directly at the 3' end of the primers [FIGS. 38-45 and Tables 27-30]. In addition to higher analytical sensitivity, it is thus also possible to advantageously construct primers for gene portions that are characterised by a high density of 5'-CG-3' dinucleotide sequences and have previously not been used for testing in accordance with the current literature recommendations [4, 16-19].

In particular, the number of PCR cycles in step b) is dependent on the starting concentration of the DNA in the sample being tested. Depending on the amount of DNA available, cycle numbers of from 5 to 50, preferably from 10 to 50, particularly preferably at least 15 and/or up to 40 are selected.

In principle, the method according to the invention can be used for any target of interest being tested. Preferably, the methylation level in DNA sequences of from three to five, preferably of up to six targets of interest are analysed in the method according to the invention. For this purpose, step b) is preferably carried out as multiplex PCR, i.e. the primer pairs for pre-amplifying the target sequences are adapted to one another such that they have approximately the same annealing temperature and do not hybridise with one another. Preferably, the primer pairs for pre-amplifying the target sequences in step b) are selected such as to produce the highest analytical and diagnostic sensitivities and specificities at the same annealing temperature, $MgCl_2$ concentration and number of cycles.

The two-stage method (BBPA-dPCR) is advantageous in that the method has a significantly higher diagnostic sensitivity and in particular higher specificity too compared with previous methods such as dPCR, MSP or MS-HRM, meaning that in principle a single tumour molecule can be detected against a large background of normal DNA (wild-type DNA). Therefore, serum samples can also be tested in addition to plasma, without having to carry out any special pre-analysis. The analytical and diagnostic sensitivity of the novel method is ultimately limited only by the sample being tested actually containing a single tumour DNA molecule that has the target gene sequence and can be transferred to the pre-amplification.

False-positive signals are prevented by simultaneously pre-amplifying unmethylated DNA fragments, even if this is a result of significantly lower efficiency towards methylated DNA sequences or, as surprisingly found, with higher efficiency towards methylated DNA sequences in samples from subjects not having tumour diseases. This is presumably due to the primers entering into competition reactions for the target sequences. In addition, the determined relative methylation levels in the targets of interest can be compared between individual patient samples despite the PCR bias since the level of the bias is the same for each sample tested at constant PCR conditions (constant annealing temperature, $MgCl_2$ concentration and number of cycles). Owing to the aforementioned advantages and the high diagnostic specificity achieved in the novel method, it is also possible to distinguish between benign hyperplasia and malignant diseases. Preferably, this is beneficial for the differential diagnosis of benign prostatic hyperplasia (BPH), prostatitis and prostate cancer (PCa) diseases since a prostate tissue biopsy is indicated when PSA values are elevated (the critical range is between 2.0 and 15.0 mg/ml; the reference range is from <2.5-4.0 mg/ml).

The higher the proportion of methylated sequences (in particular when specific to tumour DNA), the greater the likelihood of there being an advanced malignant tumour disease. If unmethylated sequences are tumour-specific, the opposite applies.

Depending on the selected primers and PCR conditions (annealing temperature, magnesium chloride concentration and number of cycles) in the pre-amplification, the percentages (fractional abundance) of methylated sequence copies pointing to the absence of a malignant disease in the form of a reference range (healthy normal range) are determined. In the embodiments, for example, a malignant tumour disease is preferably indicated by a proportion of methylated sequences of >2% in PLA2R1 (preferably 168 bp fragment), >0.1% in RASSF1A (preferably 117 bp fragment), >2% in GSTP1 (preferably 120 bp fragment) and >0.05% in GSTP1 (preferably 116 fragment). For each target sequence (and specific PCR conditions), these cut-off values between healthy and diseased samples are determined by also carrying out controls for healthy samples (e.g. DNA isolated from healthy epithelial cells from the prostate (PrEC), the breast (HMEC, MCF10A cell line) or other tissues to be tested) and diseased samples (e.g. DNA isolated from malignant LNCAP, PC-3 and DU145 prostate cells, malignant MCF-7, Cal-51, UACC-812, BT-474, MDA-MB-453 and MDA-MB231 breast tissue cells).

Patients are preferably classified as tumour patients when they present elevated values for homogeneously or heterogeneously methylated epialleles for at least one, preferably two, or even more target gene sequences.

In step c), quantification is carried out by means of digital PCR, although, by contrast to the conventional dPCR, the number of pre-amplified DNA copies used is outside the normal Poisson distribution.

Surprisingly, "overloading" the digital PCR in this way with quantities of DNA copies above a CPC value of 8 leads to increased specificity and thus considerably better distinctions between healthy samples (with no tumour disease) and malignant tumour diseases (see Table 6 in conjunction with Tables 4 and 5). For example, the quantity of samples from healthy subjects used in the dPCR produced a CPC value of 560, and the CPC value for prostate cancer patients was 1938—the values at which the best distinction (i.e. as low a value as possible for healthy samples and as high a value as possible for diseased samples) between healthy and diseased samples was achieved (Table 5).

For this purpose, the DNA pre-amplified in step b) is preferably distributed into the compartments for the digital PCR in non-diluted or slightly diluted form (e.g. up to 1:1000 after 50 cycles). Preferably, such a quantity of DNA is used in the digital PCR for there to be at least one DNA molecule in each compartment, preferably at least five molecules. Preferably, the quantity of DNA used is double that permitted by the Poisson distribution and statistics. Preferably, there are an average of at least 10, preferably at least 20, more preferably at least 50, particularly preferably at least 100 DNA molecules per compartment. In this case, this copies per compartment number (CPC) denotes the average number (arithmetic mean) of dsDNA molecules per compartment.

The number of copies of pre-amplified DNA to be used in the dPCR can be calculated as follows:

Number of copies=CPC*number of compartments

Therefore, for a preferred CPC of 8 and 5,000 compartments for example, 40,000 DNA copies are required; if there are 100,000 compartments, the number of copies required is accordingly 800,000. For a particularly preferred CPC of 50 and if there are 100,000 compartments, $5 \times 10^6$ copies must be input into the dPCR. When using the RainDrop (RainDance Technologies) digital system, for example, which has up to 1 million compartments (droplets), a preferred CPC of 10 means $1 \times 10^7$ DNA copies must be used in the dPCR; a particularly preferred CPC of 50 means $5 \times 10^7$ DNA copies must be used.

The methylated and unmethylated DNA sequences are quantified in step c) using probes that specifically hybridise with methylated regions of the pre-amplified target sequences or with the corresponding unmethylated regions.

For each target of interest, the probes for the methylated DNA sequences preferably comprise a total of at least three, preferably at least four, and up to eight, preferably up to seven 5'-CG-3' dinucleotides. For each gene, the probes for the unmethylated DNA sequences preferably comprise a total of at least three, preferably four, and up to eight, preferably up to seven 5'-CA-3' dinucleotides. Alternatively, the probes can be used to detect the complementary strand in the amplified double-strand DNA molecule. This is done either separately or together with the probe for the coding strand. To detect the complementary strand, the probes for the unmethylated DNA sequences preferably comprise three, preferably four, and up to seven 5'-TG-3' dinucleotides (instead of the 5'-CA-3' dinucleotides). The number of 5'-CG-3' dinucleotides in the probes for the methylated DNA sequences preferably corresponds to the number of 5'-CA-3' dinucleotides (or 5'-TG-3' dinucleotides) in the probes for the unmethylated DNA sequences of the same gene. Per target of interest, the aforementioned number of 5'-CG-3' or 5'-CA-3' (or 5'-TG-3') dinucleotides is either contained in one probe or distributed over a plurality of probes (in particular when it is not possible to design a probe comprising all the methylation sites due to the sequence in the target of interest). Where there are two probes for one target of interest, both probes for the methylated sequences preferably each contain three or four 5'-CG-3' dinucleotides and both probes for the unmethylated sequences preferably comprise three or four 5'-CA-3' (or 5'-TG-3') dinucleotides.

Otherwise, the digital PCR is carried out and quantified according to the usual methods. The compartments are preferably oil droplets (droplet digital PCR, ddPCR). Alternatively, the compartments are preferably arranged on a chip. However, more than one amplification cycle is preferably carried out in digital PCR, preferably at least 5, preferably at least 15, more preferably from 20 to 50, particularly preferably from 30 to 45, more preferably up to 40 cycles. For the quantification, the compartments in which amplification has taken place and with which the probes for the methylated and unmethylated DNA sequences hybridise are counted. The same primers used for the BBPA in step b) can also be used as primers for the dPCR. Alternatively and preferably, nested primers that bond to other sites on the pre-amplified sequence are used. A nested PCR can further increase the specificity. In this case, the primers can be selected according to the standard rules and the selection rules mentioned in step b) do not necessarily have to be followed. Preferably, however, the primers are selected according to the same rules as in step b).

Within the meaning of the invention, therefore, digital PCR (dPCR) is understood to be a PCR in a large number of separate compartments, preferably using a volume in the picolitre or nanolitre range. dPCR is distinguished by the compartments being quantified according to a digital result (amplification: yes or no). By counting a large number of reaction compartments (high-throughput screening preferably using from 10,000 to 100,000 compartments per PCR), statistical significance is obtained. The proportion of reaction chambers in which amplification was successful is proportional to the quantity of DNA used for the amplified DNA sequence; this is used to determine the quantity.

The probes are preferably fluorescently tagged, the probes for methylated and unmethylated sequences preferably being provided with different fluorescent markers. The fluorescent label is preferably attached to one end of the probe (preferably the 5' end). At the other end, there is preferably a quencher that is adapted to the fluorescent label and suppresses the fluorescent signal. As a result of the hybridisation with the amplified DNA, or following hybridisation and subsequent polymerase action, the quench effect is lifted and the fluorescent signal can be detected. Fluorescent labels and quenchers of this kind are well known to a person skilled in the art and are commercially available for any probe sequences.

If suitable multicolour fluorescence detection systems are available, the digital CPR is preferably also carried out as multiplex PCR. For the quantification, different colour probes are preferably used for each amplified target of interest. In this case, the probes are preferably designed such that they have a comparable hybridisation temperature.

Alternatively, the probes are used and assessed in separate batches in the dPCR. This is also applicable when the probes have different hybridisation temperatures.

If a plurality of probes are used per target of interest, the probes can have the same fluorescent markers and the signal can be integrated. Alternatively, the two aforementioned alternatives for multiplex PCR are used.

For the pre-amplification in step b), primers that amplify methylated and unmethylated DNA sequences in the genes PLA2R1, RASSF1A and GSTP1 are preferably used (methylated DNA being amplified to a greater extent than unmethylated DNA). In step c), the methylation of these targets of interest is quantified.

As shown in the embodiments (see in particular Tables 7-11), selecting these three targets of interest advantageously makes it possible to distinguish between healthy and diseased samples for all tumours tested (prostate cancer, breast cancer, ovarian cancer and renal cell cancer).

To pre-amplify methylated and unmethylated DNA sequences for the genes PLA2R1 (phospholipase A2 receptor 1, HGNC Ace. HGNC 9042, Ensembl: ENSG00000153246), RASSF1A (Rass association (Ral-GDS/AF-6) domain family member 1, HGNC Ace. HGNC 9882, Ensembl: ENSG00000068028) and GSTP1 (glutathione S-transferase pi 1, HGNC Acc HGNC 4638, Ensembl: ENSG00000084207), the following primer pairs are preferably used in step b):

| Target | Forward (5'->3') | SEQ ID | Reverse (5'->3') | SEQ ID |
|---|---|---|---|---|
| PLA2R1 (168 bp) | GGGGTAAGGAAGGTGGAGAT | 1 | ACAAACCACCTAAATTCTAATAAACAC | 2 |
| RASSF1A (117 bp) | GTTTGTTAGCGTTTAAAGTTAG | 3 | AATACGACCCTTCCCAAC | 4 |
| GSTP1 (120 bp) | GTGAAGCGGGTGTGTAAGTTT | 5 | TAAACAAACAACAAAAAAAAAAC | 6 |

Optionally, instead of the PLA2R1 (168 bp) forward primer (SEQ ID No 1), the forward primer according to SEQ ID No 7 and/or 53 is used, and/or instead of the reverse primer (SEQ ID No 2), one of the following reverse primers (SEQ ID No 8, 9, 10 or 11) is used:

| Target | Forward (5'->3') | SEQ ID | Reverse (5'->3') | SEQ ID |
|---|---|---|---|---|
| PLA2R1 (133 bp) | GGAAGGTGGAGATTACGG | 7 | GCCGAATTTACAACGAACAAC | 8 |
| PLA2R1 (150 bp) | GGGGTAAGGAAGGTGGAGAT | 53 | AATAAACACCGCGAATTTACAAC | 9 |
| PLA2R1 (161 bp) | | | ACCTAAATTCTAATAAACACCGC | 10 |
| PLA2R1 (160 bp) | | | CCTAAATTCTAATAAACACCGC | 11 |

Optionally, instead of the GSTP1 (120 bp) forward primer (SEQ ID No 5), the forward primers according to SEQ ID No 91, 93, 95 or 97 are used, and/or instead of the reverse primer (SEQ ID No 6), the reverse primers according to SEQ ID No 92, 94, 96 or 98) are used:

| Target | Forward (5'->3') | SEQ ID | Reverse (5'->3') | SEQ ID |
|---|---|---|---|---|
| GSTP1 (114 bp) | CGTAGCGGTTTTAGGGAATTT | 91 | TCCCCAACGAAACCTAAAAA | 92 |
| GSTP1 (116 bp) | ATCGTAGCGGTTTTAGGGAA | 93 | TCCCCAACGAAACCTAAAAA | 94 |
| GSTP1 (129 bp) | TGTAAGTTTCGGGATCGTAGC | 95 | TCCCCAACGAAACCTAAAAA | 96 |
| GSTP1 (132 bp) | GTGTGTAAGTTTCGGGATCG | 97 | TCCCCAACGAAACCTAAAAA | 98 |

Furthermore, instead of the GSTP1 (120 bp) forward primer (SEQ ID No 5), the forward primer according to SEQ ID No 12 is optionally used, and/or instead of the reverse primer (SEQ ID No 6), the reverse primer according to SEQ ID No 13 is used:

| Target | Forward (5'->3') | SEQ ID | Reverse (5'->3') | SEQ ID |
|---|---|---|---|---|
| GSTP1 (171 bp) | GTTCGGTTAATATGGTGAA | 12 | ACCCAAACTAAAATACAATAAC | 13 |

This primer pair is particularly preferable when the GSTP1 probes having 4 CpG sites (preferably SEQ ID No 45 and 46 or complementary sequences) are used subsequently in the dPCR, and/or when the GSTP1 probes having 5 CpG sites (preferably SEQ ID No 47 and 48 or complementary sequences) are used.

To further increase the significance of the method according to the invention or its scope of application (other tumours), in a preferred embodiment methylated and unmethylated sequences in the gene(s) AOX-1 (aldehyde oxidase 1, HGNC Acc HGNC 553, Ensembl: ENSG00000138356) and/or SERPINE-1 (serpin peptidase inhibitor, HGNC Ace HGNC 8583, Ensembl: ENSG00000106366) and/or thrombomodulin (HGNC THBD, HGNC 11784, Ensembl: ENSG00000178726) and/or septin-9 (SEPT9, HGNC 7323 Ensembl: ENSG00000184640) are additionally pre-amplified and the methylation of these genes is quantified in step c).

Preferably, the primers for pre-amplifying these targets of interest are selected as follows:

| Target | Forward (5'->3') | SEQ ID | Reverse (5'->3') | SEQ ID |
|---|---|---|---|---|
| AOX1 (180 bp) | TGGGTTGGATTTTAGGTTTTAG | 14 | CTCACCTTACGACCGTTC | 15 |
| SERPINE1 (123 bp) | AGAGCGTTGTTAAGAAGA | 16 | CTCCTACCTAAAATTCTCAAAA | 17 |

Optionally, instead of the AOX1 (180 bp) forward primer (SEQ ID No 14), the forward primer according to SEQ ID No 18 is optionally used, and/or instead of the reverse primer (SEQ ID No 15), the reverse primer according to SEQ ID No 19 is used:

| Target | Forward (5'->3') | SEQ ID | Reverse (5'->3') | SEQ ID |
|---|---|---|---|---|
| AOX1 (138 bp) | GTTGGATTTTAGGTTTTAGTAAG | 18 | GCCCGATCCATTATAATATC | 19 |

This primer pair is particularly preferable when the AOX1 probes having 4 CpG sites (preferably SEQ ID No 39 and 40 or complementary sequences) are used subsequently in the dPCR, and/or when the AOX1 probes having 5 CpG sites (preferably SEQ ID No 41 and 42 or complementary sequences) are used.

For the quantification per dPCR, probes selected from the following sequences are preferably used in step c):

| Target | methylated (5'->3') | SEQ ID | unmethylated (5'->3') | SEQ ID |
|---|---|---|---|---|
| PLA2R1 (3 CpG) | CCCAACTACTCCGCGACGCAA | 20 | AACCCAACTACTCCACAACACAAA | 21 |
| PLA2R1 (4 CpG) | CAACTACTCCGCGACGCAAACG | 22 | AACCCAACTACTCCACAACACAAACA | 23 |
| RASSF1A (3 CpG) | CGCCCAACGAATACCAACTCCCG | 24 | CACCCAACAAATACCAACTCCCACAA | 25 |
| RASSF1A (4 CpG) | CGCCCAACGAATACCAACTCCCGCG | 54 | CACCCAACAAATACCAACTCCCACAACTC | 55 |
| GSTP1 (3 CpG) | CGCAACGAAATATACGCAAC | 56 | CACAACAAAATATACACAAC | 57 |
| GSTP1 (4 CpG) | ACGAACTAACGCGCCGAAAC | 58 | ACAAACTAACACACCAAAAC | 59 |
| GSTP1 (3 CpG) | CGATCTCGACGACTCACTACAACC | 45 | CAATCTCAACAACTCACTACAACCTC | 46 |
| GSTP1 (4 CpG) | CGCGATCTCGACGACTCACTACAA | 47 | CACAATCTCAACAACTCACTACAACCT | 48 |

50

These are complementary to the coding strand. Alternatively, each (complementary) template strand can also be quantified either separately or together with the coding strand in one batch. The following (complementary) probes are suitable and preferable for this purpose:

| Target | methylated (5'->3') | SEQ ID | unmethylated (5'->3') | SEQ ID |
|---|---|---|---|---|
| PLA2R1 (3 CpG) | TTGCGTCGCGGAGTAGTTGGG | 60 | TTTGTGTTGTGGAGTAGTTGGGTT | 26 |
| PLA2R1 (4 CpG) | CGTTTGCGTCGCGGAGTAGTTG | 27 | TGTTTGTGTTGTGGAGTAGTTGGGTT | 28 |
| RASSF1A (3 CpG) | CGGGAGTTGGTATTCGTTGGGCG | 29 | TTGTGGGAGTTGGTATTTGTTGGGTG | 30 |

-continued

| Target | methylated (5'->3') | SEQ ID | unmethylated (5'->3') | SEQ ID |
|---|---|---|---|---|
| RASSF1A (4 CpG) | CGCGGGAGTTGGTATTCGTTGGGCG | 31 | GAGTTGTGGGAGTTGGTATTTGTTGGGTG | 32 |
| GSTP1 (3 CpG) | GTTGCGTATATTTCGTTGCG | 33 | GTTGTGTATATTTTGTTGTG | 34 |
| GSTP1 (4 CpG) | GTTTCGGCGCGTTAGTTCGT | 35 | GTTTTGGTGTGTTAGTTTGT | 36 |
| GSTP1 (3 CpG) | GGTTGTAGTGAGTCGTCGAGATCG | 49 | GAGGTTGTAGTGAGTCGTCGAGATCG | 50 |
| GSTP1 (4 CpG) | TTGTAGTGAGTCGTCGAGATCGCG | 51 | AGGTTGTAGTGAGTCGTCGAGATCGCG | 52 |

If methylated and unmethylated sequences of the gene(s) AOX-1 and/or SERPINE-1 are pre-amplified, probes selected from the following sequences and complementary sequences are particularly preferably used in step c) to quantify the methylation of these genes:

| Target | methylated (5'->3') | SEQ ID | unmethylated (5'->3') | SEQ ID |
|---|---|---|---|---|
| AOX1 (3 CpG) | ACTCGAACGCCCGATCCATTATAA | 37 | ACAACTCAAACACCCAATCCATTATAA | 38 |
| AOX1 (4 CpG) | CGCTAATTCGAAAACCCGAAACGA | 39 | CACTAATTCAAAAACCCAAAACAA | 40 |
| AOX1 (5 CpG) | CGCGCTAATTCGAAAACCCGAAACGA | 41 | CACACTAATTCAAAAACCCAAAACAA | 42 |
| SERPINE1 (4 CpG) | CGATTAACGATTCGTCCTACTCTAACG | 43 | CAATTAACAATTCATCCTACTCTAACA | 44 |

Alternatively or additionally, the following additional primer pairs can be used in step c):

| Target | Forward (5'->3') | SEQ ID | Reverse (5'->3') | SEQ ID |
|---|---|---|---|---|
| RASSF1A (124 bp) | GCGTTTGTTAGCGTTTAAAG | 61 | AACCGAATACGACCCTTC | 62 |
| AOX1 (138 bp) | GTTGGATTTTAGGTTTTAGTAAG | 63 | GCCCGATCCATTATAATATC | 64 |
| AOX1 (135 bp) | GGATTTTAGGTTTTAGTAAGTTTC | 65 | GCCCGATCCATTATAATATCCG | 66 |
| AOX1 (134 p) | GATTTAGGTTTTAGTAAGTTTCG | 67 | | |
| AOX1 (171 p) | TTTTAATTAAGGTTTTTTTCGTCG | 99 | CCCGATCCATTATAATATCCG | 100 |
| SERPINE1 (119 bp) | CGTTGTTAAGAAGATTTATAC | 68 | TAAACCCGAAATAAAAAATTAAA | 69 |
| TM (125 bp) | GGTCGATTCGTATGTTAGA | 70 | AACCGTACCGAAACAAAA | 71 |
| TM (144 bp) | GTTTGGGTTGGGACGGATA | 72 | AAAAACCAAAACCCCAAACA | 73 |
| TM (166 bp) | GTTTGGGGTTTTGGTTTTTG | 74 | GCAATCCGTCGCAAATCTAA | 75 |

-continued

| Target | Forward (5'->3') | SEQ ID | Reverse (5'->3') | SEQ ID |
|---|---|---|---|---|
| TM (165 bp) | | | CAATCCGTCGCAAATCTAAC | 76 |
| TM (160 bp) | TTTGTGTTTTTTGTTTCGGTAC | 101 | CACCCGACTACGACTCTACG | 102 |
| TM (159 bp) | | | ACCCGACTACGACTCTACGA | 103 |
| RASSF1A (86 bp) | TTTAGTTTGGATTTTGGGGGA | 104 | CTAACTTTAAACGCTAACAAA | 105 |
| RASSF1A (82 bp) | GTTTGGATTTTGGGGAGC | 106 | ACTTTAAACGCTAACAAACG | 107 |
| RASSF1A (82 bp) | TTTGGATTTTGGGGAGCG | 108 | CGCTAACTTTAAACGCTAAC | 109 |
| RASSF1A (86 bp) | TTTAGTTTGGATTTTGGGGAG | 110 | CGCTAACTTTAAACGCTAACAAA | 111 |
| TM (125 bp) | GGTCGATTCGTATGTTAGA | | AACCGTACCGAAACAAAA | 127 |
| TM (83 bp) | TAGCGGTAAGAAGTGTTTG | | | 128 |
| TM (70 bp) | TACGGTTTTGTCGTAGTG | | CCCAAACATATTACCCAAAC | 130 |
| TM (113 bp) | GGAGAGGTTGTCGTTATC | | CCCAAACATATTACCCAAAC | 132 |
| TM (115 bp) | | | ACCCCAAACATATTACCC | 133 |
| TM (99 bp) | GTCGAGTACGATTGTTTC | | ACGCACTATCATTAAATAACC | 135 |
| TM (97 bp) | CGGTGGTTGTCGATGTTA | | CCGCAACCGAATAACAAC | 137 |
| TM (125 bp) | TTGCGGGGTTATTTAATG | | CAACCGAATAACAACTACA | 139 |
| Septin-9 (72 bp) | GCGATTCGTTGTTTATTAG | | ATCCGAAATAATCCCATC | 141 |
| Septin-9 (169 bp) | CGGTTAGTTTTGTATTGTAG | | | 142 |
| Septin-9 (94 bp) | CGGGGTTGTTTTGTTTAAG | | CCAACACCGACAATCAAA | 144 |

The AOX1 primer pairs (SEQ ID No 63 and 64 or 65 and 66 or 65 and 67 or 99 and 100) are particularly preferable when the AOX1 probes having 4 CpG sites (preferably SEQ ID No 77 and 78 or 79 or complementary sequences) are used subsequently in the dPCR, or when the AOX1 probes having 5 CpG sites (preferably SEQ ID No 112 and 113 or 112 and 114 or complementary sequences) are used.

The thrombomodulin (TM) primer pairs (SEQ ID No 70 and 71 or 72 and 73 or 101 and 102 or 101 and 103) are particularly preferable when the TM probes having 3 CpG sites (preferably SEQ ID No 80 and 81 or complementary sequences) are used subsequently in the dPCR, and the TM primer pairs (SEQ ID No 74 and 75 or 74 and 76) are particularly preferable when the TM probes having 4 CpG sites (preferably SEQ ID No 82 and 83 or complementary sequences) are used.

The thrombomodulin (TM) primer pairs (SEQ ID No 126 and 127 or 127 and 128) are particularly preferable when the TM probes having 3 CpG sites (preferably SEQ ID No 145 and 146 or complementary sequences) are used subsequently in the dPCR, and the TM primer pairs (SEQ ID No 129 and 130 or 131 and 132) are particularly preferable when the TM probes having 5 CpG sites (preferably SEQ ID No 147 and 148 or complementary sequences) are used. The thrombomodulin (TM) primer pairs (SEQ ID No 131 and 133) are particularly preferable when the TM probes having 5 CpG sites (preferably SEQ ID No 149 and 150 or complementary sequences) are used subsequently in the dPCR, the TM primer pairs (SEQ ID No 134 and 135) are particularly preferable when the TM probes having 3 CpG sites (preferably SEQ ID No 151 and 152 or complementary sequences) are used, the TM primer pairs (SEQ ID No 136 and 137) are particularly preferable when the TM probes having 5 CpG sites (preferably SEQ ID No 153 and 154 or complementary sequences) are used, and the TM primer pairs (SEQ ID No 138 and 139) are particularly preferable when the TM probes having 4 CpG sites (preferably SEQ ID No 155 and 156 or 157 and 158 or complementary sequences) are used.

The septin-9 primer pairs (SEQ ID No 140 and 141) are particularly preferable when the TM probes having 4 CpG sites (preferably SEQ ID No 159 and 160 or complementary sequences) are used subsequently in the dPCR, the septin-9 primer pairs (SEQ ID No 141 and 142) are particularly preferable when the TM probes having 4 CpG sites (preferably SEQ ID No 161 and 162 or complementary sequences) are used, and the septin-9 primer pairs (SEQ ID No 143 and 144) are particularly preferable when the TM probes having 2 CpG sites (preferably SEQ ID No 163 and 164 or complementary sequences) are used.

The RASSF1A primer pairs (SEQ ID No 104 and 105 or 106 and 107 or 108 and 109 or 110 and 111) are particularly preferable when the RASSF1A probes having 4 CpG sites (preferably SEQ ID No 115 and 116 or 115 and 117 or 115 and 116 or complementary sequences) are used subsequently in the dPCR.

For the quantification per dPCR, probes selected from the following sequences are preferably used in step c):

| Target | methylated (5'->3') | SEQ ID | unmethylated (5'->3') | SEQ ID |
|---|---|---|---|---|
| AOX1 (4 CpG) | CGCTAATTCGAAAACCCGAAACGA | 77 | CACTAATTCAAAAACCCAAAACAA | 78 |
| AOX1 (4 CpG) | | | CACTAATTCAAAAACCCAAAACAAAAA | 79 |
| AOX1 (5 CpG) | CGCGCTAATTCGAAAACCCGAAACGA | 112 | CACACTAATTCAAAAACCCAAAACAA | 113 |
| AOX1 (5 CpG) | | | CACACTAATTCAAAAACCCAAAACAAAAA | 114 |
| RASSF1A (4 CpG) | CGCGAACCGAACGAAACCAC | 115 | CACAAACCAAACAAAACCAC | 116 |
| RASSF1A (4 CpG) | | | CACAAACCAAACAAAACCACAAA | 117 |
| RASSF1A (4 CpG) | | | AAACACAAACCAAACAAAACCACAAA | 118 |
| TM (3 CpG) | ACGCCGATAACGACAACCTCT | 80 | AAAAAGCAGATAAAGACAACCTCT | 81 |
| TM (4 CpG) | CCGACTACGACTCTACGAATACGAA | 82 | CAGACTAAGACTCTAAGAATAAGAAAAAC | 83 |
| TM (3 CpG) | ACGCCGATAACGACAACCTCT | 145 | AAGCAGATAAAGACAACCTCT | 146 |
| TM (5 CpG) | CGCCGCGTACAAACGCCGAA | 147 | AGCAGAGTACAAAAGCAGAA | 148 |
| TM (5 CpG) | AACGCGCCGCGTACAAACGC | 149 | AAAGAGCAGAGTACAAAAGC | 150 |
| TM (3 CpG) | CGCAATCCGTCGCAAATCTAACT | 151 | AGCAATCAGTAGCAAATCTAACT | 152 |
| TM (5 CpG) | AACGCCGACGACCAACGCCG | 153 | AAAGCAGAAGACCAAAGCAG | 154 |
| TM (4 CpG) | AAACGCCGACGACCAACGC | 155 | AAAAAGCAGAAGACCAAAGC | 156 |
| TM (4 CpG) | AAACGCCGACGACCAACGCC | 157 | AAAAAGCAGAAGACCAAAGCC | 158 |
| Septin-9 (4 CpG) | CGTTAACCGCGAAATCCGACATAAT | 159 | AGTTAACAGAGAAATCAGACATAAT | 160 |
| Septin-9 (4 CpG) | CGTTAACCGCGAAATCCGACATAATAA | 161 | AGTTAACAGAGAAATCAGACATAATAA | 162 |
| Septin-9 (2 CpG) | AAACGCACGCACTCACAAACT | 163 | AAAAGCAAGCACTCACAAACT | 164 |

These are complementary to the coding strand.

Alternatively, each (complementary) template strand can also be quantified either separately or together with the coding strand in one batch. The following (complementary) probes are suitable and preferable for this purpose:

| Target | methylated (5'->3') | SEQ ID | unmethylated (5'->3') | SEQ ID |
|---|---|---|---|---|
| AOX1 (4 CpG) | TCGTTTCGGGTTTTCGAATTAGCG | 84 | TTGTTTTGGGTTTTTGAATTAGTG | 85 |
| AOX1 (4 CpG) | | | TTTTTGTTTTGGGTTTTTGAATTAGTG | 86 |
| AOX1 (5 CpG) | TCGTTTCGGGTTTTCGAATTAGCGCG | 119 | TTGTTTTGGGTTTTTGAATTAGTGTG | 120 |
| AOX1 (5 CpG) | | | TTTTTGTTTTGGGTTTTTGAATTAGTGTG | 121 |
| RASSF1A (4 CpG) | GTGGTTTCGTTCGGTTCGCG | 122 | GTGGTTTTGTTTGGTTTGTG | 123 |
| RASSF1A (4 CpG) | | | TTTGTGGTTTTGTTTGGTTTGTG | 124 |
| RASSF1A (4 CpG) | | | TTTGTGGTTTTGTTTGGTTTGTGTTT | 125 |
| TM (3 CpG) | AGAGGTTGTCGTTATCGGCGT | 87 | AGAGGTTGTTGTTATTGGTGT | 88 |
| TM (4 CpG) | TTCGTATTCGTAGAGTCGTAGTCGG | 89 | TTTGTATTTGTAGAGTTGTAGTTGG | 90 |
| TM (3 CpG) | AGAGGTTGTCGTTATCGGCGT | 165 | AGAGGTTGTCTTTATCTGCTT | 166 |
| TM (5 CpG) | TTCGGCGTTTGTACGCGGCG | 167 | TTCTGCTTTTGTACTCTGCT | 168 |
| TM (5 CpG) | GCGTTTGTACGCGGCGCGTT | 169 | GCTTTTGTACTCTGCTCTTT | 170 |
| TM (3 CpG) | AGTTAGATTTGCGACGGATTGCG | 171 | AGTTAGATTTGCTACTGATTGCT | 172 |
| TM (5 CpG) | CGGCGTTGGTCGTCGGCGTT | 173 | CTGCTTTGGTCTTCTGCTTT | 174 |
| TM (4 CpG) | GCGTTGGTCGTCGGCGTTTT | 175 | GCTTTGGTCTTCTGCTTTTT | 176 |
| TM (4 CpG) | GGCGTTGGTCGTCGGCGTTTT | 177 | GGCTTTGGTCTTCTGCTTTTT | 178 |
| Septin-9 (4 CpG) | ATTATGTCGGATTTCGCGGTTAACG | 179 | ATTATGTCTGATTTCTCTGTTAACT | 180 |
| Septin-9 (4 CpG) | TTATTATGTCGGATTTCGCGGTTAACG | 181 | TTATTATGTCTGATTTCTCTGTTAACT | 182 |
| Septin-9 (2 CpG) | AGTTTGTGAGTGCGTGCGTTT | 183 | AGTTTGTGAGTGCTGCTTTT | 184 |

As in the examples, the probes are particularly preferably 5'-FAM-marked (methylated DNA) or 5'-HEX-marked (unmethylated DNA) and marked with the quencher BHQ-1 at the 3' end.

The object is also achieved by a kit for diagnosing a tumour disease in an isolated sample, containing:
i) primers for pre-amplifying methylated and unmethylated DNA sequences in the genes PLA2R1, RASSF1A and GSTP1 by means of PCR, each primer being selected such that forward and reverse primers together comprise up to seven, preferably from two to six, preferably from one to four, particularly preferably from one to three, more preferably from three to four, more preferably from four to five 5'-CG-3' dinucleotide sequences, ii) probes for quantifying the methylated and unmethylated DNA sequences in the genes PLA2R1, RASSF1A and GSTP1, each preferably comprising a fluorescent marker and a quencher as described above.

The primers used for the digital PCR are identical to those in the pre-amplification. Alternatively and preferably, the kit also contains the following:

iii) primers for the digital PCR for amplifying methylated and unmethylated DNA sequences in the genes PLA2R1, RASSF1A and GSTP1.

These additional primers are preferably used as intrinsic primers if extrinsic primers (acting as nested primers) were used in the pre-amplification.

The kit preferably contains additional components selected from the following:

iv) reaction buffers for the bias-based PCR amplification, preferably having a magnesium chloride concentration of from 0.5 to 15.0 mmol/l, preferably from 1.5 to 8 mmol/l, more preferably up to a final concentration of 3.5 mmol/l, particularly preferably of from 2.5 to 3.5 mmol/l, or alternatively a standard PCR buffer and a concentrated magnesium solution, v) reaction buffers for the dPCR, vi) deoxyribonucleotide mix, vii) a DNA polymerase such as HotStarTaq Plus, viii) control DNA, preferably an unmethylated DNA control and a methylated DNA control, ix) instructions for use and optionally analysis software.

Preferably, the primers and probes and the control DNA for the kit are selected as above for the method. This applies in particular to the preferred targets of interest PLA2R1, RASSF1A and GSTP1, but also to the optional additional targets of interest AOX1, SERPINE1, thrombomodulin (TM) and/or septin-9.

DNA isolated from primary cells or cell lines is preferably used as control DNA for the method or kit according to the invention.

Preferably, DNA from cells or cell lines in which the target sequences are not methylated are used as the unmethylated control (negative control). Particularly preferably, DNA from epithelial cells from the healthy tissue corresponding to the tumour is used as the unmethylated DNA control. For example, DNA from human prostate epithelial cells (PrEC) or human mammary epithelial cells (HMEC) is preferably used as the unmethylated control for diagnosing prostate or breast cancer, respectively. Alternatively, DNA from MCF10A cell lines is used as the negative control for detecting breast cancer.

For each target of interest, DNA from a cell line in which the target sequence is homogeneously methylated is preferably selected as the methylated control (positive control) for detecting prostate cancer. DNA from the U937 leukaemia cell line and/or the LNCaP cell line is preferably used for PLA2R1, DNA from the U937 leukaemia cell line and/or the PC-3 cell line is preferably used for RASSF1A, and DNA from the U937 leukaemia cell line, the LNCaP cell line and/or the DU-145 cell line is preferably used for GSTP1. DNA from the DU-145 cell line is preferably used as the positive controls for SERPINE1 and thrombomodulin and/or DNA from the U937 leukaemia cell line and/or PC-3 cell line is preferably used for AOX1. DNA from the LNCaP, PC-3 and DU-145 cell lines is preferably used as the positive controls for septin-9.

To detect breast cancer, DNA from the MCF-7, Cal-51, UACC-812, BT-474, MDA-MB-453 and/or MDA-MB231 cell lines is preferably used as the positive controls.

Alternatively or in addition, DNA in which two out of three or three out of four 5'-CG-3' dinucleotides are methylated is used as the positive control for heterogeneously methylated epialleles. DNA samples from the BPH-1 cell line in which epialleles have been detected and which are used as a comparison in the differential diagnosis of BPH, prostatitis and prostate cancer are particularly preferably used as controls for identifying and quantifying homogeneously and heterogeneously methylated epialleles. In particular for the genes PLA2R1, RASSF1A and/or GSTP1, DNA from the BPH-1 cell line is preferably used. When testing the benign prostate cell line BPH-1 in comparison with normal prostate epithelial cells (PrEC), the inventors were able to detect heterogeneously methylated DNA fragments, particularly in the targets of interest PLA2R1 and RASSF1A (FIGS. 18 and 19). When using probes having at least 3 CpG sites in their sequences, the heterogeneously methylated epialleles could be distinguished from the homogeneously methylated epialleles and quantified (FIG. 20-29). In this case, it was found that homogeneously methylated epialleles were specific to tumour DNA over heterogeneously methylated epialleles, and that their detection formed the basis for a clear-cut and thus more reliable differential diagnosis of benign and malignant diseases, in particular in the prostate. For this reason, probes containing at least three 5'-CG-3 or 5'-CA-3' dinucleotides in their sequence are used in the dPCR following pre-amplification. Where these probes did not make it possible in individual cases to distinguish between e.g. benign hyperplasia such as BPH and malignant diseases such as prostate cancer, probes having four, five or more 5'-CG-3' sites are used, or where this is not possible due to the gene sequences of the targets of interest or the probe design, a plurality of probes each having three 5'-CG-3' or 5'-CA-3 dinucleotides for the same target of interest are used in the dPCR (step c)) of the method or kit according to the invention. In this way, a more clear-cut distinction is possible between benign and malignant diseases since the presence of a malignant tumour is only associated with the samples in which increased levels of homogeneously methylated epialleles are initially detected and quantified (i.e. four, five or six 5'-CG-3' are methylated simultaneously). If this specification turns out to be too strict for detecting tumour DNA, resulting in the diagnostic sensitivity being too low, heterogeneously methylated epialleles having a correspondingly high number of methylated CpG sites (i.e. in each case at least two out of three 5'-CG-3' dinucleotides methylated, or a total of four out of six tested 5'-CG-3' dinucleotides simultaneously methylated) are preferably quantified and included in the data analysis. As already demonstrated by the inventors' results, heterogeneously methylated epialleles can be quantified when the aforementioned probe sequences are used (FIG. 20-29).

The invention also relates to the use of the kit for carrying out the method according to the invention.

Within the meaning of the invention, the term "tumour diagnosis" in particular includes early screening (precautionary examinations), prognosis, ongoing progress diagnosis, treatment monitoring and the detection of MRD.

In principle, the detection of circulating free tumour DNA using BBPA-dPCR can be used to diagnose any solid tumour, in particular when corresponding target gene sequences are present in bodily fluids or smears (liquid biopsies).

The method and kit according to the invention are particularly suitable for diagnosing malignant tumours such as cancers of the prostate, breast, renal cells, efferent urinary tract and bladder, pancreas, testicles, oral cavity and pharynx, gullet, larynx, thyroid, stomach, oesophagus, gut (in particular colorectal cancer), lungs, ovaries, cervix and uterus, gall bladder, malignant melanoma of the skin, astrocytoma, glioblastoma and neuroblastoma, as well as for diagnosing non-Hodgkin's lymphoma and Hodgkin's lymphoma, lymphoma of the skin, CNS, GI tract, stomach and intestinal lymphoma, and leukaemia.

In general, a preferred possible use of the method and kit is in the early detection (independent screening or precautionary examinations) of malignant diseases (including the diseases mentioned above), but in particular in combination with PSA determination and the indication for a tissue biopsy in the event of elevated PSA values and the diagnosis of prostate cancer, or in combination with mammograms and suspicious findings when diagnosing breast cancer, or in combination with the presence of a gene mutation entailing a higher family risk for breast or ovarian cancer, and the decision to opt for a prophylactic mastectomy and/or ovariectomy.

In one embodiment of the invention, screening or precautionary examinations are carried out on the basis of pooled samples, e.g. serum or plasma samples, by combining DNA sample material from e.g. 10 and 100 subjects/patients in a pool and first testing the 100-subject pool. If tumour DNA is identified in a pool of 100 subjects/patients, the samples from the 10-subject pool produced at the same time are analysed for the corresponding subjects/patient samples. If tumour DNA is detectable in one or more of these 10-subject pool samples, the individual samples are analysed. If no tumour DNA can be identified in the 100-subject pool samples, the 10-subject pool samples and individual samples are not tested. This means that a large number of samples can be screened for the presence of tumour DNA since the clear-cut amplification effect in the BBPA-dPCR method allows individual tumour DNA molecules to be detected, regardless of the concentration of background DNA.

If a tumour disease has been diagnosed, the progress of the disease can be monitored by identifying tumour DNA by means of BBPA-dPCR following surgery, chemotherapy or radiotherapy, and the presence of a minimal residual disease (MRD) can be diagnosed or ruled out. If no tumour DNA can be detected following treatment, this implies a good response to the treatment and an MRD can be ruled out. If tumour DNA can still be detected, this may indicate a need to optimise the treatment. If tumour DNA can be detected during the course of treatment when this was not the case previously, this implies a recurrence, which indicates the need to optimise the treatment again.

Advantageously, the method and kit according to the invention are particularly suitable for the differential diagnosis of benign diseases and malignant tumour diseases. The invention is most particularly suitable for the differential diagnosis of benign prostatic hyperplasia, prostatitis and prostate cancer, in particular when a prostate tissue biopsy has been indicated in line with the prior art due to elevated PSA values. Owing to the detection according to the invention of the methylation of PLA2R1, RASSF1A and GSTP1 (and optionally of AOX1, SERPINE1, thrombomodulin and/or septin-9) by means of the BBPA-dPCR, it is possible to determine the extent to which fcT-DNA can be detected in serum, plasma, urine and/or seminal fluid. On the basis of the determined methylation level, a distinction can be drawn between a benign prostatic hyperplasia, prostatitis and prostate cancer, and so unnecessary prostate tissue biopsies and operations can be prevented in many cases. If no tumour DNA can be found in e.g. a serum, plasma or urine sample by means of BBPA-dPCR, an additional PSA determination can be deferred (e.g. for three or six months). However, if there is tumour DNA detectable in the samples, a tissue biopsy is more strongly indicated.

Advantageously, the method and kit according to the invention are also particularly suitable for the differential diagnosis of breast cancer, in particular if a tissue biopsy is indicated on the basis of suspicious mammogram findings in line with the current prior art. Owing to the detection according to the invention of the methylation of PLA2R1, RASSF1A and GSTP1 (and optionally of AOX1, SERPINE1, thrombomodulin and/or septin-9) by means of the BBPA-dPCR, it is possible to determine the extent to which fcT-DNA can be detected in serum, plasma, urine and/or nipple secretions. On the basis of the determined methylation level, a distinction can be drawn between a benign microcalcification or cysts, and breast cancer, and so unnecessary tissue biopsies and operations can be prevented in many cases in the event of false-positive findings from the mammogram screening. Around two thirds of all women who begin annual mammograms from the age of 40 will be given false-positive results within the first ten years. An unnecessary biopsy is carried out in 7% of those cases [20]. Moreover, the method and corresponding kit according to the invention can reduce false-positive results in mammogram screenings.

The method and kit according to the invention are also suitable for the differential diagnosis of ovarian cancer, in particular when suspicious ultrasound findings indicate either a benign change, such as cysts, or ovarian cancer and further invasive diagnostic procedures according to the current prior art should be carried out.

In addition, in cases of a pathological gene mutation entailing a higher family risk for breast and ovarian cancer, e.g. in the BRCA1 and BRCA2 genes, the method and kit according to the invention are suitable as an additional decision-making tool as regards opting for a prophylactic mastectomy and/or ovariectomy, in particular if the patient in question is still planning a family.

The method according to the invention creates new possibilities in the diagnosis of tumour diseases, in particular in early diagnosis, since the method copies individual cf-tumour DNA copies in a suitably specific manner against a large background of normal wild-type DNA in the blood, urine or other biological samples before the subsequent quantification in the dPCR.

Even if the bias introduced leads to a change to the original ratio between methylated DNA fragments (as a sign of a malignant degeneration) and normal unmethylated wild-type DNA, the data determined by means of the BBPA-dPCR can be used for prognosis estimations (tumour load), the response to treatment (drop in fcT-DNA or constant fcT-DNA), detecting a minimal residual disease and tumour patient after-care (recurrence due to fcT-DNA increasing again). This is based on the fact that the degree of bias can be set variably in the method according to the invention by selecting the annealing temperature, magnesium concentration in the reaction buffer and the number of cycles, and that the bias is the same among the individual samples being tested when the conditions are constant, meaning that relative quantification is possible.

Another advantage of bias-inducing oligonucleotides (BIP) compared with methyl-specific oligonucleotides (MSP) is that the number of normal wild-type DNA fragments can be used as an internal control. In addition, using a primer pair that allows methylated and unmethylated DNA sequences to be simultaneously quantified prevents false results as a result of different portions of target of interest fragments and internal control gene fragments, such as ALU sequences.

The invention also relates to the primers according to sequences 1 to 19, 53, 61 to 76, 91 to 111, and 126 to 144, and to the nucleic acid probes according to sequences 20 to 52, 54 to 60, 77 to 90, 112 to 125, and 145 to 184, and to the use thereof for the aforementioned purposes.

The invention will be described in more detail on the basis of the following drawings and examples, without being limited thereto.

BRIEF DESCRIPTION OF THE DRAWING FIGURES

Reference to a Sequence Listing

This application contains a sequence listing in computer readable form; the file, 4008016A_SequenceListing.txt is 39 kb in size. The file is hereby incorporated into the instant disclosure.

Submitted herewith is a substitute sequence listing in computer readable form (text file 4008016A_SequenceListing.txt) for entry into the present application.

Figure 4:
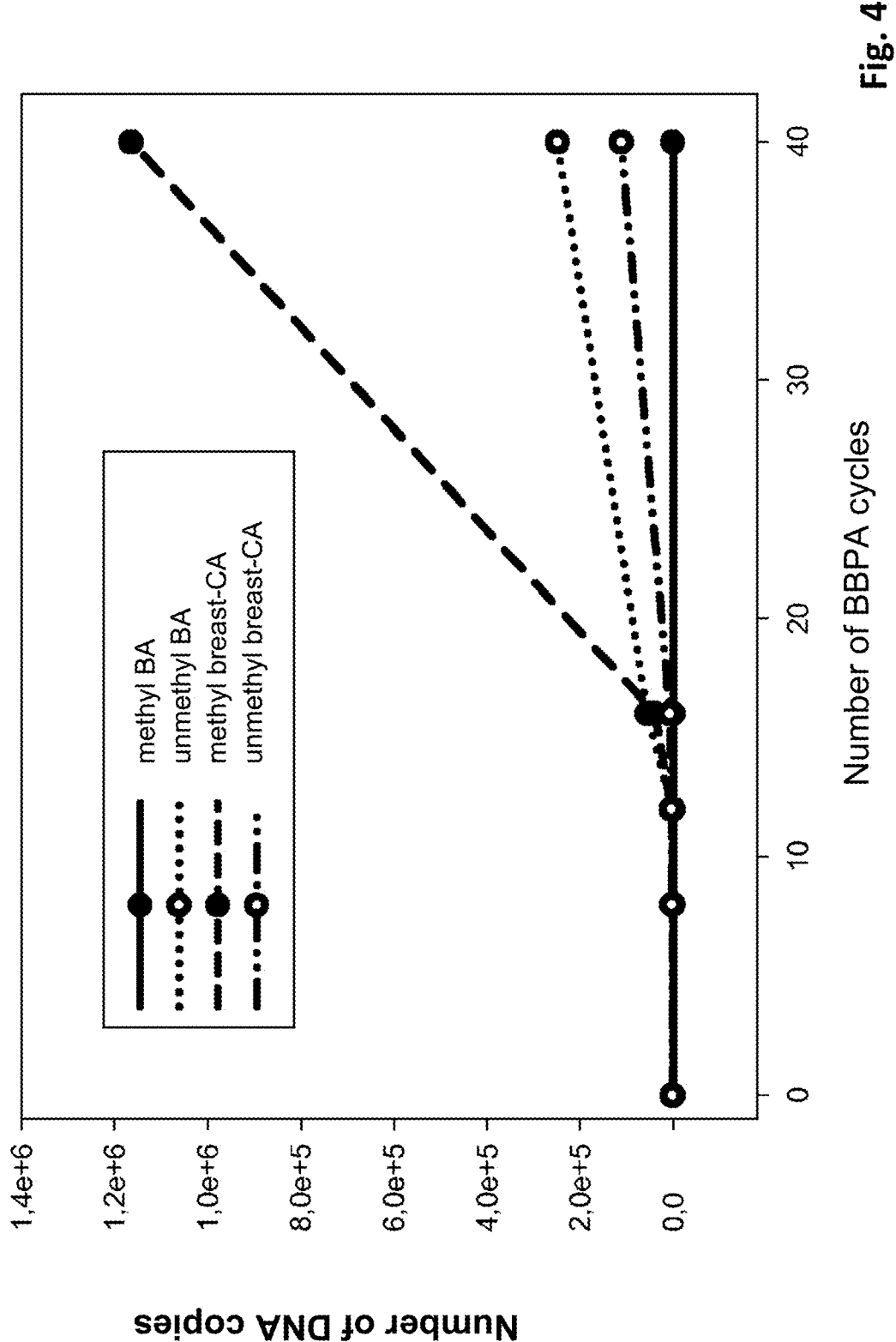
FIG. 4 shows the number of copies of methylated (methyl) and unmethylated (unmethyl) RASSF1A sequences plotted against cycle number (0 [i.e. no BBPA], 8, 12, 16 [see FIG. 3 above] and 40) at 60° C. and an MgCl$_2$ concentration of 2.5 mmol/l in the BBPA in serum pool samples from healthy subjects (BA) or female breast cancer patients (breast-CA; see also Table 3).
Figure 5:
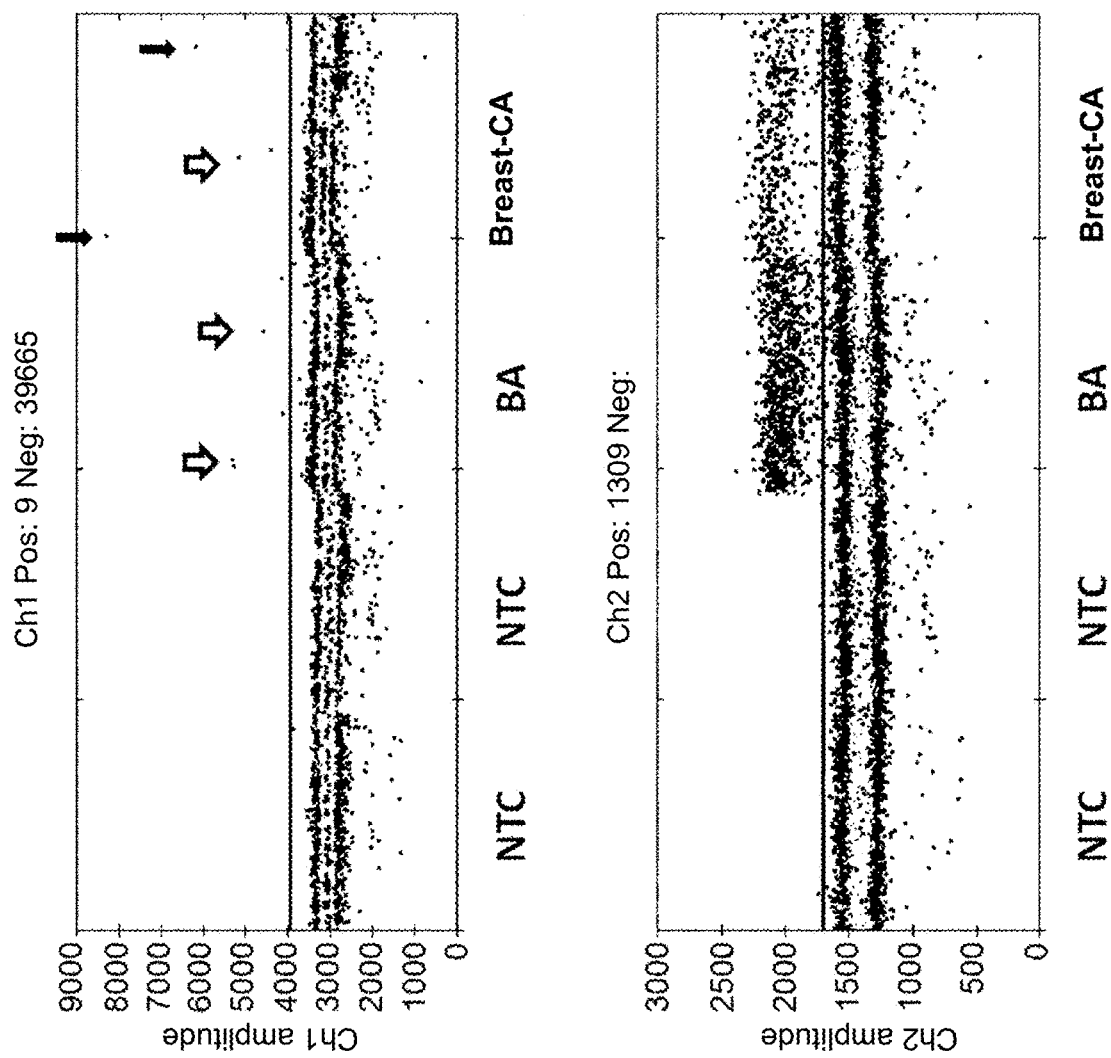

FIG. 5 (comparative data) shows the number of FAM-positive (top image) and HEX-positive (bottom image) signals for methylated and unmethylated RASSF1A sequences in dPCR without BBPA in serum sample pools from healthy subjects (BA) and female breast cancer patients (breast-CA). NTC, non-template control (no DNA). Solid arrows show two FAM-positive signals in the serum pool sample from female breast-CA patients; the empty arrows denote FAM-positive signals whose fluorescence intensity occurred in the serum pool sample from healthy subjects and in female breast-CA patients. In the bottom image, the HEX-positive signals for unmethylated RASSF1A sequences in the serum pool samples from healthy female subjects and female breast-CA patients can be seen above the threshold line; these signals are not found in the NTC samples or FAM-positive signals. Below the threshold lines, the signals from the double-negative droplets are shown. The pool samples BA and breast-CA are identical to the samples tested in FIG. 2-4.

Figure 6:
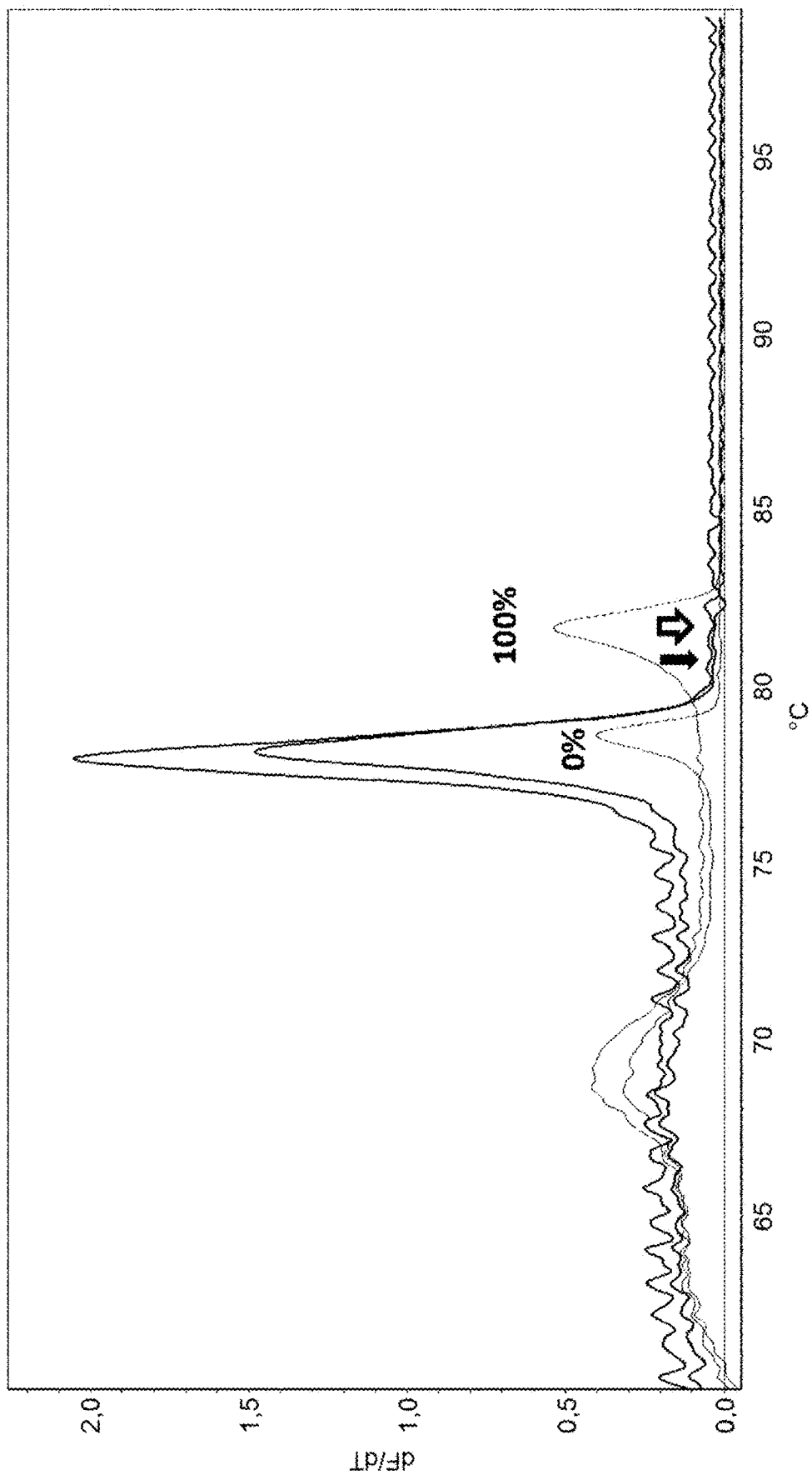

FIG. 6 (comparative data) shows the MS-HRM analysis of the RASSF1A methylation level in the serum pool from healthy female subjects (empty arrow) and subjects with breast cancer (solid arrow) by means of melting curve analysis, in which no methylated proportions could be identified. Broken lines: standard DNA samples having unmethylated (0%) and methylated (100%) DNA. The pool samples BA and breast-CA are identical to the samples tested in FIG. 2-4.

Figure 7:
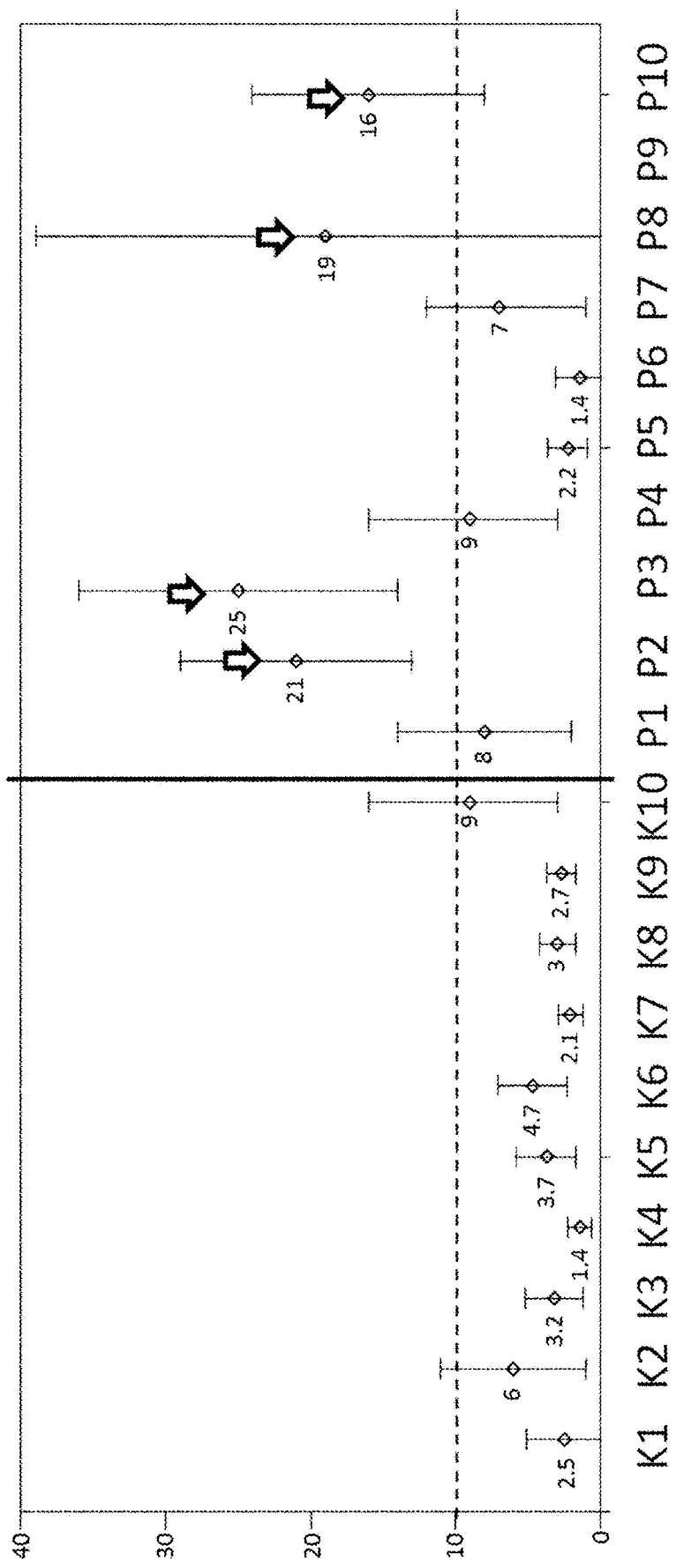

FIG. 7 (comparative data) shows the relative frequency (y-axis in %) of methylated RASSF1A sequences in cfDNA samples from serum of healthy female subjects (K1-K10, left) and female breast-CA patients (P1-P10, right) following dPCR without BBPA. In addition to the medians, the Poisson variation ranges are shown. The empty arrows show 4 out of 10 samples from female breast cancer patients correctly identified as being pathological.

Figure 8:
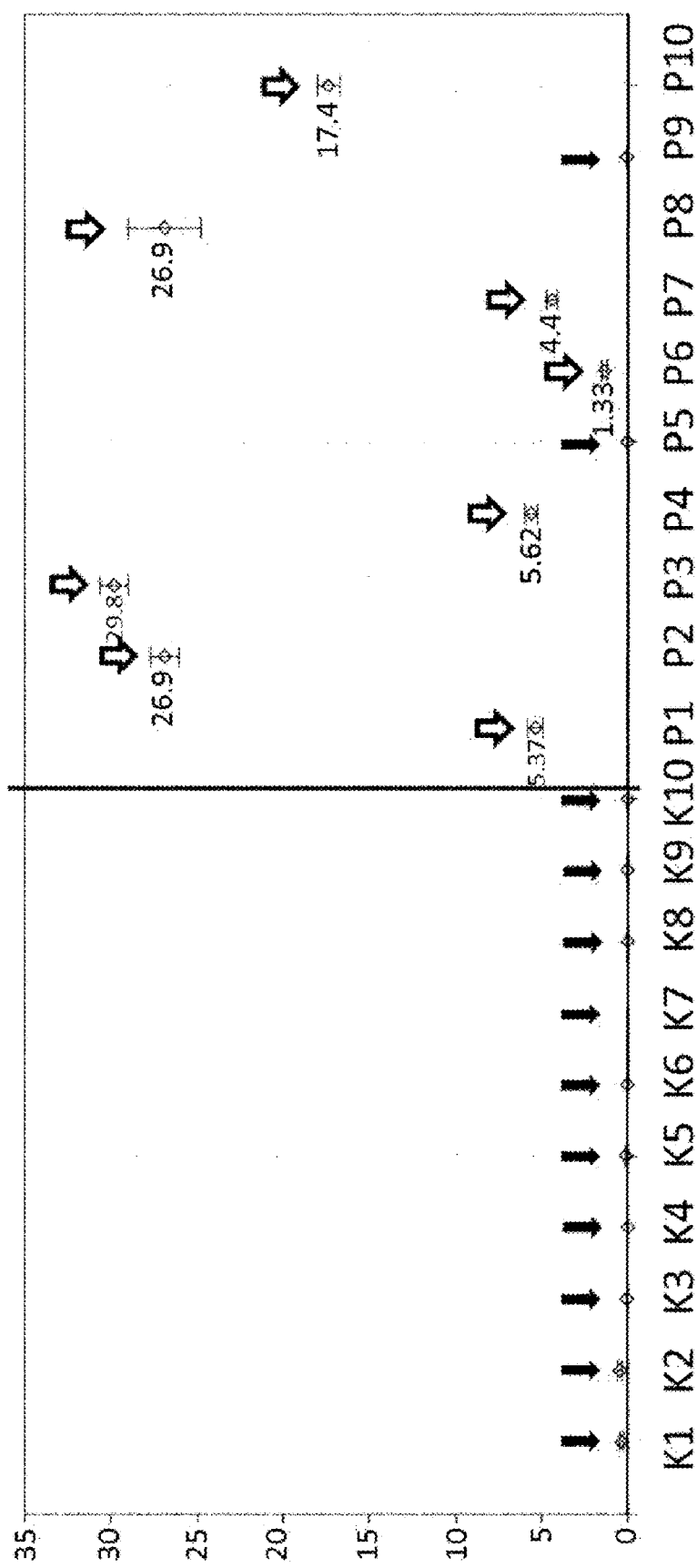

FIG. 8 shows the relative frequency (y-axis in %) of methylated RASSF1A sequences in cfDNA samples from serum of healthy female subjects (K1-K10, left) and female breast-CA patients (P1-P10, right) following BBPA-dPCR (15 cycles at 52° C. and an MgCl$_2$ concentration of 2.5 mmol/l, undiluted in the subsequent dPCR). To the left, the solid arrows show the values for the samples K1-K10 from the healthy subjects, and to the right they show two samples (P5 and P9) for which elevated RASSF1A methylation was not identified. The empty arrows show 8 out of 10 samples from female breast-CA patients for which a correct positive value was identified. The results of the BBPA-dPCR and MS-HRM analysis are compiled in Table 7.

FIG. 9 (comparative data) shows the methylation level of RASSF1A sequences in cfDNA samples from serum of healthy female subjects (K1-K10, Table 7) and breast-CA patients (P1-P10, Table 7) following the MS-HRM analysis. The arrows in C and D show the samples K8 and K9, which showed weak positive methylation levels in the MS-HRM but clearly negative results in the BBPA-dPCR (see FIG. 8). The sample P1, with which a considerably elevated RASSF1A methylation level was associated in the BBPA-dPCR (FIG. 8), produced a seemingly negative result in the MS-HRM (E and F). A, C and E: relative signal changes in relation to the 0% DNA standard; B, D and F: melting curve characteristic of MS-HRM amplified material in relation to the 0% and 100% DNA standards. The results of the MS-HRM and BBPA-dPCR analyses are compiled in Table 7.

Figure 10:
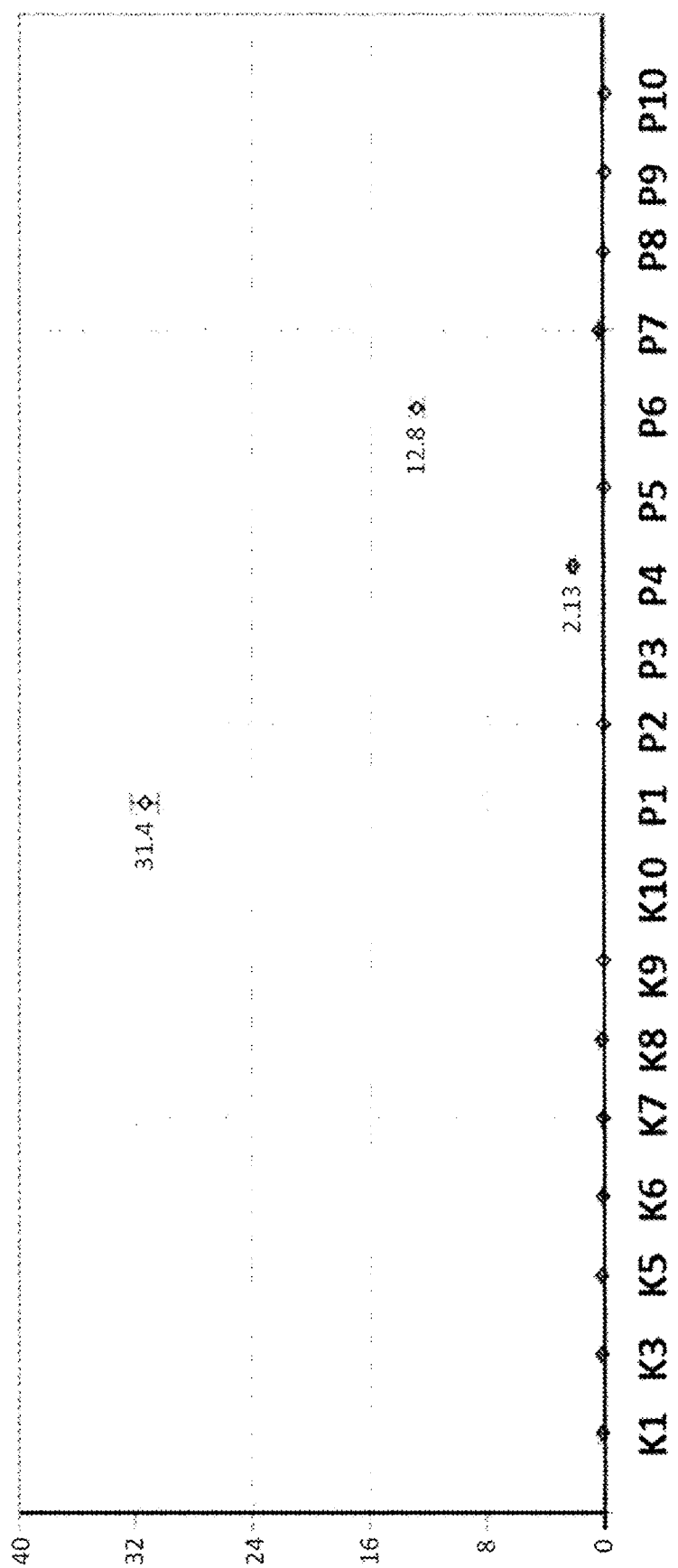

FIG. 10 shows the determination of the methylation level of the PLA2R1 gene (y-axis in %) in cfDNA samples from serum of healthy subjects (K1-K10) and prostate cancer patients (P1-P10) by means BBPA-dPCR (35 cycles at 59° C., an MgCl$_2$ concentration of 2.5 mmol/l and 1:10$^4$ dilution followed by dPCR). In the samples K10 and P3, for which no values are shown, the methylation level was 0% in both cases.

Figure 11:
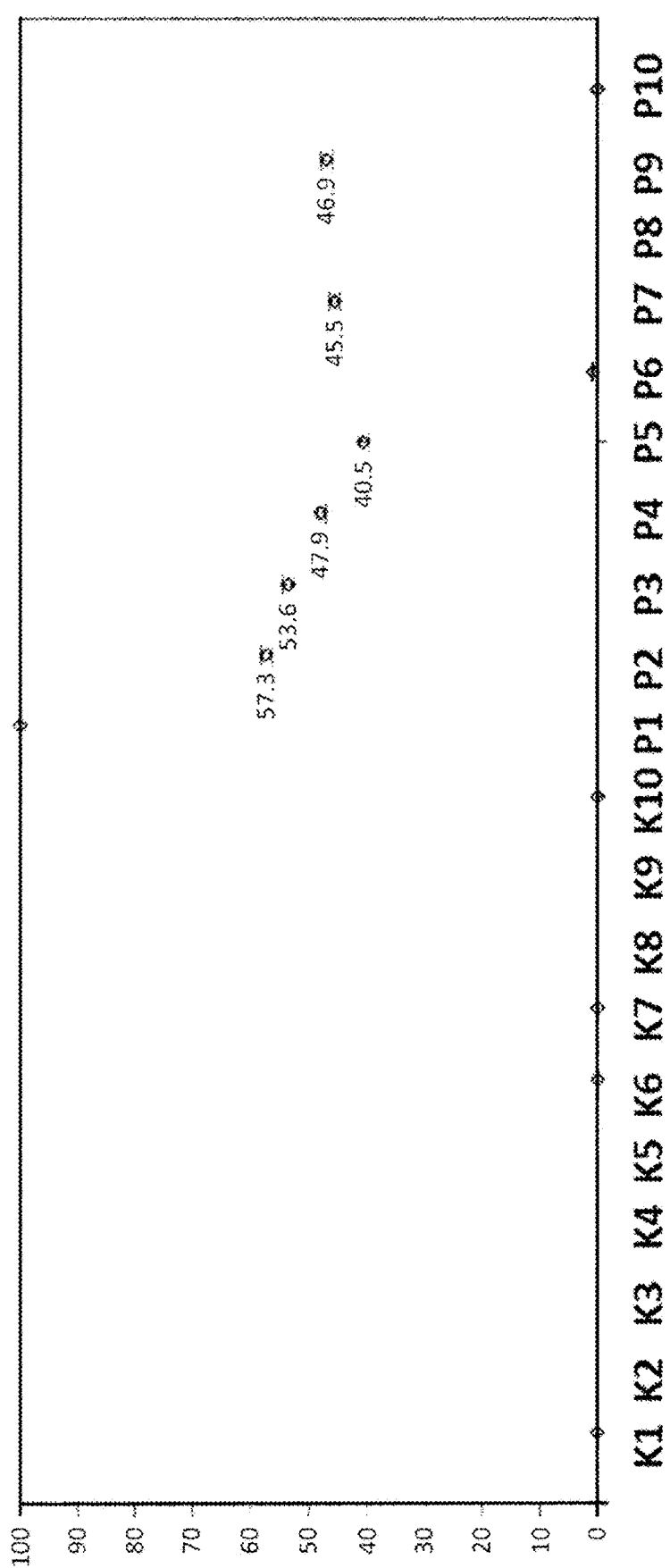

FIG. 11 shows the determination of the methylation level of the RASSF1A gene (y-axis in %) in cfDNA samples from serum of healthy subjects (K1-K10) and PCa patients (P1-P10) by means of BBPA-dPCR (50 cycles at 59° C., an MgCl$_2$ concentration of 2.5 mmol/l and 1:10$^4$ dilution followed by dPCR). In the samples K2-K5, K8, K9 and P8, for which no values are shown, the methylation level was 0% in each case.

Figure 12:
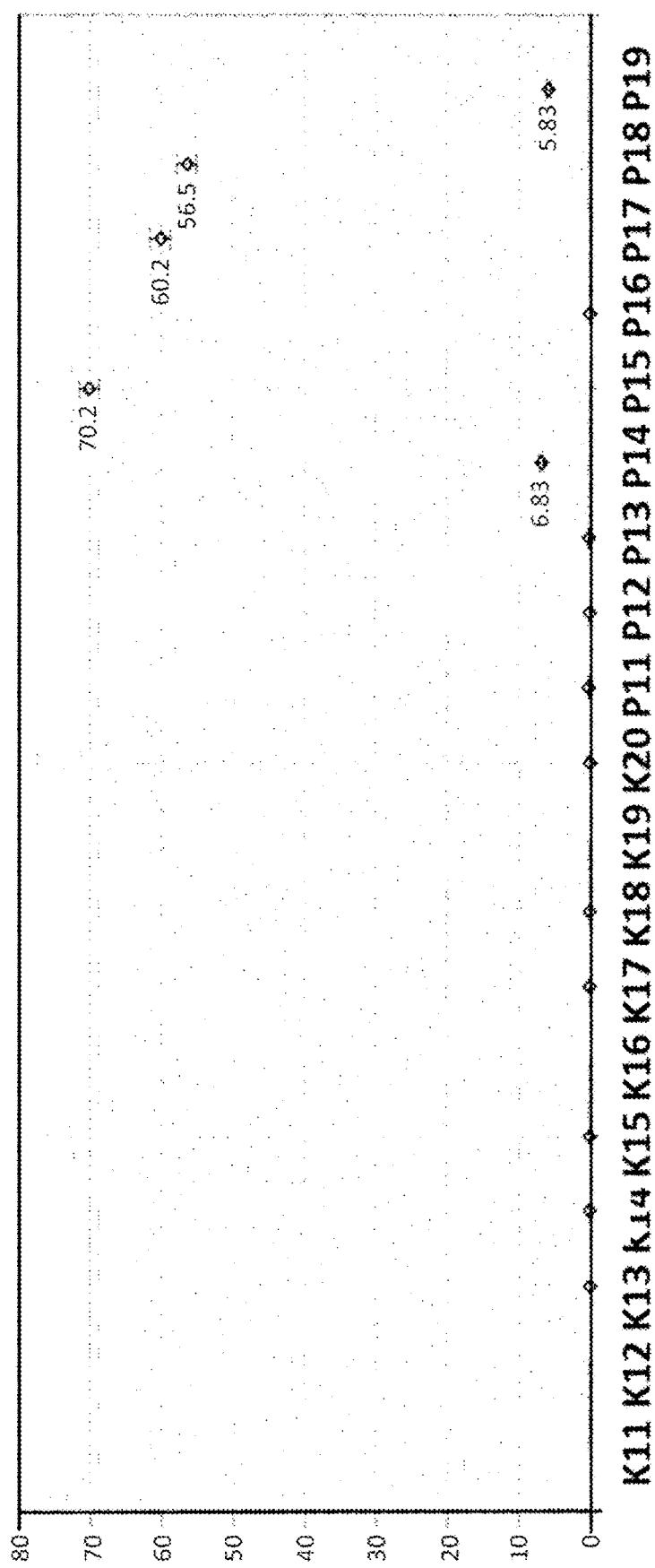

FIG. 12 shows the determination of the methylation level of the GSTP1 gene (y-axis in %) in cfDNA samples from serum of healthy subjects (K11-K20) and prostate cancer patients (P11-P19) by means of BBPA-dPCR analysis (35 cycles at 57° C., an MgCl$_2$ concentration of 2.5 mmol/l and 1:25×10$^3$ dilution followed by dPCR at 51.9° C.). In the samples K12, K12, K16 and K19, for which no values are shown, the methylation level was 0% in each case.

Figure 13:
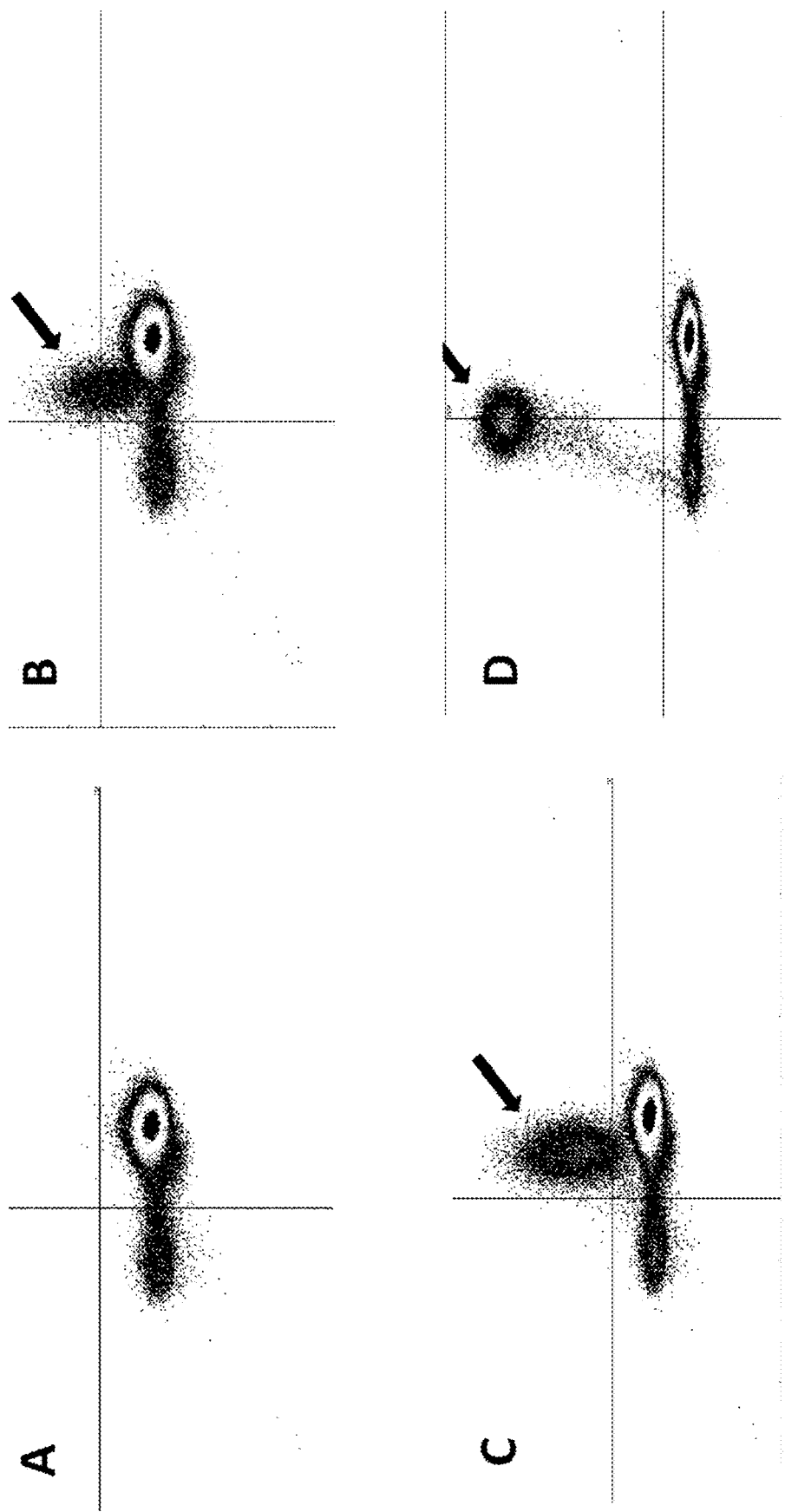

FIG. 13 is a 2D view of the FAM-positive signals (methylated DNA sequences, y-axis) and HEX-positive signals (unmethylated DNA sequences, x-axis) of the GSTP1 gene in cfDNA samples from serum of healthy subjects (K1-K7, K9 and K10, in A) and of prostate cancer patients (P1 in B, P3 in C and P6 in D; see also Table 8) by means of BBPA-dPCR (35 cycles at 57° C., an MgCl$_2$ concentration of 2.5 mmol/l and 1:25×10$^3$ dilution in the subsequent dPCR at 51.9° C.). The arrows show the positive droplets that did not occur in the samples from healthy subjects (see A).

Figure 14:
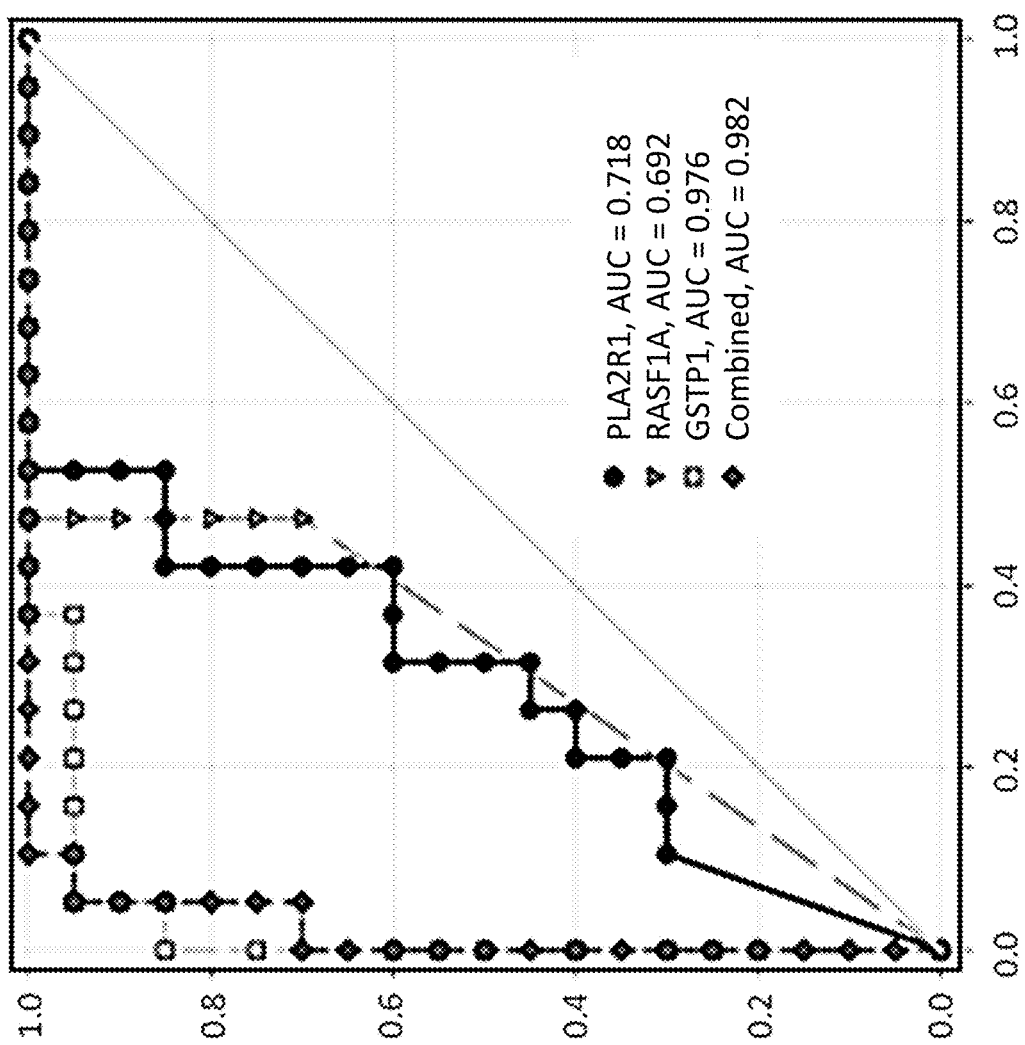

FIG. 14 shows the ROC analysis of the methylation levels of the PLA2R1, RASSF1A and GSTP1 genes, determined by means of BBPA-dPCR, alone and in combination with the test on cfDNA samples from serum of healthy subjects and prostate cancer patients (the individual results are compiled in Table 8).

Figure 15:
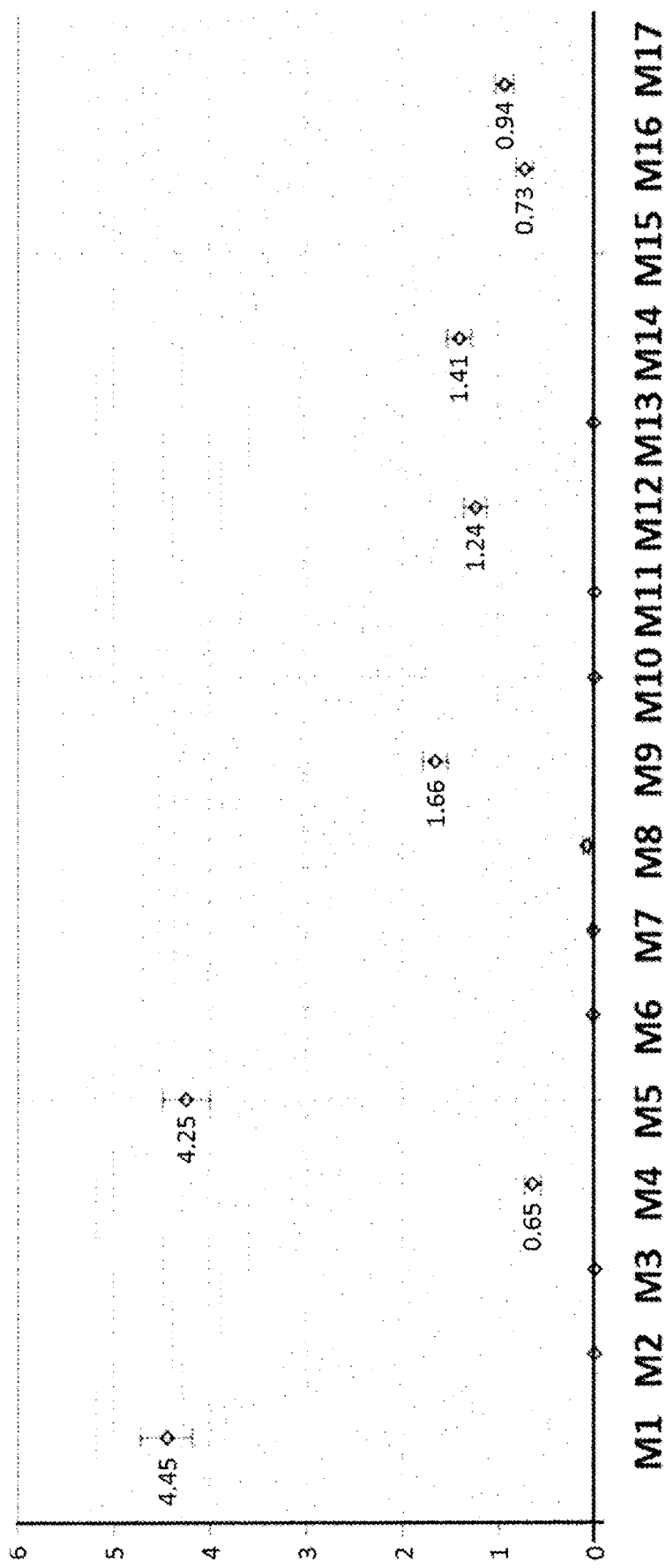

FIG. 15 shows the determination of the methylation level of the PLA2R1 gene (y-axis in %) in cfDNA samples from serum of patients having PSA values between 3.5 and 15.0 ng/ml (exception: sample M2 with a PSA value of 3115 ng/ml) by means of BBPA-dPCR (15 cycles at 59° C. and an MgCl$_2$ concentration of 2.5 mmol/l in the BBPA, and used undiluted in the dPCR at 58.8° C.). In addition to the medians, the Poisson variation ranges are shown. In the sample M15, for which no value is shown, the methylation level was 0%.

Figure 16:
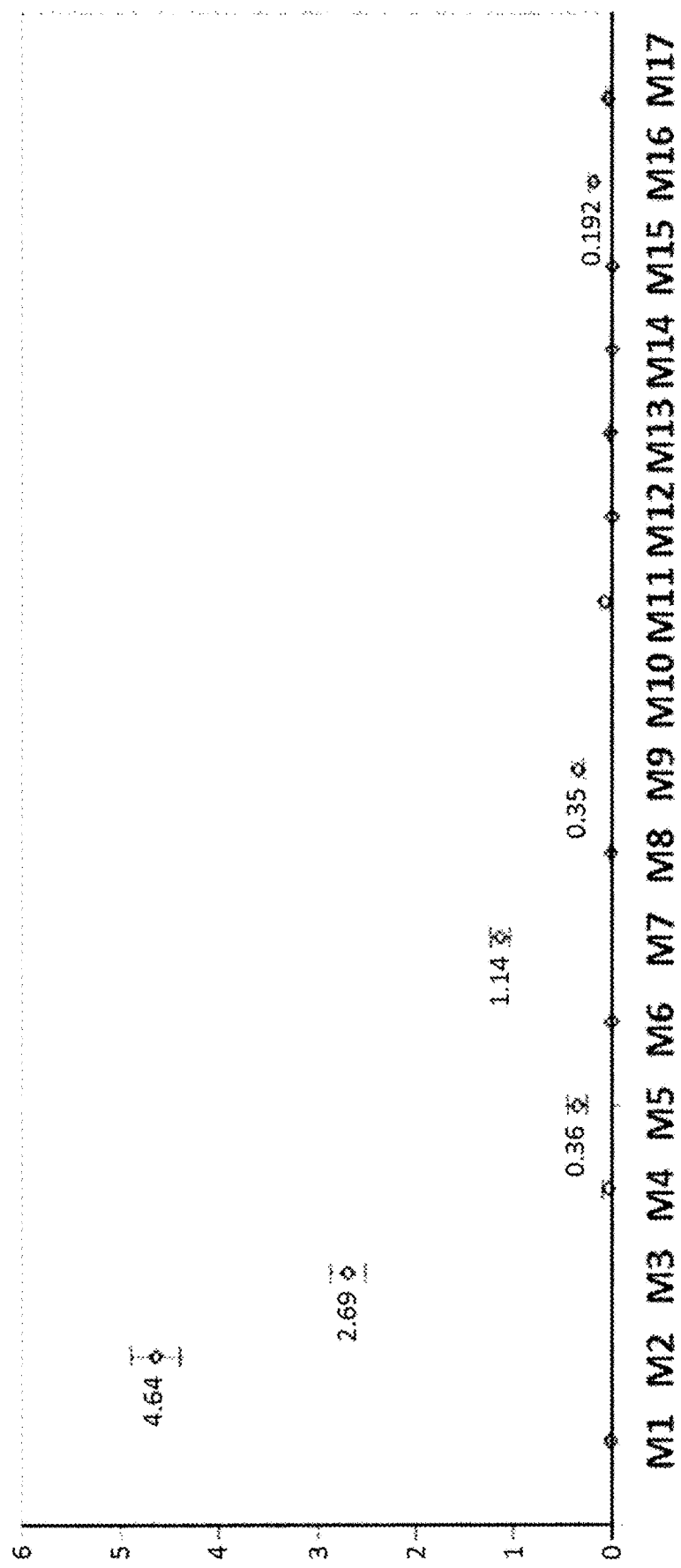

FIG. 16 shows the determination of the methylation level of the GSTP1 gene (y-axis in %) in cfDNA samples from serum of patients having PSA values between 3.5 and 15.0 ng/ml (exception: sample M2 with a PSA value of 3115 ng/ml) by means of BBPA-dPCR (15 cycles at 57° C. and an MgCl$_2$ concentration of 2.5 mmol/l in the BBPA, and used undiluted in the dPCR at 51.9° C.). In addition to the medians, the Poisson variation ranges are shown. In the sample M10, for which no value is shown, the methylation level was 0%.

Figure 17:
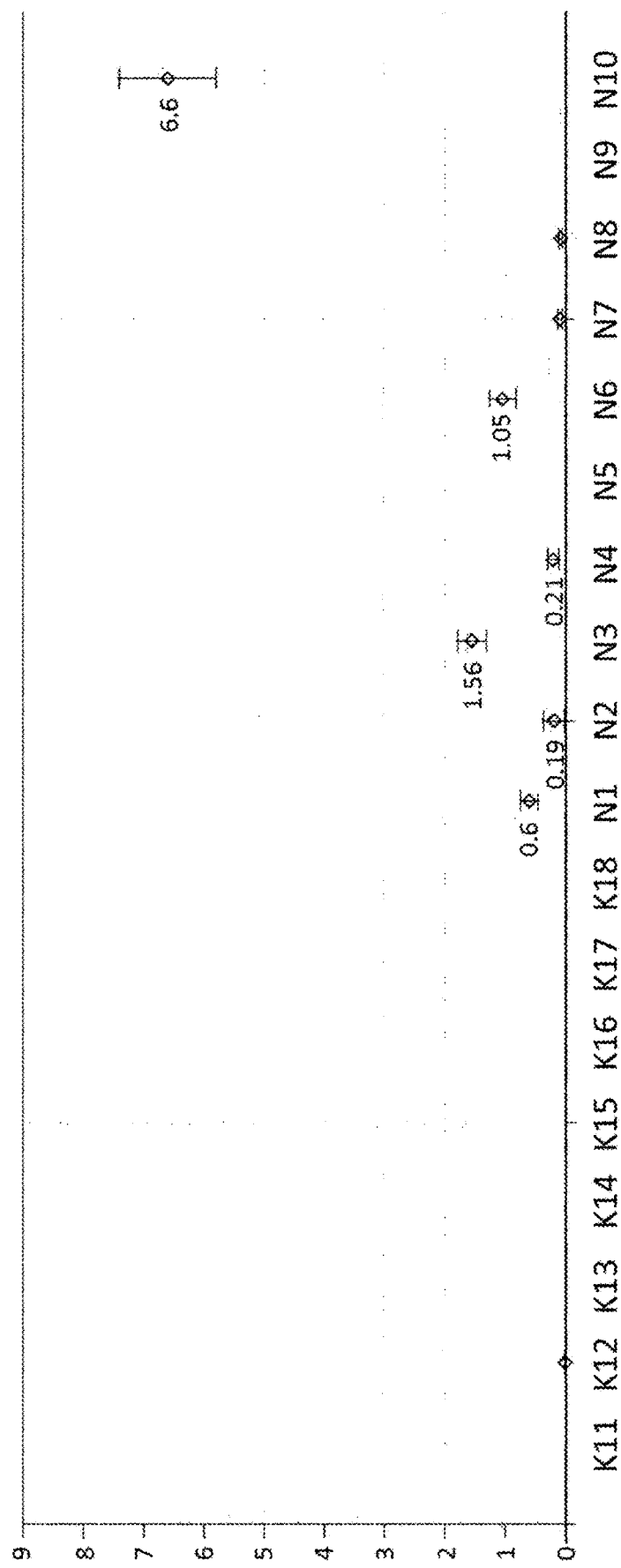

FIG. 17 shows the relative frequency of methylated PLA2R1 sequences (y-axis in %) in cfDNA samples from serum of healthy subjects (K11-K18) and renal cell cancer patients (N1-N10) following BBPA-dPCR (15 cycles at 59° C. and an MgCl$_2$ concentration of 2.5 mmol/l, undiluted in dPCR at 58.8° C.). In addition to the medians, the Poisson variation ranges are shown. In the samples K11, K13-K18, N5 and N9, for which no values are shown, the methylation level was 0%.

Figure 18:
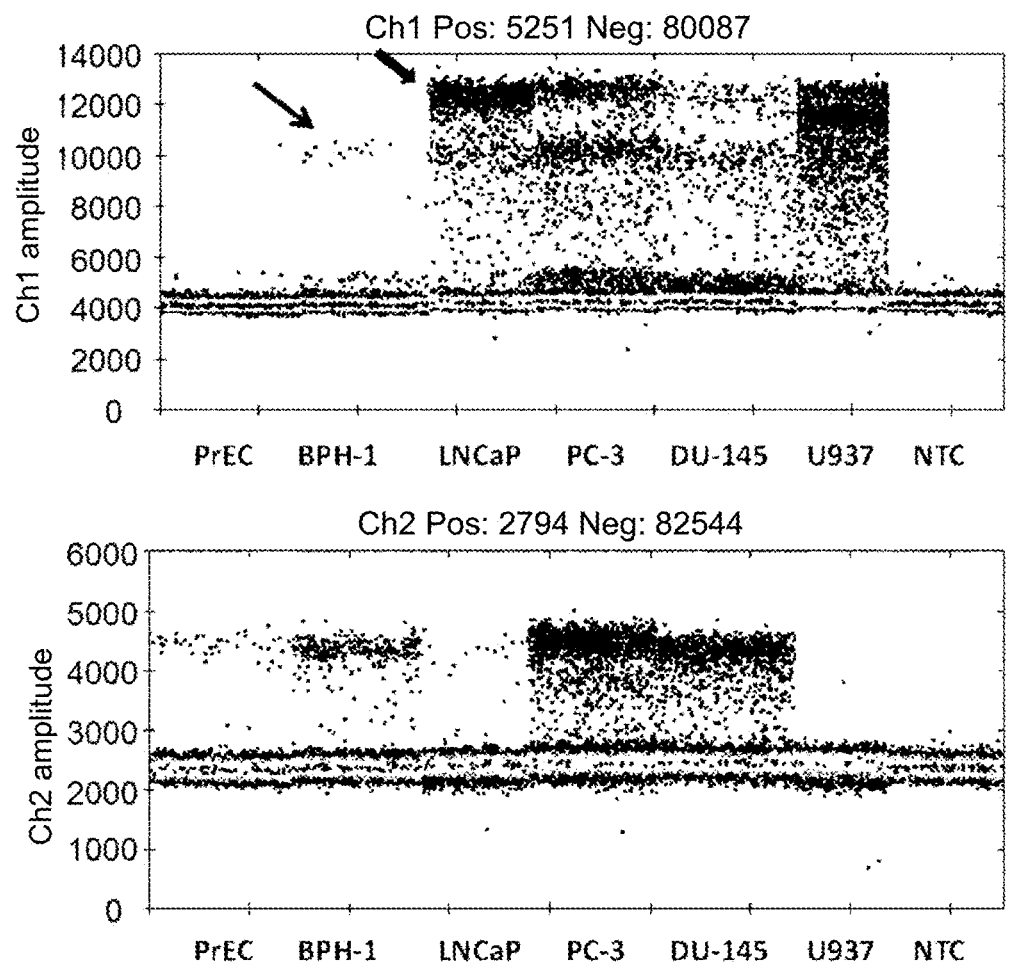

FIG. 18 (comparative data) shows FAM signals (top) for methylated PLA2R1 sequences and HEX signals (bottom) for unmethylated PLA2R1 sequences in DNA samples from PrEC, BPH-1, LNCaP, PC-3, DU-145 and U937 cell lines and non-template control (no DNA present, NTC). The bisulphite-converted DNA was quantified in the dPCR without BBPA in 40 cycles at 58.8° C. The narrow arrow shows the heterogeneously methylated epialleles that could be detected by way of mismatch in the BPH-1 cells and were also detectable in LNCaP, PC-3 and DU-145 cells. Compare this with the homogeneously methylated epialleles in the tumour cell lines LNCaP, PC-3, DU-145 and U937 (thick arrow).

Figure 19:
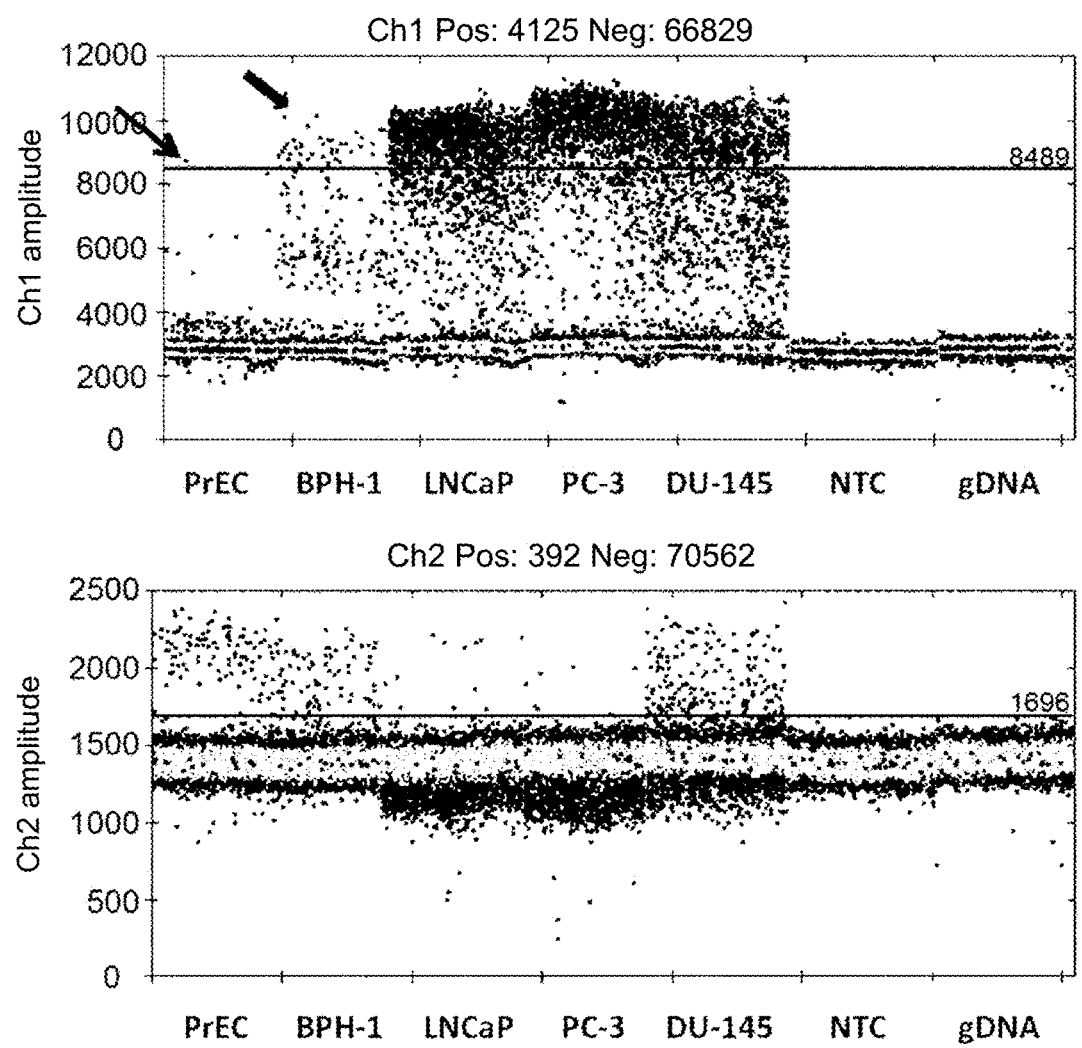

FIG. 19 (comparative data) shows FAM signals (top) for methylated RASSF1A sequences and HEX signals (bottom) for unmethylated RASSF1A sequences in DNA samples from PrEC, BPH-1, LNCaP, PC-3 and DU-145 cell lines, NTC (non-template control) and gDNA (genomic DNA control without bisulphite conversion). The bisulphite-converted DNA was quantified in the dPCR without BBPA in 40 cycles at 51.9° C. The narrow arrow shows one copy of a homogeneously methylated RASSF1A sequence in the PrEC and the thick arrow shows the numerous copies of homogeneously methylated RASSF1A sequences in the BPH-1, LNCaP, PC-3 and DU-145 cell lines. The homogeneously methylated epialleles can be quantified by the heterogeneously methylated epialleles that can be detected by way of mismatch, in particular by adjusting the thresholds accordingly (see FIG. 20 below).

Figure 20:
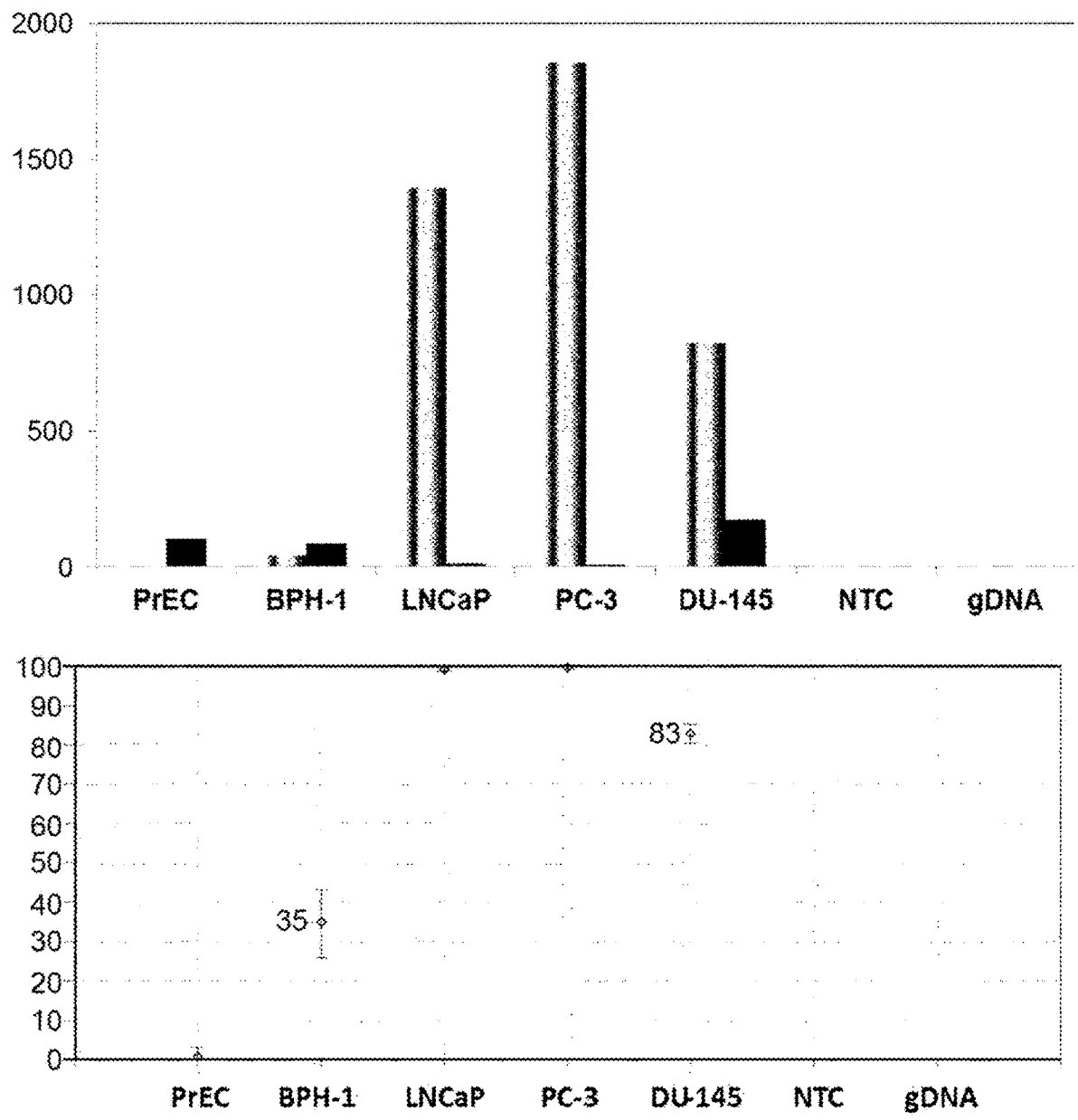

FIG. 20 shows the number of copies of methylated and unmethylated RASSF1A sequences (top image, y-axis=number of results) and the relative frequency (y-axis in %) of homogeneously methylated RASSF1A sequences (bottom image) in PrEC, BPH-1, LNCaP, PC-3 and DU-145 cells. Top image: number of positive signals for homogeneously methylated and unmethylated copies as follows: in PrEC: 1/106; BPH-1: 47/89; LNCaP: 1397/12; PC-3: 1855/9, DU-145: 825/175, NTC (non-template control): 0/0 and gDNA (genomic DNA): 0/1. Bottom image: in addition to the medians, the Poisson variation ranges are shown. The relative homogeneous RASSF1A epiallele methylation was as follows: PrEC 0.9%, BPH-1: 35.0%, LNCaP: 99.2%, PC-3: 99.6%, DU-145: 83.0%, NTC: 0% and gDNA: 0%.

Figure 21:
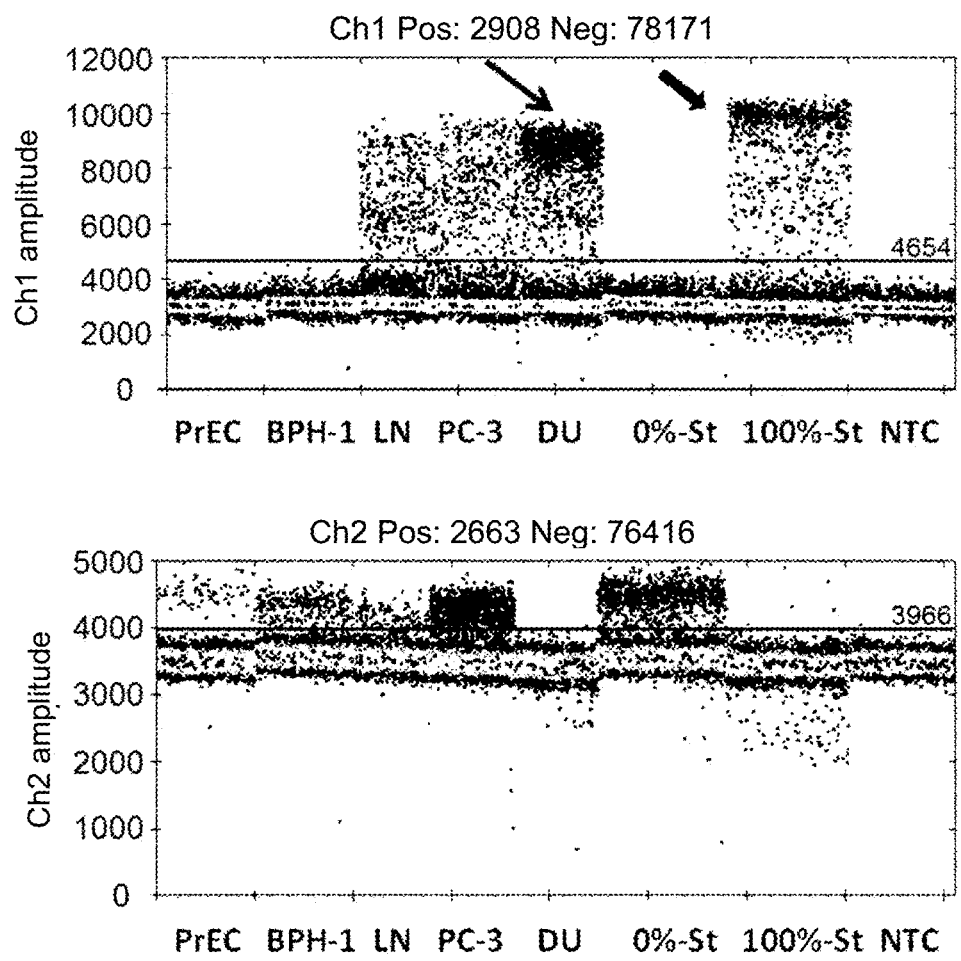

FIG. 21 shows the abundance of FAM-positive (methylated, top image) and HEX-positive (unmethylated, lower image) SERPINE1 sequences in PrEC, BPH-1, LNCaP (LN), PC-3 and DU-145 (DU) cells, in 0% and 100% DNA standards (Qiagen GmbH), and in NTC (non-template control). The thin arrow shows the main fraction of heterogeneously methylated epialleles (three out of four CpG sites methylated) in the DU-145 cell line compared with the homogeneously methylated DNA sequences in the 100% DNA standard (thick arrow). In PrEC and BPH-1, there were no 2, 3 or 4-times methylated epialleles, unlike in the malignant LNCaP, PC-3 and DU-145 cells, which were quantifiable accordingly (see FIG. 22).

Figure 22:
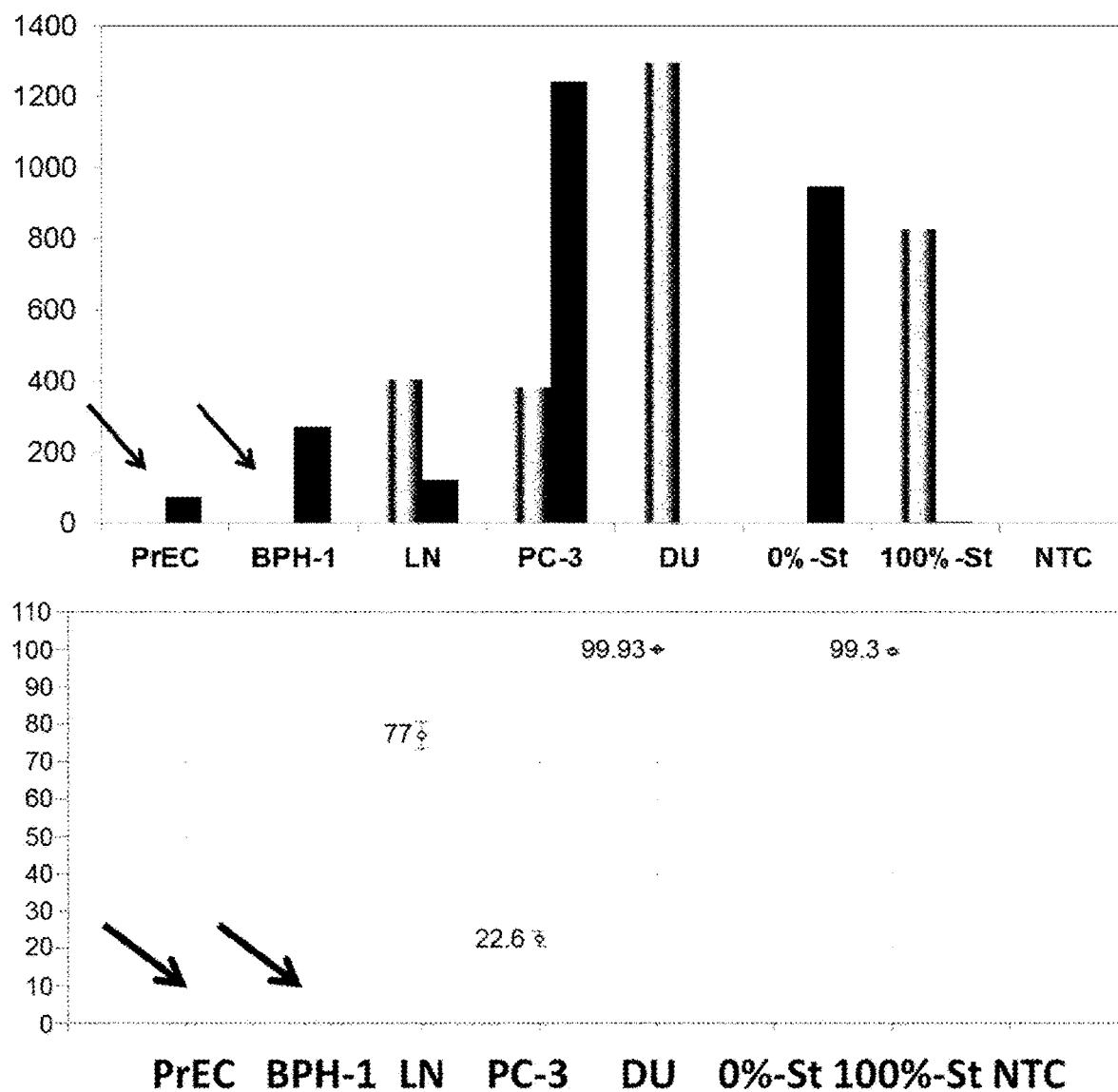

FIG. 22 in the top image shows signal frequencies (y-axis=number of events) for methylated and unmethylated SERPINE1 sequences in PrEC (0 methylated/74 unmethylated), BPH-1 (0/270), LNCaP (404/123), PC-3 (382/1241), DU-145 (1295/1), 0% DNA standard (0/947), 100% DNA standard (827/6) and non-template control (NTC: 0/1). The arrows show the undetectable copies of methylated SERPINE1 sequences in PrEC and the BPH-1 cell line. In the bottom image, the figure shows the relative frequency (y-axis in %) of all, i.e. both homogeneously and heterogeneously methylated epialleles of the SERPINE1 gene in PrEC (0%), BPH-1 (0%), LNCaP (77%), PC-3 (22.6%), DU-145 (99.93%), 0% DNA standard (0%), 100% DNA standard (99.3%) and NTC: 0%. The arrows show the 0% methylated SERPINE1 sequences in PrEC and the BPH-1 cell line.

Figure 23:
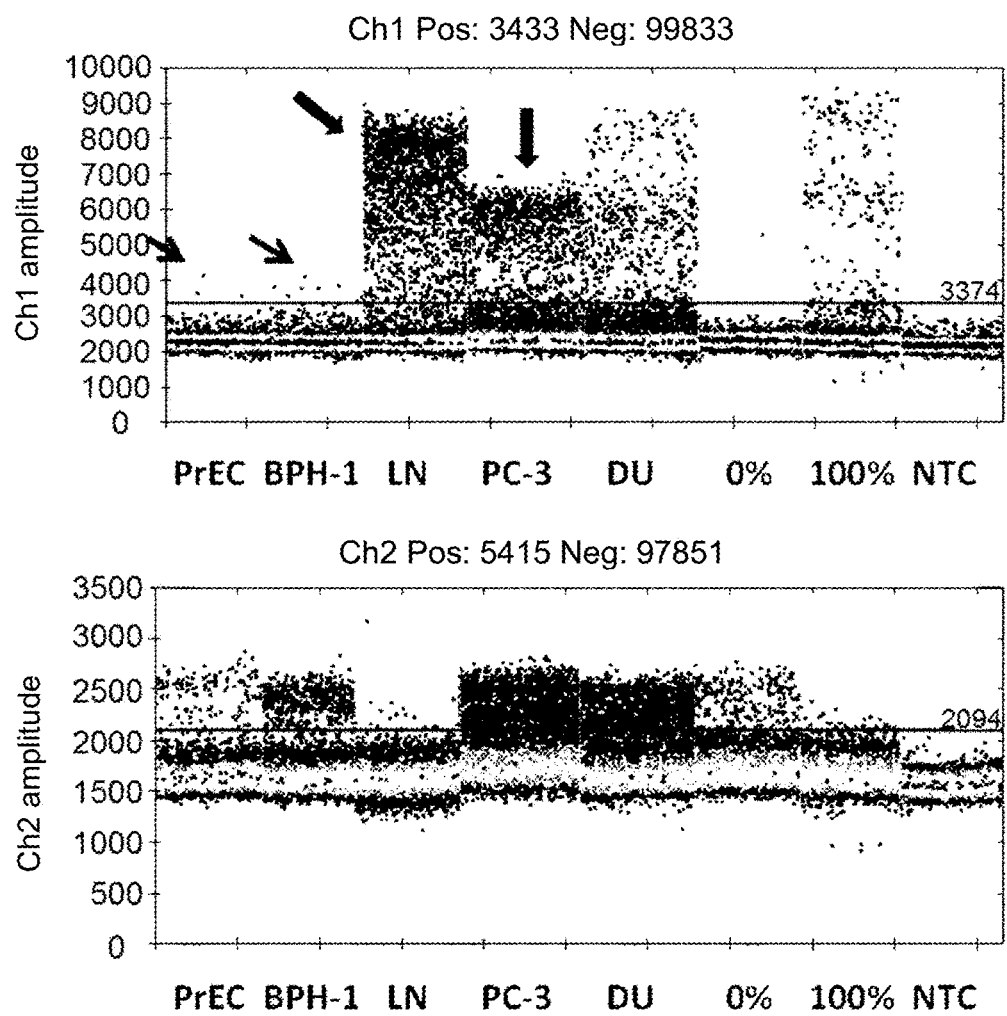

FIG. 23 shows the abundance of methylated (top image) and unmethylated (lower image) GSTP1 sequences in PrEC, BPH-1, LNCaP (LN), PC-3 and DU-145 (DU) cells, in 0% and 100% DNA standards and in NTC (non-template control). The thin arrows show heterogeneously methylated epialleles (one out of three CpG sites methylated) in PrEC and BPH-1, in contrast to the largely homogeneously 3-times methylated epialleles in LNCaP cells (thick arrow) and 2-times heterogeneously methylated alleles in PC-3 cells (second vertical thick arrow).

Figure 24:
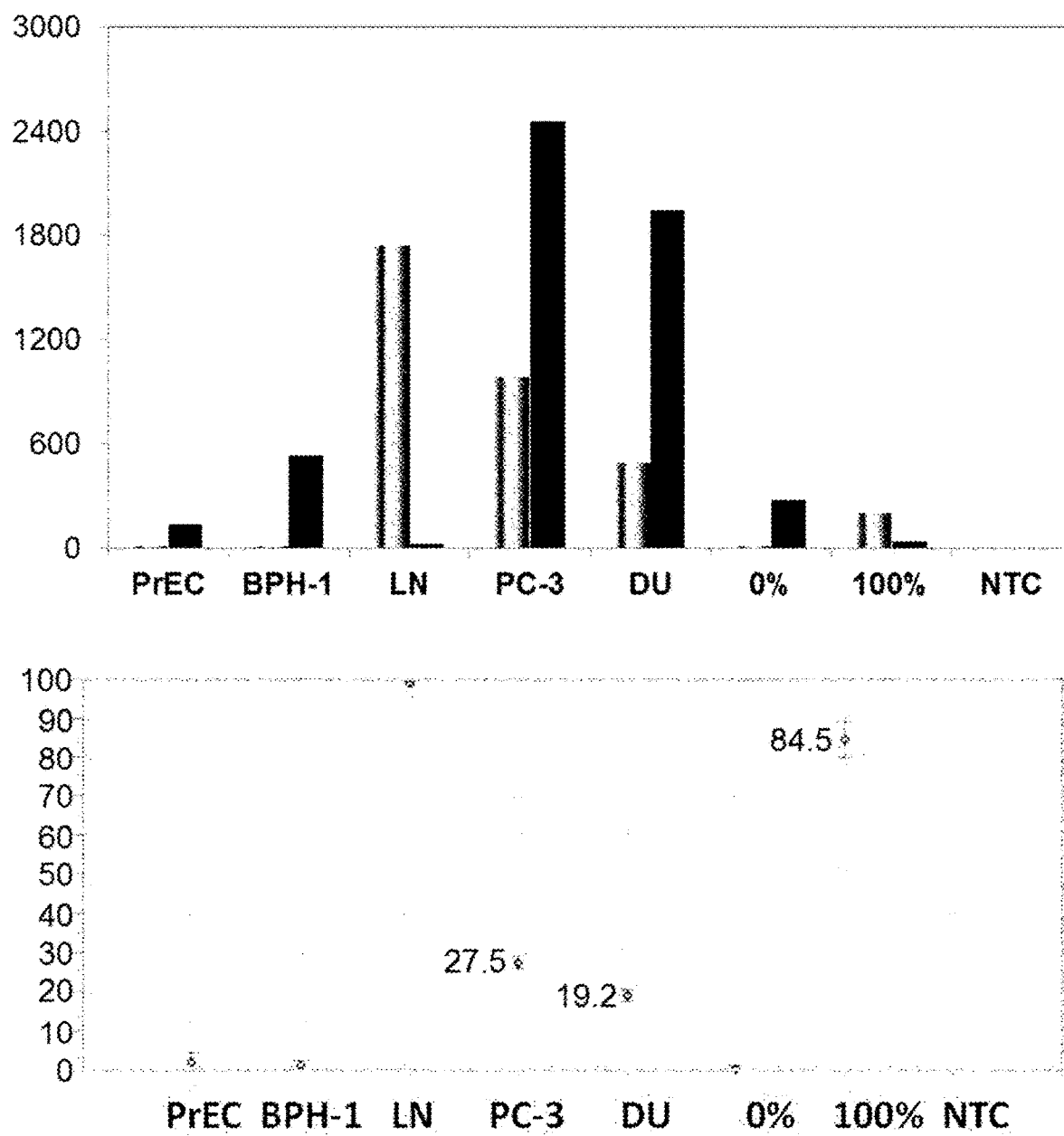

FIG. 24 in the top image shows signal frequencies (y-axis=number of events) for methylated and unmethylated GSTP1 sequences in PrEC (3 methylated/138 unmethylated), BPH-1 (8/532), LNCaP (1777/22), PC-3 (987/2460), DU-145 (490/1947) 0% DNA standard (1/279), 100% DNA standard (200/37) and non-template control (NTC: 0/0). In the bottom image, the drawing shows the relative frequency (y-axis in %) of methylated GSTP1 sequences in PrEC (2.1%), BPH-1 (1.4%), LNCaP (98.84%), PC-3 (27.5%), DU-145 (19.2%), 0% DNA standard (0.4%), 100% DNA standard (84.5%) and NTC (0%).

Figure 25:
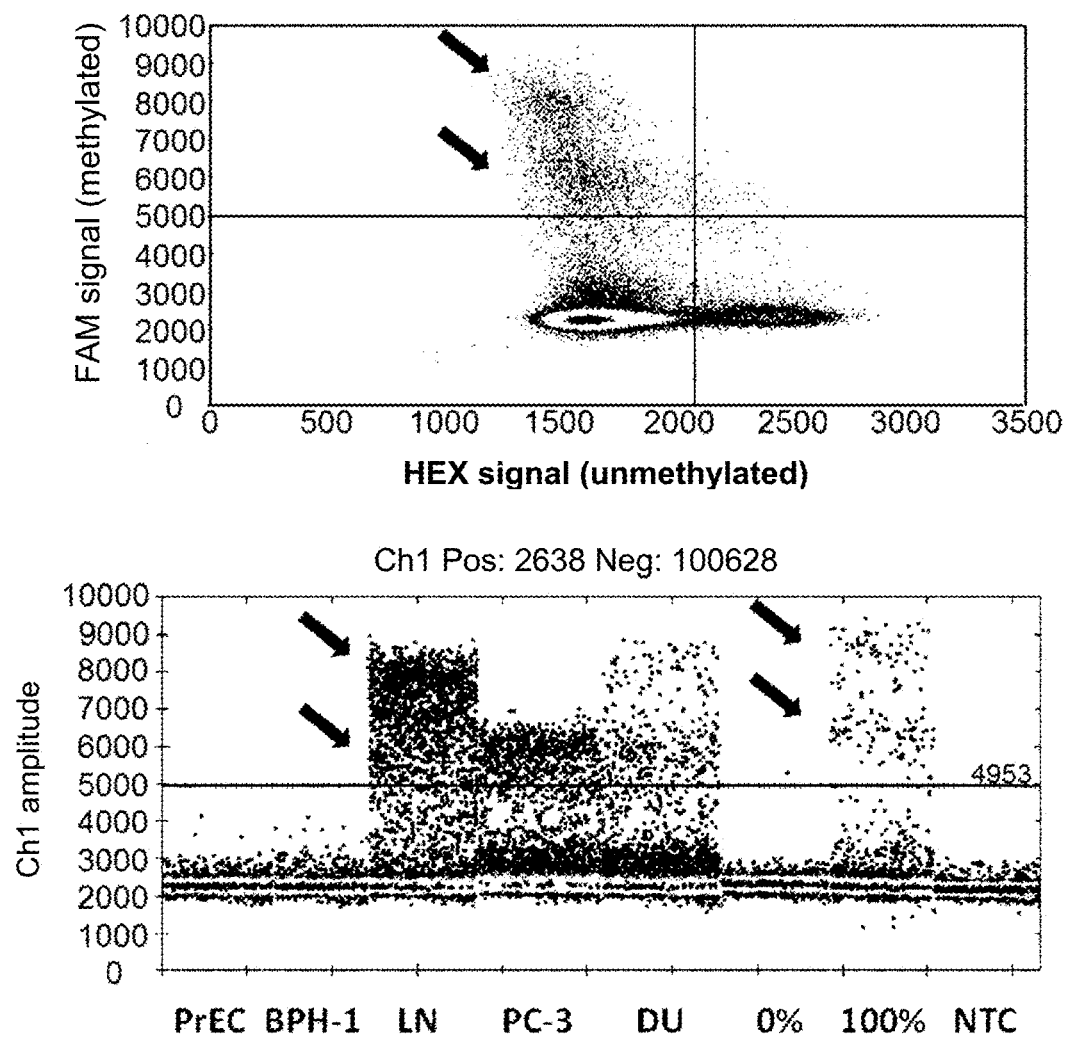

FIG. 25 is a 2D view of the FAM-positive and HEX-positive signals when determining the GSTP1 methylation (see also FIG. 23). In the top image, two populations of droplets having homogeneously (top fraction) and heterogeneously (lower fraction, two out of three CpG sites methylated) methylated epialleles are clearly visible (thick arrows). In the bottom image, where only these two populations of droplets having homogeneously (top fraction) and heterogeneously (lower fraction, two out of three CpG sites methylated) methylated epialleles are quantified (see dividing line in top and bottom image), there are no methylated GSTP1 sequences at all in PrEC and BPH-1 cells.

Figure 26:
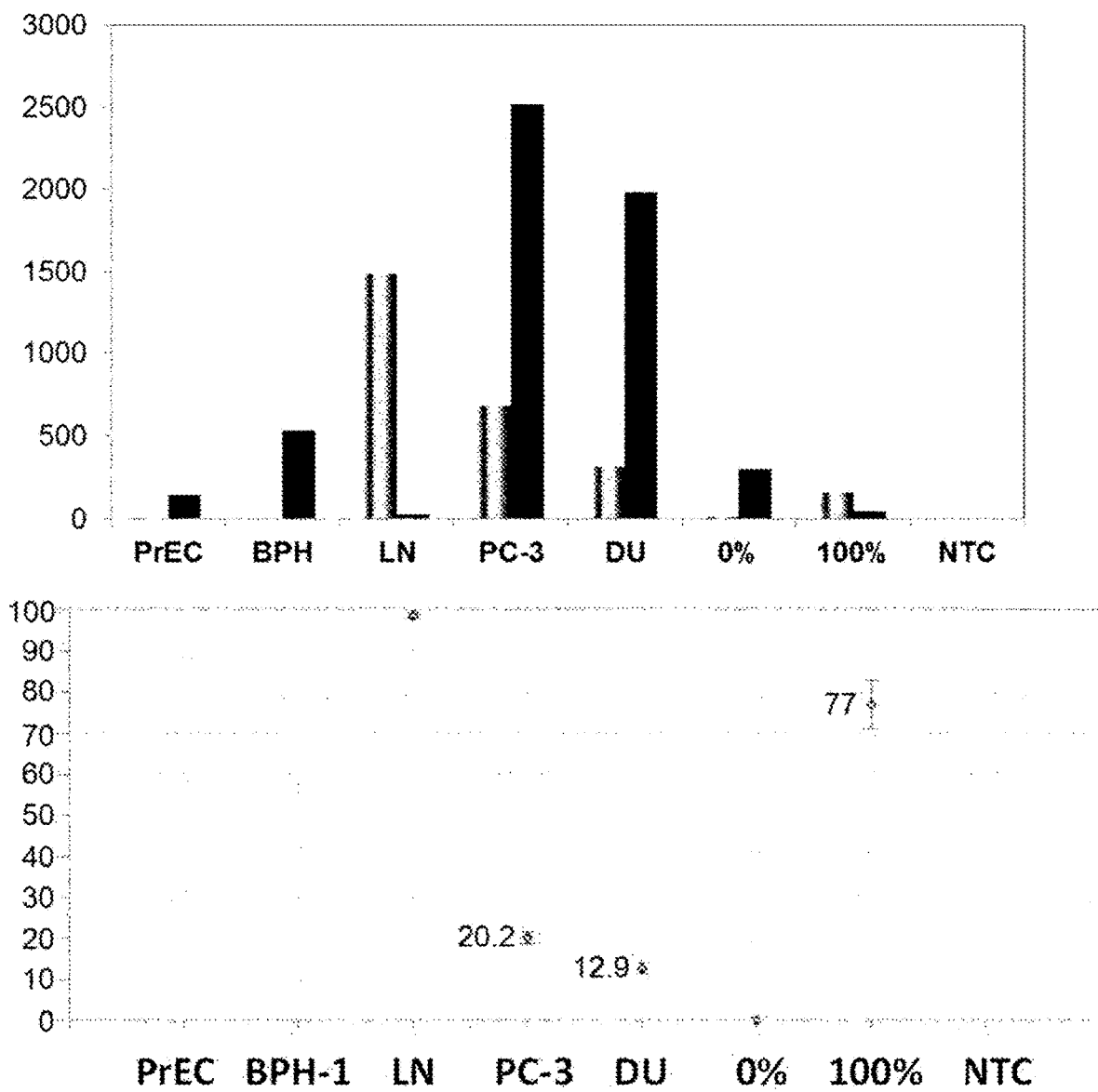

FIG. 26 in the top image shows signal frequencies (y-axis=number of events), resulting in the following positive FAM and HEX signals for methylated and unmethylated GSTP1 sequences: in PrEC (0/141), BPH-1 (0/534), LNCaP (1488/22), PC-3 (682/2515), DU145 (312/1982) 0% DNA standard (1/295), 100% DNA standard (155/46) and NTC (0/0). In the bottom image, the drawing shows relative frequencies (y-axis in %) of methylated GSTP1 sequences in PrEC (0%), BPH-1 (0%), LNCaP (98.6%), PC-3 (20.2%), DU-145 (12.9%), 0% DNA standard (0.3%), 100% DNA standard (77%) and NTC (0%). By comparison, the relative frequency was 2.1% for PrEC and 1.4% for BPH-1 cells at the corresponding threshold in FIGS. 23 and 24. For GSTP1, the 100% DNA standard is only 77% methylated, as already seen in FIG. 25 (bottom image, highlighted by two thick arrows).

Figure 27:
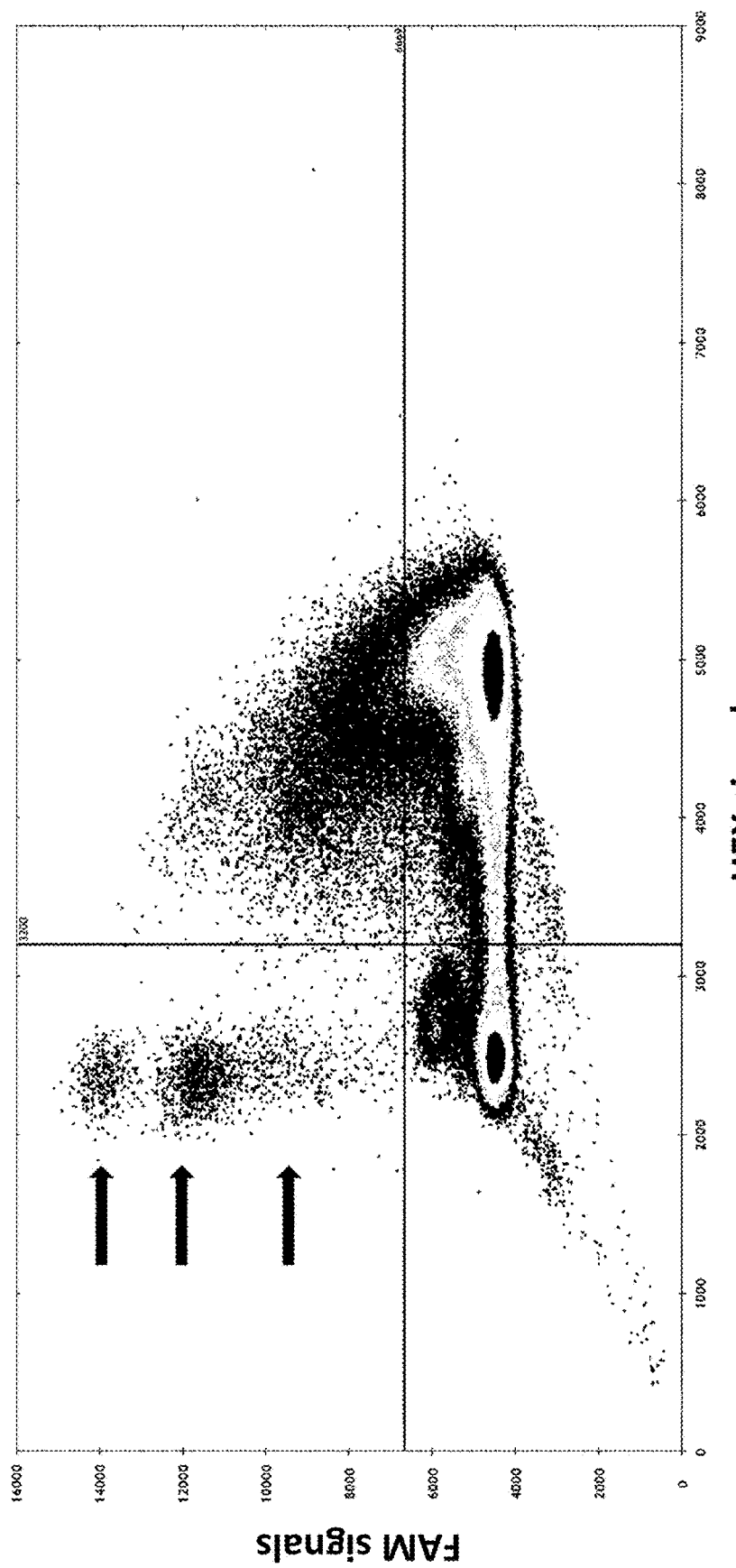

FIG. 27 is a 2D view of the FAM-positive and HEX-positive signals when determining the PLA2R1 methylation in serum samples from healthy subjects (K1-K20) and prostate cancer patients (P1-P40) after 15 BBPA cycles at 59° C. and an MgCl$_2$ concentration of 2.5 mM, followed by dPCR. The thresholds for the FAM-positive and HEX-positive signals were set such that all three fractions of FAM-positive homogeneously and heterogeneously methylated PLA2R1 epialleles highlighted with arrows were included in the calculations (Table 12).

Figure 28:
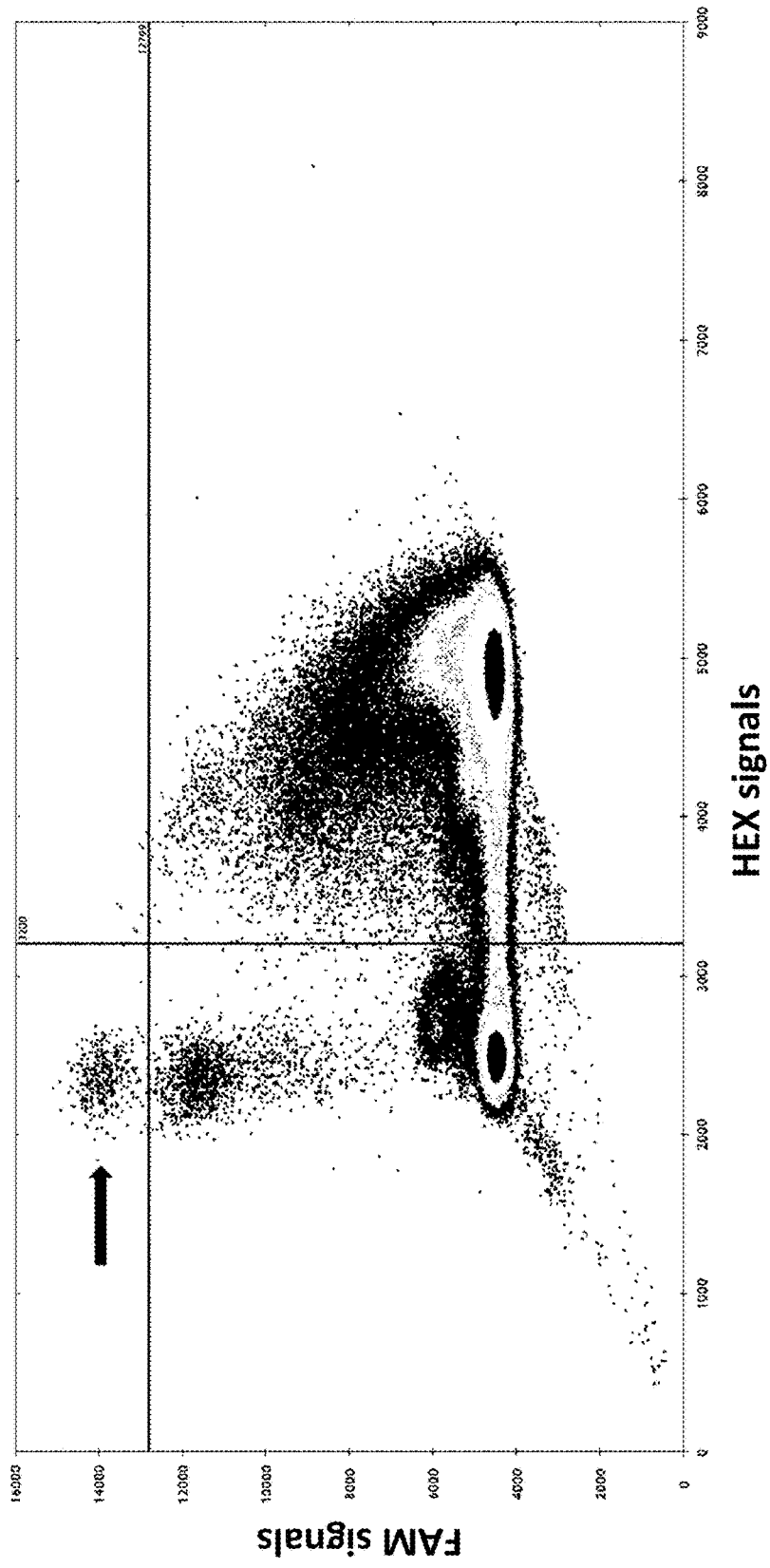

FIG. 28 is a 2D view of the FAM-positive and HEX-positive signals when determining the PLA2R1 methylation in serum samples from healthy subjects (K1-K20) and prostate cancer patients (P1-P40) after 15 BBPA cycles at 59° C. and an MgCl$_2$ concentration of 2.5 mM, followed by dPCR. The thresholds for the FAM-positive and HEX-positive signals were set such that only the fractions of FAM-positive homogeneously methylated PLA2R1 epialleles highlighted with arrows were included in the calculations (Table 12).

Figure 29:
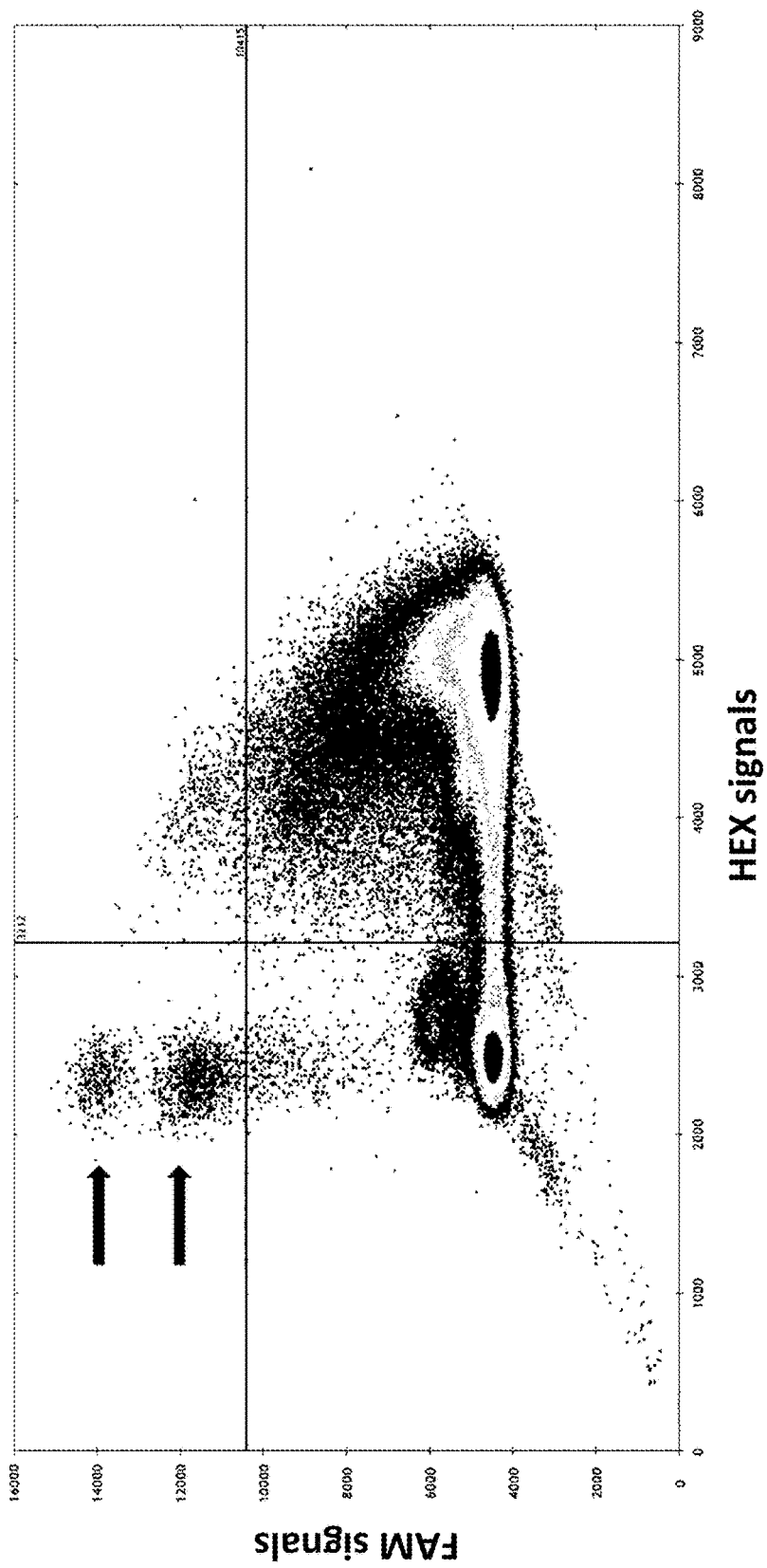

FIG. 29 is a 2D view of the FAM-positive and HEX-positive signals when determining the PLA2R1 methylation in serum samples from healthy subjects (K1-K20) and prostate cancer patients (P1-P40) after 15 BBPA cycles at 59° C. and an MgCl$_2$ concentration of 2.5 mM, followed by dPCR. The thresholds for the FAM-positive and HEX-positive signals were set such that only two fractions of FAM-positive homogeneously and heterogeneously (two out of three CpG sites) methylated PLA2R1 epialleles highlighted with arrows were included in the calculations (Table 12).

Figure 30:
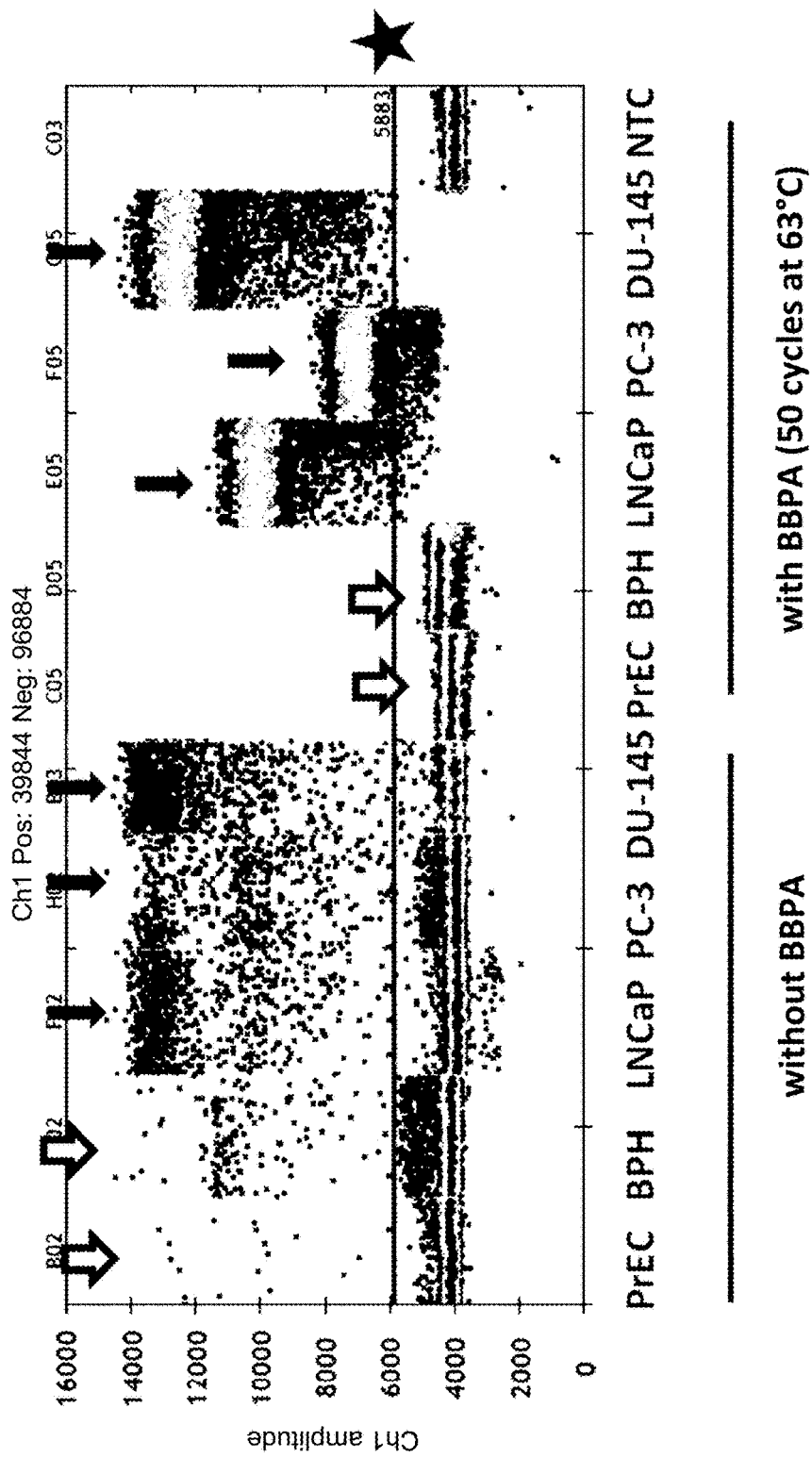

FIG. 30 shows the number of FAM-positive signals for methylated PLA2R1 sequences without BBPA (comparative data) and after 50 BBPA cycles at 63.0° C. and an MgCl$_2$ concentration of 2.5 mmol/l in normal prostate epithelial cells (PrEC), the benign prostatic hyperplasia cell line (BPH-1) and malignant prostate cancer cell lines (LNCaP, PC-3 and DU-145). The empty arrows show positive signals in DNA samples from PrEC and BPH-1 without BBPA compared with after BBPA; solid arrows show positive signals in DNA samples from LNCaP, PC-3 and DU-145 before and after BBPA; the star shows the threshold between negative and positive FAM signals.

Figure 31:
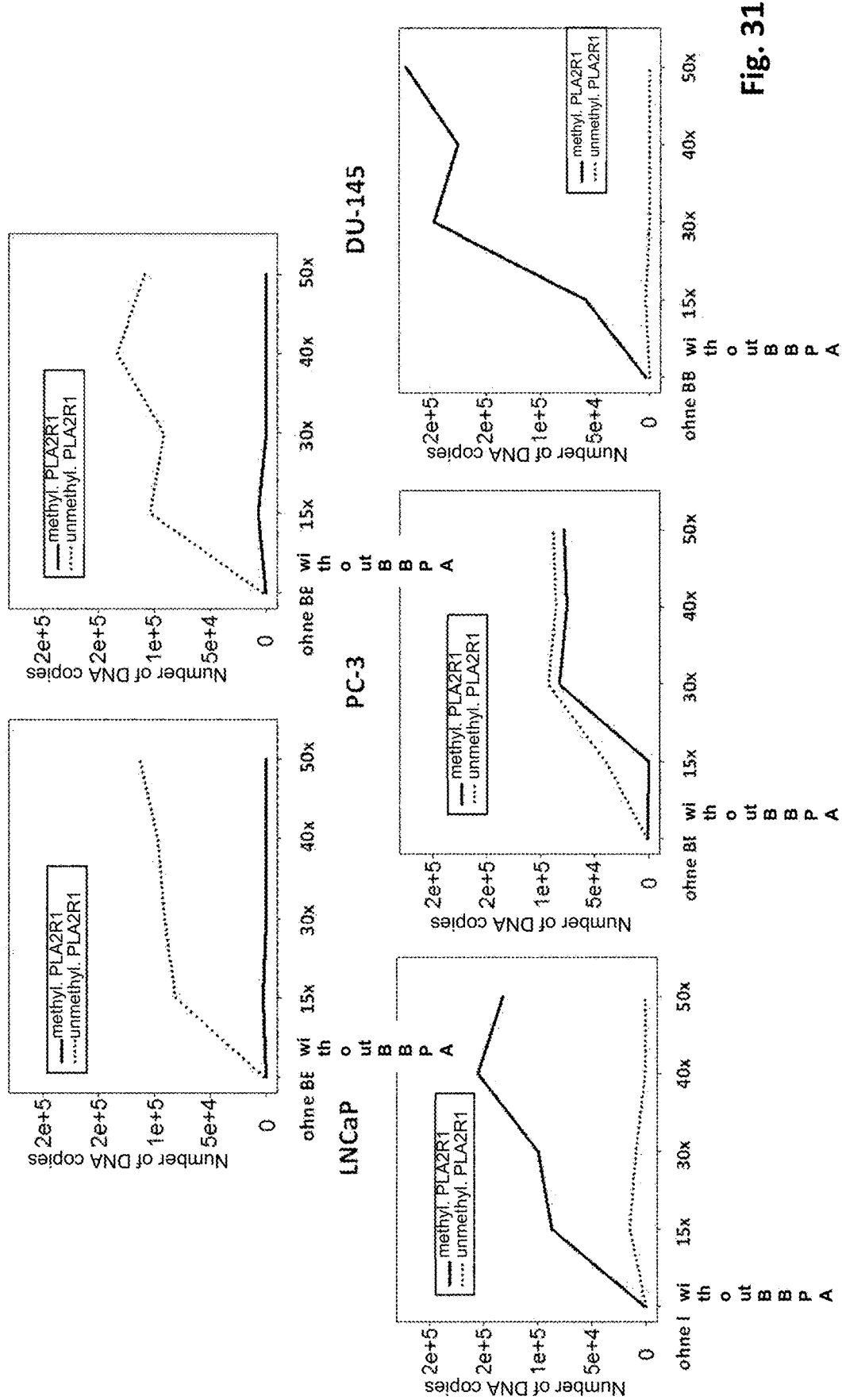

FIG. 31 shows the number of copies (y-axis) of methylated (methyl) and unmethylated (unmethyl) PLA2R1 sequences without BBPA (comparative data) and after BBPA for 15, 30, 40 and 50 cycles at 63.0° C. and an MgCl$_2$ concentration of 2.5 mmol/l in normal prostate epithelial cells (PrEC), the benign prostatic hyperplasia cell line (BPH-1) and malignant prostate cancer cell lines (LNCaP, PC-3 and DU-145). Following BBPA, 1 μl of the 25 μl PCR batches was introduced into the dPCR. To compare the number of copies with those without BBPA, the copies without BBPA were multiplied by 25.

Figure 32:
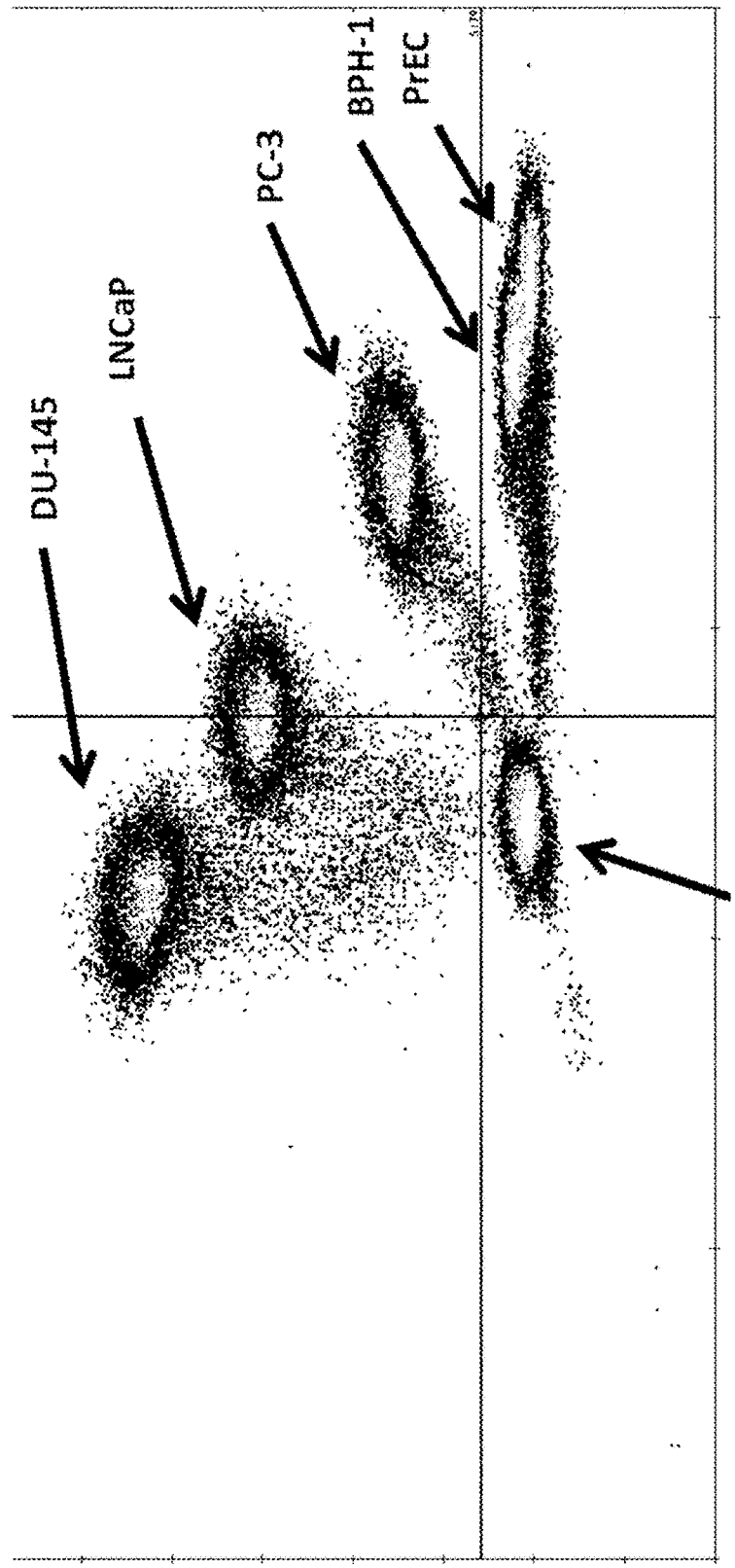

FIG. 32 shows the number of FAM-positive (y-axis, methylated) and HEX-positive (x-axis, unmethylated) signals for PLA2R1 sequences after 50 BBPA cycles at 63.0° C. and an MgCl$_2$ concentration of 2.5 mmol/l in normal prostate epithelial cells (PrEC), the benign prostatic hyperplasia cell line (BPH-1) and malignant prostate cancer cell lines (LNCaP, PC-3 and DU-145). The arrows show the scatter plots for the PrEC, BPH-1 LNCaP, PC-3 and DU-145 cell lines, and the non-template control (no DNA, NTC). The NTC are highlighted by the lower arrow having no description, and the individual values are compiled in Table 20.

Figure 33:
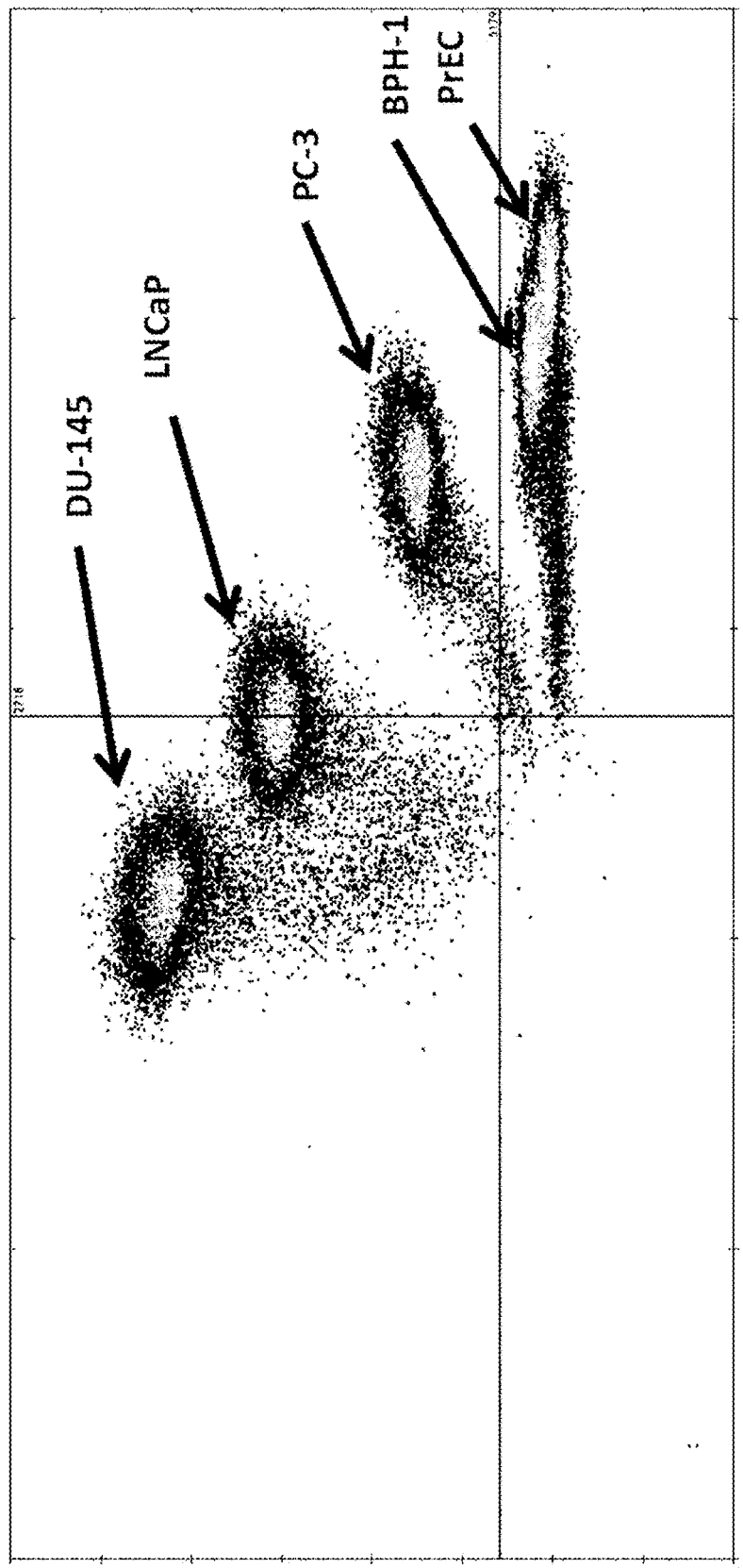

FIG. 33 shows the number of FAM-positive (y-axis, methylated) and HEX-positive (x-axis, unmethylated) signals for PLA2R1 sequences after 50 BBPA cycles at 63.0° C. in normal prostate epithelial cells (PrEC), the benign prostatic hyperplasia cell line (BPH-1) and malignant prostate cancer cell lines (LNCaP, PC-3 and DU-145). The arrows show the scatter plots for the PrEC, BPH-1, LNCaP, PC-3 and DU-145 cell lines. Unlike in FIG. 29, the non-template control is not shown, thereby demonstrating that none of the samples contained any double-negative droplets once in the dPCR. The individual values are compiled in Table 20.

Figure 34:
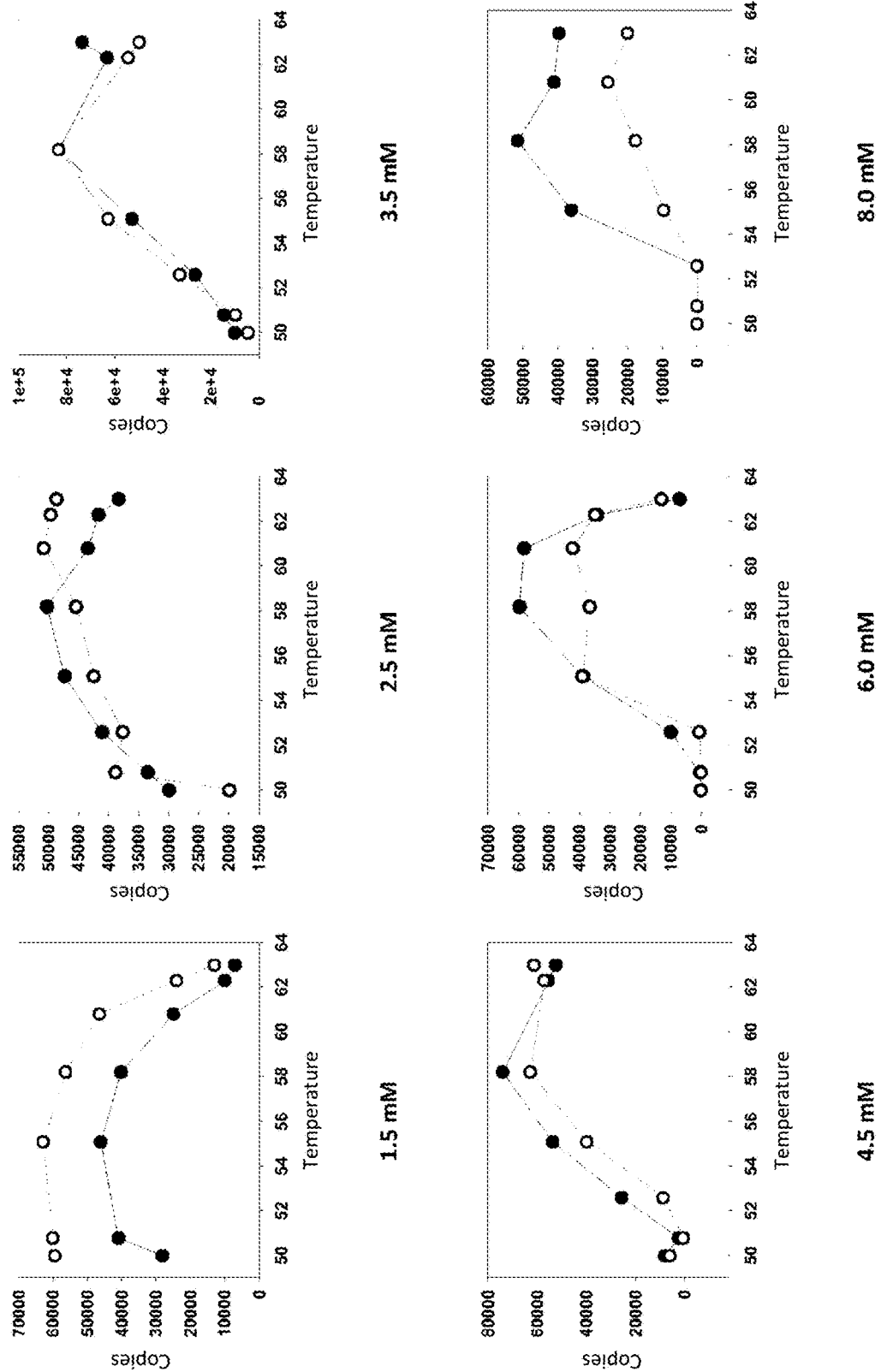

FIG. 34 shows the number of copies of methylated (solid circles) and unmethylated (empty circles) PLA2R1 DNA fragments after 16 pre-amplification cycles at increasing annealing temperatures (50-63° C.) as a function of MgCl$_2$ concentration (from 1.5 mmol/l to 8.0 mmol/l) using the primer pair 168 bp (SEQ ID: 1 and 2), and subsequent dPCR.

Figure 35:
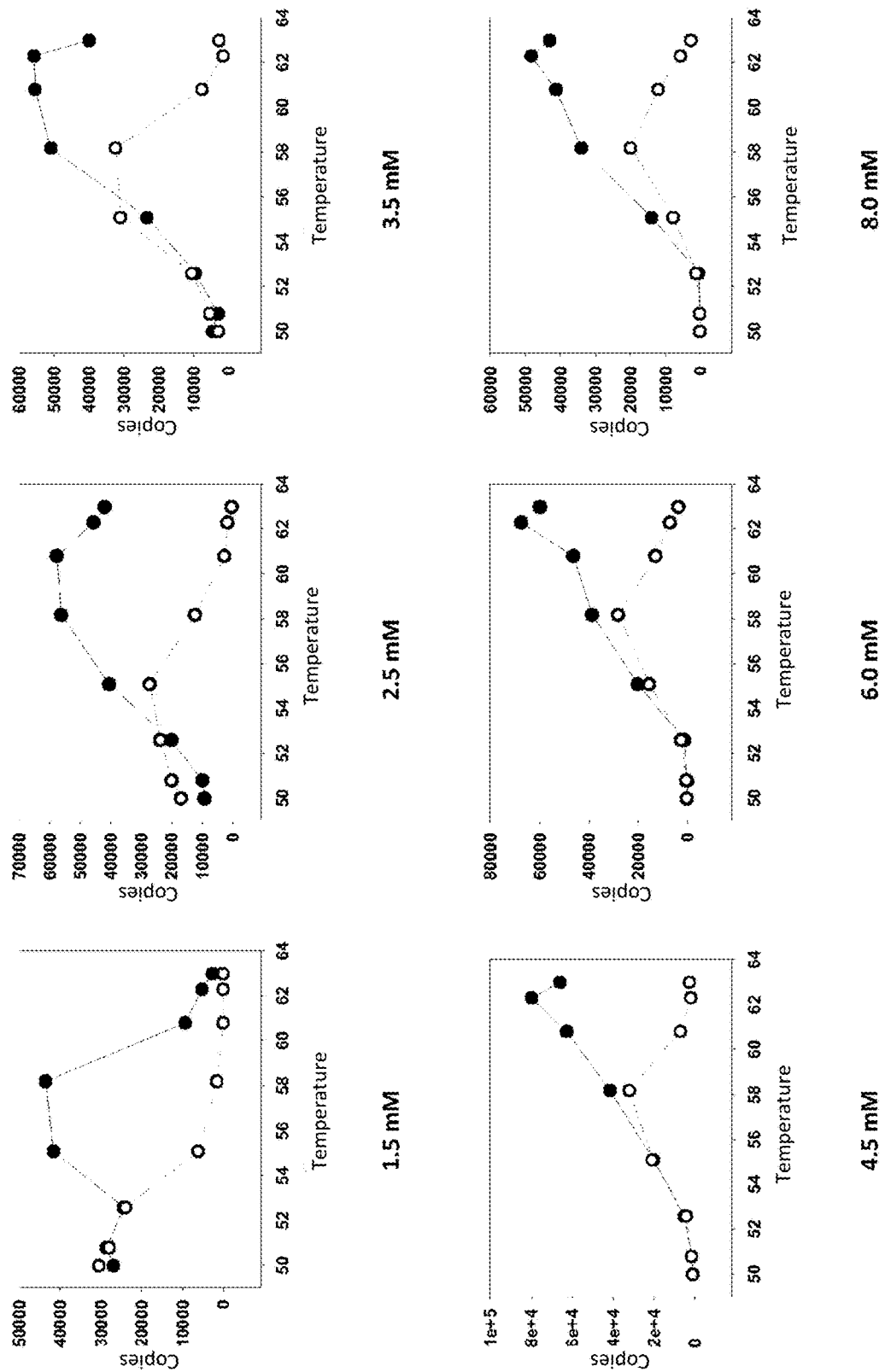

FIG. 35 shows the number of copies of methylated (solid circles) and unmethylated (empty circles) PLA2R1 DNA fragments after 16 pre-amplification cycles at increasing annealing temperatures (50-63° C.) as a function of MgCl$_2$ concentration (from 1.5 mmol/l to 8.0 mmol/l) using the primer pair 161 bp (SEQ ID: 53 and 10), and subsequent dPCR.

Figure 36:
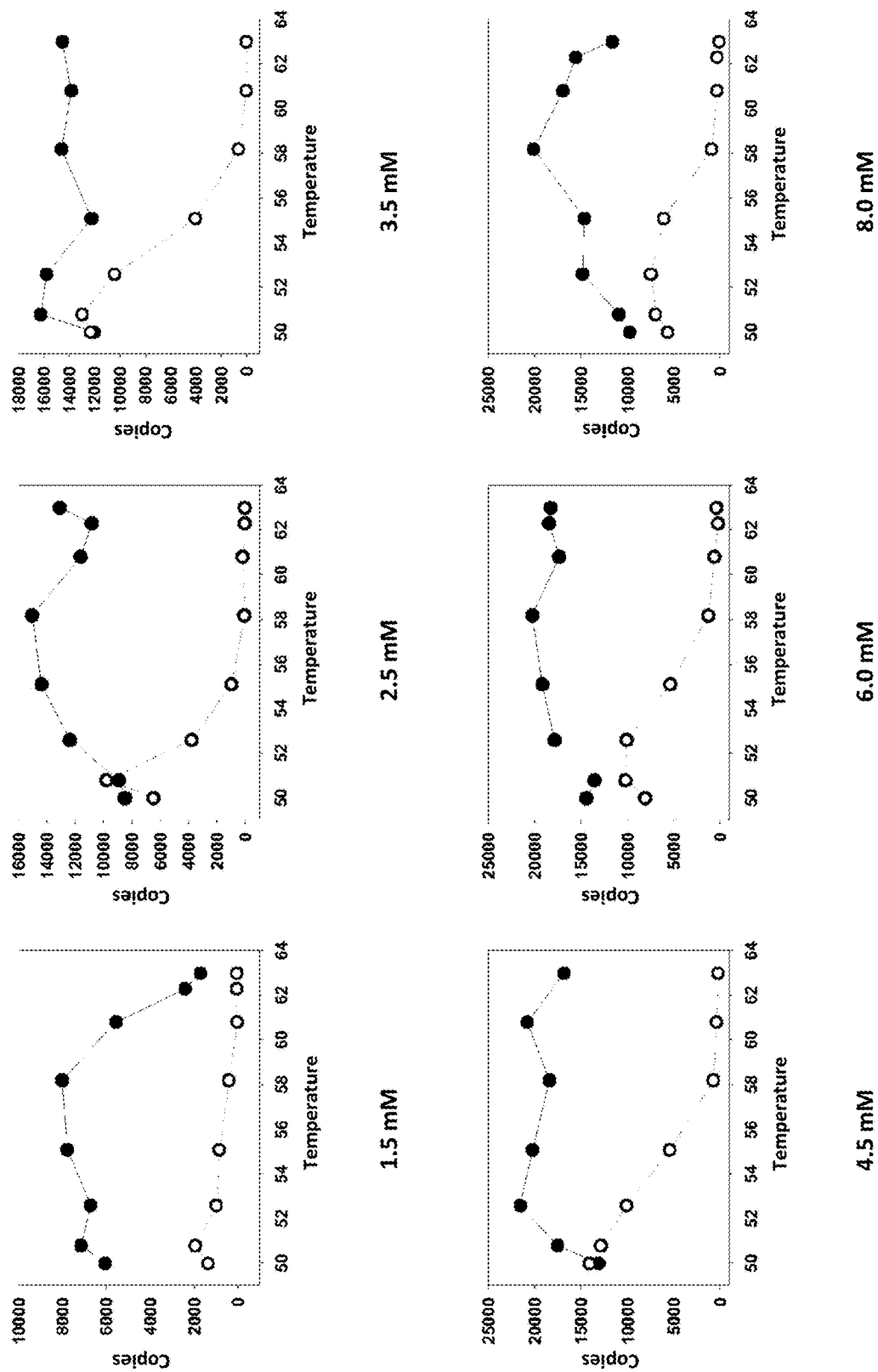

FIG. 36 shows the number of copies of methylated (solid circles) and unmethylated (empty circles) PLA2R1 DNA fragments after 16 pre-amplification cycles at increasing annealing temperatures (50-63° C.) as a function of MgCl$_2$ concentration (from 1.5 mmol/l to 8.0 mmol/l) using the primer pair 150 bp (SEQ ID: 53 and 9), and subsequent dPCR.

Figure 37:
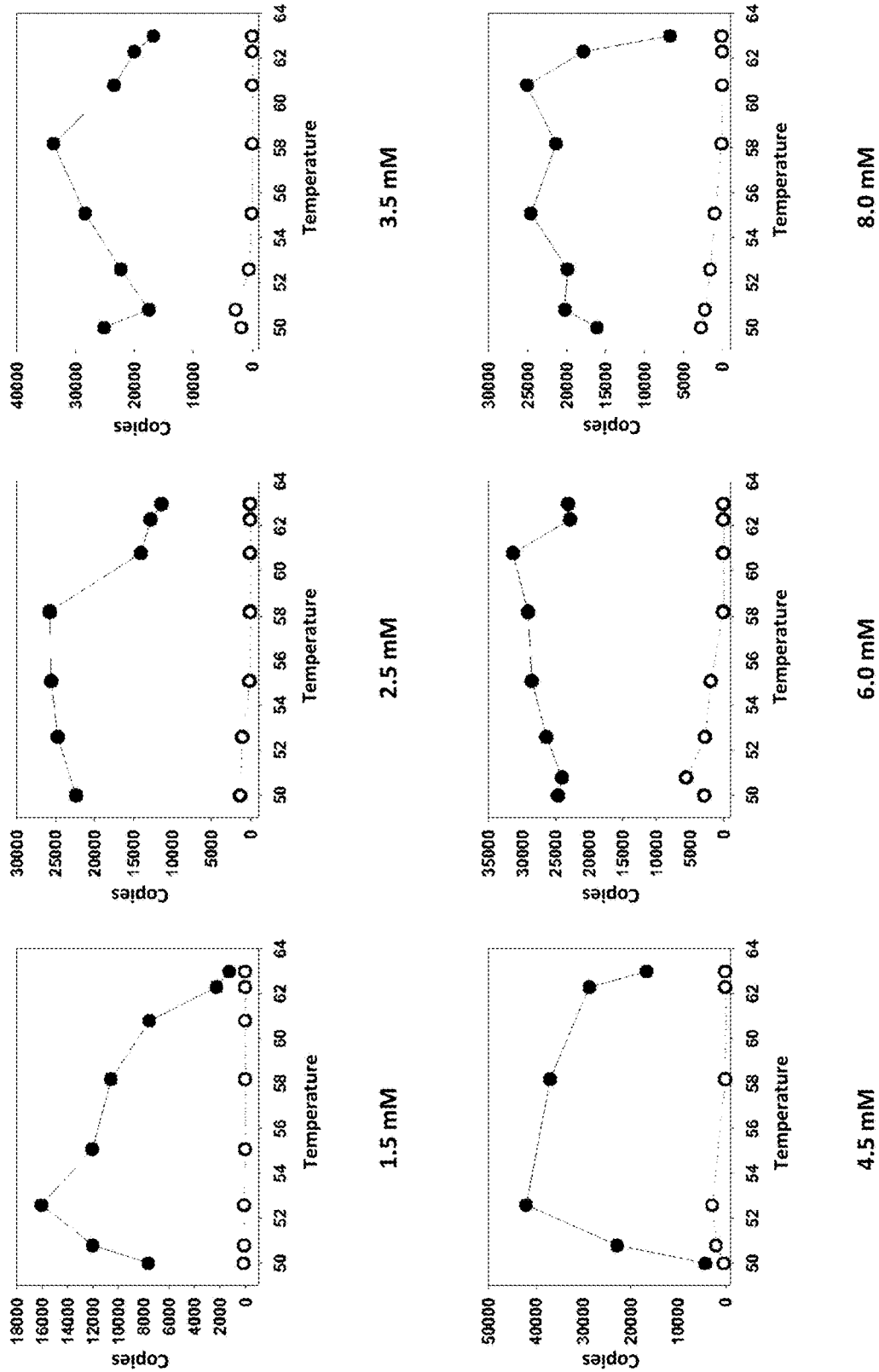

FIG. 37 shows the number of copies of methylated (solid circles) and unmethylated (empty circles) PLA2R1 DNA fragments after 16 pre-amplification cycles at increasing annealing temperatures (50-63° C.) as a function of MgCl$_2$ concentration (from 1.5 mmol/l to 8.0 mmol/l) using the primer pair 133 bp (SEQ ID: 7 and 8), and subsequent dPCR.

Figure 38:
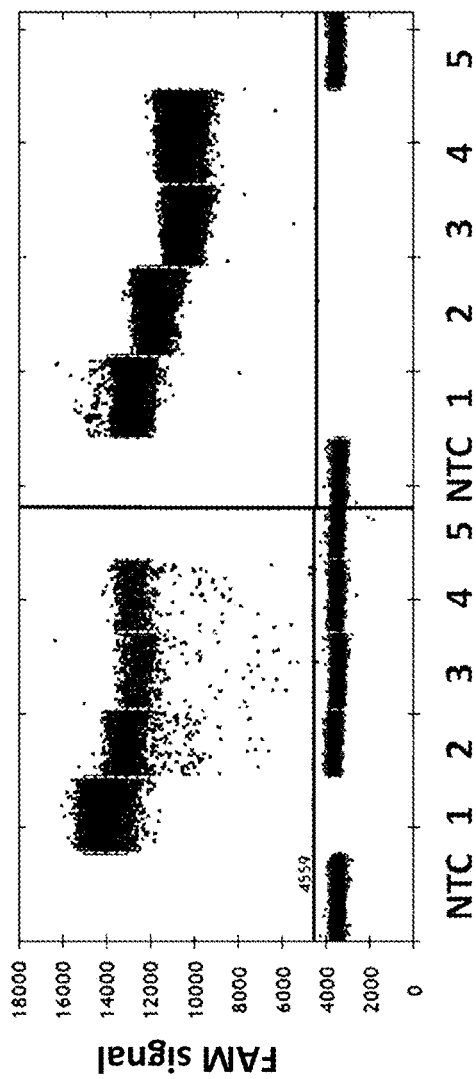
Figure 38:
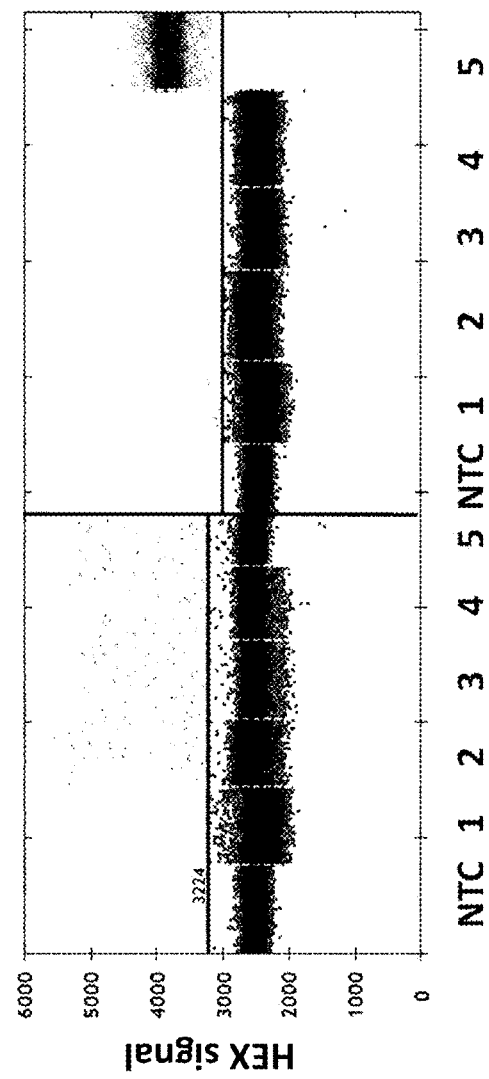

FIG. 38 shows FAM signals (methylated PLA2R1 DNA fragments [top image]) and HEX signals (unmethylated PLA2R1 DNA fragments [bottom image]) after 15 pre-amplification cycles (left of the divider) and 50 pre-amplification cycles (right of the divider) in samples having 3000 (trace 1), 20 (trace 2), 10 (trace 3), 5 (trace 4) and no copies (trace 5) of methylated PLA2R1 DNA fragments, each having a proportion of 70,000 copies of unmethylated PLA2R1 DNA fragments, using the primer pair 133 bp (SEQ ID: 7 and 8) at an MgCl$_2$ concentration of 6.0 mM and an annealing temperature of 63° C. NTC: non-template negative control. The raw data is set out in Tables 28 and 30.

Figure 39:
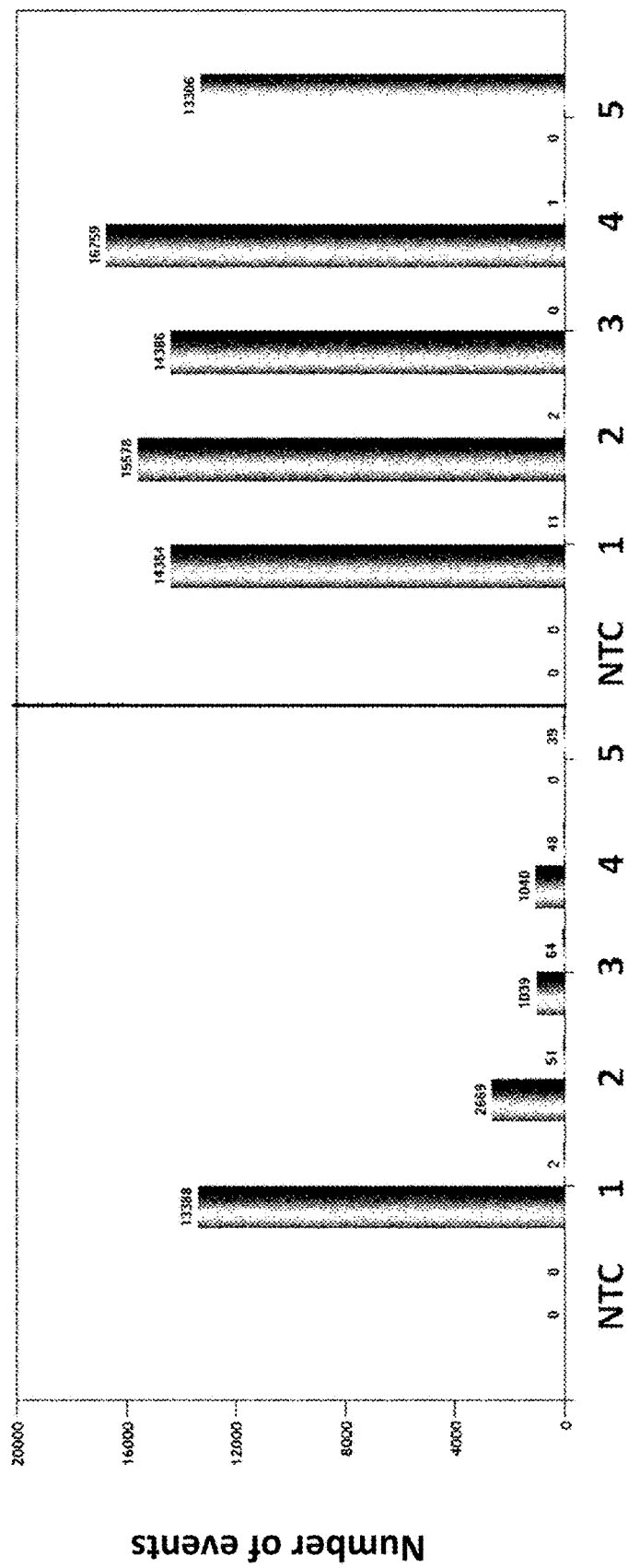

FIG. 39 shows the number of positive droplets after 15 pre-amplification cycles (left of the divider) and 50 pre-amplification cycles (right of the divider) in samples having 3000 (trace 1), 20 (trace 2), 10 (trace 3), 5 (trace 4) and no copies (trace 5) of methylated PLA2R1 DNA fragments, each having a proportion of 70,000 copies of unmethylated PLA2R1 DNA fragments, using the primer pair 133 bp (SEQ ID: 7 and 8) at an MgCl$_2$ concentration of 6.0 mmol/l and an annealing temperature of 63° C. NTC: non-template negative control. The raw data is set out in Tables 28 and 30.

Figure 40:
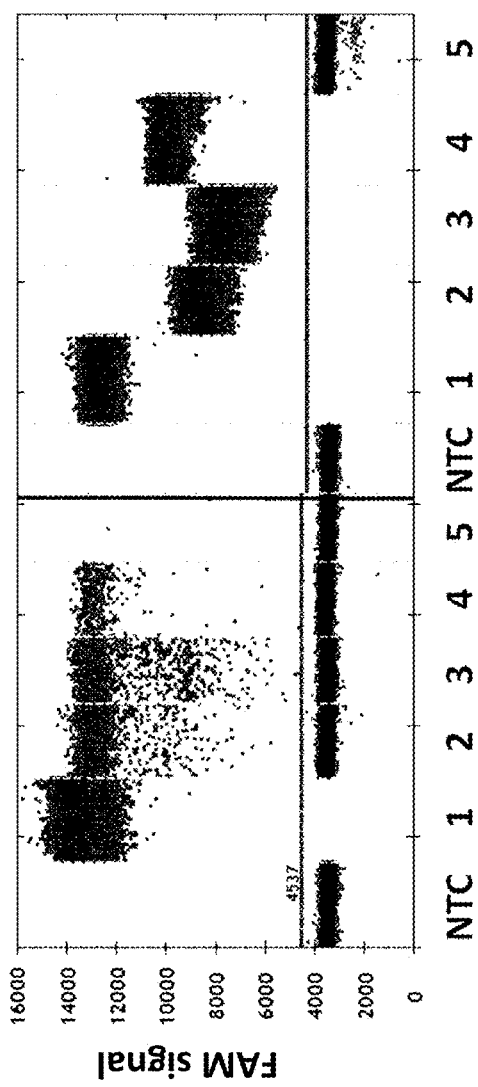
Figure 40:
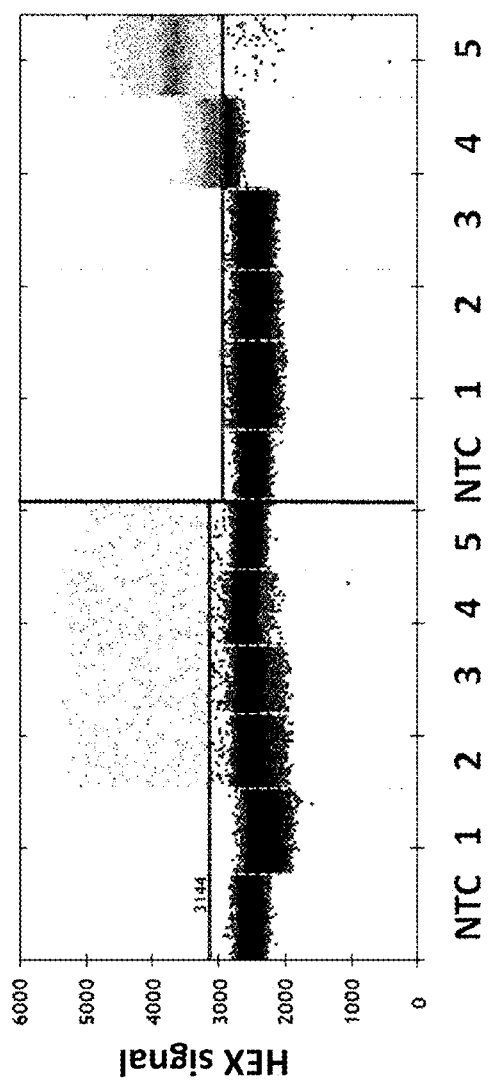

FIG. 40 shows FAM signals (methylated PLA2R1 DNA fragments [top image]) and HEX signals (unmethylated PLA2R1 DNA fragments [bottom image]) after 15 pre-amplification cycles (left of the divider) and 50 pre-amplification cycles (right of the divider) in samples having 3000 (trace 1), 20 (trace 2), 10 (trace 3), 5 (trace 4) and no copies (trace 5) of methylated PLA2R1 DNA fragments, each having a proportion of 175,000 copies of unmethylated PLA2R1 DNA fragments, using the primer pair 133 bp (SEQ ID: 7 and 8) at an MgCl$_2$ concentration of 6.0 mmol/l and an annealing temperature of 63° C. NTC: non-template negative control. The raw data is set out in Tables 28 and 30.

Figure 41:
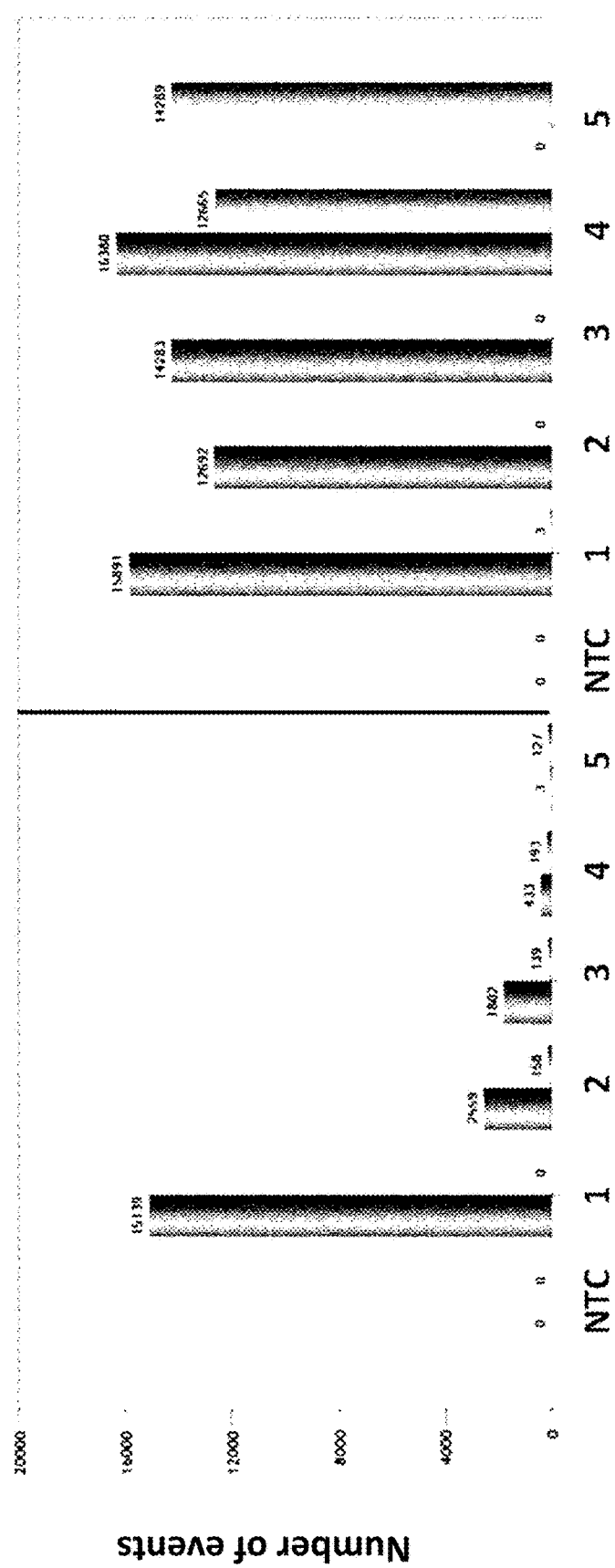

FIG. 41 shows the number of positive droplets after 15 pre-amplification cycles (left of the divider) and 50 pre-amplification cycles (right of the divider) in samples having 3000 (trace 1), 20 (trace 2), 10 (trace 3), 5 (trace 4) and no copies (trace 5) of methylated PLA2R1 DNA fragments, each having a proportion of 175,000 copies of unmethylated PLA2R1 DNA fragments, using the primer pair 133 bp (SEQ ID: 7 and 8) at an MgCl$_2$ concentration of 6.0 mmol/l and an annealing temperature of 63° C. NTC: non-template negative control. The raw data is set out in Tables 28 and 30.

Figure 42:
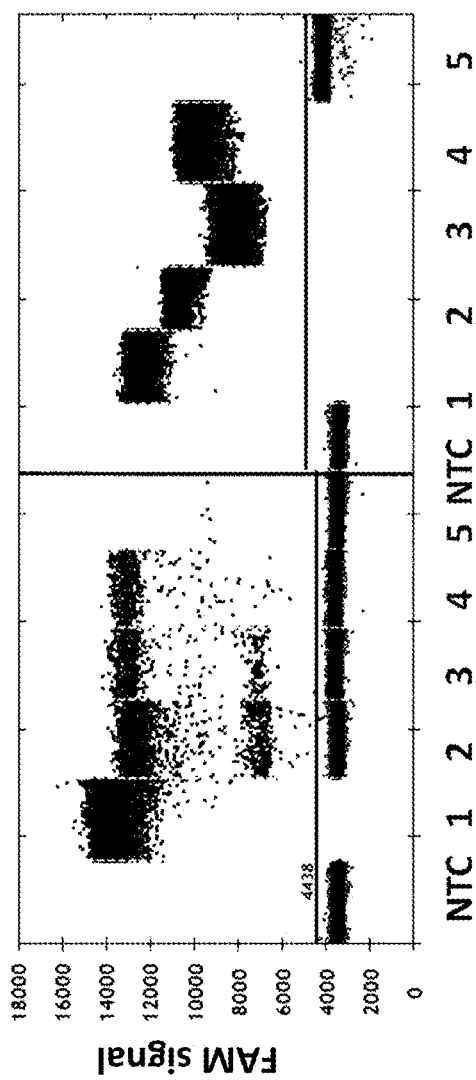
Figure 42:
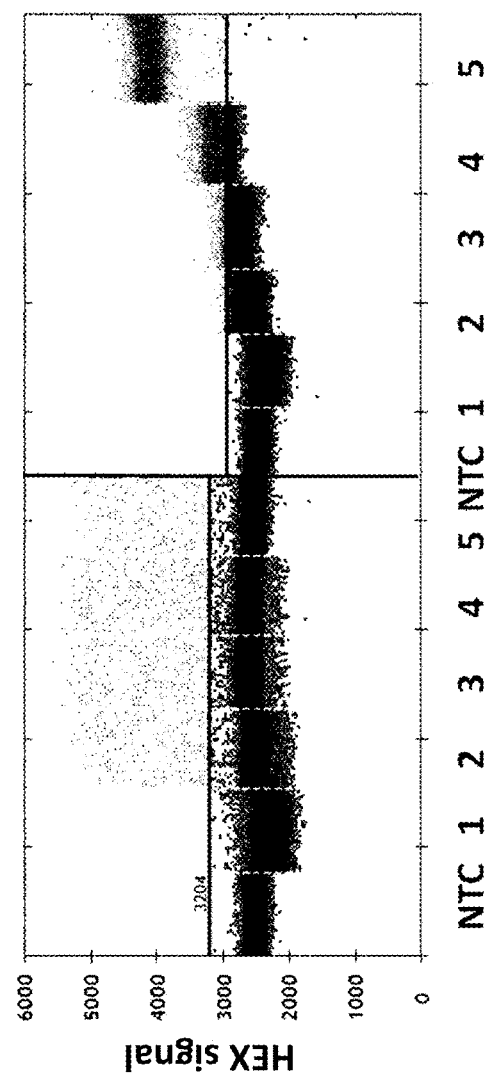

FIG. 42 shows FAM signals (methylated PLA2R1 DNA fragments [top image]) and HEX signals (unmethylated PLA2R1 DNA fragments [bottom image]) after 15 pre-amplification cycles (left of the divider) and 50 pre-amplification cycles (right of the divider) in samples having 3000 (trace 1), 20 (trace 2), 10 (trace 3), 5 (trace 4) and no copies (trace 5) of methylated PLA2R1 DNA fragments, each having a proportion of 350,000 copies of unmethylated PLA2R1 DNA fragments, using the primer pair 133 bp (SEQ ID: 7 and 8) at an MgCl$_2$ concentration of 6.0 mmol/l and an annealing temperature of 63° C. NTC: non-template negative control. The raw data is set out in Tables 28 and 30.

Figure 43:
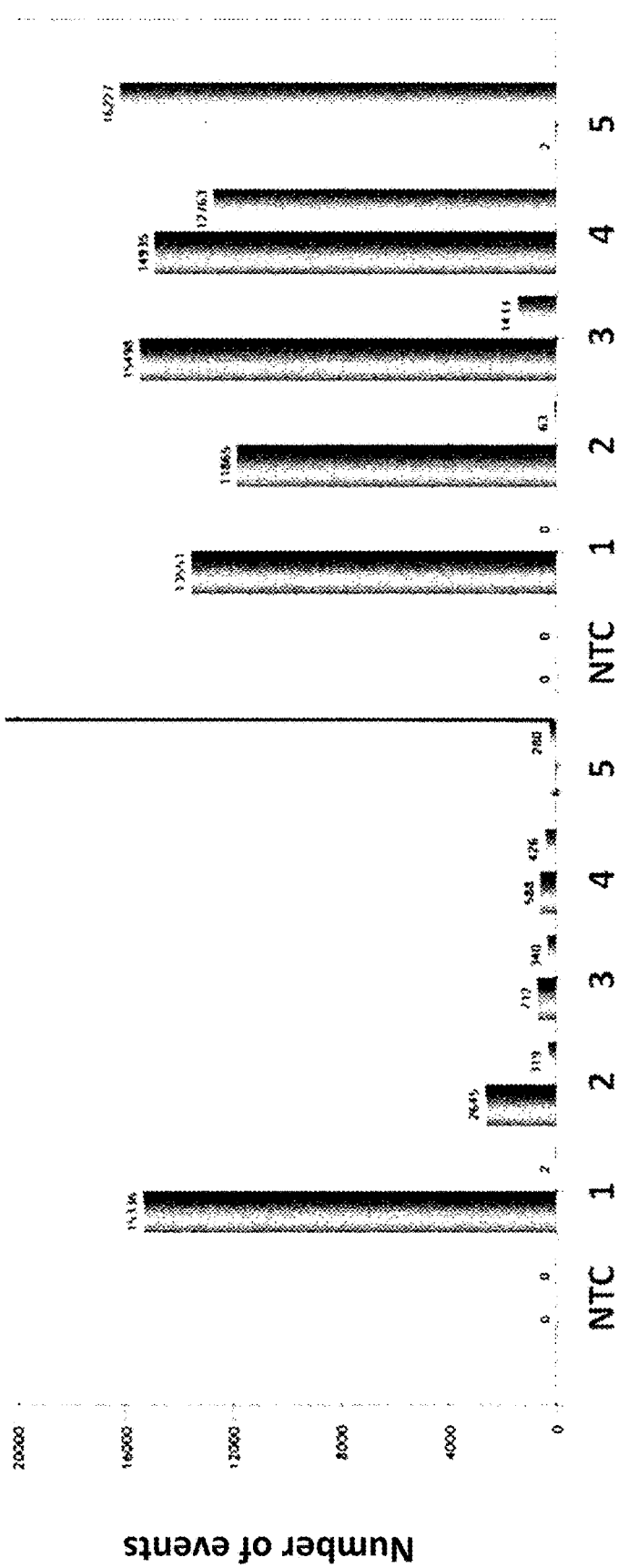

FIG. 43 shows the number of positive droplets after 15 pre-amplification cycles (left of the divider) and 50 pre-amplification cycles (right of the divider) in samples having 3000 (trace 1), 20 (trace 2), 10 (trace 3), 5 (trace 4) and no copies (trace 5) of methylated PLA2R1 DNA fragments, each having a proportion of 350,000 copies of unmethylated PLA2R1 DNA fragments, using the primer pair 133 bp (SEQ ID: 7 and 8) at an MgCl$_2$ concentration of 6.0 mmol/l and an annealing temperature of 63° C. NTC: non-template negative control. The raw data is set out in Tables 28 and 30.

Figure 44:
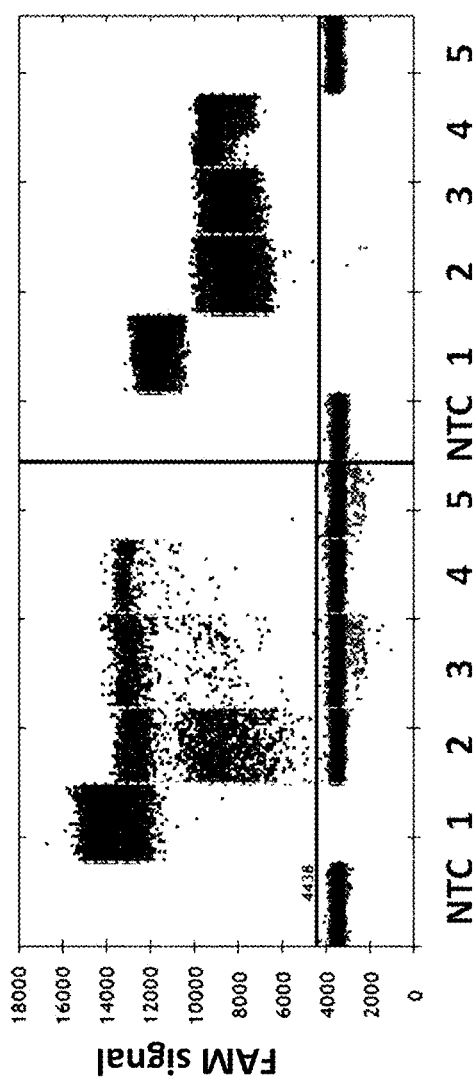
Figure 44:
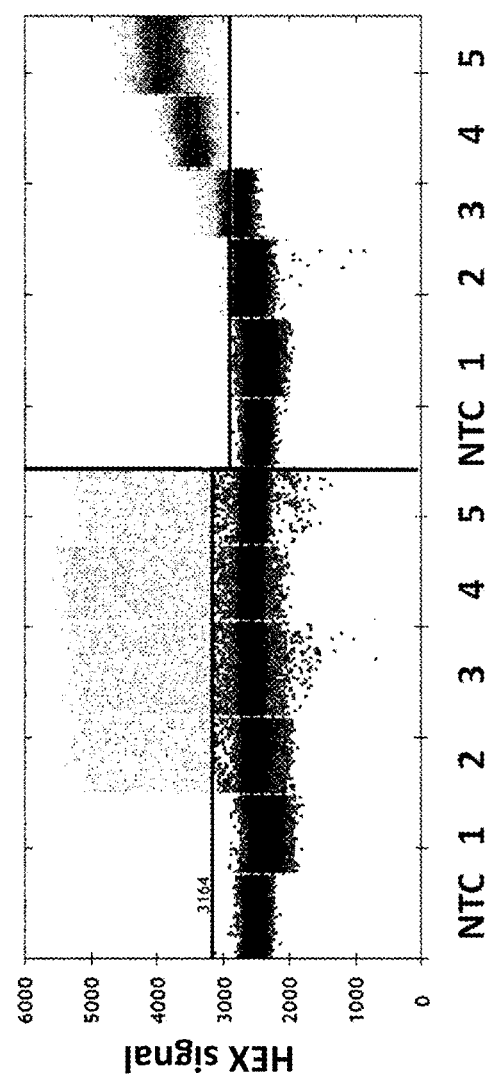

FIG. 44 shows FAM signals (methylated PLA2R1 DNA fragments [top image]) and HEX signals (unmethylated PLA2R1 DNA fragments [bottom image]) after 15 pre-amplification cycles (left of the divider) and 50 pre-amplification cycles (right of the divider) in samples having 3000 (trace 1), 20 (trace 2), 10 (trace 3), 5 (trace 4) and no copies (trace 5) of methylated PLA2R1 DNA fragments, each having a proportion of 700,000 copies of unmethylated PLA2R1 DNA fragments, using the primer pair 133 bp (SEQ ID: 7 and 8) at an MgCl$_2$ concentration of 6.0 mM and an annealing temperature of 63° C. NTC: non-template negative control. The raw data is set out in Tables 28 and 30.

Figure 45:
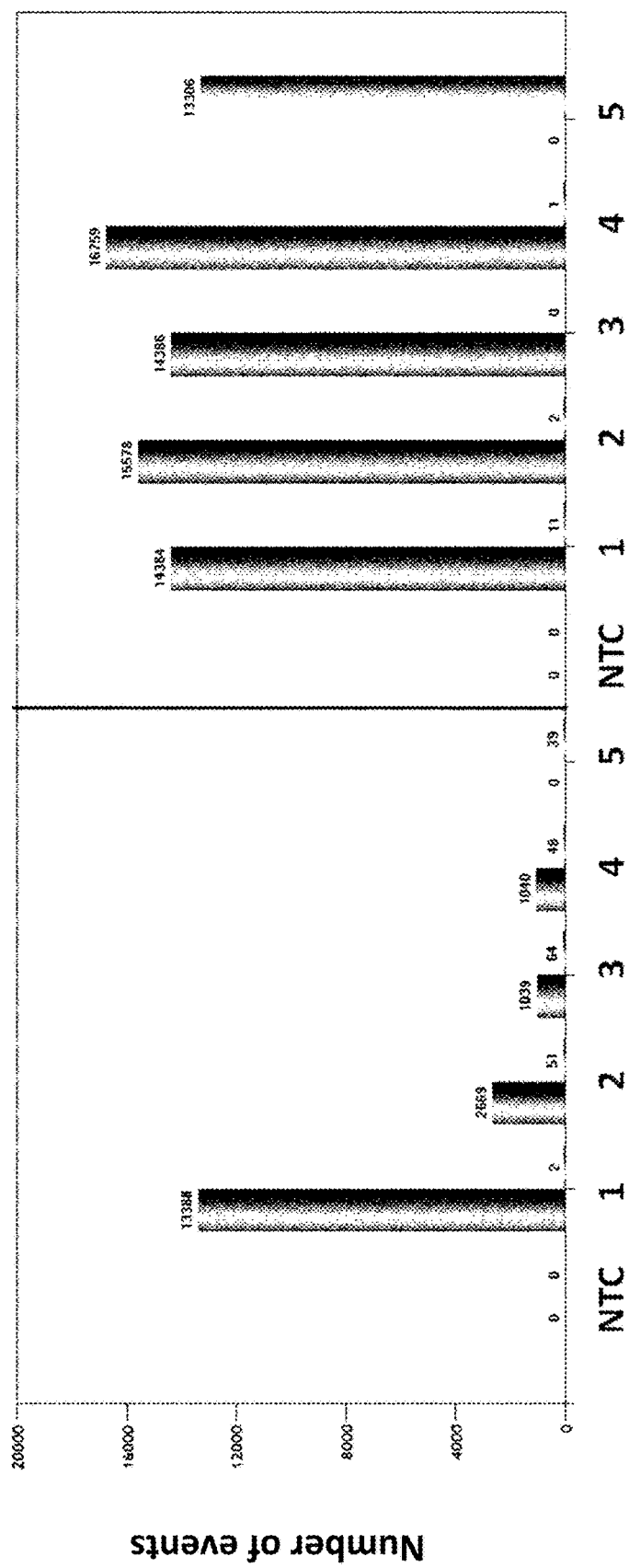

FIG. 45 shows the number of positive droplets after 15 pre-amplification cycles (left of the divider) and 50 pre-amplification cycles (right of the divider) in samples having 3000 (trace 1), 20 (trace 2), 10 (trace 3), 5 (trace 4) and no copies (trace 5) of methylated PLA2R1 DNA fragments, each having a proportion of 700,000 copies of unmethylated PLA2R1 DNA fragments, using the primer pair 133 bp (SEQ ID: 7 and 8) at an MgCl$_2$ concentration of 6.0 mmol/l and an annealing temperature of 63° C. NTC: non-template negative control. The raw data is set out in Tables 28 and 30.

Figure 46:
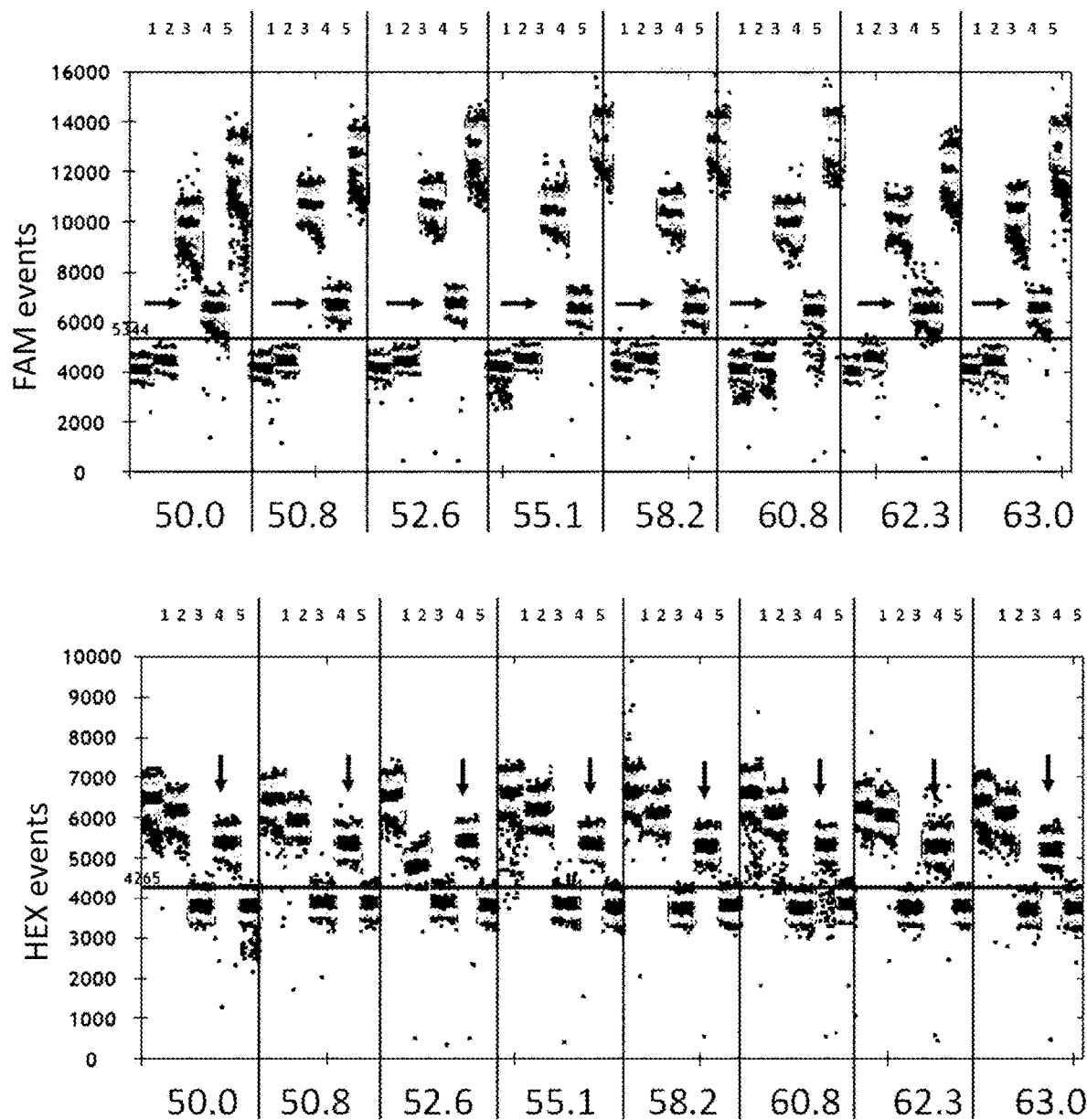

FIG. 46 shows FAM signals (methylated PLA2R1 DNA fragments, top image) and HEX signals (unmethylated PLA2R1 DNA fragments, bottom image) from normal PrEC (position 1), benign BPH cells (position 2), malignant LNCaP (position 3), PC-3 (position 4) and DU-145 cells (position 5) after 50 pre-amplification cycles at an MgCl$_2$ concentration of 2.5 mM and increasing annealing temperatures (50-63° C.) using the primer pair 168 bp (SEQ ID: 1 and 2), and subsequent dPCR. The arrows show the development of the FAM and HEX signals as a function of the annealing temperature for PC-3 cells.

Figure 47:
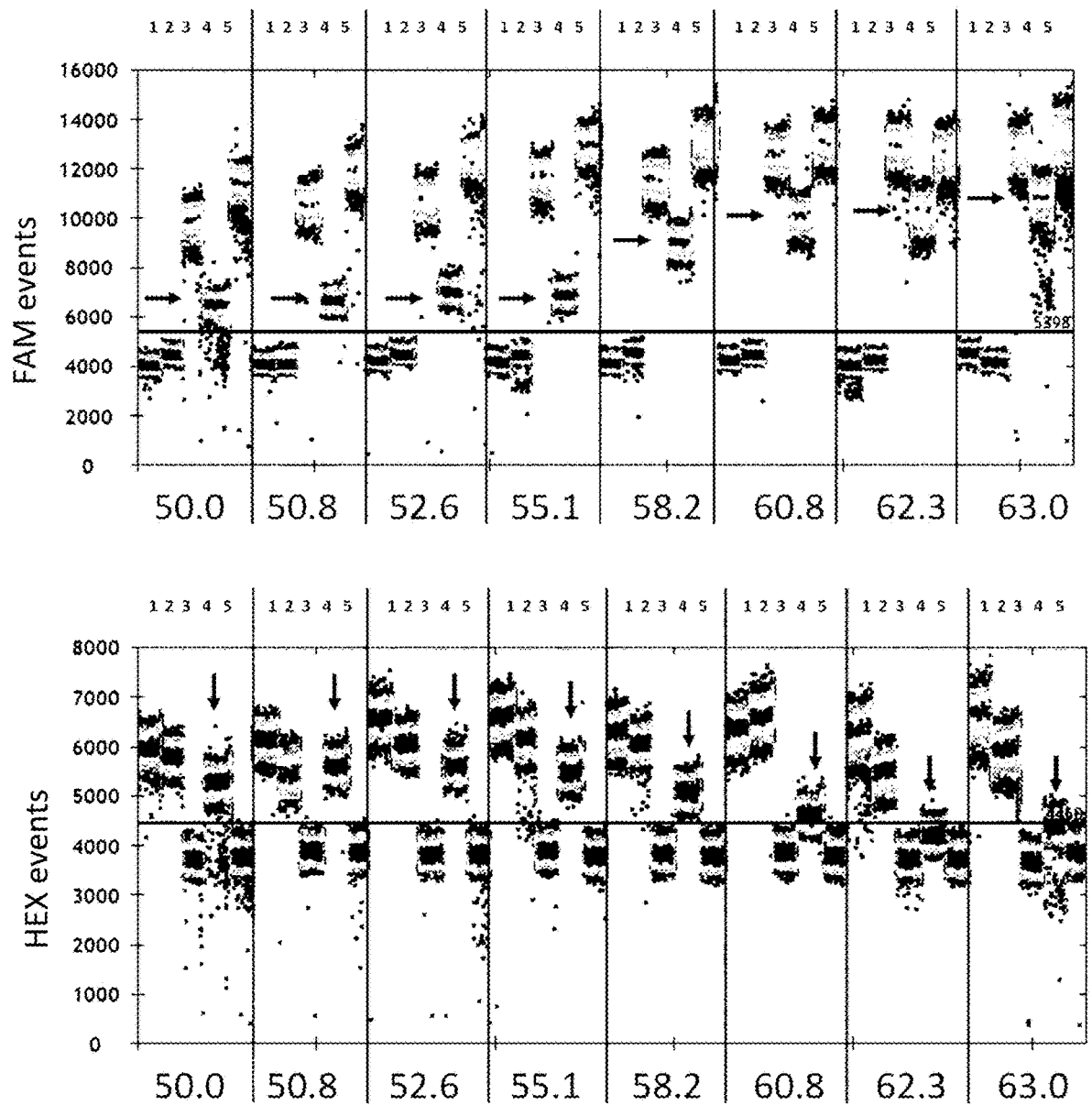

FIG. 47 shows FAM signals (methylated PLA2R1 DNA fragments, top image) and HEX signals (unmethylated PLA2R1 DNA fragments, bottom image) from normal PrEC (position 1), benign BPH cells (position 2), malignant LNCaP (position 3), PC-3 (position 4) and DU-145 cells (position 5) after 50 pre-amplification cycles at an MgCl$_2$ concentration of 2.5 mmol/l and increasing annealing temperatures (50-63° C.) using the primer pair 161 bp (SEQ ID: 53 and 10), and subsequent dPCR. The arrows show the development of the FAM and HEX signals as a function of the annealing temperature for PC-3 cells.

Figure 48:
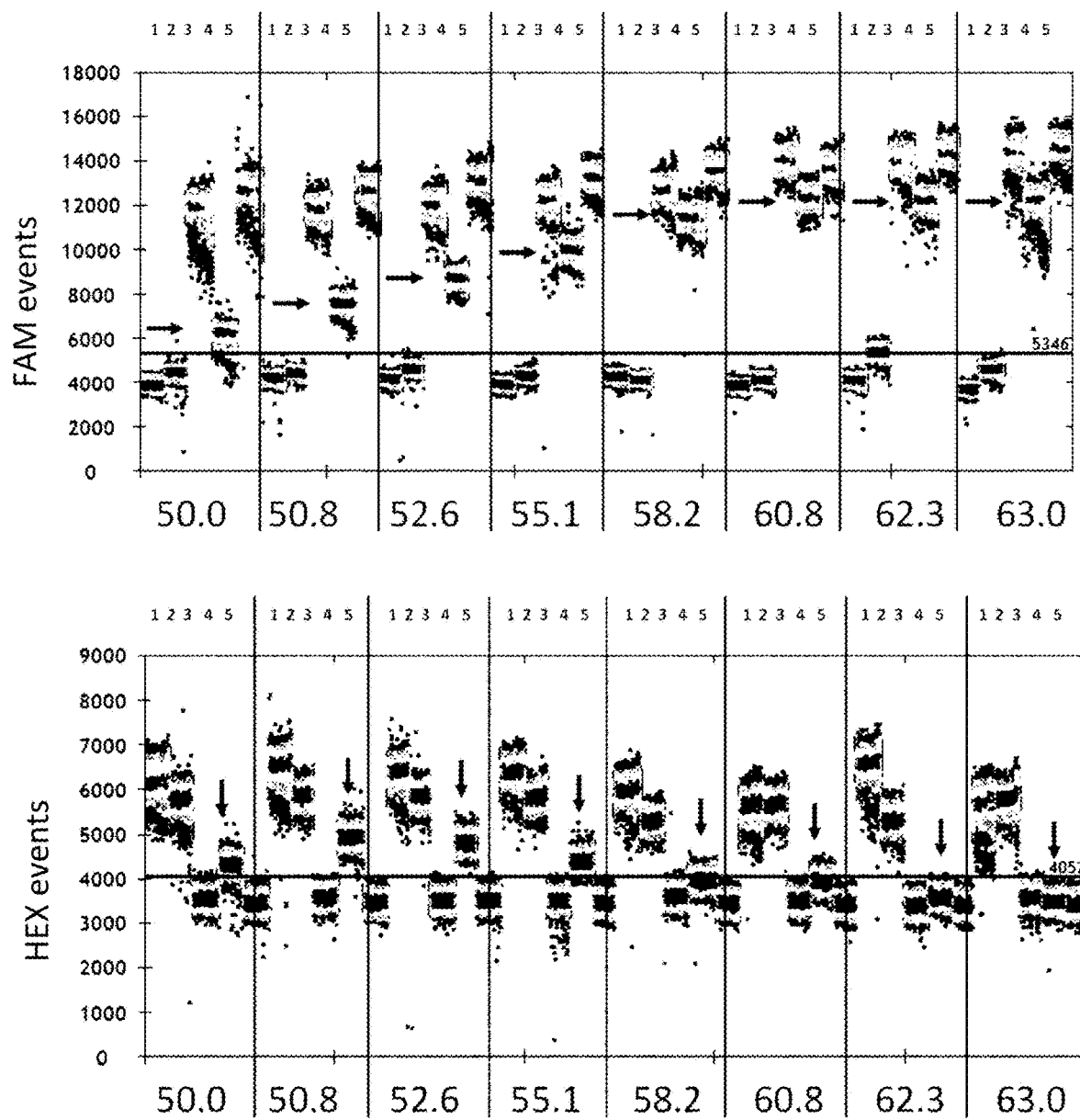

FIG. 48 shows FAM signals (methylated PLA2R1 DNA fragments, top image) and HEX signals (unmethylated PLA2R1 DNA fragments, bottom image) from normal PrEC (position 1), benign BPH cells (position 2), malignant LNCaP (position 3), PC-3 (position 4) and DU-145 cells (position 5) after 50 pre-amplification cycles at an MgCl$_2$ concentration of 2.5 mmol/l and increasing annealing temperatures (50-63° C.) using the primer pair 150 bp (SEQ ID: 53 and 9), and subsequent dPCR. The arrows show the development of the FAM and HEX signals as a function of the annealing temperature for PC-3 cells.

Figure 49:
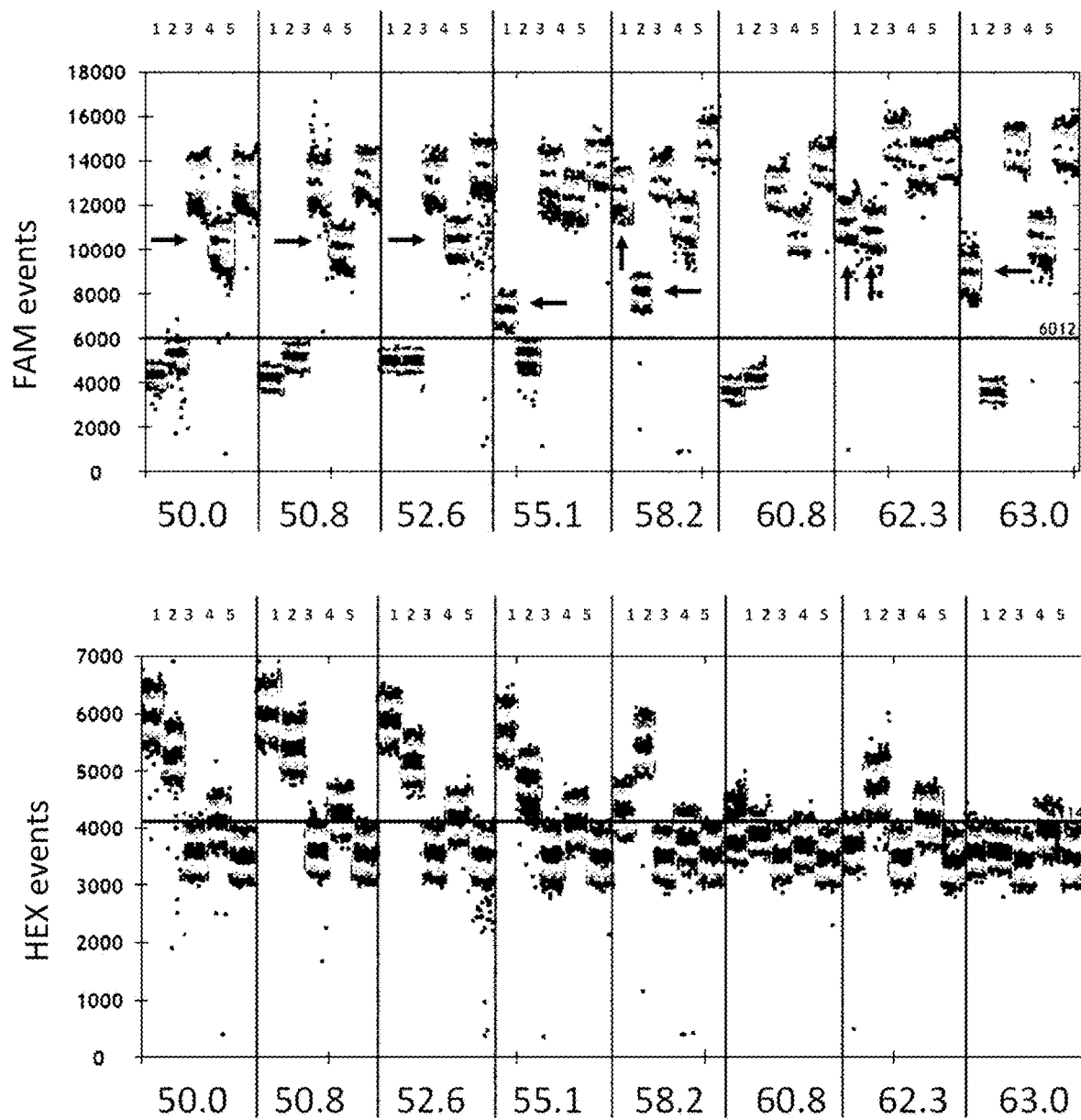

FIG. 49 shows FAM signals (methylated PLA2R1 DNA fragments, top image) and HEX signals (unmethylated PLA2R1 DNA fragments, bottom image) from normal PrEC (position 1), benign BPH cells (position 2), malignant LNCaP (position 3), PC-3 (position 4) and DU-145 cells (position 5) after 50 pre-amplification cycles at an MgCl$_2$ concentration of 2.5 mmol/l and increasing annealing temperatures (50-63° C.) using the primer pair 133 bp (SEQ ID: 7 and 8), and subsequent dPCR. The arrows show the development of the FAM signals up to 52.6° C. for the PC-3 cells and above 52.6° C. for PrEC and BPH-1.

Figure 50:
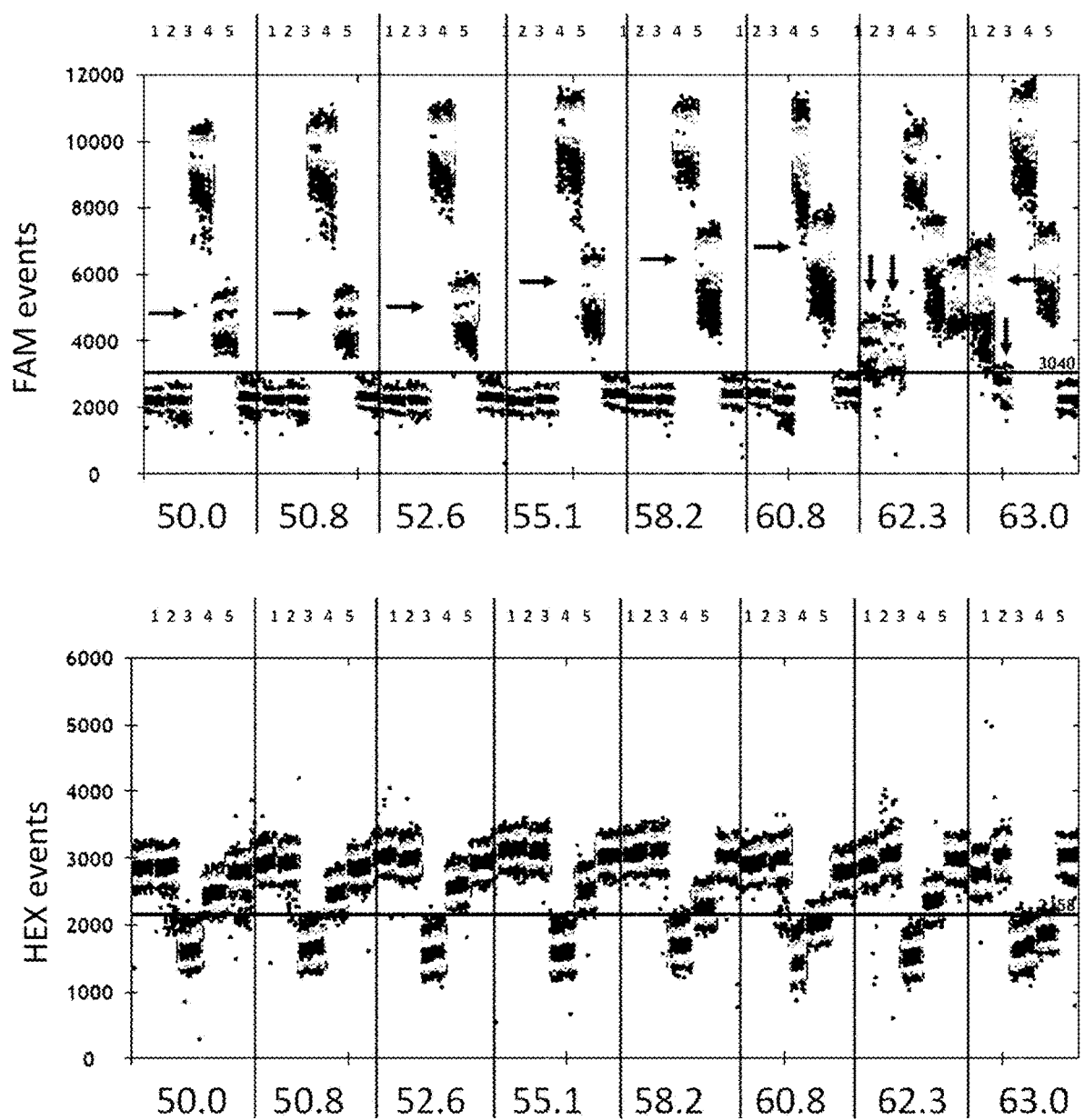

FIG. 50 shows FAM signals (methylated GSPT1 DNA fragments, top image) and HEX signals (unmethylated GSPT1 DNA fragments, bottom image) from normal PrEC (position 1), benign BPH cells (position 2), malignant LNCaP (position 3), PC-3 (position 4) and DU-145 cells (position 5) after 50 pre-amplification cycles at an $MgCl_2$ concentration of 2.5 mmol/l and increasing annealing temperatures (50-63° C.) using the primer pair 120 bp (SEQ ID: 5 and 6), and subsequent dPCR. The arrows show the development of the FAM signals up to 60.8° C. for the PC-3 cells and above 60.8° C. for PrEC and BPH-1.

Figure 51:
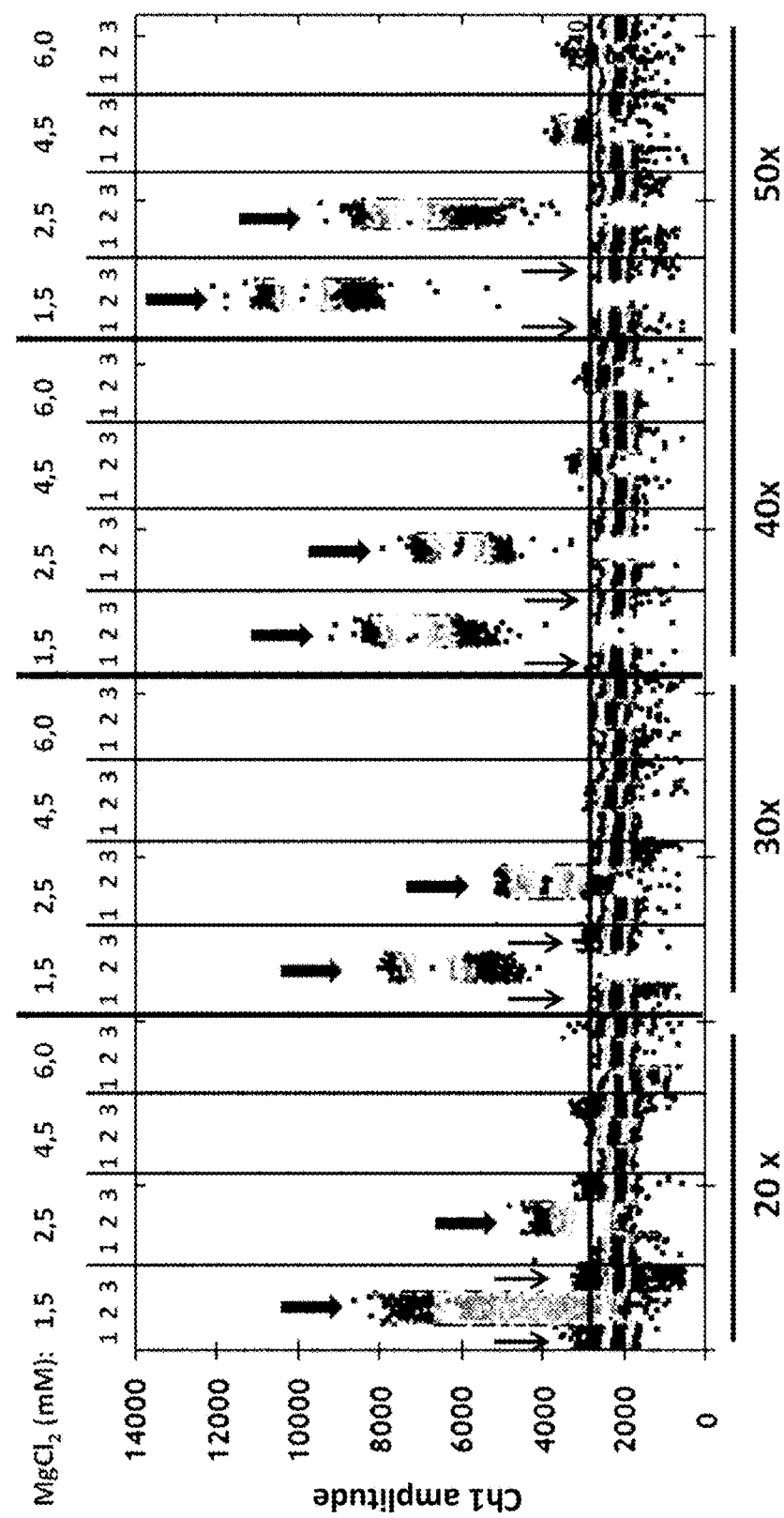

FIG. 51 shows FAM signals (methylated GSTP1 DNA fragments) as a function of the number of cycles (20×, 30×, 40× and 50×) and $MgCl_2$ concentration in the reaction buffer (1.5, 2.5, 4.5 and 6.0 mmol/l) in the pre-amplification using the primer pair 120 bp (SEQ ID: 5 and 6) at an annealing temperature of 50.7° C. Trace 1: 0% methylated standard NDA, trace 2: 50% methylated standard DNA and trace 3: non-template negative control. The thin arrows show the scatter signals for 0% methylated standard DNA and non-template negative controls, and the thick arrows show the increasing signal intensities for the 50% methylated standard DNA as the number of cycles increases (shown at the bottom).

Figure 52:
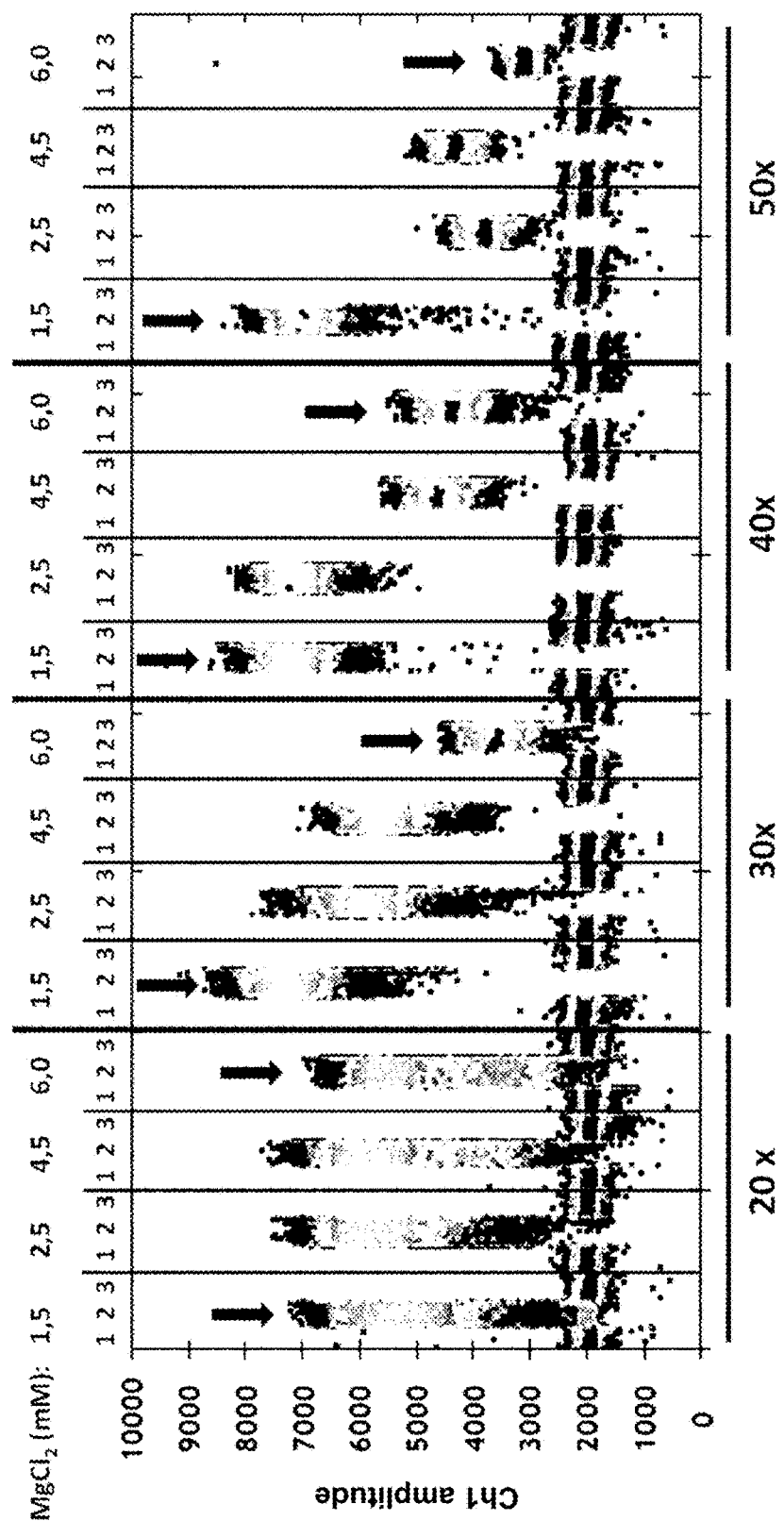

FIG. 52 shows FAM signals (methylated GSTP1 DNA fragments) as a function of the number of cycles (20×, 30×, 40× and 50×) and $MgCl_2$ concentration in the reaction buffer (1.5, 2.5, 4.5 and 6.0 mmol/l) in the pre-amplification using the primer pair 116 bp (SEQ ID: 84 and 85) at an annealing temperature of 53.8° C. Trace 1: 0% methylated standard NDA, trace 2: 50% methylated standard DNA and trace 3: non-template negative control. The arrows shows the intensities of the FAM signals for 50% methylated standard DNA as a function of the number of cycles in samples having $MgCl_2$ concentrations of from 1.5 to 6.0 mmol/l.

Figure 53:
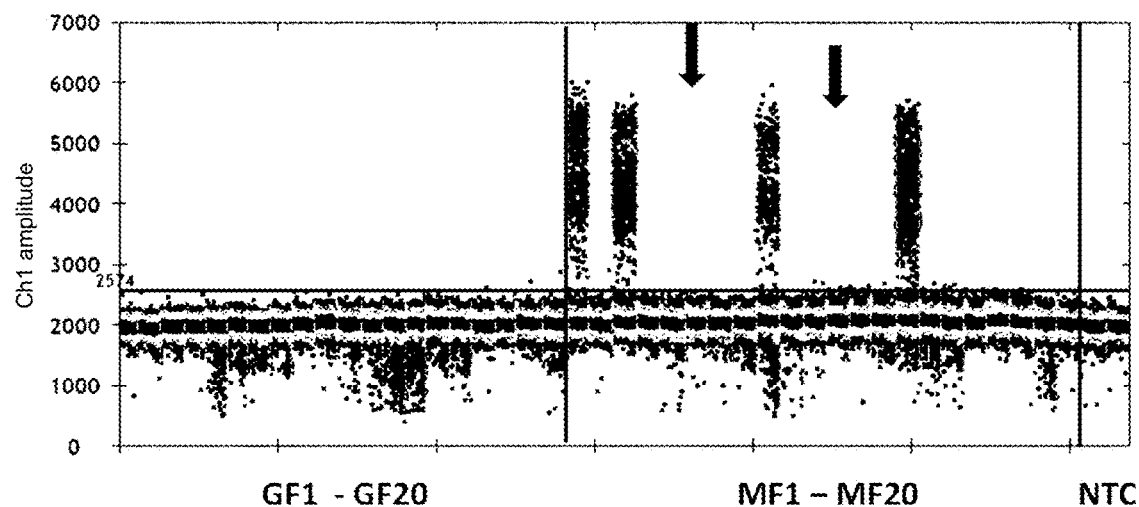
Figure 53:
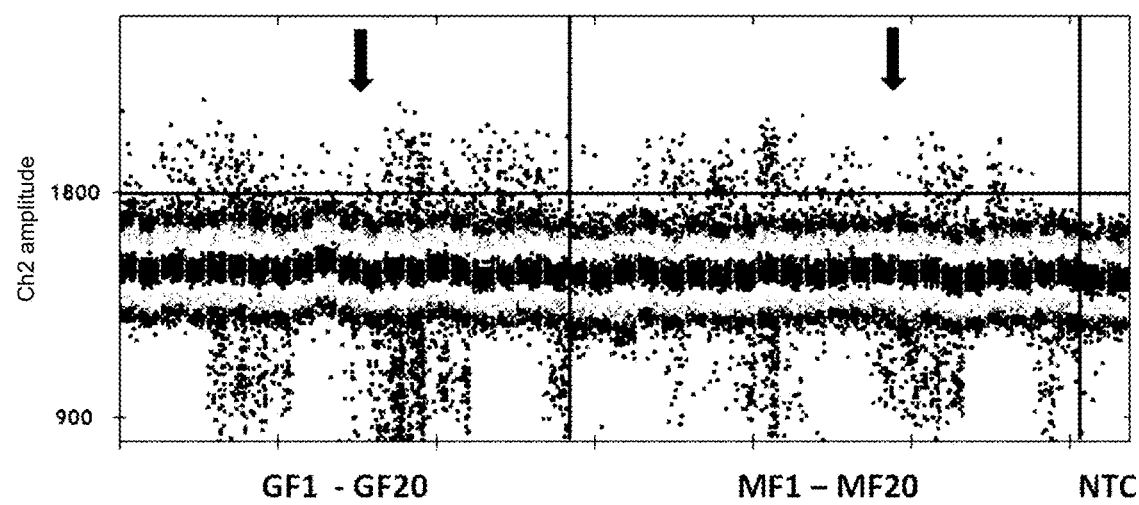

FIG. 53 shows FAM signals (methylated GSTP1 DNA fragments, top image) and HEX signals (unmethylated GSTP1 DNA fragments, bottom image) in serum samples from healthy subjects (GF1-GF20; to the left, separated by the first division line) and serum samples from female breast cancer patients (MF1-MF20; to the right of the first division line) and non-template control (NTC, no DNA or genomic DNA, without bisulphite conversion, right of the second division line in each case) after 15 BBPA cycles using the GSTP1 116 bp primers (SEQ ID: 93 and 94) and at an $MgCl_2$ concentration of 1.5 mmol/l and a temperature of 53.8° C., and subsequent dPCR. The arrows in the top image show the additional patient samples that showed positive results for GSTP1 methylation at an $MgCl_2$ concentration of 4.5 mM (FIG. 54), and the arrows in the bottom image show the weak HEX signals obtained at an $MgCl_2$ concentration of 1.5 mM.

Figure 54:
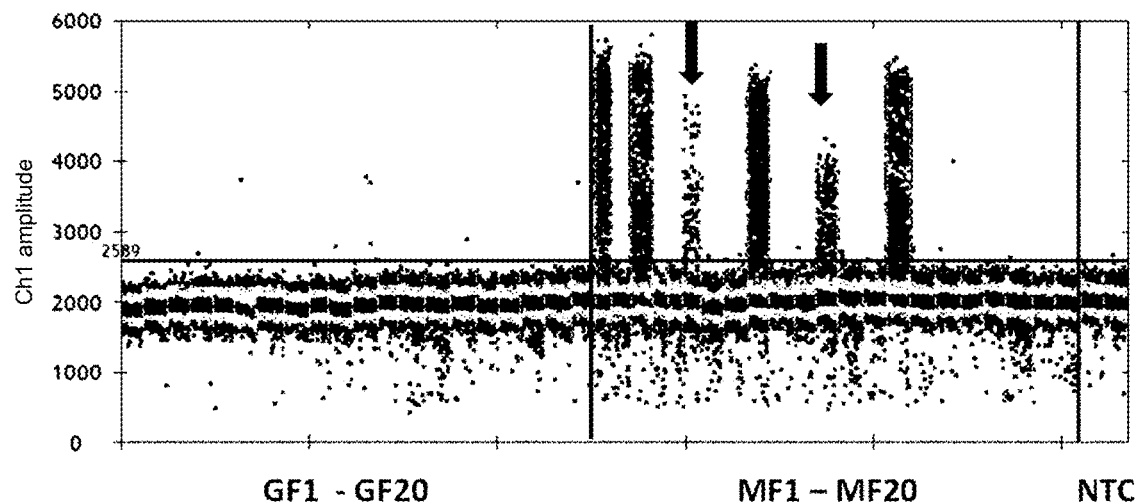
Figure 54:
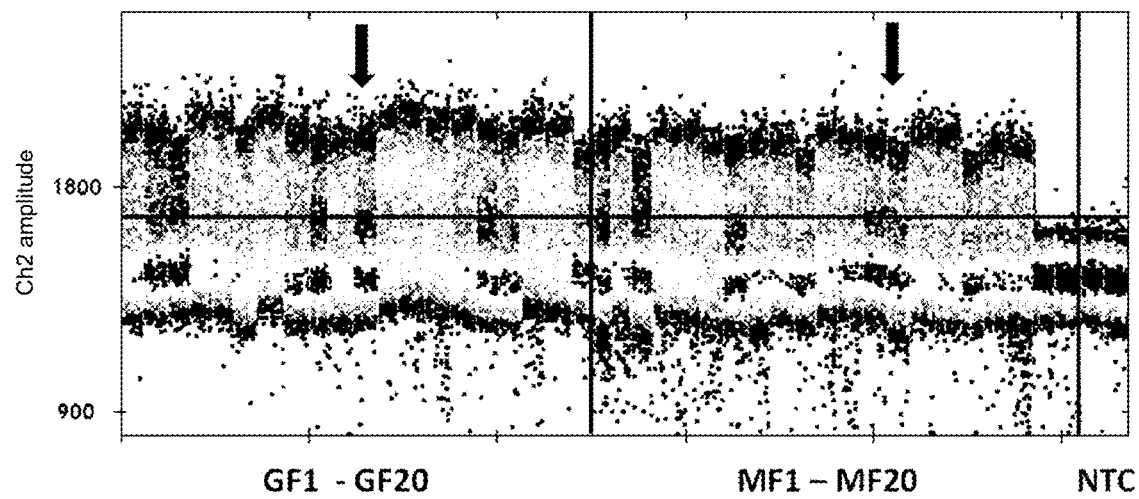

FIG. 54 shows FAM signals (methylated GSTP1 DNA fragments, top image) and HEX signals (unmethylated GSTP1 DNA fragments, bottom image) in serum samples from healthy subjects (GF1-GF20; to the left, separated by the first division line) and serum samples from female breast cancer patients (MF1-MF20; to the right of the first division line) and non-template control (NTC, no DNA or genomic DNA, without bisulphite conversion, right of the second division line in each case) after 15 BBPA cycles using the GSTP1 116 bp primers (SEQ ID: 93 and 94) and at an $MgCl_2$ concentration of 4.5 mmol/l and a temperature of 53.8° C., and subsequent dPCR. The arrows in the top image show the additional patient samples that showed positive results for GSTP1 methylation at an $MgCl_2$ concentration of 4.5 mM compared with 1.5 mM (FIG. 53), and the arrows in the bottom image show the strong HEX signals obtained at an $MgCl_2$ concentration of 4.5 mM.

Figure 55:
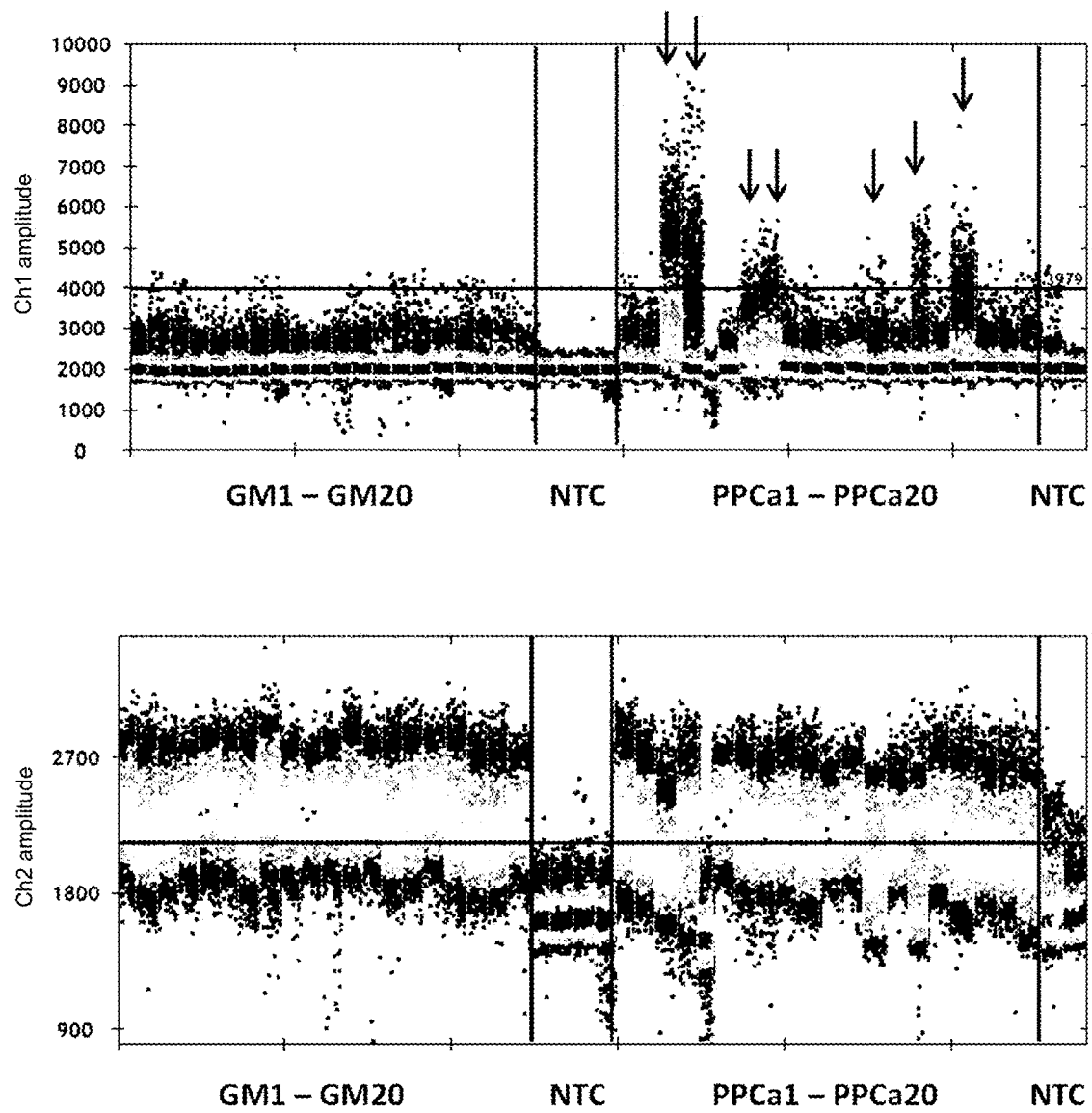

FIG. 55 shows FAM signals (methylated GSTP1 DNA fragments, top image) and HEX signals (unmethylated GSTP1 DNA fragments, bottom image) in serum samples from healthy subjects (GM1-GM20; to the left, separated by the first division line), non-template control (NTC, no DNA in the dPCR, to the right of the first division line, serum samples from prostate cancer patients (PCa; PPCa1-PPCa20, to the right of the second division line) and non-template controls (NTC, no DNA or genomic DNA, without bisulphite conversion, to the right of the third division line) after 15 BBPA cycles using the GSTP1 120 bp primers (SEQ ID: 5 and 5) and at an $MgCl_2$ concentration of 2.5 mmol/l and a temperature of 50.7° C., and subsequent dPCR. The arrows show the serum samples from PCa patients in which the FAM signals could be significantly distinguished from those in the serum samples from healthy subjects (Table 13).

Figure 56:
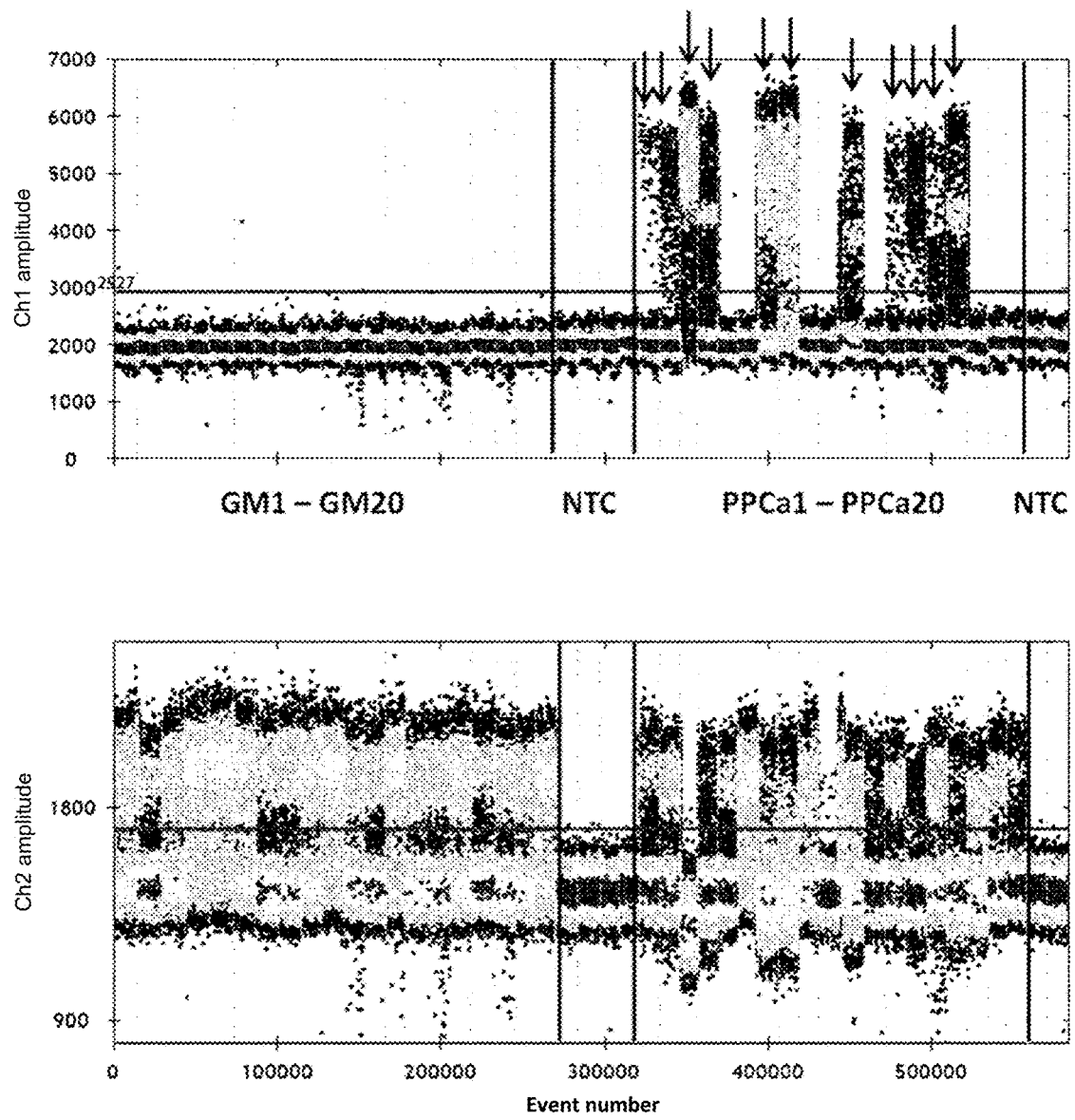

FIG. 56 shows FAM signals (methylated GSTP1 DNA fragments, top image) and HEX signals (unmethylated GSTP1 DNA fragments, bottom image) in serum samples from healthy subjects (GM1-GM20; to the left, separated by the first division line), non-template control (NTC, no DNA in the dPCR, to the right of the first division line), serum samples from prostate cancer patients (PPCa1-PPCa20, to the right of the second division line) and non-template controls (NTC, no DNA or genomic DNA, without bisulphite conversion, to the right of the third division line) after 15 BBPA cycles using the GSTP1 116 bp primers (SEQ ID: 93 and 94) and at an $MgCl_2$ concentration of 4.5 mmol/l and a temperature of 53.8° C., and subsequent dPCR. The arrows show the serum samples from PCa patients in which the FAM signals could be significantly distinguished from those in the serum samples from healthy subjects (Table 14).

Figure 57:
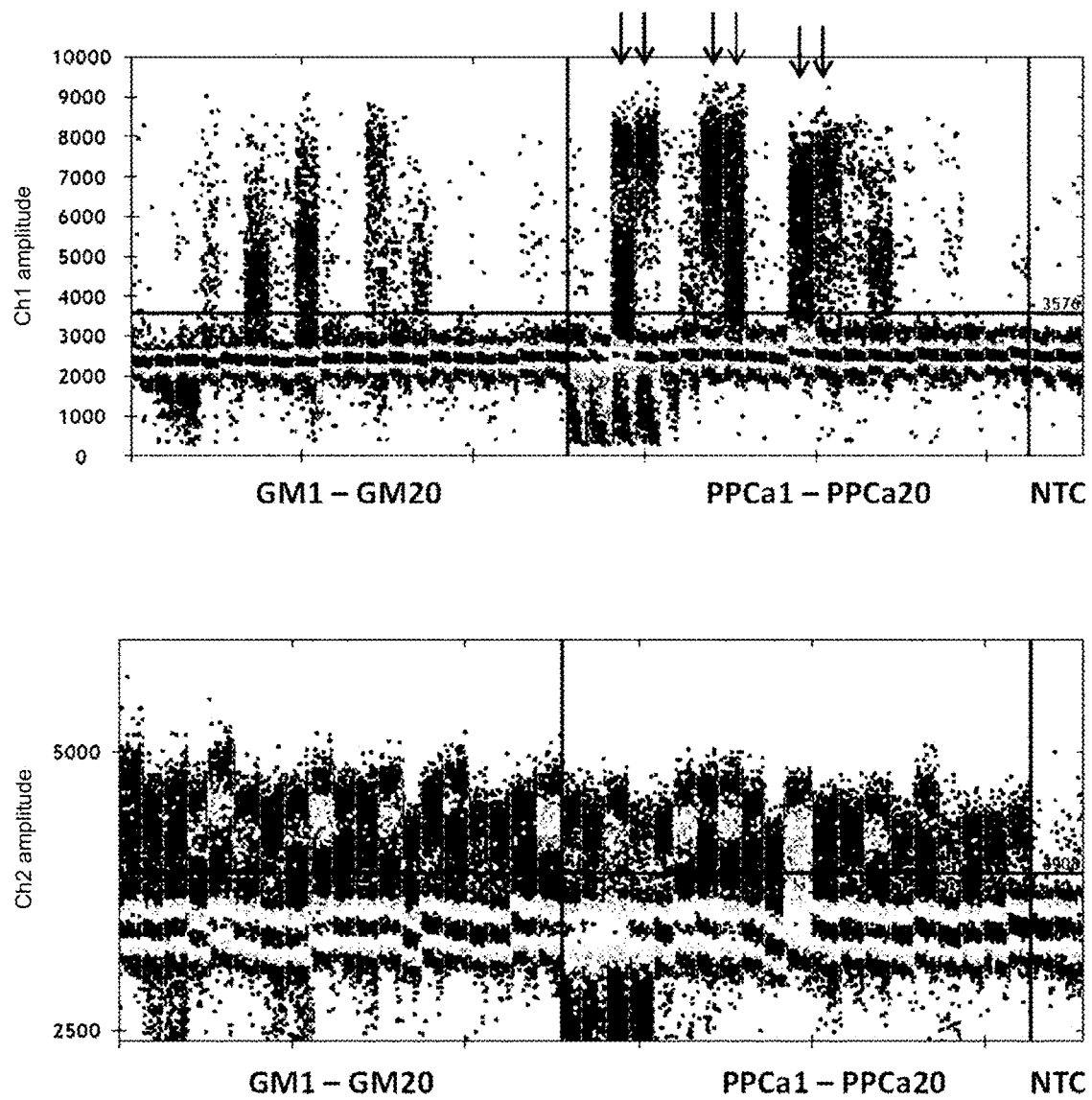

FIG. 57 shows FAM signals (methylated SERPINE1 DNA fragments, top image) and HEX signals (unmethylated SERPINE1 DNA fragments, bottom image) in serum samples from healthy subjects (GM1-GM20; to the left, separated by the first division line), serum samples from prostate cancer patients (PPCa1-PPCa20; to the right of the first division line) and non-template controls (NTC, no DNA or genomic DNA, without bisulphite conversion, to the right of the second division line) after 15 BBPA cycles using the SERPINE1 123 bp primers (SEQ ID: 16 and 17) and at an $MgCl_2$ concentration of 3.5 mmol/l and a temperature of 52.0° C., and subsequent dPCR. The arrows show the serum samples from PCa patients in which the FAM signals could be significantly distinguished from those in the serum samples from healthy subjects (Table 15).

Figure 58:
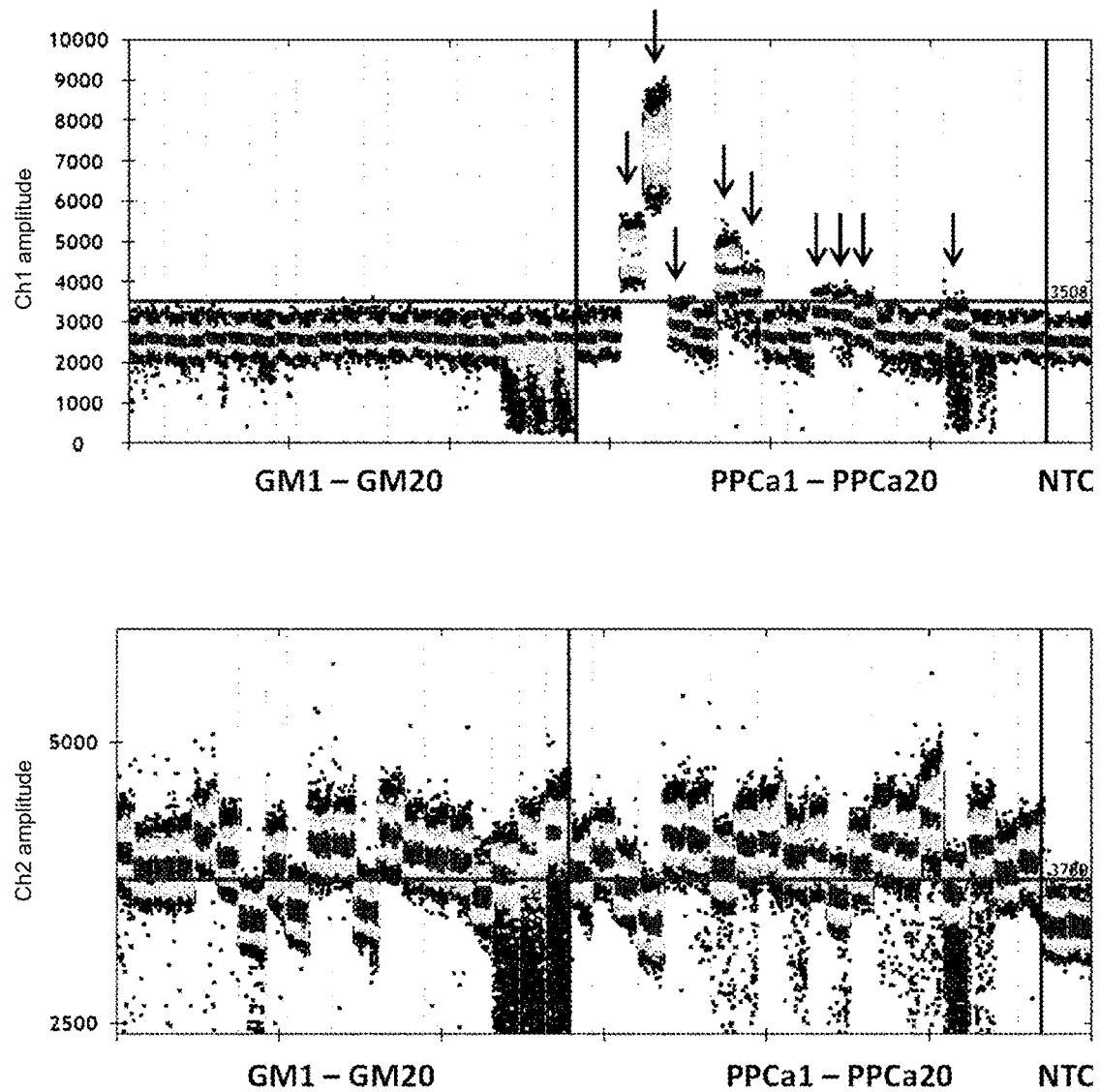

FIG. 58 shows FAM signals (methylated SERPINE1 DNA fragments, top image) and HEX signals (unmethylated SERPINE1 DNA fragments, bottom image) in serum samples from healthy subjects (GM1-GM20; to the left, separated by the first division line), serum samples from prostate cancer patients (PPCa1-PPCa20; to the right of the first division line) and non-template controls (NTC, no DNA or genomic DNA, without bisulphite conversion, to the right of the second division line) after 50 BBPA cycles using the SERPINE1 123 bp primers (SEQ ID: 16 and 17) and at an $MgCl_2$ concentration of 3.5 mmol/l and a temperature of 52.0° C., and subsequent dPCR. The arrows show the serum samples from PCa patients in which the FAM signals could be significantly distinguished from those in the serum samples from healthy subjects (Table 16).

Figure 59:
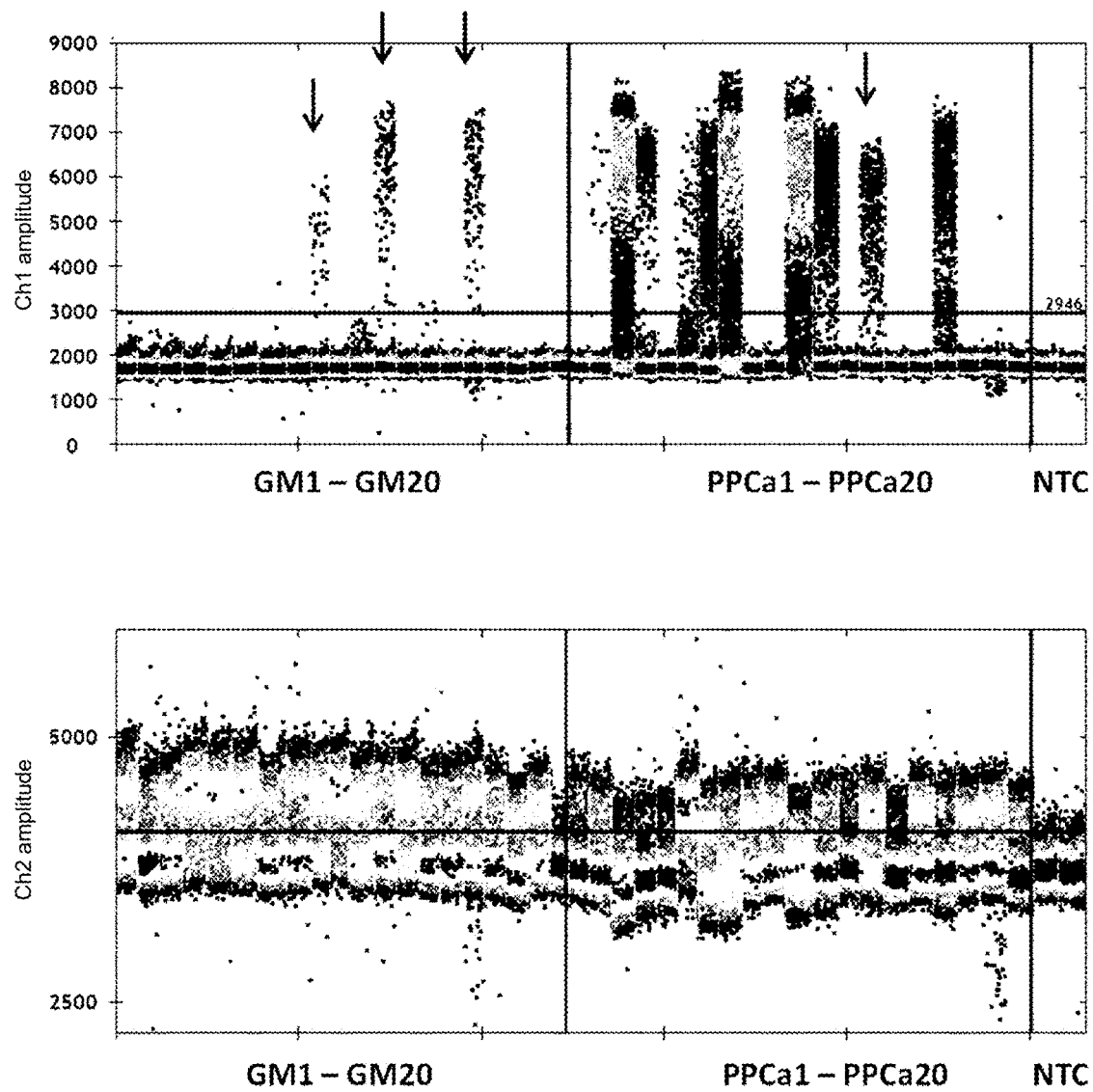

FIG. 59 shows FAM signals (methylated AOX1 DNA fragments, top image) and HEX signals (unmethylated AOX1 DNA fragments, bottom image) in serum samples from healthy subjects (GM1-GM20; to the left, separated by the first division line), serum samples from prostate cancer patients (PPCa1-PPCa20; to the right of the first division line) and non-template controls (NTC, no DNA or genomic DNA, without bisulphite conversion, to the right of the second division line) after 15 BBPA cycles using the AOX1 138 bp primers (SEQ ID: 18 and 19) and at an $MgCl_2$ concentration of 2.5 mmol/l and a temperature of 50.0° C., and subsequent dPCR. The arrows show the FAM signals in serum samples from three healthy subjects and a PCa patient in which the intensity dropped considerably after 30 BBPA cycles (FIG. 60 and Tables 17 and 18).

Figure 60:
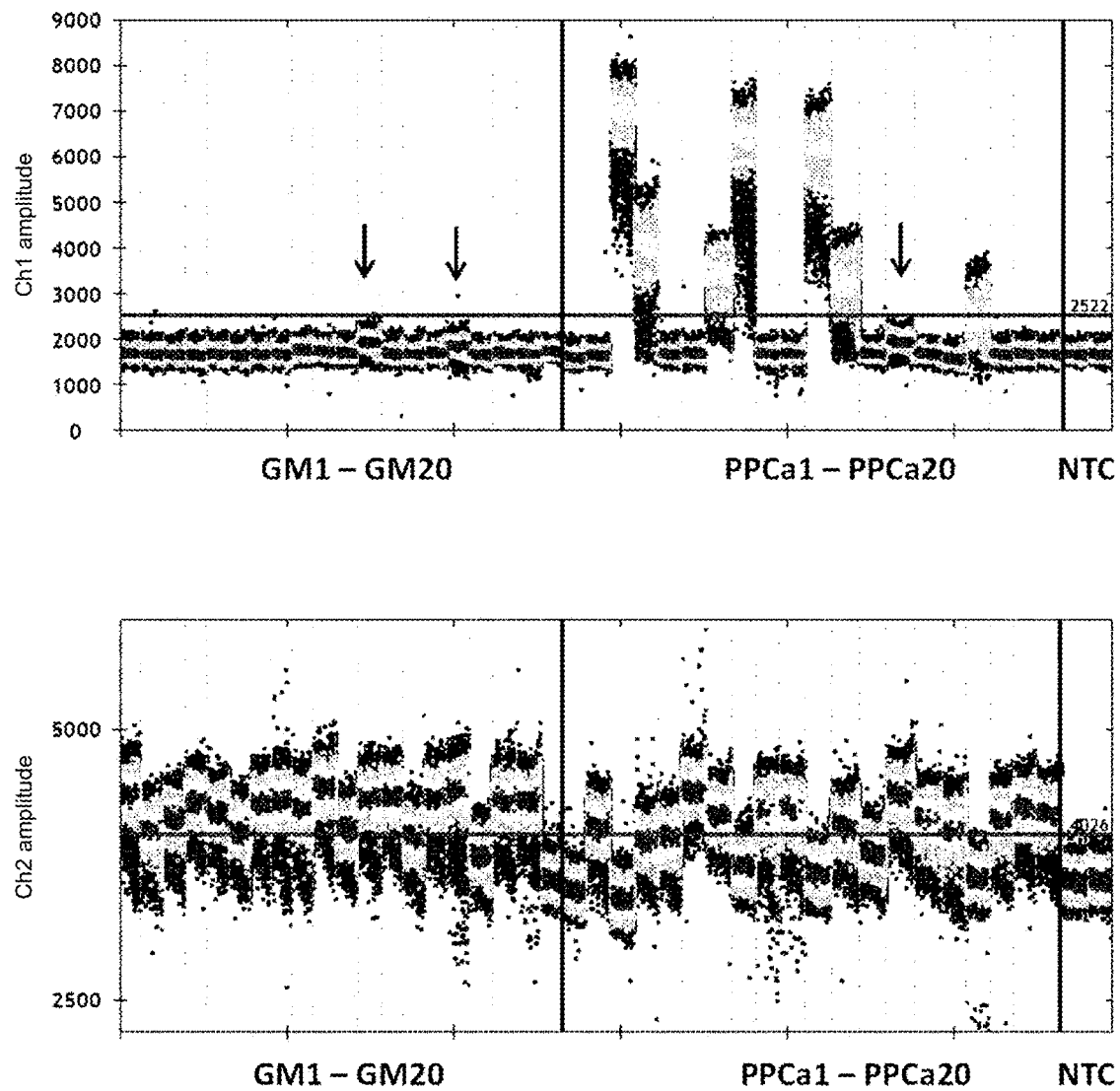

FIG. 60 shows FAM signals (methylated AOX1 DNA fragments, top image) and HEX signals (unmethylated AOX1 DNA fragments, bottom image) in serum samples from healthy subjects (GM1-GM20; to the left, separated by the first division line), serum samples from prostate cancer patients (PPCa1-PPCa20; to the right of the first division line) and non-template controls (NTC, no DNA or genomic DNA, without bisulphite conversion, to the right of the second division line) after 30 BBPA cycles using the AOX1 138 bp primers (SEQ ID: 18 and 19) and at an $MgCl_2$ concentration of 2.5 mmol/l and a temperature of 50.0° C., and subsequent dPCR. The arrows show the FAM signals in serum samples from healthy subjects and one PCa patient in which the intensity dropped considerably after 30 BBPA cycles compared with 15 cycles (FIG. 59). The arrow to the right shows the results for patient PPCa14, in which values were still considerably elevated after 15 BBPA cycles but were significantly lower after 30 cycles, unlike e.g. patients PPCa12 and 17, and could no longer be distinguished from those of healthy subjects GM12 and 16. If the threshold is set such that these samples do not show any FAM-positive signals, seven serum samples from PCa patients show considerably elevated FAM signal values and are significantly different from those of healthy subjects (Tables 17 and 18).

Figure 61:
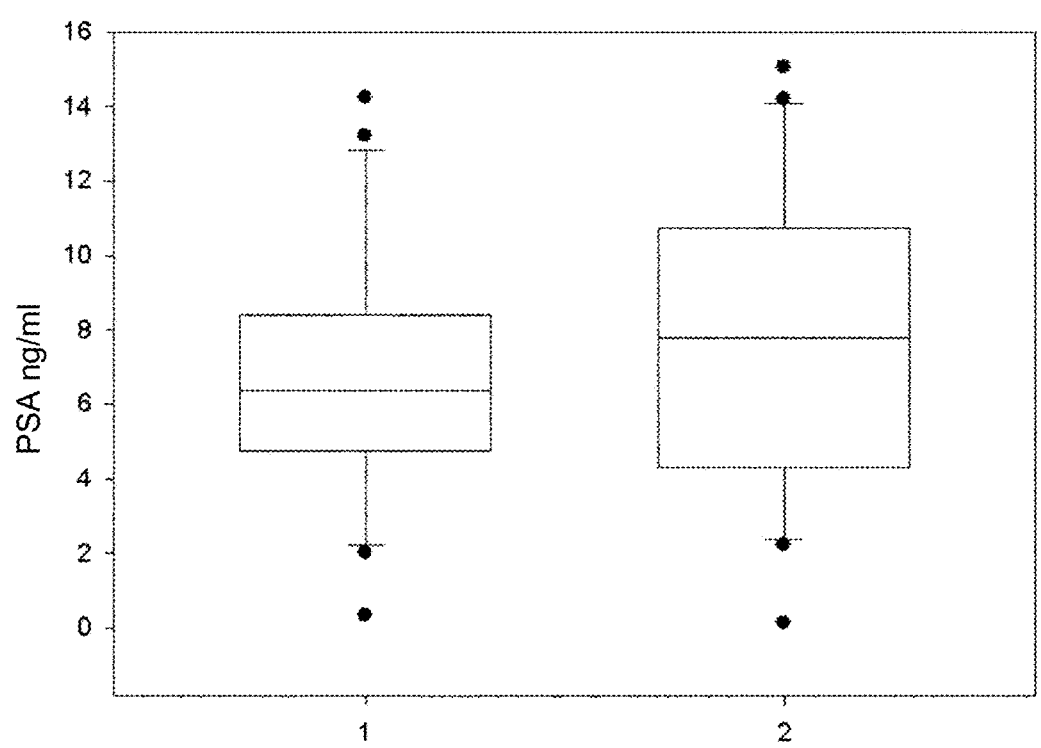

FIG. 61 is a box plot for the PSA concentration values (ng/ml) that were detected in the serum from 20 patients suffering from benign prostatic hyperplasia (BPH, No 1 left) and 20 PCa patients (No 2 right) and do not differ significantly (p<0.552).

GENERAL SPECIFICATIONS

Isolation and Bisulphite Conversion of Circulating Free DNA (cfDNA):

Firstly, the circulating free DNA (cfDNA) is isolated from the sample being tested, e.g. from 1-5 ml serum samples using QIAamp Circulating Nucleic Acid Kit from Qiagen GmbH (Hilden, Del.) following the test kit description, and then eluted into samples of 25 µl each.

Bisulphite Conversion of the cfDNA:

The bisulphite conversion of 20 µl samples of the cfDNA is carried out using the EpiTect Fast Bisulfite Conversion Kit from Qiagen GmbH following the test kit description. Following elution, 15 µl of bisulphite-treated cfDNA solution is obtained.

Bias-Based Pre-Amplification (BBPA) of Samples:

Following bisulphite conversion, the DNA concentrations in the DNA samples are determined using the Quantus™ Fluorometer (Promega). Where the DNA concentration was below or above 1 ng/µl, 2 or 1 µl of the bisulphite-treated DNA was added to the BBPA, respectively.

Master Mix for the BBPA:

| Reagent | Vol. [µl] | Final concentration |
|---|---|---|
| PCR buffer [15 mM MgCl] | 2.50 | 1.5 mmol/l |
| dNTPs [2.5 mM] | 2.00 | 200 µmol/l |
| forward primer | 1.00 | 400 nmol/l |
| reverse primer | 1.00 | 400 nmol/l |
| HotStarTaq Plus [5 U/µl] | 0.125 | 0.625 U |
| $MgCl_2$ [25 mM] | 0-13.50, preferably 1.00-2.00 | 0 to +13.5, preferably +1-2 mmol/l |
| RNase-Free Distilled Water | 2.875-17.375, preferably 13.50-15.50 | |
| Carrier DNA | 1.00-2.00 | |
| Final volume | 25.00 | | mM = mmol/l

Primers for the BBPA:

| Target | Forward (5'->3') | SEQ ID | Reverse (5'->3') | SEQ ID BBPA | Annealing temperature |
|---|---|---|---|---|---|
| PLA2R1 (168 bp) | GGGGTAAGGAAGGTGGAGAT | 1 | ACAAACCACCTAAATTCTAATAAACAC | 2 | 63.0° C. and 2.5 mM $MgCl_2$ |
| RASSF1A (117 bp) | GTTTGTTAGCGTTTAAAGTTAG | 3 | AATACGACCCTTCCCAAC | 4 | 52.0° C. and 2.5 mM $MgCl_2$ |
| GSTP1 (120 bp) | GTGAAGCGGGTGTGTAAGTTT | 5 | TAAACAAACAACAAAAAAAAAC | 6 | 50.7° C. and 2.5 mM $MgCl_2$ |
| GSTP1 (116 bp) | ATCGTAGCGGTTTTAGGGAA | 93 | TCCCCAACGAAACCTAAAAA | 94 | 53.8° C. and 4.5 mM $MgCl_2$ |
| PLA2R1 (150 bp) | GGGGTAAGGAAGGTGGAGAT | 53 | AATAAACACCGCGAATTTACAAC | 9 | 59.5° C. and 2.5 mM $MgCl_2$ |
| PLA2R1 (161 bp) | | | ACCTAAATTCTAATAAACACCGC | 10 | 62.5° C. and 2.5 mM $MgCl_2$ |

-continued

| Target | Forward (5'->3') | SEQ ID | Reverse (5'->3') | SEQ ID | Conditions |
|---|---|---|---|---|---|
| PLA2R1 (160 bp) | | | CCTAAATTCTAATAAACAC<u>CG</u>C | 11 | 62.5° C. and 2.5 mM MgCl$_2$ |
| PLA2R1 (133 bp) | GGAAGGTGGAGATTA<u>CG</u>G | 7 | G<u>CG</u>AATTTACAA<u>CG</u>AACAA<u>C</u> | 8 | 50.0° C. and 1.5 mM MgCl$_2$ or 63.0° C. and 6.0 mM MgCl$_2$ |
| AOX1 (180 bp) | TGGGTTGGATTTTAGGTTTTAG | 14 | CTCACCTTA<u>CG</u>AC<u>CG</u>TTC | 15 | 52.6° C. and 2.5 mM MgCl$_2$ |
| SERPINE1 (123 bp) | AGAG<u>CG</u>TTGTTAAGAAGA | 16 | CTCCTACCTAAAATTCTCAAAA | 17 | 52.0° C. and 3.5 mM MgCl$_2$ |
| AOX1 (138 bp) | GTTGGATTTTAGGTTTTAGTAAG | 18 | GCC<u>CG</u>ATCCATTATAATATC | 19 | 50.0° C. and 2.5 mM MgCl$_2$ |

| Target | Forward (5'->3') | SEQ ID | Reverse (5'->3') | SEQ ID |
|---|---|---|---|---|
| RASSF1A (124 bp) | G<u>CG</u>TTTGTTAG<u>CG</u>TTTAAAG | 61 | AAC<u>CG</u>AATA<u>CG</u>ACCCTTC | 62 |
| GSTP1 (114 bp) | <u>CG</u>TAG<u>CG</u>GTTTTAGGGAATTT | 91 | TCCCCAA<u>CG</u>AAACCTAAAAA | 92 |
| GSTP1 (129 bp) | TGTAAGTTT<u>CG</u>GGAT<u>CG</u>TAG<u>C</u> | 95 | TCCCCAA<u>CG</u>AAACCTAAAAA | 96 |
| GSTP1 (132 bp) | GTGTGTAAGTTT<u>CG</u>GGAT<u>CG</u> | 97 | TCCCCAA<u>CG</u>AAACCTAAAAA | 98 |
| AOX1 (138 bp) | GTTGGATTTTAGGTTTTAGTAAG | 63 | G<u>CC<u>CG</u>ATCCATTATAATATC | 64 |
| AOX1 (135 bp) | GGATTTTAGGTTTTAGTAAGTTT<u>C</u> | 65 | GCC<u>CG</u>ATCCATTATAATATC<u>CG</u> | 66 |
| AOX1 (134 bp) | GATTTTAGGTTTTAGTAAGTTT<u>CG</u> | 67 | | |
| SERPINE1 (119 bp) | <u>CG</u>TTGTTAAGAAGATTTATA<u>C</u> | 68 | TAAACC<u>CG</u>AAATAAAAAATTAAA | 69 |
| TM (125 bp) | GGT<u>CG</u>ATT<u>CG</u>TATGTTAGA | 70 | 5'-AAC<u>CG</u>TAC<u>CG</u>AAACAAAA | 71 |
| TM (144 bp) | GTTTGGGTTGGGA<u>CG</u>GATA | 72 | 5'-AAAAACCAAAACCCCAAACA | 73 |
| TM (166 bp) | GTTTGGGGTTTTGGTTTTTG | 74 | 5'-<u>G</u>CAATC<u>CG</u>TCGCAAATCTAA | 75 |
| TM (165 bp) | | | 5'-CAATC<u>CG</u>T<u>CG</u>CAAATCTAAC | 76 |

Since methylated DNA fragments were detected in serum samples from tumour patients and in cfDNA samples from serum of healthy subjects following pre-amplification and dPCR using methyl-specific primers, which was not the case when using a less methyl-specific primer pair, the methyl-specific primers were altered empirically such that unmethylated DNA fragments were also amplified as well as the methylated fragments, thereby producing a bias in favour of methylated DNA sequences as far as possible during the amplification. The aforementioned primers were obtained in the process. For the RASSF1A gene, for example, an oligonucleotide pair (amplified material size 117 bp) was generated that amplifies both methylated and unmethylated DNA fragments over a wide temperature range and at the same time has a clear bias in favour of methylated DNA fragments. A similar process was carried out for the targets of interest PLA2R1 (FIG. 34-37), GSTP1 (Table 15), SERPINE1, AOX1 and thrombomodulin, without methylated fragments alone being amplified.

In the following examples, the aforementioned primers were used for both BBPA and dPCR. It goes without saying that other primers (nested PCR primers) that hybridise (anneal) with the sequence portions pre-amplified by the BBPA can also be used for the dPCR. The primers used in the dPCR must include the DNA sequence for which the probes used are specific. Since bias is ruled out in the dPCR, the primers in this case can be selected according to conventional rules, or the BBPA-specific primers are also used in the dPCR.

Temperature and Time Schedule for the BBPA:

| PCR | Temperature | Time |
|---|---|---|
| Denaturing: | 95° C. | 5 minutes |
| PCR cycle: 5×-50× | 94° C. (denaturing) | 10 seconds |
| | Primer-specific temperatures (Annealing: 40-72° C., preferably 50-72° C.) | 30 seconds |
| | 72° C. (elongation) | 30 seconds |
| | 4° C. | Stop |

Master Mix for ddPCR:

| Component | Batch vol. [µl] | Final concentration |
|---|---|---|
| 2× ddPCR super mix (BioRad) | 10.0 | |
| 20× primer/probe mix | 1.0 | 900 mmol/l/250 nmol/l |
| DNA | 2.0 | |
| RNase-Free Distilled Water | 7.0 | |
| Final volume | 20.0 | |

Probes: For the dPCR

| Target | methylated (5'->3') | SEQ ID | unmethylated (5'->3') | SEQ ID | Hybridisation temp. |
|---|---|---|---|---|---|
| PLA2R1 (3 CpG) | CCCAACTACTCCGCGACGCAA | 20 | AACCCAACTACTCCACAACACAAA | 21 | 58.8° C. |
| PLA2R1 (4 CpG) | CAACTACTCCGCGACGCAAACG | 22 | AACCCAACTACTCCACAACACAAACA | 23 | 51.9° C. |
| RASSF1A (3 CpG) | CGCCCAACGAATACCAACTCCCG | 24 | CACCCAACAAATACCAACTCCCACAA | 25 | 51.9° C. |
| RASSF1A (4 CpG) | CGCCCAACGAATACCAACTCCCGCG | 54 | CACCCAACAAATACCAACTCCCACAACTC- | 55 | 51.9° C. |
| GSTP1 (3 CpG) | CGCAACGAAATATACGCAAC | 56 | CACAACAAAATATACACAAC | 57 | 50.7° C. |
| GSTP1 (4 CpG) | ACGAACTAACGCGCCGAAAC | 58 | ACAAACTAACACACCAAAAC | 59 | 51.9° C. |
| AOX1 (3 CpG) | ACTCGAACGCCCGATCCATTATAA | 37 | ACAACTCAAACACCCAATCCATTATAA | 38 | 50.7° C. |
| AOX1 (4 CpG) | CGCTAATTCGAAACCCGAAACGA | 39 | CACTAATTCAAAAACCCAAAACAA | 40 | 53.8° C. |
| AOX1 (5 CpG) | CGCGCTAATTCGAAAACCCGAACGA | 41 | CACACTAATTCAAAAACCCAAAACAA | 42 | 51.9° C. |
| SERPINE1 (4 CpG) | CGATTAACGATTCGTCCTACTCTAACG | 43 | CAATTAACAATTCATCCTACTCTAACA | 44 | 58.8° C. |

| Target | methylated (5'->3') | SEQ ID | unmethylated (5'->3') | SEQ ID |
|---|---|---|---|---|
| AOX1 (4 CpG) | CGCTAATTCGAAAACCCGAAACGA | 77 | CACTAATTCAAAAACCCAAAACAA | 78 |
| AOX1 (4 CpG) | | | CACTAATTCAAAAACCCAAAACAAAAA | 79 |
| TM (3 CpG) | ACGCCGATAACGACAACCTCT | 80 | AAAAAGCAGATAAAGACAACCTC | 81 |
| TM (4 CpG) | CCGACTACGACTCTACGAATACGAA | 82 | CAGACTAAGACTCTAAGAATAAGAAAAC | 83 |

In the examples, all the probes are 5' FAM-marked (methylated DNA) or 5' HEX-marked (unmethylated DNA) and marked with the quencher BHQ-1 at the 3' end.
Producing the Droplets (Droplet Generator [BioRad]):
20 μl master mix with DNA sample
+70 μl oil in corresponding cartridges (BioRad);
Generation of around 20,000 oil/emulsion droplets,
35 μl of which into the subsequent dPCR
Temperature and Time Schedule for the dPCR by Means of T100-PCR Device (BioRad):

| PCR | Temperature | Time |
|---|---|---|
| Denaturing: | 95° C. | 10 minutes |
| PCR cycle: 40× | 94° C. (denaturing) | 30 seconds |
| | Primer-specific and probe-specific temperature (annealing and elongation, 50-72° C.) | 1 minute |
| | 98° C. (droplet stabilisation) | 10 minutes |
| | 20° C. | Stop |

Droplet Fluorescence Measurement:
The droplet fluorescence is measured by means of QY100 (BioRad) following the manufacturer's description.
Gene Selection
On the basis of tests carried out on prostate cells (normal PrEC and BPH-1, and malignant LNCaP, PC-3 and DU-145 cell lines), breast cancer cells (normal HMEC and malignant Cal-51, BT-474, MCF-7 and MDA-MB-453 cell lines), leukaemia cell lines (U937 and Jurkat cells), the hepatoma cell line (HepG2) and normal endothelial cells (HUVEC and HCAEC), the genes PLA2R1, RASSF1A and GSTP1 were selected, as well as the genes SERPINE1 (PAI-1) and AOX1. Another gene candidate is thrombomodulin (TM). In the genes uPA, Del-1 and Jam-C, elevated methylation values in the prostate tumour cell lines were only found in individual cases. The gene PLA2G5 showed elevated methylation values even in normal PrEC and is thus unsuitable for use as a biomarker for diagnosing tumour diseases.

Figure 1:
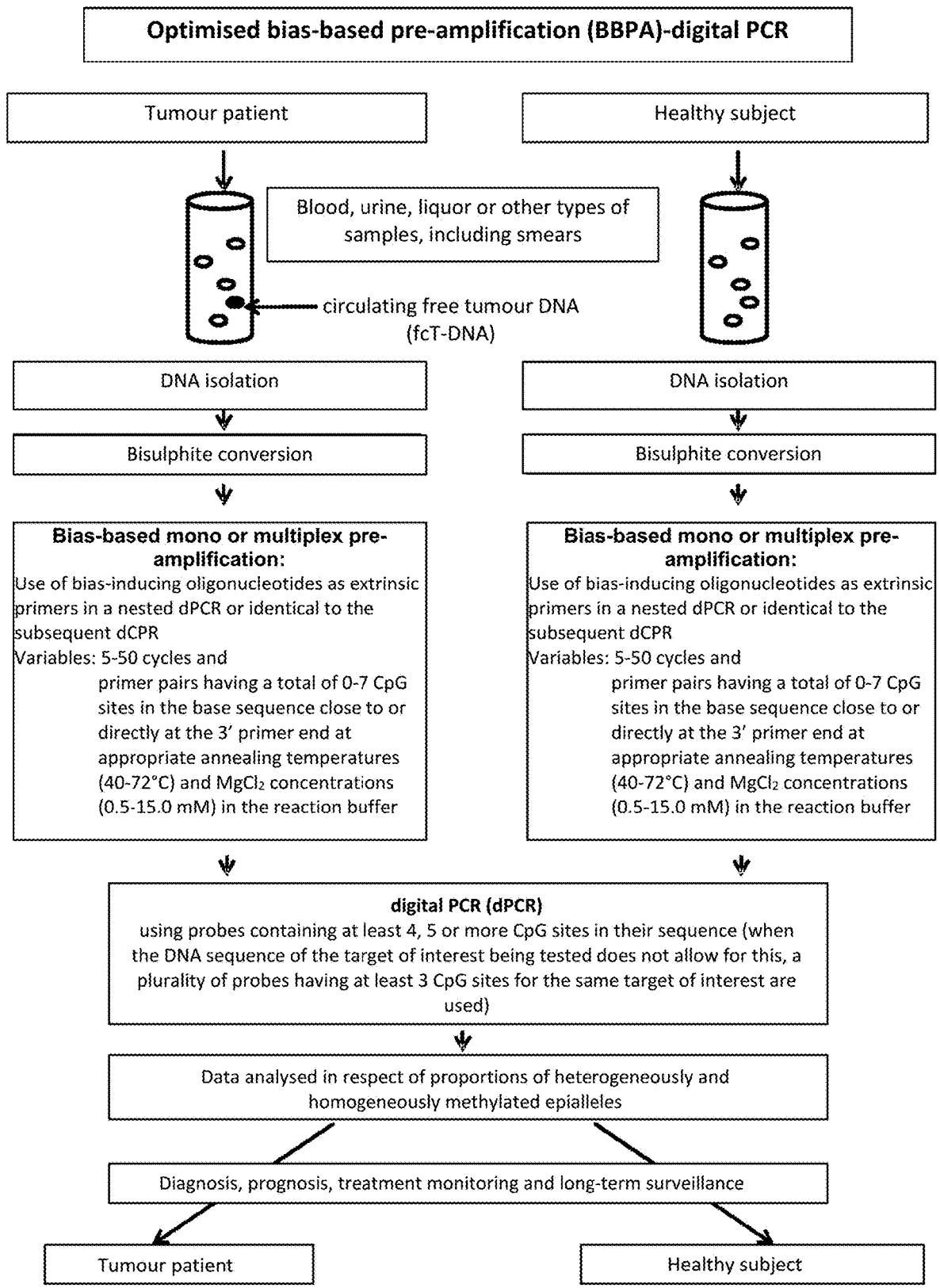
FIG. 1 is an outline of the preferred implementation of the BBPA-dPCR according to the invention.
Figure 2:
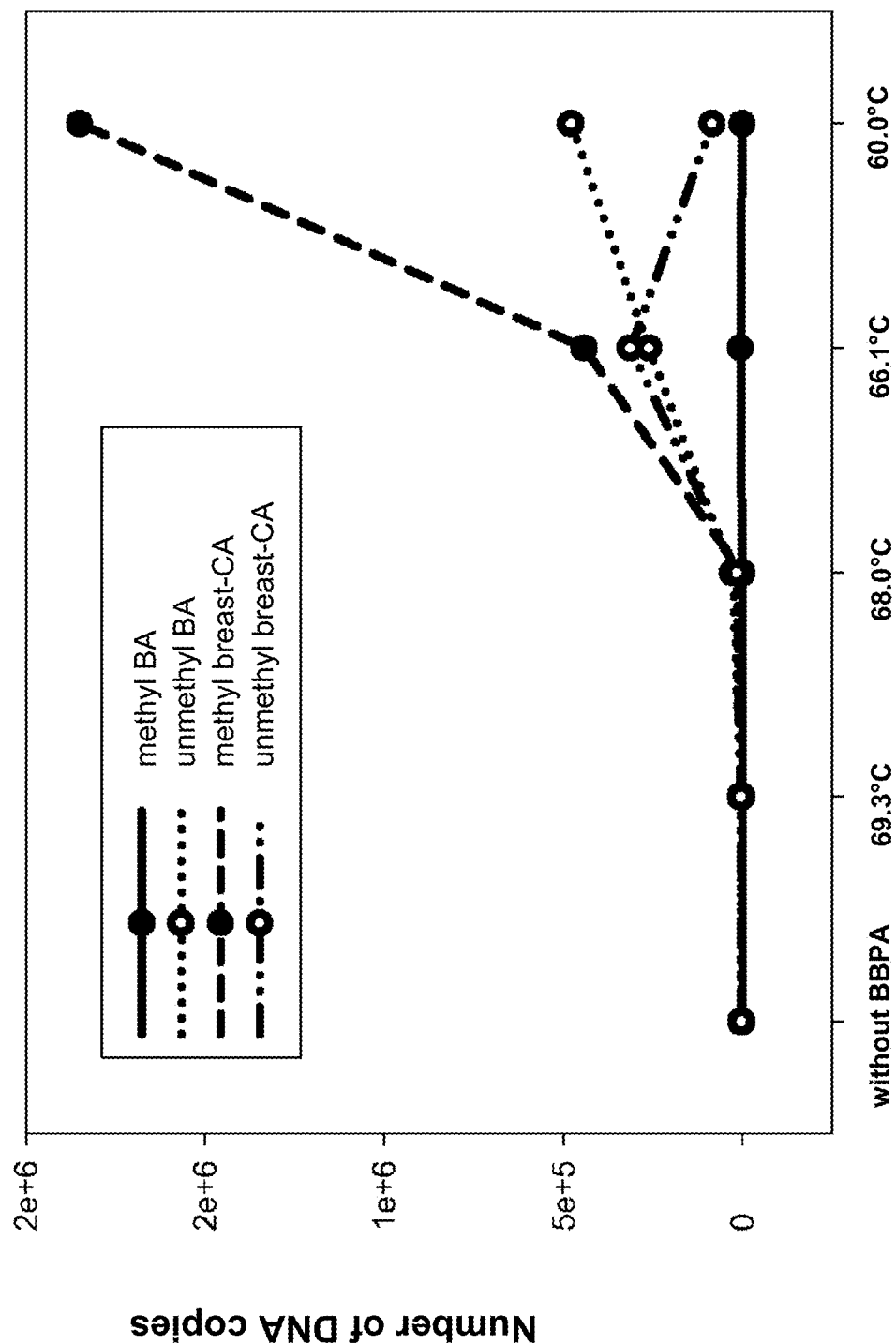
FIG. 2 shows the number of copies of methylated (methyl) and unmethylated (unmethyl) RASSF1A sequences plotted against annealing temperature for 30 cycles and at an MgCl$_2$ concentration of 2.5 mmol/l in the BBPA in serum pool samples from healthy subjects (BA) or female breast cancer patients (breast-CA; see also Table 2).

Embodiment 1: BBPA-dPCR Results on the Basis of RASSF1 Methylation in Serum Pool Samples from Female Breast Cancer Patients Compared with Healthy Subjects When using the bias-inducing RASSF1 (117 bp) primer pair (SEQ ID No 3 and 4), it was surprisingly found that, as the cycle number increased and without the pre-amplified material being additionally diluted, the differential between the determined methylation levels of the RASSF1A gene among healthy female subjects and female breast cancer patients increased more and more, to the extent that the values from healthy female subjects approached 0% and those from the female breast cancer patients approached 100%. For example, it was found that using the above primer pair at an annealing temperature of from 66.1° C. to 60.0° C. increased the number of copies of methylated sequences to a greater extent in the breast cancer patient samples compared with unmethylated sequences (FIG. 2). However, it was unexpected that the methylated DNA copies occurring in the fcDNA of healthy subjects, even when only in small numbers, were preferably not copied over unmethylated DNA copies. On the contrary, the unmethylated DNA copies were copied to a greater extent compared with the methylated copies in the healthy samples (Table 2). Without the BBPA, the methylation level (fractional abundance) was 0.6% (Poisson probability range: 0-1.2%) in healthy subjects and 1.5% (Poisson probability range: 0.8-2.1%) in breast cancer patients (Table 2).

TABLE 1

Overview of the gene methylations tested (%) in prostate cells (normal PrEC and BPH -1, and malignant LNCaP, PC-3 and DU-145 cell lines), breast cancer cells (normal HMEC and malignant Cal-51, BT-474, MCF-7 and MDA-MB-453 cell lines), leukaemia cell lines (U937 and Jurkat cells), the hepatoma cell line (HepG2) and normal endothelial cells (HUVEC and HCAEC)

| Cell type | PLA2R1 | PLA2G5 | PAI-1 | uPA | Del-1 | Jam-C | RASSF1A | AOX1 | GSTP1 | TM |
|---|---|---|---|---|---|---|---|---|---|---|
| PrEC | 2.2 | 25 | 0 | 0 | 5 | 0 | 2 | 0 | 0.7 | 0 |
| BPH-1 | 6 | n.d. | 0 | n.d. | n.d. | n.d. | 7 | 8 | 0.6 | n.d. |
| LNCaP | 99 | 70 | 30 | 65 | 30 | 0 | 94 | 46 | 99 | 17 |
| PC-3 | 43 | 40 | 16 | 0 | 0 | 0 | 96 | 69 | 26 | 28 |
| DU145 | 24 | 100 | 64 | 0 | 0 | 23 | 55 | 64 | 18 | 64 |
| U937 | 100 | 100 | 9 | n.d. | 100 | n.d. | 5 | n.d. | n.d. | n.d. |
| Jurkat | 100 | 65 | 1 | n.d. | 10 | n.d. | 80 | n.d. | n.d. | n.d. |
| HepG2 | 42 | 19 | 1 | n.d. | 7 | n.d. | 70 | n.d. | n.d. | n.d. |
| HUVEC | 1 | 12 | n.d. | n.d. | 0 | n.d. | 4 | n.d. | n.d. | n.d. |
| HCAEC | 2 | 0 | 1 | n.d. | 0 | n.d. | 3 | n.d. | n.d. | n.d. |
| HMEC | 1 | 5 | 0 | 0 | 0 | 0 | 3 | n.d. | n.d. | 0 |
| Cal-51 | 5 | 11 | 40 | 0 | 95 | 20 | 100 | n.d. | n.d. | 70 |
| BT-474 | 8 | 85 | 48 | 47 | 0 | 100 | 100 | n.d. | n.d. | 55 |
| MCF-7 | 9 | 59 | 75 | 75 | 0 | 100 | 95 | n.d. | n.d. | 45 |
| MDA-MB-453 | 71 | 35 | 65 | 100 | 65 | 100 | 70 | n.d. | n.d. | 0 | n.d. = no data

TABLE 2

Number of copies of methylated (Met) and unmethylated (Unm) RASSF1A sequences as a function of annealing temperature (60.0-69.3° C.) for 30 BBPA cycles in serum pool samples of healthy subjects (BA) or female breast cancer patients (PatP). Following BBPA, 1 μl of the 25 μl PCR batches were added to the dPCR, and so the values after the BBPA were multiplied by 25 for comparison. "without" in the Temp/° C. column signifies without prior BBPA.

| Sample | Target | Copies/ 20 μl well | 1:25 | Positive | Negative | Ch1+ Ch2+ | Ch1+ Ch2− | Ch1− Ch2+ | Ch1− Ch2− | Accepted droplets | Fractional abundance | Poisson fractional abundance max. | Poisson fractional abundance min. | Temp/ ° C. |
|---|---|---|---|---|---|---|---|---|---|---|---|---|---|---|
| BA | RASSF1 Met | 9 | 9 | 4 | 10353 | 0 | 4 | 669 | 9684 | 10357 | 0.6 | 1.2 | 0 | without |
| BA | RASSF1 Unm | 1580 | 1580 | 669 | 9688 | | | | | | | | | without |
| PatP | RASSF1 Met | 40 | 40 | 19 | 11016 | 1 | 18 | 1202 | 9814 | 11035 | 1.5 | 2.1 | 0.8 | without |
| PatP | RASSF1 Unm | 2720 | 2720 | 1203 | 9832 | | | | | | | | | without |
| BA 30× | RASSF1 Met | 2 | 50 | 1 | 11872 | 1 | 0 | 65 | 11807 | 11873 | 1.5 | 5 | 0 | 69.3 |
| BA 30× | RASSF1 Unm | 132 | 3300 | 66 | 11807 | | | | | | | | | 69.3 |
| PatP 30× | RASSF1 Met | 11.2 | 280 | 6 | 12562 | 0 | 6 | 73 | 12489 | 12568 | 8 | 14 | 2 | 69.3 |
| PatP 30× | RASSF1 Unm | 138 | 3450 | 73 | 12495 | | | | | | | | | 69.3 |
| BA 30× | RASSF1 Met | 18 | 450 | 8 | 10515 | 4 | 4 | 447 | 10068 | 10523 | 1.7 | 2.9 | 0.5 | 68.0 |
| BA 30× | RASSF1 Unm | 1030 | 25750 | 451 | 10072 | | | | | | | | | 68.0 |
| PatP 30× | RASSF1 Met | 32 | 800 | 19 | 13584 | 0 | 19 | 351 | 13233 | 13603 | 5.1 | 7.3 | 2.8 | 68.0 |
| PatP 30× | RASSF1 Unm | 616 | 15400 | 351 | 13252 | | | | | | | | | 68.0 |
| BA 30× | RASSF1 Met | 162 | 4050 | 71 | 10332 | 35 | 36 | 3692 | 6640 | 10403 | 1.52 | 1.87 | 1.17 | 66.1 |
| BA 30× | RASSF1 Unm | 10440 | 261000 | 3727 | 6676 | | | | | | | | | 66.1 |
| PatP 30× | RASSF1 Met | 17660 | 441500 | 6583 | 5888 | 2325 | 4258 | 2801 | 3087 | 12471 | 58.6 | 59.5 | 57.7 | 66.1 |
| PatP 30× | RASSF1 Unm | 12460 | 311500 | 5126 | 7345 | | | | | | | | | 66.1 |
| BA 30× | RASSF1 Met | 0 | 0 | 0 | 10851 | 0 | 0 | 6036 | 4815 | 10851 | 0 | 0 | 0 | 60.0 |
| BA 30× | RASSF1 Unm | 19120 | 478000 | 6036 | 4815 | | | | | | | | | 60.0 |
| PatP 30× | RASSF1 Met | 74000 | 1850000 | 12234 | 550 | 1678 | 10556 | 12 | 538 | 12784 | 95.69 | 95.91 | 95.46 | 60.0 |
| PatP 30× | RASSF1 Unm | 3340 | 83500 | 1690 | 11094 | | | | | | | | | 60.0 |

TABLE 3

Number of copies of methylated (methyl) and unmethylated (unmethyl) RASSF1A sequences as a function of number of BBPA cycles(0 × [i.e. without BBPA], 8×, 12×, 16× and 40× ) at 60.0° C. in serum pool samples of healthy subjects (BA) or breast cancer patients (PatP). Following BBPA, 1 μl of the 25 μl PCR batches was added to the dPCR, and so the values following the BBPA were multiplied by 25 for comparison.

| Sample | Copies/ 20 μL well | 1:25 | Positive | Negative | Ch1+ Ch2+ | Ch1+ Ch2− | Ch1− Ch2+ | Ch1− Ch2− | Accepted droplets | Fractional abundance | Poisson fractional abundance min. | Poisson fractional abundance max. |
|---|---|---|---|---|---|---|---|---|---|---|---|---|
| BA (0×) methyl. | 12 | 12 | 5 | 9728 | 1 | 4 | 567 | 9161 | 9733 | 0.8 | 0.1 | 1.6 |
| BA (0×) unmeth. | 1420 | 1420 | 568 | 9165 | | | | | | | | |
| PatP (0×) methyl. | 40 | 40 | 19 | 11241 | 4 | 15 | 907 | 10334 | 11260 | 2 | 1.1 | 2.8 |
| PatP (0×) unmeth. | 1980 | 1980 | 911 | 10349 | | | | | | | | |
| BA 8× methyl. | 2.2 | 55 | 1 | 11053 | 1 | 0 | 20 | 11033 | 11054 | 5 | 0 | 15 |

TABLE 3-continued

Number of copies of methylated (methyl) and unmethylated (unmethyl) RASSF1A sequences as a function of number of BBPA cycles(0 × [i.e. without BBPA], 8×, 12×, 16× and 40× ) at 60.0° C. in serum pool samples of healthy subjects (BA) or breast cancer patients (PatP). Following BBPA, 1 μl of the 25 μl PCR batches was added to the dPCR, and so the values following the BBPA were multiplied by 25 for comparison.

| Sample | Copies/ 20 μL well | 1:25 | Positive | Negative | Ch1+ Ch2+ | Ch1+ Ch2− | Ch1− Ch2+ | Ch1− Ch2− | Accepted droplets | Fractional abundance | Poisson fractional abundance min. | Poisson fractional abundance max. |
|---|---|---|---|---|---|---|---|---|---|---|---|---|
| BA 8× unmeth. | 44 | 1100 | 21 | 11033 | | | | | | | | |
| PatP 8× methyl. | 22 | 550 | 8 | 8730 | 2 | 6 | 36 | 8694 | 8738 | 17 | 6 | 29 |
| PatP 8× unmeth. | 102 | 2550 | 38 | 8700 | | | | | | | | |
| BA 12× methyl. | 7 | 175 | 3 | 10206 | 3 | 0 | 43 | 10163 | 10209 | 6 | 0 | 13 |
| BA 12× unmeth. | 106 | 2650 | 46 | 10163 | | | | | | | | |
| PatP 12× methyl. | 150 | 3750 | 63 | 9832 | 0 | 63 | 58 | 9774 | 9895 | 52 | 43 | 61 |
| PatP 12× unmeth. | 138 | 3450 | 58 | 9837 | | | | | | | | |
| BA 6× methyl. | 8.4 | 210 | 4 | 11236 | 2 | 2 | 1014 | 10222 | 11240 | 0.37 | 0 | 0.76 |
| BA 16× unmeth. | 2220 | 55500 | 1016 | 10224 | | | | | | | | |
| PatP 16× methyl. | 1544 | 38600 | 755 | 11125 | 8 | 747 | 144 | 10981 | 11880 | 83.6 | 81.2 | 86 |
| PatP 16× unmeth. | 302 | 7550 | 152 | 11728 | | | | | | | | |
| BA 40× methyl. | 30 | 750 | 16 | 12592 | 6 | 10 | 4345 | 8247 | 12608 | 0.3 | 0.15 | 0.45 |
| BA 40 unmeth. | 9960 | 249000 | 4351 | 8257 | | | | | | | | |
| PatP 40× methyl. | 46580 | 1164500 | 9298 | 1490 | 1665 | 7633 | 198 | 1292 | 10788 | 91.26 | 90.85 | 91.67 |
| PatP 40× unmeth. | 4460 | 111500 | 1863 | 8925 | | | | | | | | |

Figure 3:
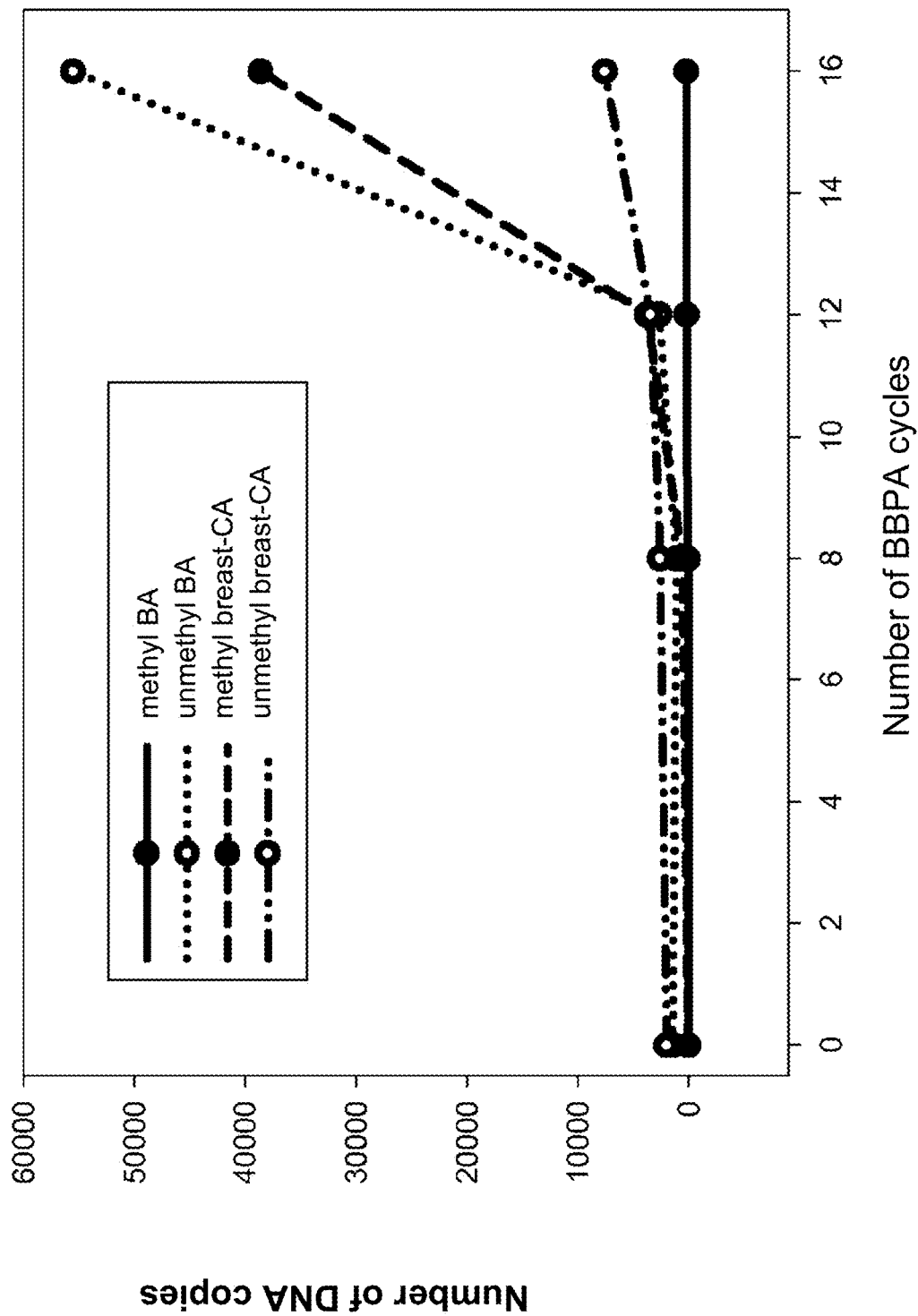
FIG. 3 shows the number of copies of methylated (methyl) and unmethylated (unmethyl) RASSF1A sequences plotted against cycle number (0 [i.e. no BBPA], 8, 12 and 16) at 60° C. and an MgCl$_2$ concentration of 2.5 mmol/l in the BBPA in serum pool samples from healthy subjects (BA) or female breast cancer patients (breast-CA; see also Table 3).

This unusual behaviour also became clear when the annealing temperature was kept constant at 60.0° C. and the copying was analysed according to number of cycles. In this case, too, the methylated fraction increased compared with the unmethylated fraction in the cfDNA samples of tumour patients, even after just 16 cycles, and further increased sharply after 40 cycles (FIGS. 3 and 4). By contrast, in healthy subjects there was a significant increase in the unmethylated DNA fraction, whereas the proportion of methylated DNA only rose slightly (FIGS. 3 and 4; Table 3). Without the BBPA, the methylation level (fractional abundance) was 0.8% (Poisson probability range: 0.1-1.6%) in healthy subjects and 2.0% (Poisson probability range: 1.1-2.8%) in breast cancer patients (Table 3).

This phenomenon cannot yet be fully explained. It first accounts for the observation that, as the number of PCR cycles is increased, the fractional methylation level of the RASSF1A gene determined (ratio between methylated and unmethylated DNA fragments in relation to the overall quantity of methylated and unmethylated DNA fragments) in the healthy cfDNA samples approached 0% whereas the methylation level in the breast cancer patients' cfDNA samples approached 100%.

In this way, a clear-cut distinction can be made between healthy and diseased subjects on the basis of the determination of the methylation of e.g. the RASSF1A gene; this is not possible using dPCR alone or MS-HRM. For example, in the same serum pool samples using dPCR alone, fractional methylation levels of the RASSF1A gene of 0.5% (Poisson probability range: 0.05-0.99%) could be detected in healthy subjects and of 1.00% (Poisson probability range: 0-2.00%) in female breast cancer patients (FIG. 5); in other words, they could not be distinguished to a statistically significant degree.

In addition, the same pool samples did not show any significant differences in the melting curve characteristics as a result of MS-HRM analysis between healthy subjects and breast cancer patients (FIG. 6).

Embodiment 2: BBPA-dPCR Results on the Basis of RASSF1 Methylation in Serum Pool Samples from Prostate Cancer Patients Compared with Healthy Subjects The phenomenon first observed in breast cancer patients, whereby the values for RASSF1A methylation deviated increasingly between healthy and diseased subjects when a selective annealing temperature and increasing number of cycles are used (i.e. increasing pre-amplified numbers of copies), was also observed in serum pool samples from prostate cancer patients compared with healthy subjects (Tables 4 and 5). For example, in this case too there was a large difference between healthy subjects and prostate cancer patients when the pre-amplification was carried out at 59° C. instead of 52° C., and after 50 cycles different quantities of the pre-amplified DNA copies (e.g. $1:10^7$ diluted compared with dilution of $1:10^5$, i.e. 100-times less diluted) were analysed in the dPCR (Table 4). This was also observed when the annealing temperature was constant at 59° C. and 35 or 50 cycles were carried out in the pre-amplification (Table 5).

TABLE 4

Relative frequency of methylated RASSF1A sequences in cfDNA samples from a serum pool of healthy subjects (BA) and prostate cancer patients (Pat) following BBPA (50 cycles at 52° C. and 59° C.) as a function of the quantity of DNA used in the dPCR (dilutions of $1:10^7$, $1:10^6$ and $1:10^5$).

| BBPA | BA | Pat |
|---|---|---|
| 50 cycles at 52° C. and dilution of $1:10^7$ | 2.52% | 9.52% |
| 50 cycles at 59° C. and dilution of $1:10^7$ | 0.91% | 81.9% |
| 50 cycles at 52° C. and dilution of $1:10^6$ | 0.153% | 9.73% |
| 50 cycles at 59° C. and dilution of $1:10^6$ | 0.067% | 96.26% |
| 50 cycles at 52° C. and dilution of $1:10^5$ | 0% | 11.6% |
| 50 cycles at 59° C. and dilution of $1:10^5$ | 0.006% | 99.09% |

TABLE 5

Relative frequency of methylated RASSF1A sequences in cfDNA samples from a serum pool of healthy subjects (BA) and prostate cancer patients (Pat) following BBPA (35 and 50 cycles at 59° C.) as a function of the quantity of DNA used in the dPCR (dilutions of $1:10^7$ to $1:10^3$).

| BBPA | BA | Pat |
|---|---|---|
| 35 cycles at 59° C. and dilution of $1:10^7$ | 4.7% | 65.7% |
| 50 cycles at 59° C. and dilution of $1:10^7$ | 0.42% | 79.8% |
| 35 cycles at 59° C. and dilution of $1:10^6$ | 2.7% | 65.6% |
| 50 cycles at 59° C. and dilution of $1:10^6$ | 0.011% | 92.0% |
| 35 cycles at 59° C. and dilution of $1:10^5$ | 1.1% | 75.2% |
| 50 cycles at 59° C. and dilution of $1:10^5$ | 0.006% | 96.5% |
| 35 cycles at 59° C. and dilution of $1:10^4$ | 0.01% | 70.2% |
| 50 cycles at 59° C. and dilution of $1:10^4$ | 0% | 98.5% |
| 35 cycles at 59° C. and dilution of $1:10^3$ | 0% | 75.5% |
| 50 cycles at 59° C. and dilution of $1:10^3$ | 0.004% | 96.3% |

TABLE 6

Absolute number of copies of methylated (methyl) and unmethylated (unmethyl) RASSF1A sequences in cfDNA samples from a serum pool of healthy subjects (BA) and prostate cancer patients (PatP) following BBPA (50 cycles at 59° C., undiluted [und.]). The resultant number of DNA copies after the corresponding dilutions (1:103, 1:104, 1:105, 1:106 and 1:107) used in the dPCR are shown. On this basis, the CPCs for the tests shown in Tables 4 and 5, in which there was an average droplet number of 12,000, were calculated according to the formula: CPC (copies per compartment) = copies/number of compartments, for the samples from healthy subjects (BA CPC) and prostate cancer patients (PatP CPC).

| Samples | und. | $1:10^7$ | $1:10^6$ | $1:10^5$ | $1:10^4$ | $1:10^3$ |
|---|---|---|---|---|---|---|
| BA methyl | $2.4 \times 10^8$ | 24 | 240 | 2400 | 24000 | 240000 |
| BA unmethyl | $6.7 \times 10^{10}$ | 6700 | 67000 | 670000 | $6.7 \times 10^6$ | $6.7 \times 10^7$ |
| PatP methyl | $1.828 \times 10^{11}$ | 18280 | 182800 | $1.828 \times 10^6$ | $1.828 \times 10^6$ | $1.828 \times 10^7$ |
| PatP unmethyl | $4.98 \times 10^{10}$ | 4980 | 49800 | 49800 | 498000 | $4.98 \times 10^6$ |
| BA total DNA copies | | 6724 | 67240 | 672400 | $6.72 \times 10^6$ | $6.72 \times 10^7$ |
| BA CPC | | 0.56 | 5.6 | 56.0 | 560 | 5603 |
| PatP total DNA copies | | 23260 | 232600 | $2.33 \times 10^6$ | $2.33 \times 10^7$ | $2.33 \times 10^8$ |
| PatP CPC | | 1.9 | 19.4 | 193.8 | 1938 | 19383 |

For the dPCR, a maximum CPC value of 8 is given according to the prior art for the Poisson distribution and the associated statistics to apply [9]. However, the data presented here shows that, at a CPC value >8, the distinction between healthy and diseased subjects is even more clearcut. A CPC of 8 means that a maximum of 80,000 DNA copies are used in a dPCR having 10,000 compartments (e.g. oil-emulsion droplets or "nano-chambers" on a fixed support). In theory, after 35 or 50 amplification cycles the initial DNA copies are copied $3.43 \times 10^{10}$ or $1.12 \times 10^{15}$ times, if 100% PCR efficiency is assumed. In the example shown, after 50 cycles there were $1.828 \times 10^{11}$ methylated and $4.98 \times 10^{10}$ unmethylated RASSF1A DNA fragment copies in the samples from prostate cancer patients, and $2.4 \times 10^8$ methylated and $6.7 \times 10^{10}$ unmethylated RASSF1A DNA fragment copies in the samples from healthy subjects (Table 6). If, for example, the batch having the greatest separation (distinction) is selected, i.e. 50 cycles at 59° C. and dilution of $1:10^4$, in which 0% RASSF1A methylation was found in healthy subjects (BA) and 98.5% methylation was found in diseased subjects (PatP), the CPC value was 560 for the BA sample and 1938 for the PatP sample (Table 6).

On the basis of this clear distinction, the BBPA-dPCR in principle makes it possible to give a yes/no answer as regards the presence of tumour-specific DNA in the sample being tested (liquid biopsy) and therefore of a tumour disease. By means of the varying manipulated variable in the form of the number of cycles, without non-specific signals also being amplified at the same time, it is possible to specifically detect just one single tumour DNA molecule against a large background of normal DNA in a sample being tested. Detection that is this sensitive and in particular this specific is not possible with dPCR alone.

Embodiment 3: BBPA-dPCR Results on the Basis of RASSF1 Methylation in Individual Serum Samples from Female Breast Cancer Patients—Comparison with dPCR Alone and with MS-HRM In 10 serum samples from healthy subjects not suffering from tumour diseases and 10 female breast cancer patients, it was observed in the RASSF1A methylation analysis that only 4 patients (P2, P3, P8 and P19) were correctly identified as having positive results using dPCR alone (FIG. 7; Table 7), whereas 8 of the 10 female breast-CA patients (P1-P4, P6-P8 and P10) were correctly identified on the basis of the RASSF1A methylation analysis using the BBPA-dPCR according to the invention (FIG. 8; Table 7).

Figure 9A:
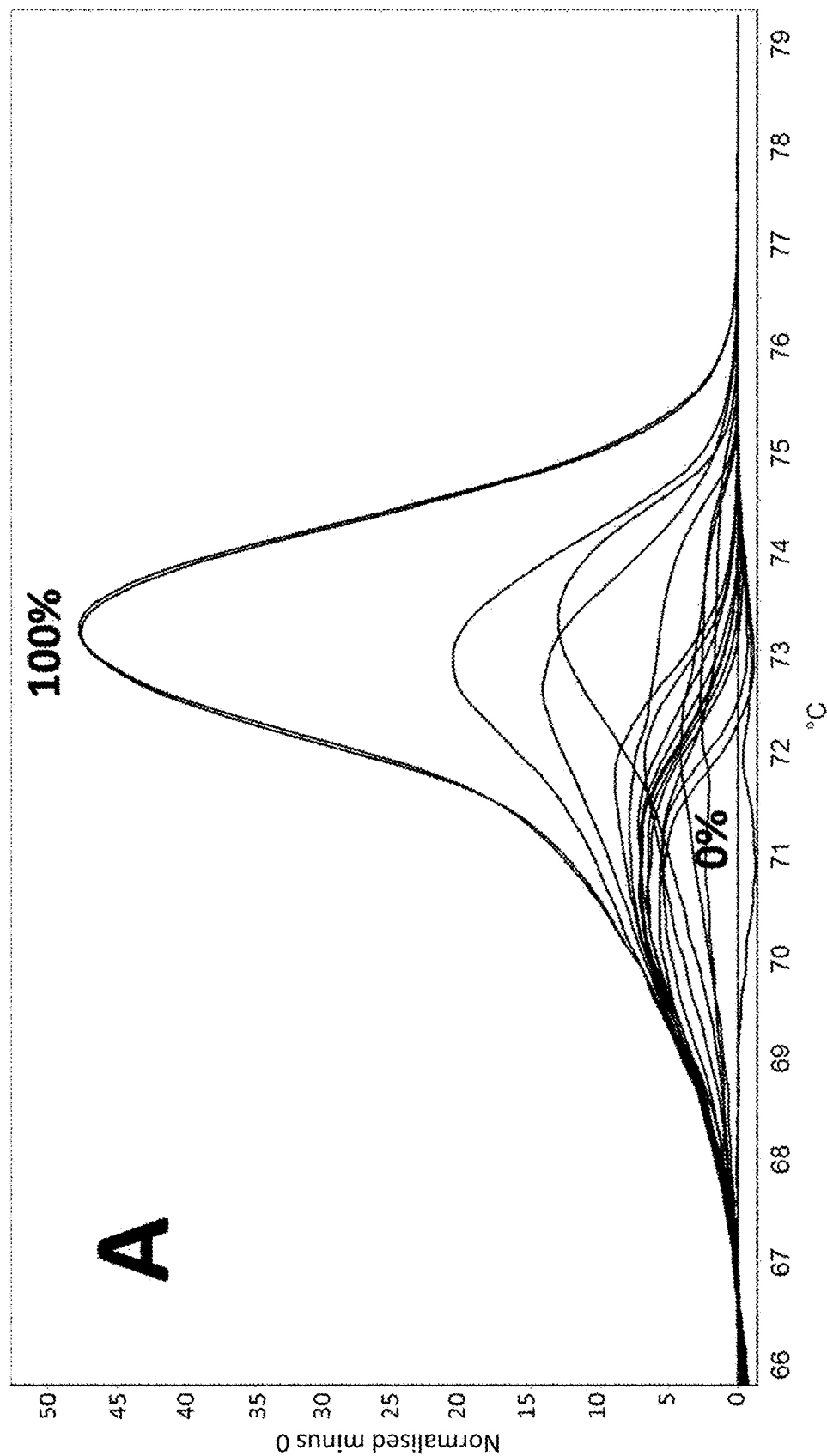
Figure 9B:
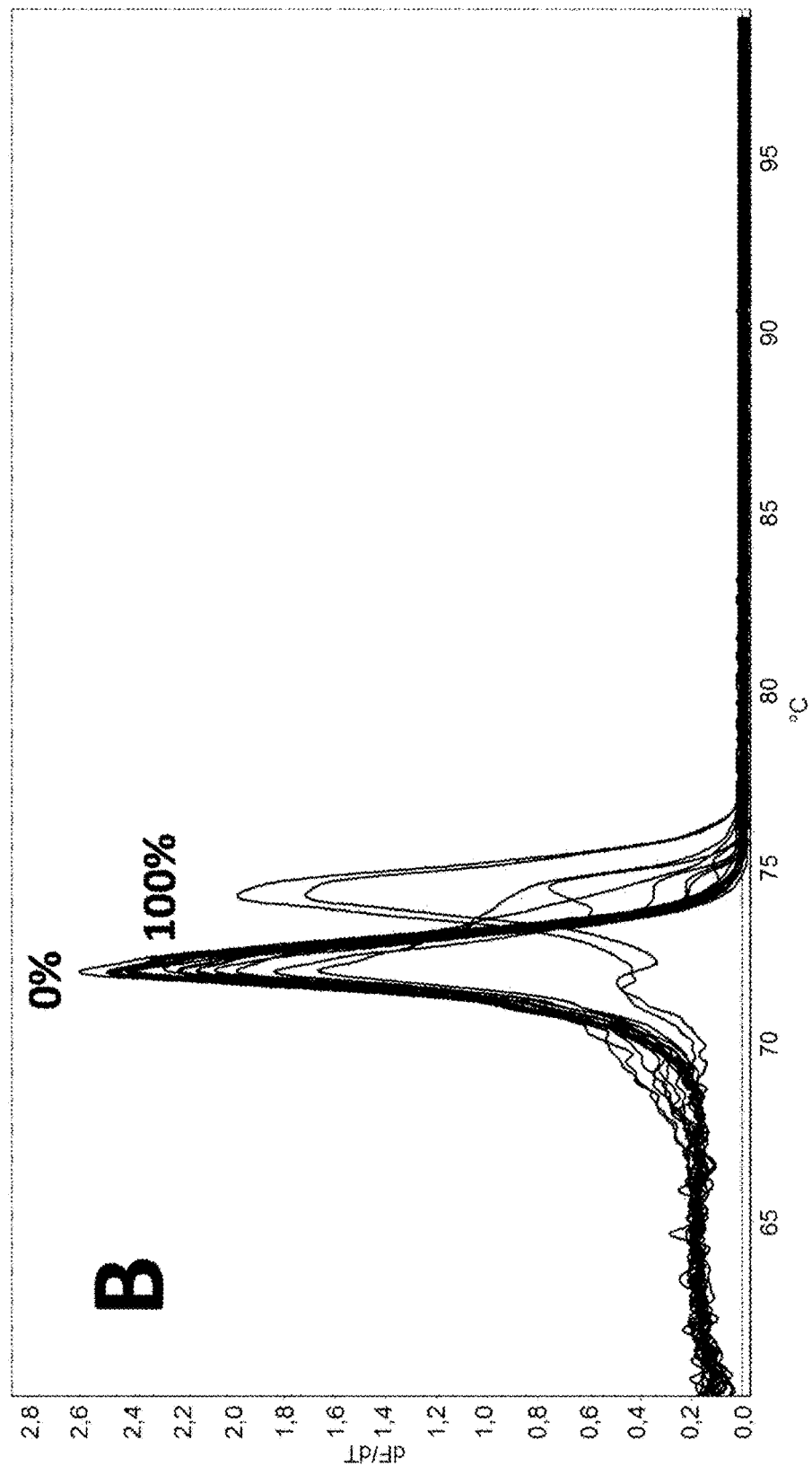
Figure 9C:
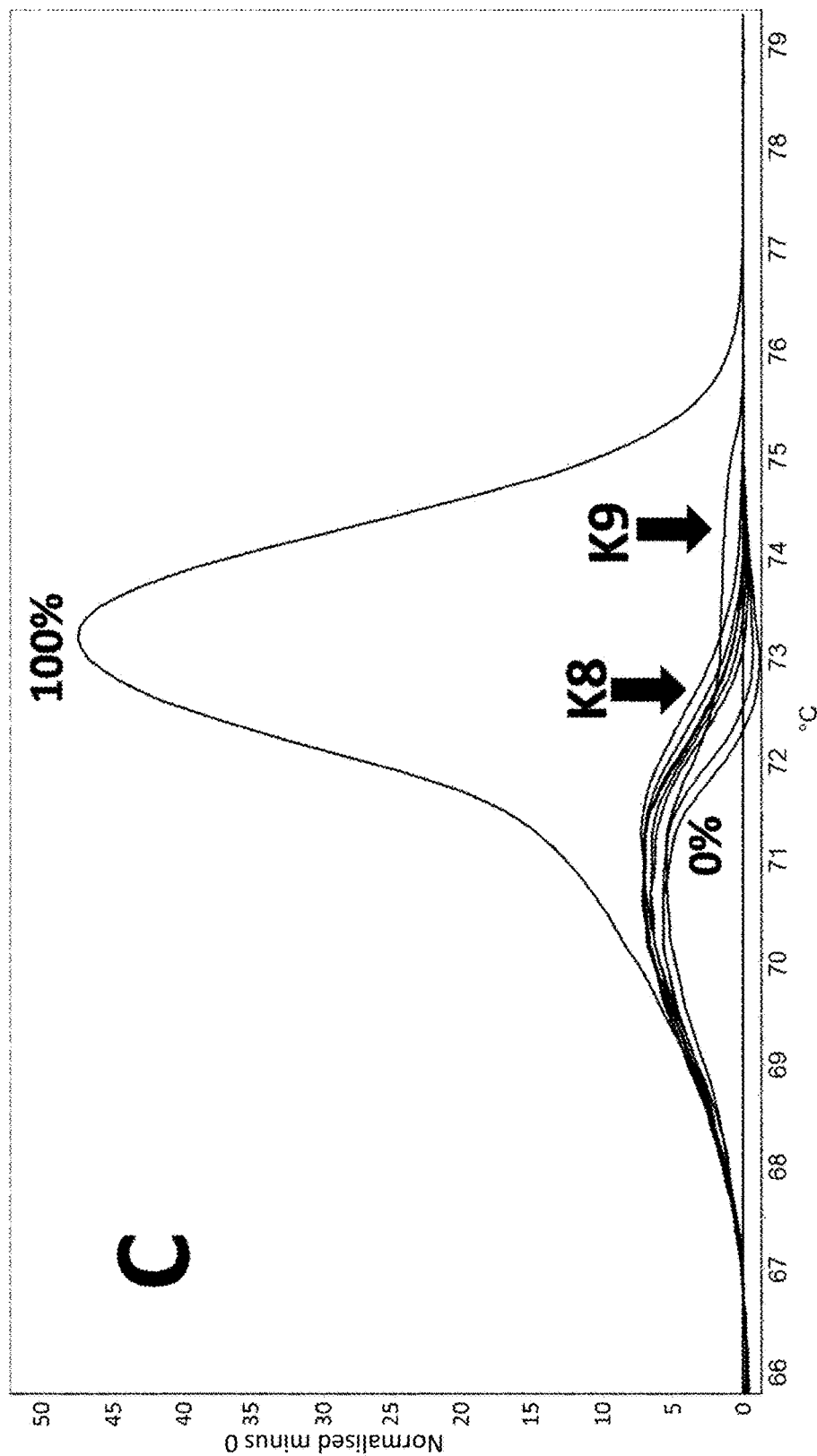
Figure 9D:
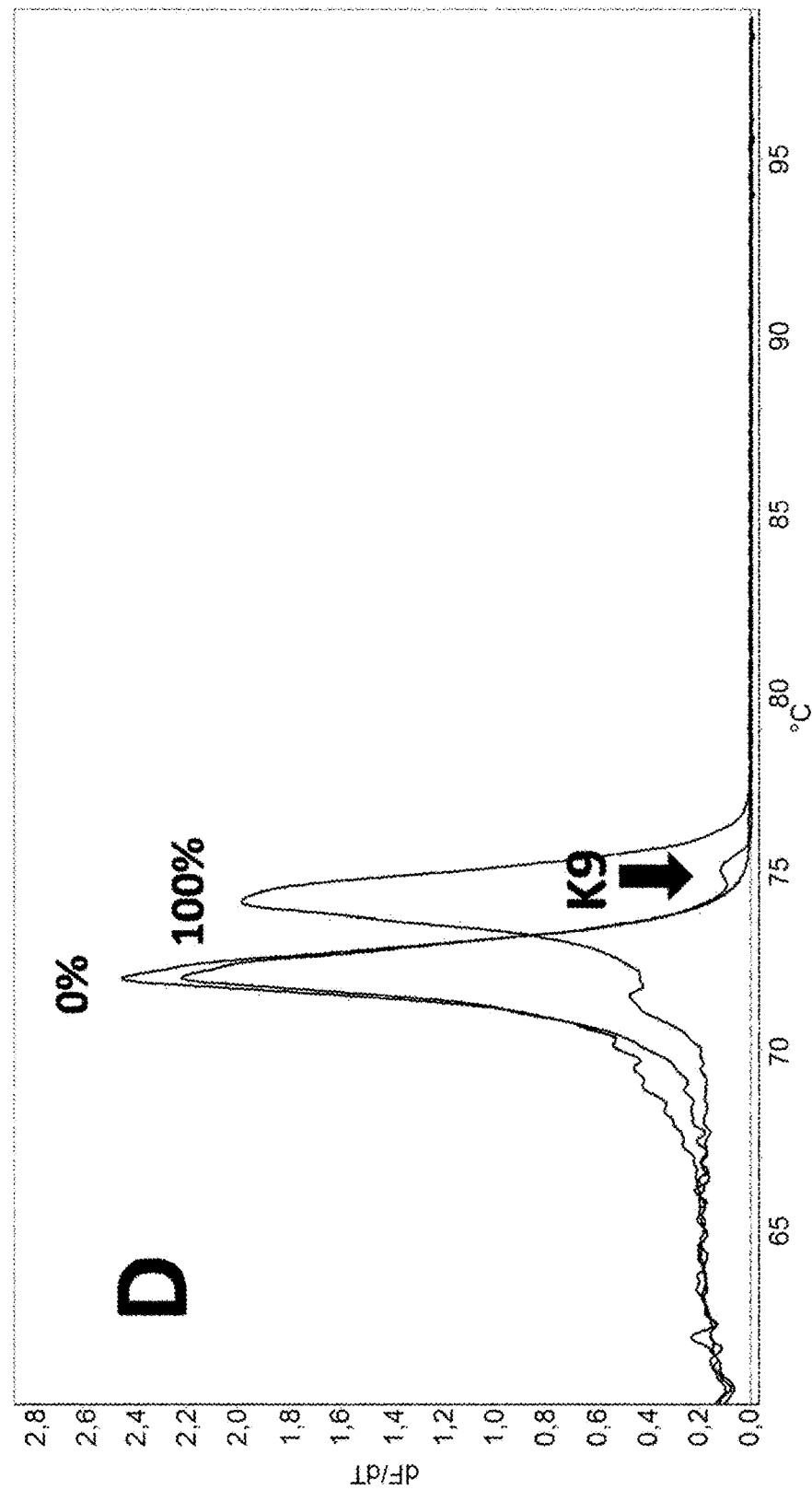
Figure 9E:
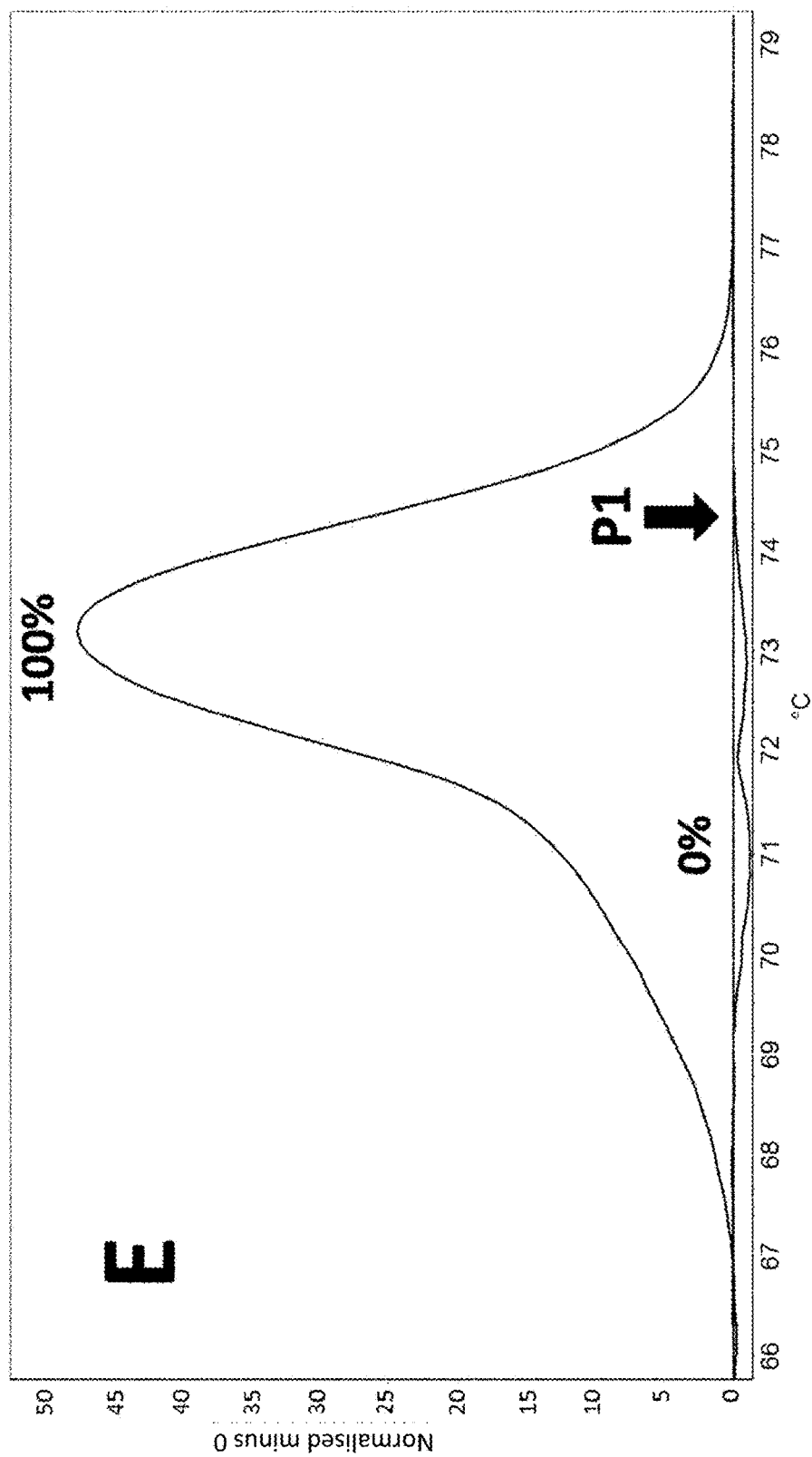

In an MS-HRM analysis carried out concurrently on the identical cfDNA samples, one sample from the healthy subject group showed considerably elevated RASSF1A methylation (FIGS. 9C and 9D, sample ID K9; Table 7) and less elevated RASSF1A methylation in another sample (FIG. 9C, sample ID K8; Table 7). By contrast, a positive RASSF1 result was not detected by means of MS-HRM analysis in one sample (P1) from the female breast cancer patient group (FIG. 9F), yet the BBPA-dPCR analysis showed considerably elevated RASSF1A methylation in this sample (FIG. 8 and Table 7).

TABLE 7

Overview of the RASSF1A methylation levels in serum from healthy subjects (K1-K10) and female breast cancer patients (P1-P10) obtained by means of dPCR alone, MS-HRM and the BBPA-dPCR technique (items in bold: methylation values of >9% as the cut-off value for dPCR alone and of >0.460% in the BBPA-dPCR analysis; a semi-quantitative assessment was carried out in the MS-HRM analysis)

| ID | RASSF1A in dPCR alone in % (comparative data) | RASSF1A by means of MS-HRM analysis (comparative data) | RASSF1A by means of BBPA-dPCR analysis in % |
|---|---|---|---|
| K1 | 2.5 | – | 0.38 |
| K2 | 6 | – | 0.46 |
| K3 | 3.2 | – | 0.058 |
| K4 | 1.4 | – | 0.004 |
| K5 | 3.7 | – | 0.103 |
| K6 | 4.7 | – | 0.017 |
| K7 | 2.1 | – | 0 |
| K8 | 3 | (+) | 0.009 |
| K9 | 2.7 | + | 0.005 |
| K10 | 9 | – | 0.010 |
| P1 | 8 | – | 5.37 |
| P2 | 21 | ++ | 26.9 |
| P3 | 25 | +++ | 29.8 |
| P4 | 9 | ++ | 5.62 |
| P5 | 2.2 | – | 0.006 |
| P6 | 1.4 | ++ | 1.33 |
| P7 | 7 | + | 4.4 |
| P8 | 19 | +++ | 26.9 |
| P9 | 0 | – | 0.04 |
| P10 | 16 | + | 17.4 |

Overall, 2 out of 10 samples from the healthy subject group were erroneously deemed pathological in the MS-HRM analysis, yet this was not the case with BBPA-dPCR (Table 7). In MS-HRM alone, therefore, the diagnostic sensitivity (i.e. diseased subjects correctly diagnosed) was 70% and the diagnostic specificity (i.e. healthy subjects correctly diagnosed) was 80%. In dPCR alone, the diagnostic sensitivity was 40% and the diagnostic specificity was 100%, based on an RASSF1A methylation threshold of <9.1% for healthy subjects. In BBPA-dPCR, the diagnostic sensitivity was 80% and the diagnostic specificity was 100%, based on an RASSF1A methylation threshold of <0.460% for healthy subjects. To detect a tumour disease early (screening or precautionary examinations), a diagnostic sensitivity and specificity of close to 100% is necessary in order to exclude false positives (healthy subjects erroneously diagnosed as diseased) and false negatives (diseased subjects not detected).

As shown in further examples below, in BBPA-dPCR the diagnostic sensitivity can be increased by combining a plurality of candidate genes in the methylation test. In addition, using 5 ml serum instead of 1 ml serum, as was the case here, can also increase the diagnostic sensitivity. Moreover, multiplex use of primers in the BBPA can increase the diagnostic sensitivity since this provides the entire set of isolated DNA for analysing the individual candidate genes in the subsequent dPCR.

As shown in embodiment 12, the diagnostic sensitivity of the method can also be increased by using a plurality of primer pairs for the same gene in the pre-amplification, including the sequences that are detected by the probes in the dPCR.

Embodiment 4: BBPA-dPCR Results on the Basis of PLA2R1, RASSF1A, GSTP1 and AOX1 Methylations in Prostate Cancer Patient Sera In a further test carried out on a group of 19 prostate cancer patients (PCa) and a comparison group of 20 subjects with no tumour disease, it was found that using BBPA-dPCR to determine methylations in PLA2R1 (using the primer pair SEQ ID No 1 and 2 and probe pair SEQ ID No 20 and 21), RASSF1A (primer pair SEQ ID No 3 and 4 and probe pair SEQ ID No 24 and 25), GSTP1 (primer pair SEQ ID No 5 and 6 and probe pair SEQ ID No 56 and 57) and AOX1 (primer pair SEQ ID No 14 and 15 and probe pair SEQ ID No 37 and 38) led to higher values being detectable in 18 out of the 19 patients for at least one of the genes tested compared with the healthy subjects (FIG. 10-12; Table 8).

For these tests, the 2D evaluation shows a distinct population of double-marked droplets (FAM and HEX-positive) that were clearly different from those of unmethylated cfDNA (only HEX-positive) when the BBPA was carried out using an accordingly high number of cycles and the resulting amplified material was analysed in the dPCR in less diluted form (FIG. 13). For the combined BBPA-dPCR-based tests on the PLA2R1, RASSF1A, GSTP1 and AOX1 targets of interest, a diagnostic sensitivity of 95% and a diagnostic specificity of 100% were produced. The ROC analysis showed an AUC value of 0.718 for the PLA2R1 methylation, a value of 0.692 for RASSF1A and a value of 0.976 for GSTP1. When the three biomarkers were combined, the AUC value was 0.982 for the distinction between PCa patients against healthy subjects on the basis of serum tests (FIG. 14).

TABLE 8

Overview of the methylation level determination for the PLA2R1, RASSF1A, GSTP1 and AOX1 genes by means of BBPA-dPCR analyses in % in cfDNA samples of serum from healthy subjects (K1-K20) and PCa patients (P1-19) and the PSA concentrations (ng/ml) (items in bold: values of >2.0% for PLA2R1, >0.1% for RASSF1A, >2.1% for GSTP1 and >1.0% for the AOX1 gene).

| ID | PSA ng/ml | PLA2R1 in % | RASSF1A in, % | GSTP1 in % | AOX1 in % |
|---|---|---|---|---|---|
| K1 |  | 0.080 | 0.076 | 0.007 | 0 |
| K2 |  | 0 | 0 | 0.003 | 0 |
| K3 |  | 0.120 | 0 | 0.0026 | 0.006 |
| K4 |  | 0 | 0 | 0.021 | 0 |
| K5 |  | 0.130 | 0.0027 | 0.007 | 0.018 |
| K6 |  | 0.090 | 0.006 | 0.0029 | 0.039 |
| K7 |  | 0.070 | 0 | 0.018 | 0.138 |
| K8 |  | 0.150 | 0 | 2.05 | 1.1 |
| K9 |  | 0.027 | 0 | 0.0029 | 0 |
| K10 |  | 0 | 0.002 | 0.0026 | 0 |
| K11 |  | 0 | 0 | 0 | 0.017 |
| K12 |  | 1.970 | 0.003 | 0 | 0 |
| K13 |  | 1.250 | 0.003 | 0.009 | 0 |
| K14 |  | 0.008 | 0 | 0.0014 | 0 |
| K15 |  | 0 | 0 | 0.004 | 0.034 |
| K16 |  | 0.011 | 0 | 0 | 0.02 |
| K17 |  | 0 | 0 | 0.0025 | 0 |
| K18 |  | 0.270 | 0 | 0.007 | 0 |
| K19 |  | 0.910 | 0 | 0 | 0 |
| K20 |  | 0.074 | 0 | 0.009 | 0 |
| P1 | 52.49 | 31.400 | 100 | 43.9 | 0 |
| P2 | 37.48 | 0.047 | 57.3 | 5.58 | 0 |
| P3 | 73.66 | 0 | 53.6 | 19.2 | 0 |
| P4 | 86.31 | 2.130 | 47.9 | 19.7 | 55.7 |
| P5 | 33.63 | 0.015 | 40.5 | 0.28 | 0 |
| P6 | 75.53 | 12.800 | 0.8 | 84.5 | 93.3 |
| P7 | 79.68 | 0.360 | 45.5 | 2.82 | 0.018 |
| P8 | 23.84 | 0.089 | 0 | 0.129 | 0.05 |
| P9 | 28.51 | 0.0022 | 46.9 | 0.118 | 0 |

TABLE 8-continued

Overview of the methylation level determination for the PLA2R1, RASSF1A, GSTP1 and AOX1 genes by means of BBPA-dPCR analyses in % in cfDNA samples of serum from healthy subjects (K1-K20) and PCa patients (P1-19) and the PSA concentrations (ng/ml) (items in bold: values of >2.0% for PLA2R1, >0.1% for RASSF1A, >2.1% for GSTP1 and >1.0% for the AOX1 gene).

| ID | PSA ng/ml | PLA2R1 in % | RASSF1A in, % | GSTP1 in % | AOX1 in % |
|---|---|---|---|---|---|
| P10 | 37.98 | 0.0024 | 0 | 5.11 | 0.22 |
| P11 | 26.78 | 5.560 | 0 | 0.166 | 0.14 |
| P12 | 20.74 | 3.690 | 0 | 0.048 | 0 |
| P13 | 24.96 | 2.360 | 0 | 0.131 | 0 |
| P14 | 18.65 | 0.290 | 0 | 6.83 | 66.2 |
| P15 | 77.99 | 0.087 | 0 | 70.2 | 99.8 |
| P16 | 25.63 | 4.450 | 52.1 | 0.011 | 0 |
| P17 | 38.26 | 3.770 | 0 | 60.2 | 90.01 |
| P18 | 59.93 | 20.30 | 0 | 56.5 | 91.95 |
| P19 | 54.74 | 0 | 29.4 | 5.83 | 46.1 |

In addition to the high AUC values, the BBPA-dPCR showed low intra and interassay variation coefficients (VC) of from 3-10%, significantly below the VC achieved by means of MS-HRM analyses, which attained values of 50-100%, in particular in the 1-3% methylation range. Moreover, an analytical sensitivity of <0.003% was achieved by means of the BBPA-dPCR, even though only 1 ml serum was available for these tests. There were no plasma samples available either, only serum samples. Plasma samples are preferably used for testing cfDNA since the coagulation that occurs in serum samples results in high amounts of DNA being released from blood leucocytes and so high background concentrations of unmethylated DNA must be anticipated. The results showed that using BBPA-dPCR made it possible to detect cf-tumour DNA to a very sensitive degree, even against a large background of normal DNA. In addition, the serum samples were not specially treated pre-analysis, including rapid centrifuging of the serum followed by freezing until the cfDNA was isolated. By comparison, the sensitivity of the MS-HRM technique was at most 1% in some tests. One reason for the negative results (in the BBPA-dPCR test) in the sample from patient P8 (Table 8) could be that too little serum was used (1 ml), meaning that there may not have been any methylated DNA copies in the tested sample.

For this reason, serum samples showing PSA values of between 3.5 and 15.0 ng/ml were analysed next, 3-5 ml of each being available. Said PSA concentration range is the critical range for indicating a prostate tissue biopsy. In 17 serum samples, the PLA2R1 and GSTP1 methylations were determined using the BBPA-dPCR. In this case, significant differences were detected in terms of the sample methylations (FIGS. 15 and 16; Table 9).

TABLE 9

Overview of the PLA2R1 and GSTP1 methylation level determination, the overall PSA concentrations (reference range: <4 ng/ml) and the quotient of free PSA to total PSA (reference range: <20%); items in bold: values above the cut-off value of >0.1% for the methylations of the PLA2R1 and GSTP1 genes).

| ID | PSA ng/ml | fPSA/ total PSA in % | PLA2R1 in % | GSTP1 in % | Result |
|---|---|---|---|---|---|
| M1 | 6.88 | 11.48 | 4.45 | 0.02 | Prostate biopsy with 1/16 cylinders positive on the right |
| M2 | 3114.7 | no data | 0.003 | 4.64 | Metastatic prostate cancer |
| M3 | 6.51 | 24.6 | 0.0021 | 2.69 | |
| M4 | 13.87 | 12.11 | 0.65 | 0.04 | Prostate biopsy positive |
| M5 | 6.19 | 7.11 | 4.25 | 0.36 | ? |
| M6 | 3.52 | 52.27 | 0.019 | 0.009 | |
| M7 | 3.48 | 24.1 | 0.017 | 1.14 | |
| M8 | 4.36 | 19.5 | 0.085 | 0.016 | |
| M9 | 4.86 | 10.7 | 1.66 | 0.35 | ? |
| M10 | 6.24 | 8.49 | 0.005 | 0 | |
| M11 | 8.64 | 9.84 | 0.008 | 0.077 | |
| M12 | 7.49 | 4.27 | 1.24 | 0.0039 | Prostate biopsy with 1/12 cylinders positive |
| M13 | 8.9 | 30.79 | 0.011 | 0.023 | |
| M14 | 8.32 | 22.5 | 1.41 | 0.005 | Prostate biopsy carried out, results pending |
| M15 | 4.26 | 16.9 | 0 | 0.0025 | |
| M16 | 14.88 | 7.6 | 0.73 | 0.192 | Moderately enlarged prostate with partially obstructive lateral lobes |
| M17 | 10.17 | 5.9 | 0.94 | 0.048 | Metastatic colon Ca, 14/23 LM, pM1a (hepatic) |

If a cut-off value of <0.1% is taken as the basis for the methylation of the two biomarkers, the indication for a biopsy could be reinforced in 7 samples (M1, M4, M5, M9, M12, M16 and M17, Table 9), the indication being made due to a quotient of free PSA to total PSA of <20%. In 4 samples having a quotient of free PSA to total PSA of <20%, no elevated values could be found for the tested biomarkers, meaning that no tissue biopsy would be indicated in these cases (M8, M10, M11 and M15, Table 9). By contrast, in 3 samples (M3, M7 and M14), increased values for the PLA2R1 and GSTP1 methylations were shown, despite the free PSA proportion being >20%. In patient samples M1, M2, M4 and M12, prostate cancer had already been detected. A prostate biopsy had already taken place in another sample (M14) (Table 9).

Embodiment 5: Combination of BBPA-dPCR for RASSF1A Methylation with MS-HRM for PLA2R1 Methylations in Prostate Cancer Patient Serum Using BBPA-dPCR, the RASSF1A methylation was analysed in a further 27 patient samples. There were no longer any sufficiently isolated DNA samples available for the PLA2R1 methylation determination by means of BBPA-dPCR, and so the RASSF1A results were combined with the PLA2R1 results that had been tested in the MS-HRM analysis. The results showed significantly higher values for the RASSF1A methylation in the samples I1, I2, I18, I19, I21 and I24. It is noteworthy that PCa had already been detected in samples I19, I21 and I24 (Table 10). In sample I12, no elevated RASSF1A methylation was detected although the patient was suffering from PCa with PSA-positive metastasis. It was found, however, that there was a considerably methylated sub-fraction of the PLA2R1 gene in this sample (Table 10). A positive PLA2R1 methylation result without the RASSF1A methylation being elevated at the same time was also found in another PCa patient (sample I17, Table 10). The patient who gave sample I2 had also undergone a prostate biopsy. The extent of the prostate cancer in the patients of samples I1, I11 and I18 is not yet known. This question can only be answered in the future.

TABLE 10

Overview of the methylation level determination in RASSF1A by means of BBPA-dPCR and PLA2R1 by means of MS-HRM, and the overall PSA concentrations (reference range: <4 ng/ml) and the quotient of free to total PSA (reference range: <20%); in bold: values above the cut-off value of >0.1% for RASSF1A methylation, a semi-quantitative evaluation was carried out in the MS-HRM analysis of the PLA2R1 gene, PCa, prostate cancer).

| ID | PSA ng/ml | fPSA/ total PSA in % | RASSF1A in % by means of BBPA-dPCR | PLA2R1 by means of MS-HRM | Clinical finding |
|---|---|---|---|---|---|
| I1 | 3.25 | 18.2 | 6.7 | + | ? |
| I2 | 9.33 | 7.8 | 36.0 | ++ | Prostate biopsy carried out, results pending |
| I3 | 4.14 | 12.3 | 0.147 | − | |
| I4 | 3.88 | 26 8 | 0.166 | − | P biopsy in 2011 and 2014 both negative |
| I5 | 3.41 | 32.8 | 0 | − | Prostatitis |
| I6 | 3.47 | 17.0 | 0.017 | − | |
| I7 | 7.77 | 21.5 | 0.046 | − | |
| I8 | 4.82 | 30.3 | 0.5 | − | |
| I9 | 3.41 | 23.2 | 0.202 | − | |
| I10 | 4.78 | 16.9 | 0.6 | − | |
| I11 | 4.79 | 23.8 | 0.011 | ++ | ? |
| I12 | 3.30 | 27.6 | 0.023 | +++ | Prostate cancer with PSA-positive metastasis |
| I13 | 5.03 | 27.6 | 0.24 | − | |
| I14 | 6.67 | 8.9 | 0.28 | − | |
| I15 | 5.03 | 18.1 | 0.49 | − | |
| I16 | 8.28 | 10.6 | 0.71 | − | |
| I17 | 5.71 | 18.6 | 0.36 | ++ | Prostate CA, radiotherapy July 2013 |
| I18 | 5.73 | 14.1 | 19.9 | + | ? |
| I19 | 7.44 | 2.2 | 21.1 | ++ | Prostate CA in prostate biopsy (3 of 14 cylinders positive) |
| I20 | 3.17 | 44.5 | 0.025 | − | |
| I21 | 3.45 | 8.4 | 36.3 | − | PSA, fPSA and BBPA-dPCR from blood taken September 2013; July 2015 histologically proven prostate CA with bone metastasis |
| I22 | 3.85 | 19 0 | 0.3 | − | quarterly PSA checks |
| I23 | 5.63 | 8.9 | 1.1 | − | |
| I24 | 2.54 | 1.2 | 34.5 | + | Prostate CA in prostate biopsy (4 of 12 cylinders positive) |

Embodiment 6: BBPA-dPCR for RASSF1A and GSTP1 Methylation in Renal Cell Cancer Patient Serum In another test, ten serum samples from patients suffering from renal cell cancer were analysed against eight healthy samples.

Likewise, the results showed elevated PLAR21 methylation (when using primer pair SEQ ID No 1 and 2 and probe pair SEQ ID No 20 and 21) in the samples N1-N4, N6-N8 and N10, whereas the methylation in the cfDNA samples from healthy subjects was less than 0.005% (FIG. 17). Together with the determination of the RASSF1A methylation (using primer pair SEQ ID No 3 and 4 and probe pair SEQ ID No 24 and 25) and GSTP1 methylation (primer pair SEQ ID No 5 and 6 and probe pair SEQ ID No 56 and 57), all the serum samples were able to be identified as pathological to a greater extent (Table 11).

TABLE 11

Overview of the determination of the PLA2R1, RASSF1A and GSTP1 methylation levels in serum samples from patients with renal cell cancer (NZK1-10; values in bold are elevated methylation values [>0.1%])

| ID | PLA2R1 in % | RASSF1A in % | GSTP1 in % |
|---|---|---|---|
| NZK1 | 0.60 | 0 | 9.5 |
| NZK2 | 0.19 | 10.9 | 0 |
| NZK3 | 1.56 | 3.52 | 30.0 |
| NZK4 | 0.21 | 0 | 12.6 |
| NZK5 | 0 | 2.6 | 0 |
| NZK6 | 1.05 | 13.8 | 5.4 |
| NZK7 | 0.097 | 14.5 | 0 |
| NZK8 | 0.082 | 10.7 | 0 |
| NZK9 | 0 | 16.6 | 0 |
| NZK10 | 6.6 | 0 | 0 |

Embodiment 7: BBPA-dPCR for PLA2R1, RASSF1A and GSTP1 Methylation for Distinguishing Between Benign Prostatic Hyperplasia and Prostate Cancer in Patient Serum Since prostate cancers, breast cancers and renal cell cancers were able to be unambiguously associated with patients using the new BBPA-dPCR methods, the question arises as to how far it is possible to reliably distinguish between a benign prostatic hyperplasia (BPH) and a PCa using BBPA-dPCR when PSA values are elevated, in order to prevent unnecessary prostate tissue biopsies. For this purpose, the malignant prostate cell lines LNCaP, PC-3 and DU-145 cells, and the benign prostatic hyperplasia cell line BPH-1 were tested.

It was found that, in the benign prostate cell line BPH-1 compared with normal prostate epithelial cells (PrEC), heterogeneously methylated DNA fragments were already present, particularly in the targets of interest PLA2R1 and RASSF1A (FIGS. 18 and 19). When using probes having at least 3 CpG sites in their sequences, these heterogeneously methylated epialleles could be distinguished from the homogeneously methylated epialleles and quantified (FIG. 20). Homogeneously methylated epialleles, i.e. having three out of three CpG sites methylated, appear to be specific for cf-tumour DNA when distinguishing between BPH and PCa, and can form a basis for a reliable differential diagnosis of benign and malignant prostate diseases.

In the case of SERPINE1 methylation (using primer pair SEQ ID No 16 and 17 and probe pair SEQ ID No 43 and 44), there were no homogeneously or heterogeneously methylated epialleles found in the DNA samples from PrEC and BPH-1, and so this gene is also a candidate gene for the differential diagnosis of BPH and prostate cancer (FIGS. 21 and 22).

For the GSTP1 gene, it was also found that there were no homogeneously or heterogeneously methylated epialleles (two out of three CpG sites methylated) detected in PrEC or BPH-1 cells (FIGS. 23 and 24), unlike the malignant prostate cancer cell lines LNCaP, PC-3 and DU-145. Interestingly, the malignant cell line PC-3 mainly showed heterogeneously methylated epialleles (two out of three CpG sites methylated) that are clearly different from those in PrEC and BPH-1 (FIGS. 25 and 26). In these, there were only low concentrations of heterogeneously methylated epialleles (one out of three CpG sites methylated), which could be easily separated from those of the malignant cell lines by increasing the threshold set (FIGS. 25 and 26).

Embodiment 8: Distinguishing Between Healthy Subjects, Benign and Malignant Prostate Diseases by Including and Quantifying PLA2R1 Epialleles There was also an improved distinction between healthy subjects and prostate cancer patients in the determination and quantification of PLA2R1 epialleles. Where three epiallele fractions were included in the determination (see FIG. 27), only 4 out of the 40 PCa patients (P1, P5, P21 and P30; fractional methylation abundance cut-off value of <3.25%) could be clearly distinguished from the healthy subjects (Table 12). Where only the homogeneously methylated PLA2R1 epialleles, i.e. three out of three CpG sites methylated, were determined and quantified (see FIG. 28), 5 out of the 40 PCa patients could be identified (P1, P12, P17, P21 and P30; fractional methylation abundance cut-off value of <0.011%; Table 12). Interestingly, when only homogeneously methylated PLA2R1 epialleles were included and quantified, P12 and P17 were identified as PCa patients, yet P5 was not, even though P5 had been identified as such when three PLA2R1 epialleles were included previously.

By contrast, P1, P21 and P30, as well as P5, P12 and P17, and P15, P33, P34 and P38 were identified as PCa patients when two of the PLA2R1 epialleles (homogeneously and heterogeneously methylated epialleles having two out of three CpG sites methylated) were quantified, i.e. 10 out of the 40 PCa patients were identified to a diagnostic specificity of 100% (fractional methylation abundance cut-off value of <0.123%; Table 12). Since there was only 200 μl serum available for these tests, the diagnostic sensitivity of 25% achieved here when two PLA2R1 epialleles were included can be increased further by using a greater volume of serum and/or when combined with other gene sequences.

TABLE 12

Overview of the determination of the PLA2R1 methylation levels in serum samples from healthy subjects (K1-20) and prostate cancer patients (P1-40) when one, two or three PLA2R1 epialleles are included (FIG. 27-29). The number of copies per 20 μl, ratio (ratio of methylated to unmethylated), FM (fractional methylation, i.e. the proportion of methylated fragments against unmethylated fragments) and TH (thresholds) are listed. Values in bold are elevated methylation values compared with the cut-off values. M: methylated, U: unmethylated DNA fragments and NTC: negative control with no DNA template

| | | 3 epialleles included | | | | 1 epiallele included | | | | 2 epialleles included | | | |
| --- | --- | --- | --- | --- | --- | --- | --- | --- | --- | --- | --- | --- | --- |
| ID | Target | Copies/ 20 μl | Ratio | FM | TH | Copies/ 20 μl | Ratio | FM | TH | Copies/ 20 μl | Ratio | FM | TH |
| K1 | M | 904 | 0.0203 | 1.99 | 6669 | 0 | 0 | 0 | 12799 | 40 | 0.00091 | 0.091 | 10415 |
| | U | 44600 | | | 3200 | 44600 | | | 3200 | 44600 | | | 3212 |
| K2 | M | 816 | 0.0108 | 1.07 | 6669 | 0 | 0 | 0 | 12799 | 0 | 0 | 0 | 10415 |
| | U | 75600 | | | 3200 | 75600 | | | 3200 | 75400 | | | 3212 |
| K3 | M | 966 | 0.0105 | 1.04 | 6669 | 0 | 0 | 0 | 12799 | 0 | 0 | 0 | 10415 |
| | U | 92000 | | | 3200 | 92000 | | | 3200 | 91800 | | | 3212 |
| K4 | M | 2900 | 0.0315 | 3.05 | 6669 | 0 | 0 | 0 | 12799 | 24 | 0.00026 | 0.026 | 10415 |
| | U | 91800 | | | 3200 | 91800 | | | 3200 | 91600 | | | 3212 |
| K5 | M | 1300 | 0.013 | 1.29 | 6669 | 0 | 0 | 0 | 12799 | 0 | 0 | 0 | 10415 |
| | U | 99600 | | | 3200 | 99600 | | | 3200 | 99400 | | | 3212 |
| K6 | M | 200 | 0.0026 | 0.26 | 6669 | 0 | 0 | 0 | 12799 | 0 | 0 | 0 | 10415 |
| | U | 77600 | | | 3200 | 77600 | | | 3200 | 77600 | | | 3212 |
| K7 | M | 266 | 0.0031 | 0.31 | 6669 | 0 | 0 | 0 | 12799 | 0 | 0 | 0 | 10415 |
| | U | 84800 | | | 3200 | 84800 | | | 3200 | 84600 | | | 3212 |
| K8 | M | 712 | 0.008 | 0.79 | 6669 | 0 | 0 | 0 | 12799 | 0 | 0 | 0 | 10415 |
| | U | 89600 | | | 3200 | 89600 | | | 3200 | 89400 | | | 3212 |
| K9 | M | 2060 | 0.0299 | 2.91 | 6669 | 2.2 | 3.00E−05 | 0.003 | 12799 | 18 | 0.00026 | 0.026 | 10415 |
| | U | 68600 | | | 3200 | 68600 | | | 3200 | 68400 | | | 3212 |
| K10 | M | 0 | 0 | 0 | 6669 | 0 | 0 | 0 | 12799 | 0 | 0 | 0 | 10415 |
| | U | 74000 | | | 3200 | 74000 | | | 3200 | 73800 | | | 3212 |
| K11 | M | 3.4 | 5.00E−05 | 0.005 | 6669 | 0 | 0 | 0 | 12799 | 0 | 0 | 0 | 10415 |
| | U | 72000 | | | 3200 | 72000 | | | 3200 | 71800 | | | 3212 |
| K12 | M | 1110 | 0.0124 | 1.22 | 6669 | 0 | 0 | 0 | 12799 | 4.6 | 5.00E−05 | 0.005 | 10415 |
| | U | 90000 | | | 3200 | 90000 | | | 3200 | 89600 | | | 3212 |
| K13 | M | 20 | 0.00025 | 0.025 | 6669 | 0 | 0 | 0 | 12799 | 0 | 0 | 0 | 10415 |
| | U | 77800 | | | 3200 | 77800 | | | 3200 | 77600 | | | 3212 |
| K14 | M | 814 | 0.012 | 1.19 | 6669 | 0 | 0 | 0 | 12799 | 1.8 | 2.6E−05 | 0.0026 | 10415 |
| | U | 68000 | | | 3200 | 68000 | | | 3200 | 67800 | | | 3212 |
| K15 | M | 786 | 0.0112 | 1.11 | 6669 | 0 | 0 | 0 | 12799 | 0 | 0 | 0 | 10415 |
| | U | 70200 | | | 3200 | 70200 | | | 3200 | 70000 | | | 3212 |
| K16 | M | 10 | 0.00014 | 0.014 | 6669 | 0 | 0 | 0 | 12799 | 0 | 0 | 0 | 10415 |
| | U | 77000 | | | 3200 | 77000 | | | 3200 | 76600 | | | 3212 |
| K17 | M | 218 | 0.0023 | 0.23 | 6669 | 0 | 0 | 0 | 12799 | 0 | 0 | 0 | 10415 |
| | U | 94600 | | | 3200 | 94600 | | | 3200 | 94200 | | | 3212 |
| K18 | M | 162 | 0.0022 | 0.21 | 6669 | 0 | 0 | 0 | 12799 | 0 | 0 | 0 | 10415 |
| | U | 75400 | | | 3200 | 75400 | | | 3200 | 75400 | | | 3212 |
| K19 | M | 48 | 0.0006 | 0.06 | 6669 | 0 | 0 | 0 | 12799 | 0 | 0 | 0 | 10415 |
| | U | 79600 | | | 3200 | 79600 | | | 3200 | 79400 | | | 3212 |
| K20 | M | 2160 | 0.0336 | 3.25 | 6669 | 7.2 | 0.00011 | 0.011 | 12799 | 78 | 0.00123 | 0.123 | 10415 |
| | U | 64000 | | | 3200 | 64000 | | | 3200 | 64000 | | | 3212 |
| P1 | M | 940 | 0.09 | 8.2 | 6669 | 288 | 0.0275 | 2.67 | 12799 | 590 | 0.056 | 5.3 | 10415 |
| | U | 10480 | | | 3200 | 10480 | | | 3200 | 10460 | | | 3212 |
| P2 | M | 0 | 0 | 0 | 6669 | 0 | 0 | 0 | 12799 | 0 | 0 | 0 | 10415 |
| | U | 51800 | | | 3200 | 51800 | | | 3200 | 51800 | | | 3212 |

TABLE 12-continued

Overview of the determination of the PLA2R1 methylation levels in serum samples from healthy subjects (K1-20) and prostate cancer patients (P1-40) when one, two or three PLA2R1 epialleles are included (FIG. 27-29). The number of copies per 20 μl, ratio (ratio of methylated to unmethylated), FM (fractional methylation, i.e. the proportion of methylated fragments against unmethylated fragments) and TH (thresholds) are listed. Values in bold are elevated methylation values compared with the cut-off values. M: methylated, U: unmethylated DNA fragments and NTC: negative control with no DNA template

| | | 3 epialleles included | | | | 1 epiallele included | | | | 2 epialleles included | | | |
| --- | --- | --- | --- | --- | --- | --- | --- | --- | --- | --- | --- | --- | --- |
| ID | Target | Copies/ 20 μl | Ratio | FM | TH | Copies/ 20 μl | Ratio | FM | TH | Copies/ 20 μl | Ratio | FM | TH |
| P3 | M | 0 | 0 | 0 | 6669 | 0 | 0 | 0 | 12799 | 0 | 0 | 0 | 10415 |
| | U | 27940 | | | 3200 | 27940 | | | 3200 | 27940 | | | 3212 |
| P4 | M | 564 | 0.0134 | 1.32 | 6669 | 0 | 0 | 0 | 12799 | 52 | 0.0012 | 0.12 | 10415 |
| | U | 42200 | | | 3200 | 42200 | | | 3200 | 42200 | | | 3212 |
| P5 | M | 1520 | 0.061 | 5.76 | 6669 | 2.4 | 9.00E−05 | 0.009 | 12799 | 394 | 0.0158 | 1.55 | 10415 |
| | U | 24980 | | | 3200 | 24980 | | | 3200 | 24960 | | | 3212 |
| P6 | M | 0 | 0 | 0 | 6669 | 0 | 0 | 0 | 12799 | 0 | 0 | 0 | 10415 |
| | U | 7000 | | | 3200 | 7000 | | | 3200 | 7000 | | | 3212 |
| P7 | M | 0 | 0 | 0 | 6669 | 0 | 0 | 0 | 12799 | 0 | 0 | 0 | 10415 |
| | U | 21000 | | | 3200 | 21000 | | | 3200 | 20980 | | | 3212 |
| P8 | M | 2360 | 0.0301 | 2.92 | 6669 | 0 | 0 | 0 | 12799 | 30 | 0.00038 | 0.038 | 10415 |
| | U | 78600 | | | 3200 | 78600 | | | 3200 | 78400 | | | 3212 |
| P9 | M | 1360 | 0.0159 | 1.57 | 6669 | 7.8 | 9.00E−05 | 0.009 | 12799 | 50 | 0.00058 | 0.058 | 10415 |
| | U | 85400 | | | 3200 | 85400 | | | 3200 | 84800 | | | 3212 |
| P10 | M | 0 | 0 | 0 | 6669 | 0 | 0 | 0 | 12799 | 0 | 0 | 0 | 10415 |
| | U | 5200 | | | 3200 | 5200 | | | 3200 | 5200 | | | 3212 |
| P11 | M | 790 | 0.0133 | 1.31 | 6669 | 3.8 | 6.00E−05 | 0.006 | 12799 | 30 | 0.00051 | 0.051 | 10415 |
| | U | 59400 | | | 3200 | 59400 | | | 3200 | 59200 | | | 3212 |
| P12 | M | 1920 | 0.0267 | 2.6 | 6669 | 20 | 0.00029 | 0.029 | 12799 | 166 | 0.0023 | 0.23 | 10415 |
| | U | 71800 | | | 3200 | 71800 | | | 3200 | 71600 | | | 3212 |
| P13 | M | 710 | 0.0126 | 1.24 | 6669 | 0 | 0 | 0 | 12799 | 64 | 0.00112 | 0.112 | 10415 |
| | U | 56400 | | | 3200 | 56400 | | | 3200 | 56400 | | | 3212 |
| P14 | M | 4.2 | 0.00018 | 0.018 | 6669 | 0 | 0 | 0 | 12799 | 4.2 | 0.00018 | 0.018 | 10415 |
| | U | 23480 | | | 3200 | 23480 | | | 3200 | 23460 | | | 3212 |
| P15 | M | 634 | 0.0334 | 3.24 | 6669 | 0 | 0 | 0 | 12799 | 250 | 0.0132 | 1.3 | 10415 |
| | U | 18960 | | | 3200 | 18960 | | | 3200 | 18920 | | | 3212 |
| P16 | M | 4.8 | 8.00E−05 | 0.008 | 6669 | 0 | 0 | 0 | 12799 | 0 | 0 | 0 | 10415 |
| | U | 60600 | | | 3200 | 60600 | | | 3200 | 60400 | | | 3212 |
| P17 | M | 762 | 0.0283 | 2.75 | 6669 | 176 | 0.0066 | 0.65 | 12799 | 432 | 0.0161 | 1.58 | 10415 |
| | U | 26900 | | | 3200 | 26900 | | | 3200 | 26860 | | | 3212 |
| P18 | M | 0 | 0 | 0 | 6669 | 0 | 0 | 0 | 12799 | 0 | 0 | 0 | 10415 |
| | U | 22080 | | | 3200 | 22080 | | | 3200 | 22060 | | | 3212 |
| P19 | M | 0 | 0 | 0 | 6669 | 0 | 0 | 0 | 12799 | 0 | 0 | 0 | 10415 |
| | U | 43580 | | | 3200 | 43580 | | | 3200 | 43460 | | | 3212 |
| P20 | M | 34 | 0.00031 | 0.031 | 6669 | 0 | 0 | 0 | 12799 | 0 | 0 | 0 | 10415 |
| | U | 107200 | | | 3200 | 107200 | | | 3200 | 106400 | | | 3212 |
| P21 | M | 1580 | 0.069 | 6.42 | 6669 | 202 | 0.0088 | 0.87 | 12799 | 700 | 0.0305 | 2.96 | 10415 |
| | U | 23000 | | | 3200 | 23000 | | | 3200 | 23000 | | | 3212 |
| P22 | M | 0 | 0 | 0 | 6669 | 0 | 0 | 0 | 12799 | 0 | 0 | 0 | 10415 |
| | U | 9060 | | | 3200 | 9060 | | | 3200 | 9060 | | | 3212 |
| P23 | M | 0 | 0 | 0 | 6669 | 0 | 0 | 0 | 12799 | 0 | 0 | 0 | 10415 |
| | U | 5420 | | | 3200 | 5420 | | | 3200 | 5420 | | | 3212 |
| P24 | M | 0 | 0 | 0 | 6669 | 0 | 0 | 0 | 12799 | 0 | 0 | 0 | 10415 |
| | U | 992 | | | 3200 | 992 | | | 3200 | 992 | | | 3212 |
| P25 | M | 0 | 0 | 0 | 6669 | 0 | 0 | 0 | 12799 | 0 | 0 | 0 | 10415 |
| | U | 342 | | | 3200 | 342 | | | 3200 | 342 | | | 3212 |
| P26 | M | 1.8 | 0.00012 | 0.012 | 6669 | 0 | 0 | 0 | 12799 | 1.8 | 0.00012 | 0.012 | 10415 |
| | U | 15740 | | | 3200 | 15740 | | | 3200 | 15720 | | | 3212 |
| P27 | M | 0 | 0 | 0 | 6669 | 0 | 0 | 0 | 12799 | 0 | 0 | 0 | 10415 |
| | U | 500 | | | 3200 | 500 | | | 3200 | 500 | | | 3212 |
| P28 | M | 890 | 0.0108 | 1.06 | 6669 | 0 | 0 | 0 | 12799 | 4.2 | 5.00E−05 | 0.005 | 10415 |
| | U | 82800 | | | 3200 | 82800 | | | 3200 | 82400 | | | 3212 |
| P29 | M | 680 | 0.0114 | 1.13 | 6669 | 0 | 0 | 0 | 12799 | 26 | 0.00044 | 0.044 | 10415 |
| | U | 59400 | | | 3200 | 59400 | | | 3200 | 59400 | | | 3212 |
| P30 | M | 2360 | 0.0585 | 5.53 | 6669 | 64 | 0.0016 | 0.16 | 12799 | 454 | 0.0112 | 1.11 | 10415 |
| | U | 40440 | | | 3200 | 40440 | | | 3200 | 40400 | | | 3212 |
| P31 | M | 244 | 0.0032 | 0.32 | 6669 | 0 | 0 | 0 | 12799 | 0 | 0 | 0 | 10415 |
| | U | 77200 | | | 3200 | 77200 | | | 3200 | 77000 | | | 3212 |
| P32 | M | 3.4 | 0.00019 | 0.019 | 6669 | 0 | 0 | 0 | 12799 | 3.4 | 0.00019 | 0.019 | 10415 |
| | U | 18480 | | | 3200 | 18480 | | | 3200 | 18460 | | | 3212 |
| P33 | M | 454 | 0.0244 | 2.38 | 6669 | 0 | 0 | 0 | 12799 | 152 | 0.0081 | 0.81 | 10415 |
| | U | 18660 | | | 3200 | 18660 | | | 3200 | 18640 | | | 3212 |
| P34 | M | 654 | 0.0178 | 1.74 | 6669 | 0 | 0 | 0 | 12799 | 46 | 0.0013 | 0.13 | 10415 |
| | U | 36840 | | | 3200 | 36840 | | | 3200 | 36820 | | | 3212 |
| P35 | M | 0 | 0 | 0 | 6669 | 0 | 0 | 0 | 12799 | 0 | 0 | 0 | 10415 |
| | U | 46000 | | | 3200 | 46000 | | | 3200 | 46000 | | | 3212 |

TABLE 12-continued

Overview of the determination of the PLA2R1 methylation levels in serum samples from healthy subjects (K1-20) and prostate cancer patients (P1-40) when one, two or three PLA2R1 epialleles are included (FIG. 27-29). The number of copies per 20 µl, ratio (ratio of methylated to unmethylated), FM (fractional methylation, i.e. the proportion of methylated fragments against unmethylated fragments) and TH (thresholds) are listed. Values in bold are elevated methylation values compared with the cut-off values. M: methylated, U: unmethylated DNA fragments and NTC: negative control with no DNA template

|  |  | 3 epialleles included | | | | 1 epiallele included | | | | 2 epialleles included | | | |
| --- | --- | --- | --- | --- | --- | --- | --- | --- | --- | --- | --- | --- | --- |
| ID | Target | Copies/ 20 µl | Ratio | FM | TH | Copies/ 20 µl | Ratio | FM | TH | Copies/ 20 µl | Ratio | FM | TH |
| P36 | M | 0 | 0 | 0 | 6669 | 0 | 0 | 0 | 12799 | 0 | 0 | 0 | 10415 |
|  | U | 28920 |  |  | 3200 | 28920 |  |  | 3200 | 28900 |  |  | 3212 |
| P37 | M | 0 | 0 | 0 | 6669 | 0 | 0 | 0 | 12799 | 0 | 0 | 0 | 10415 |
|  | U | 82 |  |  | 3200 | 82 |  |  | 3200 | 72 |  |  | 3212 |
| P38 | M | 676 | 0.0279 | 2.71 | 6669 | 0 | 0 | 0 | 12799 | 148 | 0.0061 | 0.61 | 10415 |
|  | U | 24240 |  |  | 3200 | 24240 |  |  | 3200 | 24200 |  |  | 3212 |
| P39 | M | 0 | 0 | 0 | 6669 | 0 | 0 | 0 | 12799 | 0 | 0 | 0 | 10415 |
|  | U | 73000 |  |  | 3200 | 73000 |  |  | 3200 | 72800 |  |  | 3212 |
| P40 | M | 62 | 0.0026 | 0.26 | 6669 | 0 | 0 | 0 | 12799 | 14 | 0.00062 | 0.062 | 10415 |
|  | U | 23440 |  |  | 3200 | 23440 |  |  | 3200 | 23420 |  |  | 3212 |
| NTC | M | 0 | 0 | 0 | 6669 | 0 | 0 | 0 | 12799 | 0 | 0 | 0 | 10415 |
|  | U |  |  |  | 3200 | 0 |  |  | 3200 | 0 |  |  | 3212 |
| NTC | M | 0 | 0 | 0 | 6669 | 0 | 0 | 0 | 12799 | 0 | 0 | 0 | 10415 |
|  | U |  |  |  | 3200 | 0 |  |  | 3200 | 0 |  |  | 3212 |
| NTC | M | 0 | 0 | 0 | 6669 | 0 | 0 | 0 | 12799 | 0 | 0 | 0 | 10415 |
|  | U |  |  |  | 3200 | 0 |  |  | 3200 | 0 |  |  | 3212 |

Since there is enough DNA isolated from cell lines, which is often not the case in liquid biopsies such as serum, plasma or seminal fluid, the question arose as to how the fractional PLA2R1 methylation abundance in normal PrEC and BPH-1 cells in which homogeneously and heterogeneously methylated epiallele copies occurred separately would behave following BBPA-dPCR compared with dPCR alone. Compared with dPCR alone (left side of FIG. 30), after 50 pre-amplification cycles at 63° C., the resultant PLA2R1 methylation level moved towards 0% in normal PrEC and non-malignant BPH-1 cells in this case too, and the methylation of malignant prostate cancer cell lines could be clearly distinguished from the BPH-1 cell line (right side of FIG. 30). This is again because of the phenomenon whereby the unmethylated sequences in the PrEC and BPH-1 cells were copied to a greater extent as the number of BBPA cycles increased, despite the samples containing a certain number of methylated PLA2R1 fragments, albeit a small quantity, and without the methylated fragments being copied to the same extent (FIG. 31). Conversely, the LNCaP and DU-145 cell DNA samples showed a clearly preferable amplification of the methylated sequences over the unmethylated sequences. In the PC-3 cells, the methylated and unmethylated PLA2R1 sequences were copied in a more or less comparably efficient manner (FIG. 31).

The 2D view of the FAM-positive and HEX-positive signals after 50 BBPA cycles demonstrated that the BPH-1 cell population could be clearly set apart from the PC-3, LNCaP and DU-145 cells (FIG. 32). Without showing the NTC, i.e. the double-negative droplets, it was also found that after 50 cycles there were no longer any double-negative droplets in all cell samples. This means that the dPCR was heavily overloaded with pre-amplified DNA copies and the Poisson distribution and statistics no longer applied, and the malignant prostate cell lines could be separated so effectively from BPH-1 despite this or precisely because of this (FIG. 33). In dPCR alone, fractional methylation levels of 2.1% (1.1-3.1%) and 8.3% (7.0-9.5%) were still produced for PrEC and BPH-1, respectively. In BBPA-dPCR, the methylation level in both cell lines was 0%, whereas the methylation level for the malignant prostate cell lines LNCaP, PC-3 and DU-145 correlated well with the data from dPCR alone (Table 20).

Embodiment 9: Determining the Bias in Favour of Methylated and Unmethylated PLA2R1 Gene Sequences According to Primer Design, Annealing Temperature, $MgCl_2$ Concentration and Number of BBPA Cycles On the basis of tests carried out on the PLA2R1 gene and different primer pairs and using dPCR, it was possible to show how the PCR bias for methylated DNA sequences over unmethylated DNA sequences varied depending on the $MgCl_2$ concentrations and annealing temperatures. Using these results, it is possible to develop new test systems for each gene to be tested in which individual tumour DNA fragments are detected to a highly sensitive and specific degree, even against a large background of wild-type DNA. By accordingly adjusting the $MgCl_2$ concentration, annealing temperatures, number of cycles and primer design, the rates at which methylated and unmethylated sequences are amplified can be adjusted such as to produce an optimum bias depending on whether methylated or unmethylated sequences are to be used as the target for identifying tumour-specific DNA. Where unmethylated sequences are the target of interest, primer pairs having no CpG sites are preferably used. If this is not possible due to the gene sequences, primers should be designed such as to contain as few CpG sequences as possible and with these generally arranged towards the 5' end of the primer. In addition, the $MgCl_2$ concentrations and annealing temperatures should be set such that unmethylated sequences are preferably copied over methylated sequences.

For example, when using samples having 50% methylated and 50% unmethylated DNA copies and the primer pair having no CpG sites (primer pair 168 bp) at an $MgCl_2$ concentration of 1.5 mM over the entire temperature range of from 50-63° C., bias in favour of unmethylated DNA sequences was shown (FIG. 34). At an MgCl$_2$ concentration of 2.5-4.5 mM, there was no significant bias detectable for this primer pair. For this primer pair and an MgCl$_2$ concentration of 6.0 mM, and in particular of 8.0 mM, there was, however, a clear bias in favour of methylated DNA sequences in the temperature ranges of from 58.2-60.8° C. and of from 55.1-63.0° C., respectively (FIG. 34).

When using primer pairs having one CpG site (PL-161 bp) or two CpG sites (PL-150 bp), there was a bias towards methylated sequences compared with primers having no CpG sites (PL-168 bp); the level of this bias can be adjusted accordingly by means of the MgCl$_2$ concentration and annealing temperature (FIGS. 35 and 36).

The greatest bias was found when the primers contained four CpG sites, in which one cytosine group was arranged directly at the 3' end of a primer, the amplification efficiency dropping significantly depending on the selected MgCl$_2$ concentration as the annealing temperatures were increased (FIG. 37). For example, at an MgCl$_2$ concentration of 1.5 mM, the amplification efficiency for methylated sequences dropped continuously once the annealing temperature rose above 52.6° C. (FIG. 37).

Bias in favour of methylated DNA sequences depending on the primer design, annealing temperature and MgCl$_2$ concentration was also shown for the RASSF1A and GSTP1 primers (Table 21 and 22).

Embodiment 10: Analytical Sensitivity and Specificity of BBPA-dPCR According to Primer Design, Annealing Temperature, MgCl$_2$ Concentration and Number of BBPA Cycles To determine the conditions under which the greatest analytical sensitivity can be achieved, in particular against a large background of wild-type DNA and without increasing numbers of false-positive signals (a basic requirement for the test procedure to have high analytical and diagnostic sensitivity), test samples were generated containing a small proportion of methylated DNA fragments (DNA from U937 leukaemia cells) compared with an increasing proportion of normal wild-type DNA. To do so, genomic DNA from healthy subjects' blood leucocytes was amplified in a PCR. In this way, it was possible to generate samples that contained a sufficiently large quantity of unmethylated, normal wild-type DNA and to which no methylated DNA or only small quantities of methylated DNA were added, i.e. 5, 10, 20 or 3000 copies of methylated DNA fragments. The background was formed by 70,000, 175,000, 350,000 and 700,000 copies of unmethylated DNA. In samples having 700,000 unmethylated DNA fragments, for example, the resultant proportions of methylated PLA2R1 DNA fragments were 0%, 0.0007%, 0.0014%, 0.0028% and 0.43%.

In a subsequent dPCR, i.e. without pre-amplification beforehand, when primer pairs having no CpG sites (PLA2R1 168 bp) and four CpG sites (PLA2R1 133 bp) were used, it was found that the methylated copies were easily detectable in the samples having 70,000 unmethylated copies using both primer pairs (Tables 23 and 24). When the unmethylated copies were increased further, i.e. in the samples having 175,000, 350,000 and 700,000 unmethylated copies, and the primer pair having no CpG sites was used, an increasingly lower number of the 3,000 methylated DNA fragments was detected (from 2,780 with 70,000 unmethylated copies, to 1,968, 560 and 114 methylated copies, respectively, as the unmethylated copies increased to 175,000, 350,000 and 700,000; Table 23). A similar drop was also observed when this primer pair was used in the samples having 5, 10 and 20 copies of methylated DNA (Table 23). By contrast, when the primer pair having four CpG sites was used (PLA2R1 133 bp), all 3,000 copies of methylated DNA were detectable even in the samples having 175,000, 350,000 and 700,000 unmethylated copies (Table 24). However, the low concentrations of methylated DNA fragments could not be reliably detected here either as the background of unmethylated DNA increased (Table 24).

Next, therefore, investigations were carried out as to the conditions under which improved sensitivity for detecting low concentrations of tumour DNA against a large background of wild-type DNA could be achieved without generating greater numbers of false-positive signals. This implies that the values obtained in the samples having no copies of methylated DNA are clearly distinguished from those having just five copies of methylated DNA.

When using the primer pairs having one CpG site (PLA2R1 168 bp) or two CpG sites (PLA2R1 150 bp) compared with the primer pair having no CpG sites (PLA2R1 168 bp), increased analytical sensitivity was detectable following 15 pre-amplification cycles at an annealing temperature of 63° C. and an MgCl$_2$ concentration of 2.5 mM (Table 25 and 26).

In this case, however, increased sensitivity and in particular considerably better analytical specificity was also surprisingly shown for the primer pair having four CpG sites (PLA2R1 133 bp) when the MgCl$_2$ concentration and annealing temperature were selected accordingly. While only the 3,000 methylated copies could be detected at an MgCl$_2$ concentration of 6.0 mM and an annealing temperature of 50° C., and not the 5, 10 and 20 copies of methylated DNA, it was possible to distinguish between the samples having the low proportion of methylated DNA when the MgCl$_2$ concentration was reduced to 1.5 mM and the annealing temperature remained at 50° C. (Tables 27 and 29). By comparison, if the annealing temperature was increased to 63° C. and the MgCl$_2$ concentration left at 1.5 mM, the samples having no copies and five copies of methylated DNA against a background of 700,000 unmethylated DNA copies could not be distinguished from one another after 15 cycles or 50 cycles (Tables 28 and 29). This changed when the MgCl$_2$ concentration was increased to 6.0 mM at an annealing temperature of 63° C. In this case, increased analytical sensitivity and specificity was found in all samples after 15 cycles when the primer pair having four CpG sites (PLA2R1 133 bp) was used. If the number of cycles was increased from 15 to 50, i.e. the CPC (copies per compartment) was far beyond the maximum of 8 recommended in the prior art [9], the best results in terms of analytical sensitivity and specificity were found; these were 100% in each case. While the signals from the samples having no methylated copies could be already be unambiguously and significantly distinguished from those having five copies of methylated DNA after 15 cycles, none of the samples having no copies of methylated DNA showed positive signals after 50 cycles (with the exception of the sample containing 350,000 copies of unmethylated DNA, in which case one droplet out of the total of 16,235 droplets showed a false positive for FAM signals), whereas significantly elevated FAM signals could be detected in all the other samples containing methylated DNA fragments (Tables 28 and 30; FIG. 38-45).

The reason for the high analytical sensitivities and specificities achieved under the selected reaction conditions could be a special competition reaction among the primers having four CpG sites, in which a cytosine group is located directly at the 3' end (PLA2R1 133 bp), for the methylated and unmethylated DNA fragments. For example, it can be seen in the 2D graphic that, after 50 pre-amplification cycles, the 70,000 unmethylated DNA copies only led to one positive HEX signal when there were absolutely no copies of methylated DNA in the initial samples (FIGS. 38 and 39). Even five copies of methylated DNA prevented 70,000 copies of unmethylated DNA leading to an increase in HEX signals after 50 pre-amplification cycles. If the number of copies of unmethylated DNA was increased to 175,000, ten copies of methylated DNA (no longer five) were sufficient to fully prevent positive HEX signals being generated (FIGS. 40 and 41). If the unmethylated DNA copies were increased further to 350,000 and 700,000, ultimately only the 3,000 copies of methylated DNA were sufficient to prevent the generation of positive HEX signals (FIGS. 42 and 44). Under these strict reaction conditions, the competition reaction appears to prevent false-positive signals; this was not the case previously with PCR using methyl-specific primers MSP [4, 16-19]. If account is taken of the large signal differences between the samples having five or no copies of methylated PLA2R1 DNA fragments against backgrounds of 700,000 unmethylated DNA copies (FIG. 44), it can be assumed that even a single methylated PLA2R1 fragment can be reliably detected using the primer pair having four CpG sites (PLA2R1 133 bp) at an $MgCl_2$ concentration of 6.0 mM and a temperature of 63° C. This would result in an analytical sensitivity of 1 to 700,000 (ratio of $1.4 \times 10^{-6}$) or a methylation level of 0.00014%.

TABLE 13

FAM signals (methylated GSTP1 DNA fragments) and HEX signals (unmethylated GSTP1 DNA fragments) in serum samples from healthy subjects (GF1-GF20), serum samples from female breast cancer patients (MF1-MF20) and non-template control (NTC, no DNA or genomic DNA, without bisulphite conversion) after 15 BBPA cycles using the GSTP1 120 bp primers (SEQ ID: 5 and 6) at an $MgCl_2$ concentration of 2.5 mM and a temperature of 50.7° C., and subsequent dPCR. Cut-off value: <0.07%; raw data for FIG. 55.

| Pos. | Sample | Copies/ 20 μl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| A01 | GM1 | 0 | 0 | 11659 | 0 | 0 | 9615 | 2044 | 11659 | 0 | 0 | 3979 |
| A01 |  | 40960 | 9615 | 2044 | 0 | 0 | 9615 | 2044 | 11659 |  |  | 2133 |
| B01 | GM2 | 9.2 | 5 | 12808 | 3 | 2 | 7860 | 4948 | 12813 | 0.00041 | 0.041 | 3979 |
| B01 |  | 22380 | 7863 | 4950 | 3 | 2 | 7860 | 4948 | 12813 |  |  | 2133 |
| C01 | GM3 | 9.6 | 5 | 12273 | 4 | 1 | 9038 | 3235 | 12278 | 0.00031 | 0.031 | 3979 |
| C01 |  | 31380 | 9042 | 3236 | 4 | 1 | 9038 | 3235 | 12278 |  |  | 2133 |
| D01 | GM4 | 0 | 0 | 12271 | 0 | 0 | 10748 | 1523 | 12271 | 0 | 0 | 3979 |
| D01 |  | 49000 | 10748 | 1523 | 0 | 0 | 10748 | 1523 | 12271 |  |  | 2133 |
| E01 | GM5 | 0 | 0 | 13518 | 0 | 0 | 12481 | 1037 | 13518 | 0 | 0 | 3979 |
| E01 |  | 60400 | 12481 | 1037 | 0 | 0 | 12481 | 1037 | 13518 |  |  | 2133 |
| F01 | GM6 | 0 | 0 | 10542 | 0 | 0 | 9441 | 1101 | 10542 | 0 | 0 | 3979 |
| F01 |  | 53200 | 9441 | 1101 | 0 | 0 | 9441 | 1101 | 10542 |  |  | 2133 |
| G01 | GM7 | 7.8 | 4 | 12116 | 2 | 2 | 8646 | 3470 | 12120 | 0.00026 | 0.026 | 3979 |
| G01 |  | 29420 | 8648 | 3472 | 2 | 2 | 8646 | 3470 | 12120 |  |  | 2133 |
| H01 | GM8 | 3.8 | 2 | 12457 | 1 | 1 | 11087 | 1370 | 12459 | 7.00E−05 | 0.007 | 3979 |
| H01 |  | 52000 | 11088 | 1371 | 1 | 1 | 11087 | 1370 | 12459 |  |  | 2133 |
| A02 | GM9 | 0 | 0 | 12452 | 0 | 0 | 10674 | 1778 | 12452 | 0 | 0 | 3979 |
| A02 |  | 45800 | 10674 | 1778 | 0 | 0 | 10674 | 1778 | 12452 |  |  | 2133 |
| B02 | GM10 | 0 | 0 | 12588 | 0 | 0 | 11275 | 1313 | 12588 | 0 | 0 | 3979 |
| B02 |  | 53200 | 11275 | 1313 | 0 | 0 | 11275 | 1313 | 12588 |  |  | 2133 |
| C02 | GM11 | 0 | 0 | 12385 | 0 | 0 | 11107 | 1278 | 12385 | 0 | 0 | 3979 |
| C02 |  | 53400 | 11107 | 1278 | 0 | 0 | 11107 | 1278 | 12385 |  |  | 2133 |
| D02 | GM12 | 5.6 | 3 | 12540 | 2 | 1 | 10747 | 1793 | 12543 | 0.00012 | 0.012 | 3979 |
| D02 |  | 45800 | 10749 | 1794 | 2 | 1 | 10747 | 1793 | 12543 |  |  | 2133 |
| E02 | GM13 | 0 | 0 | 11600 | 0 | 0 | 10610 | 990 | 11600 | 0 | 0 | 3979 |
| E02 |  | 58000 | 10610 | 990 | 0 | 0 | 10610 | 990 | 11600 |  |  | 2133 |
| F02 | GM14 | 19.2 | 10 | 12310 | 6 | 4 | 8428 | 3882 | 12320 | 0.0007 | 0.07 | 3979 |
| F02 |  | 27140 | 8434 | 3886 | 6 | 4 | 8428 | 3882 | 12320 |  |  | 2133 |
| G02 | GM15 | 9.8 | 5 | 12025 | 4 | 1 | 9614 | 2411 | 12030 | 0.00026 | 0.026 | 3979 |
| G02 |  | 37820 | 9618 | 2412 | 4 | 1 | 9614 | 2411 | 12030 |  |  | 2133 |
| H02 | GM16 | 1.6 | 1 | 13960 | 1 | 0 | 12996 | 964 | 13961 | 2.7E−05 | 0.0027 | 3979 |
| H02 |  | 62800 | 12997 | 964 | 1 | 0 | 12996 | 964 | 13961 |  |  | 2133 |
| A03 | GM17 | 13.2 | 7 | 12464 | 5 | 2 | 9108 | 3356 | 12471 | 0.00043 | 0.043 | 3979 |
| A03 |  | 30880 | 9113 | 3358 | 5 | 2 | 9108 | 3356 | 12471 |  |  | 2133 |
| B03 | GM18 | 3.8 | 2 | 12154 | 0 | 2 | 6479 | 5675 | 12156 | 0.00022 | 0.022 | 3979 |
| B03 |  | 17920 | 6479 | 5677 | 0 | 2 | 6479 | 5675 | 12156 |  |  | 2133 |
| C03 | GM19 | 1.8 | 1 | 12487 | 0 | 1 | 7424 | 5063 | 12488 | 9.00E−05 | 0.009 | 3979 |
| C03 |  | 21240 | 7424 | 5064 | 0 | 1 | 7424 | 5063 | 12488 |  |  | 2133 |
| D03 | GM20 | 0 | 0 | 14041 | 0 | 0 | 11809 | 2232 | 14041 | 0 | 0 | 3979 |
| D03 |  | 43280 | 11809 | 2232 | 0 | 0 | 11809 | 2232 | 14041 |  |  | 2133 |
| E03 | ddNTC | 0 | 0 | 11889 | 0 | 0 | 2 | 11887 | 11889 | 0 | 0 | 3979 |
| E03 |  | 4 | 2 | 11887 | 0 | 0 | 2 | 11887 | 11889 |  |  | 2133 |
| F03 | ddNTC | 0 | 0 | 13770 | 0 | 0 | 1 | 13769 | 13770 | 0 | 0 | 3979 |
| F03 |  | 1.8 | 1 | 13769 | 0 | 0 | 1 | 13769 | 13770 |  |  | 2133 |
| G03 | ddNTC | 0 | 0 | 12580 | 0 | 0 | 11 | 12569 | 12580 | 0 | 0 | 3979 |
| G03 |  | 20 | 11 | 12569 | 0 | 0 | 11 | 12569 | 12580 |  |  | 2133 |
| H03 | ddNTC | 0 | 0 | 12067 | 0 | 0 | 4 | 12063 | 12067 | 0 | 0 | 3979 |
| H03 |  | 7.8 | 4 | 12063 | 0 | 0 | 4 | 12063 | 12067 |  |  | 2133 |
| A04 | PPCa1 | 9.8 | 5 | 11906 | 3 | 2 | 8509 | 3397 | 11911 | 0.00033 | 0.033 | 3979 |
| A04 |  | 29500 | 8512 | 3399 | 3 | 2 | 8509 | 3397 | 11911 |  |  | 2133 |
| B04 | PPCa2 | 2 | 1 | 12218 | 0 | 1 | 6498 | 5720 | 12219 | 0.00011 | 0.011 | 3979 |
| B04 |  | 17860 | 6498 | 5721 | 0 | 1 | 6498 | 5720 | 12219 |  |  | 2133 |

TABLE 13-continued

FAM signals (methylated GSTP1 DNA fragments) and HEX signals (unmethylated GSTP1 DNA fragments) in serum samples from healthy subjects (GF1-GF20), serum samples from female breast cancer patients (MF1-MF20) and non-template control (NTC, no DNA or genomic DNA, without bisulphite conversion) after 15 BBPA cycles using the GSTP1 120 bp primers (SEQ ID: 5 and 6) at an MgCl$_2$ concentration of 2.5 mM and a temperature of 50.7° C., and subsequent dPCR. Cut-off value: <0.07%; raw data for FIG. 55.

| Pos. | Sample | Copies/ 20 μl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| C04 | PPCa3 | 2580 | 1356 | 11727 | 389 | 967 | 2516 | 9211 | 13083 | 0.436 | 30.4 | 3979 |
| C04 |  | 5900 | 2905 | 10178 | 389 | 967 | 2516 | 9211 | 13083 |  |  | 2133 |
| D04 | PPCa4 | 696 | 380 | 12663 | 110 | 270 | 7269 | 5394 | 13043 | 0.0354 | 3.42 | 3979 |
| D04 |  | 19620 | 7379 | 5664 | 110 | 270 | 7269 | 5394 | 13043 |  |  | 2133 |
| E04 | PPCa5 | 2.6 | 1 | 8926 | 1 | 0 | 4 | 8922 | 8927 | 0 | 0 | 3979 |
| E04 |  | 14 | 5 | 8922 | 1 | 0 | 4 | 8922 | 8927 |  |  | 2133 |
| F04 | PPCa6 | 0 | 0 | 13126 | 0 | 0 | 11605 | 1521 | 13126 | 0 | 0 | 3979 |
| F04 |  | 50800 | 11605 | 1521 | 0 | 0 | 11605 | 1521 | 13126 |  |  | 2133 |
| G04 | PPCa7 | 76 | 40 | 12261 | 32 | 8 | 7991 | 4270 | 12301 | 0.0031 | 0.31 | 3979 |
| G04 |  | 24860 | 8023 | 4278 | 32 | 8 | 7991 | 4270 | 12301 |  |  | 2133 |
| H04 | PPCa8 | 226 | 118 | 12178 | 96 | 22 | 7170 | 5008 | 12296 | 0.0108 | 1.07 | 3979 |
| H04 |  | 21040 | 7266 | 5030 | 96 | 22 | 7170 | 5008 | 12296 |  |  | 2133 |
| A05 | PPCa9 | 11.4 | 6 | 12345 | 4 | 2 | 8044 | 4301 | 12351 | 0.00046 | 0.046 | 3979 |
| A05 |  | 24800 | 8048 | 4303 | 4 | 2 | 8044 | 4301 | 12351 |  |  | 2133 |
| B05 | PPCa10 | 5 | 3 | 13879 | 0 | 3 | 7226 | 6653 | 13882 | 0.00029 | 0.029 | 3979 |
| B05 |  | 17300 | 7226 | 6656 | 0 | 3 | 7226 | 6653 | 13882 |  |  | 2133 |
| C05 | PPCa11 | 0 | 0 | 13220 | 0 | 0 | 7999 | 5221 | 13220 | 0 | 0 | 3979 |
| C05 |  | 21860 | 7999 | 5221 | 0 | 0 | 7999 | 5221 | 13220 |  |  | 2133 |
| D05 | PPCa12 | 3.8 | 2 | 12680 | 1 | 1 | 9583 | 3097 | 12682 | 0.00011 | 0.011 | 3979 |
| D05 |  | 33160 | 9584 | 3098 | 1 | 1 | 9583 | 3097 | 12682 |  |  | 2133 |
| E05 | PPCa13 | 26 | 16 | 14337 | 0 | 16 | 4798 | 9539 | 14353 | 0.0027 | 0.27 | 3979 |
| E05 |  | 9580 | 4798 | 9555 | 0 | 16 | 4798 | 9539 | 14353 |  |  | 2133 |
| F05 | PPCa14 | 3.6 | 2 | 13179 | 0 | 2 | 7233 | 5946 | 13181 | 0.00019 | 0.019 | 3979 |
| F05 |  | 18720 | 7233 | 5948 | 0 | 2 | 7233 | 5946 | 13181 |  |  | 2133 |
| G05 | PPCa15 | 210 | 100 | 11137 | 9 | 91 | 4348 | 6789 | 11237 | 0.0182 | 1.79 | 3979 |
| G05 |  | 11540 | 4357 | 6880 | 9 | 91 | 4348 | 6789 | 11237 |  |  | 2133 |
| H05 | PPCa16 | 9 | 5 | 12963 | 3 | 2 | 8580 | 4383 | 12968 | 0.00036 | 0.036 | 3979 |
| H05 |  | 25520 | 8583 | 4385 | 3 | 2 | 8580 | 4383 | 12968 |  |  | 2133 |
| A06 | PPCa17 | 316 | 202 | 14943 | 101 | 101 | 6978 | 7965 | 15145 | 0.0213 | 2.09 | 3979 |
| A06 |  | 14820 | 7079 | 8066 | 101 | 101 | 6978 | 7965 | 15145 |  |  | 2133 |
| B06 | PPCa18 | 8.6 | 5 | 13773 | 3 | 2 | 5824 | 7949 | 13778 | 0.0007 | 0.07 | 3979 |
| B06 |  | 12940 | 5827 | 7951 | 3 | 2 | 5824 | 7949 | 13778 |  |  | 2133 |
| C06 | PPCa19 | 7.4 | 4 | 12673 | 0 | 4 | 4727 | 7946 | 12677 | 0.0007 | 0.07 | 3979 |
| C06 |  | 10980 | 4727 | 7950 | 0 | 4 | 4727 | 7946 | 12677 |  |  | 2133 |
| D06 | PPCa20 | 24 | 14 | 13839 | 0 | 14 | 4895 | 8944 | 13853 | 0.0023 | 0.23 | 3979 |
| D06 |  | 10260 | 4895 | 8958 | 0 | 14 | 4895 | 8944 | 13853 |  |  | 2133 |
| E06 | gDNA 15 | 14.6 | 8 | 12975 | 0 | 8 | 879 | 12096 | 12983 | 0.009 | 0.9 | 3979 |
| E06 |  | 1640 | 879 | 12104 | 0 | 8 | 879 | 12096 | 12983 |  |  | 2133 |
| F06 | NTC 15 | 0 | 0 | 13676 | 0 | 0 | 53 | 13623 | 13676 | 0 | 0 | 3979 |
| F06 |  | 92 | 53 | 13623 | 0 | 0 | 53 | 13623 | 13676 |  |  | 2133 |

TABLE 14

FAM signals (methylated GSTP1 DNA fragments) and HEX signals (unmethylated GSTP1 DNA fragments) in serum samples from healthy subjects (GF1-GF20), serum samples from female breast cancer patients (MF1-MF20) and non-template control (NTC, no DNA or genomic DNA, without bisulphite conversion) after 15 BBPA cycles using the GSTP1 116 bp primers (SEQ ID: 93 and 94) at an MgCl$_2$ concentration of 4.5 mM and a temperature of 53.8° C., and subsequent dPCR. Cut-off value: <0.023%; raw data for FIG. 56.

| Pos. | Sample | Copies/ 20 μl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| A01 | GM1 | 1.4 | 1 | 15767 | 0 | 1 | 7390 | 8377 | 15768 | 0.0001 | 0.01 | 2927 |
| A01 |  | 14880 | 7390 | 8378 | 0 | 1 | 7390 | 8377 | 15768 |  |  | 1705 |
| B01 | GM2 | 0 | 0 | 14360 | 0 | 0 | 2251 | 12109 | 14360 | 0 | 0 | 2927 |
| B01 |  | 4020 | 2251 | 12109 | 0 | 0 | 2251 | 12109 | 14360 |  |  | 1705 |
| C01 | GM3 | 0 | 0 | 14640 | 0 | 0 | 6362 | 8278 | 14640 | 0 | 0 | 2927 |
| C01 |  | 13420 | 6362 | 8278 | 0 | 0 | 6362 | 8278 | 14640 |  |  | 1705 |
| D01 | GM4 | 0 | 0 | 14771 | 0 | 0 | 10267 | 4504 | 14771 | 0 | 0 | 2927 |
| D01 |  | 27940 | 10267 | 4504 | 0 | 0 | 10267 | 4504 | 14771 |  |  | 1705 |
| E01 | GM5 | 0 | 0 | 14872 | 0 | 0 | 11131 | 3741 | 14872 | 0 | 0 | 2927 |
| E01 |  | 32480 | 11131 | 3741 | 0 | 0 | 11131 | 3741 | 14872 |  |  | 1705 |
| F01 | GM6 | 1.8 | 1 | 13135 | 0 | 1 | 7488 | 5647 | 13136 | 9.00E−05 | 0.009 | 2927 |
| F01 |  | 19860 | 7488 | 5648 | 0 | 1 | 7488 | 5647 | 13136 |  |  | 1705 |
| G01 | GM7 | 0 | 0 | 13798 | 0 | 0 | 3363 | 10435 | 13798 | 0 | 0 | 2927 |
| G01 |  | 6580 | 3363 | 10435 | 0 | 0 | 3363 | 10435 | 13798 |  |  | 1705 |
| H01 | GM8 | 0 | 0 | 13949 | 0 | 0 | 4887 | 9062 | 13949 | 0 | 0 | 2927 |
| H01 |  | 10140 | 4887 | 9062 | 0 | 0 | 4887 | 9062 | 13949 |  |  | 1705 |

TABLE 14-continued

FAM signals (methylated GSTP1 DNA fragments) and HEX signals (unmethylated GSTP1 DNA fragments) in serum samples from healthy subjects (GF1-GF20), serum samples from female breast cancer patients (MF1-MF20) and non-template control (NTC, no DNA or genomic DNA, without bisulphite conversion) after 15 BBPA cycles using the GSTP1 116 bp primers (SEQ ID: 93 and 94) at an MgCl$_2$ concentration of 4.5 mM and a temperature of 53.8° C., and subsequent dPCR. Cut-off value: <0.023%; raw data for FIG. 56.

| Pos. | Sample | Copies/ 20 µl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| A02 | GM9 | 0 | 0 | 12667 | 0 | 0 | 6686 | 5981 | 12667 | 0 | 0 | 2927 |
| A02 |  | 17660 | 6686 | 5981 | 0 | 0 | 6686 | 5981 | 12667 |  |  | 1705 |
| B02 | GM10 | 0 | 0 | 13982 | 0 | 0 | 10312 | 3670 | 13982 | 0 | 0 | 2927 |
| B02 |  | 31480 | 10312 | 3670 | 0 | 0 | 10312 | 3670 | 13982 |  |  | 1705 |
| C02 | GM11 | 2 | 1 | 12293 | 1 | 0 | 3608 | 8685 | 12294 | 0.00023 | 0.023 | 2927 |
| C02 |  | 8180 | 3609 | 8685 | 1 | 0 | 3608 | 8685 | 12294 |  |  | 1705 |
| D02 | GM12 | 0 | 0 | 13369 | 0 | 0 | 3709 | 9660 | 13369 | 0 | 0 | 2927 |
| D02 |  | 7640 | 3709 | 9660 | 0 | 0 | 3709 | 9660 | 13369 |  |  | 1705 |
| E02 | GM13 | 0 | 0 | 11019 | 0 | 0 | 7254 | 3765 | 11019 | 0 | 0 | 2927 |
| E02 |  | 25260 | 7254 | 3765 | 0 | 0 | 7254 | 3765 | 11019 |  |  | 1705 |
| F02 | GM14 | 0 | 0 | 13031 | 0 | 0 | 4748 | 8283 | 13031 | 0 | 0 | 2927 |
| F02 |  | 10660 | 4748 | 8283 | 0 | 0 | 4748 | 8283 | 13031 |  |  | 1705 |
| G02 | GM15 | 0 | 0 | 15122 | 0 | 0 | 4572 | 10550 | 15122 | 0 | 0 | 2927 |
| G02 |  | 8480 | 4572 | 10550 | 0 | 0 | 4572 | 10550 | 15122 |  |  | 1705 |
| H02 | GM16 | 0 | 0 | 12342 | 0 | 0 | 5999 | 6343 | 12342 | 0 | 0 | 2927 |
| H02 |  | 15660 | 5999 | 6343 | 0 | 0 | 5999 | 6343 | 12342 |  |  | 1705 |
| A03 | GM17 | 0 | 0 | 14605 | 0 | 0 | 2825 | 11780 | 14605 | 0 | 0 | 2927 |
| A03 |  | 5060 | 2825 | 11780 | 0 | 0 | 2825 | 11780 | 14605 |  |  | 1705 |
| B03 | GM18 | 0 | 0 | 12935 | 0 | 0 | 3736 | 9199 | 12935 | 0 | 0 | 2927 |
| B03 |  | 8020 | 3736 | 9199 | 0 | 0 | 3736 | 9199 | 12935 |  |  | 1705 |
| C03 | GM19 | 0 | 0 | 12230 | 0 | 0 | 4769 | 7461 | 12230 | 0 | 0 | 2927 |
| C03 |  | 11620 | 4769 | 7461 | 0 | 0 | 4769 | 7461 | 12230 |  |  | 1705 |
| D03 | GM20 | 0 | 0 | 12400 | 0 | 0 | 7509 | 4891 | 12400 | 0 | 0 | 2927 |
| D03 |  | 21880 | 7509 | 4891 | 0 | 0 | 7509 | 4891 | 12400 |  |  | 1705 |
| E03 | ddNTC | 0 | 0 | 13014 | 0 | 0 | 1 | 13013 | 13014 | 0 | 0 | 2927 |
| E03 |  | 1.8 | 1 | 13013 | 0 | 0 | 1 | 13013 | 13014 |  |  | 1705 |
| F03 | ddNTC | 0 | 0 | 13618 | 0 | 0 | 2 | 13616 | 13618 | 0 | 0 | 2927 |
| F03 |  | 3.4 | 2 | 13616 | 0 | 0 | 2 | 13616 | 13618 |  |  | 1705 |
| G03 | ddNTC | 0 | 0 | 12250 | 0 | 0 | 0 | 12250 | 12250 | 0 | 0 | 2927 |
| G03 |  | 0 | 0 | 12250 | 0 | 0 | 0 | 12250 | 12250 |  |  | 1705 |
| H03 | ddNTC | 0 | 0 | 12222 | 0 | 0 | 2 | 12220 | 12222 | 0 | 0 | 2927 |
| H03 |  | 3.8 | 2 | 12220 | 0 | 0 | 2 | 12220 | 12222 |  |  | 1705 |
| A04 | PPCa1 | 166 | 87 | 12317 | 5 | 82 | 1552 | 10765 | 12404 | 0.052 | 5 | 2927 |
| A04 |  | 3160 | 1557 | 10847 | 5 | 82 | 1552 | 10765 | 12404 |  |  | 1705 |
| B04 | PPCa2 | 716 | 372 | 12047 | 27 | 345 | 3074 | 8973 | 12419 | 0.106 | 9.6 | 2927 |
| B04 |  | 6760 | 3101 | 9318 | 27 | 345 | 3074 | 8973 | 12419 |  |  | 1705 |
| C04 | PPCa3 | 69400 | 9844 | 546 | 7 | 9837 | 0 | 546 | 10390 | 4400 | 99.977 | 2927 |
| C04 |  | 16 | 7 | 10383 | 7 | 9837 | 0 | 546 | 10390 |  |  | 1705 |
| D04 | PPCa4 | 5720 | 2688 | 9783 | 36 | 2652 | 602 | 9181 | 12471 | 4.62 | 82.2 | 2927 |
| D04 |  | 1236 | 638 | 11833 | 36 | 2652 | 602 | 9181 | 12471 |  |  | 1705 |
| E04 | PPCa5 | 1.8 | 1 | 12478 | 0 | 1 | 1634 | 10844 | 12479 | 0.0006 | 0.06 | 2927 |
| E04 |  | 3300 | 1634 | 10845 | 0 | 1 | 1634 | 10844 | 12479 |  |  | 1705 |
| F04 | PPCa6 | 0 | 0 | 11920 | 0 | 0 | 8589 | 3331 | 11920 | 0 | 0 | 2927 |
| F04 |  | 30000 | 8589 | 3331 | 0 | 0 | 8589 | 3331 | 11920 |  |  | 1705 |
| G04 | PPCa7 | 26300 | 8374 | 4070 | 496 | 7878 | 994 | 3076 | 12444 | 8.76 | 89.8 | 2927 |
| G04 |  | 3000 | 1490 | 10954 | 496 | 7878 | 994 | 3076 | 12444 |  |  | 1705 |
| H04 | PPCa8 | 33740 | 9434 | 2953 | 937 | 8497 | 761 | 2192 | 12387 | 9.7 | 90.68 | 2927 |
| H04 |  | 3460 | 1698 | 10689 | 937 | 8497 | 761 | 2192 | 12387 |  |  | 1705 |
| A05 | PPCa9 | 0 | 0 | 12183 | 0 | 0 | 3952 | 8231 | 12183 | 0 | 0 | 2927 |
| A05 |  | 9220 | 3952 | 8231 | 0 | 0 | 3952 | 8231 | 12183 |  |  | 1705 |
| B05 | PPCa10 | 0 | 0 | 12193 | 0 | 0 | 15 | 12178 | 12193 | 0 | 0 | 2927 |
| B05 |  | 28 | 15 | 12178 | 0 | 0 | 15 | 12178 | 12193 |  |  | 1705 |
| C05 | PPCa11 | 1000 | 136 | 3161 | 32 | 104 | 977 | 2184 | 3297 | 0.115 | 10.3 | 2927 |
| C05 |  | 8600 | 1009 | 2288 | 32 | 104 | 977 | 2184 | 3297 |  |  | 1705 |
| D05 | PPCa12 | 9060 | 3807 | 8097 | 316 | 3491 | 2737 | 5360 | 11904 | 1.3 | 56.5 | 2927 |
| D05 |  | 6980 | 3053 | 8851 | 316 | 3491 | 2737 | 5360 | 11904 |  |  | 1705 |
| E05 | PPCa13 | 0 | 0 | 13326 | 0 | 0 | 852 | 12474 | 13326 | 0 | 0 | 2927 |
| E05 |  | 1560 | 852 | 12474 | 0 | 0 | 852 | 12474 | 13326 |  |  | 1705 |
| F05 | PPCa14 | 342 | 180 | 12273 | 21 | 159 | 2173 | 10100 | 12453 | 0.075 | 7 | 2927 |
| F05 |  | 4560 | 2194 | 10259 | 21 | 159 | 2173 | 10100 | 12453 |  |  | 1705 |
| G05 | PPCa15 | 1364 | 733 | 12280 | 6 | 727 | 357 | 11923 | 13013 | 2.05 | 67.2 | 2927 |
| G05 |  | 666 | 363 | 12650 | 6 | 727 | 357 | 11923 | 13013 |  |  | 1705 |
| H05 | PPCa16 | 508 | 265 | 12143 | 18 | 247 | 3706 | 8437 | 12408 | 0.06 | 5.7 | 2927 |
| H05 |  | 8400 | 3724 | 8684 | 18 | 247 | 3706 | 8437 | 12408 |  |  | 1705 |
| A06 | PPCa17 | 8280 | 3811 | 9026 | 94 | 3717 | 853 | 8173 | 12837 | 4.6 | 82.1 | 2927 |
| A06 |  | 1800 | 947 | 11890 | 94 | 3717 | 853 | 8173 | 12837 |  |  | 1705 |
| B06 | PPCa18 | 0 | 0 | 12031 | 0 | 0 | 2732 | 9299 | 12031 | 0 | 0 | 2927 |
| B06 |  | 6060 | 2732 | 9299 | 0 | 0 | 2732 | 9299 | 12031 |  |  | 1705 |
| C06 | PPCa19 | 0 | 0 | 11204 | 0 | 0 | 2358 | 8846 | 11204 | 0 | 0 | 2927 |
| C06 |  | 5560 | 2358 | 8846 | 0 | 0 | 2358 | 8846 | 11204 |  |  | 1705 |
| D06 | PPCa20 | 0 | 0 | 12688 | 0 | 0 | 1224 | 11464 | 12688 | 0 | 0 | 2927 |

TABLE 14-continued

FAM signals (methylated GSTP1 DNA fragments) and HEX signals (unmethylated GSTP1 DNA fragments) in serum samples from healthy subjects (GF1-GF20), serum samples from female breast cancer patients (MF1-MF20) and non-template control (NTC, no DNA or genomic DNA, without bisulphite conversion) after 15 BBPA cycles using the GSTP1 116 bp primers (SEQ ID: 93 and 94) at an $MgCl_2$ concentration of 4.5 mM and a temperature of 53.8° C., and subsequent dPCR. Cut-off value: <0.023%; raw data for FIG. 56.

| Pos. | Sample | Copies/ 20 µl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| D06 |  | 2380 | 1224 | 11464 | 0 | 0 | 1224 | 11464 | 12688 |  |  | 1705 |
| E06 | gDNA 15 | 0 | 0 | 12039 | 0 | 0 | 1 | 12038 | 12039 | 0 | 0 | 2927 |
| E06 |  | 2 | 1 | 12038 | 0 | 0 | 1 | 12038 | 12039 |  |  | 1705 |
| G06 | NTC 15 | 0 | 0 | 13354 | 0 | 0 | 1 | 13353 | 13354 | 0 | 0 | 2927 |
| G06 |  | 1.8 | 1 | 13353 | 0 | 0 | 1 | 13353 | 13354 |  |  | 1705 |

TABLE 15

FAM signals (methylated SERPINE1 DNA fragments) and HEX signals (unmethylated SERPINE1 DNA fragments) in serum samples from healthy subjects (GF1-GF20), serum samples from female breast cancer patients (MF1-MF20) and non-template control (NTC, no DNA or genomic DNA, without bisulphite conversion) after 15 BBPA cycles using the SERPINE1 123 bp primers (SEQ ID: 16 and 17) at an $MgCl_2$ concentration of 3.5 mM and a temperature of 52.0° C., and subsequent dPCR. Cut-off value: <25.9%; raw data for FIG. 57.

| Pos. | Sample | Copies/ 20 µl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| A01 | GM1 | 20 | 12 | 14245 | 4 | 8 | 1132 | 13113 | 14257 | 0.01 | 1 | 3576 |
| A01 |  | 1960 | 1136 | 13121 | 4 | 8 | 1132 | 13113 | 14257 |  |  | 3908 |
| B01 | GM2 | 2 | 1 | 12114 | 0 | 1 | 487 | 11627 | 12115 | 0.002 | 0.2 | 3576 |
| B01 |  | 966 | 487 | 11628 | 0 | 1 | 487 | 11627 | 12115 |  |  | 3908 |
| C01 | GM3 | 24 | 15 | 14517 | 3 | 12 | 1088 | 13429 | 14532 | 0.013 | 1.3 | 3576 |
| C01 |  | 1840 | 1091 | 13441 | 3 | 12 | 1088 | 13429 | 14532 |  |  | 3908 |
| D01 | GM4 | 210 | 102 | 11324 | 10 | 92 | 1724 | 9600 | 11426 | 0.054 | 5.2 | 3576 |
| D01 |  | 3880 | 1734 | 9692 | 10 | 92 | 1724 | 9600 | 11426 |  |  | 3908 |
| E01 | GM5 | 18 | 11 | 14493 | 2 | 9 | 3160 | 11333 | 14504 | 0.0031 | 0.31 | 3576 |
| E01 |  | 5780 | 3162 | 11342 | 2 | 9 | 3160 | 11333 | 14504 |  |  | 3908 |
| F01 | GM6 | 766 | 487 | 14709 | 36 | 451 | 1940 | 12769 | 15196 | 0.234 | 19 | 3576 |
| F01 |  | 3280 | 1976 | 13220 | 36 | 451 | 1940 | 12769 | 15196 |  |  | 3908 |
| G01 | GM7 | 86 | 52 | 14280 | 0 | 52 | 455 | 13825 | 14332 | 0.113 | 10.1 | 3576 |
| G01 |  | 760 | 455 | 13877 | 0 | 52 | 455 | 13825 | 14332 |  |  | 3908 |
| H01 | GM8 | 966 | 562 | 13412 | 51 | 511 | 1501 | 11911 | 13974 | 0.349 | 25.9 | 3576 |
| H01 |  | 2780 | 1552 | 12422 | 51 | 511 | 1501 | 11911 | 13974 |  |  | 3908 |
| A02 | GM9 | 14 | 1 | 1724 | 0 | 1 | 0 | 1724 | 1725 | 0 | 0 | 3576 |
| A02 |  | 0 | 0 | 1725 | 0 | 0 | 0 | 1725 | 1725 |  |  | 3908 |
| B02 | GM10 | 50 | 25 | 11855 | 4 | 21 | 2835 | 9020 | 11880 | 0.0077 | 0.77 | 3576 |
| B02 |  | 6420 | 2839 | 9041 | 4 | 21 | 2835 | 9020 | 11880 |  |  | 3908 |
| C02 | GM11 | 5.2 | 3 | 13687 | 1 | 2 | 1253 | 12434 | 13690 | 0.0023 | 0.23 | 3576 |
| C02 |  | 2260 | 1254 | 12436 | 1 | 2 | 1253 | 12434 | 13690 |  |  | 3908 |
| D02 | GM12 | 552 | 305 | 12830 | 43 | 262 | 851 | 11979 | 13135 | 0.333 | 25 | 3576 |
| D02 |  | 1660 | 894 | 12241 | 43 | 262 | 851 | 11979 | 13135 |  |  | 3908 |
| E02 | GM13 | 102 | 58 | 13391 | 4 | 54 | 2469 | 10922 | 13449 | 0.021 | 2.1 | 3576 |
| E02 |  | 4780 | 2473 | 10976 | 4 | 54 | 2469 | 10922 | 13449 |  |  | 3908 |
| F02 | GM14 | 304 | 140 | 10770 | 3 | 137 | 718 | 10052 | 10910 | 0.189 | 15.9 | 3576 |
| F02 |  | 1600 | 721 | 10189 | 3 | 137 | 718 | 10052 | 10910 |  |  | 3908 |
| G02 | GM15 | 10.4 | 6 | 13536 | 1 | 5 | 589 | 12947 | 13542 | 0.01 | 1 | 3576 |
| G02 |  | 1048 | 590 | 12952 | 1 | 5 | 589 | 12947 | 13542 |  |  | 3908 |
| H02 | GM16 | 10.4 | 6 | 13557 | 2 | 4 | 1605 | 11952 | 13563 | 0.0035 | 0.35 | 3576 |
| H02 |  | 2960 | 1607 | 11956 | 2 | 4 | 1605 | 11952 | 13563 |  |  | 3908 |
| A03 | GM17 | 3.8 | 2 | 12274 | 0 | 2 | 287 | 11987 | 12276 | 0.007 | 0.7 | 3576 |
| A03 |  | 556 | 287 | 11989 | 0 | 2 | 287 | 11987 | 12276 |  |  | 3908 |
| B03 | GM18 | 0 | 0 | 12516 | 0 | 0 | 530 | 11986 | 12516 | 0 | 0 | 3576 |
| B03 |  | 1018 | 530 | 11986 | 0 | 0 | 530 | 11986 | 12516 |  |  | 3908 |
| C03 | GM19 | 36 | 24 | 15274 | 4 | 20 | 1133 | 14141 | 15298 | 0.02 | 2 | 3576 |
| C03 |  | 1820 | 1137 | 14161 | 4 | 20 | 1133 | 14141 | 15298 |  |  | 3908 |
| D03 | GM20 | 10.4 | 6 | 13578 | 2 | 4 | 3671 | 9907 | 13584 | 0.0014 | 0.14 | 3576 |
| D03 |  | 7420 | 3673 | 9911 | 2 | 4 | 3671 | 9907 | 13584 |  |  | 3908 |
| A04 | PPCa1 | 48 | 24 | 11619 | 4 | 20 | 327 | 11292 | 11643 | 0.072 | 6.7 | 3576 |
| A04 |  | 678 | 331 | 11312 | 4 | 20 | 327 | 11292 | 11643 |  |  | 3908 |
| B04 | PPCa2 | 8.4 | 5 | 14014 | 0 | 5 | 383 | 13631 | 14019 | 0.013 | 1.3 | 3576 |
| B04 |  | 652 | 383 | 13636 | 0 | 5 | 383 | 13631 | 14019 |  |  | 3908 |
| C04 | PPCa3 | 6440 | 3173 | 10077 | 283 | 2890 | 1916 | 8161 | 13250 | 1.51 | 60.1 | 3576 |
| C04 |  | 4280 | 2199 | 11051 | 283 | 2890 | 1916 | 8161 | 13250 |  |  | 3908 |
| D04 | PPCa4 | 910 | 540 | 13698 | 0 | 540 | 158 | 13540 | 14238 | 3.5 | 77.6 | 3576 |
| D04 |  | 262 | 158 | 14080 | 0 | 540 | 158 | 13540 | 14238 |  |  | 3908 |
| E04 | PPCa5 | 28 | 14 | 11907 | 0 | 14 | 257 | 11650 | 11921 | 0.054 | 5.1 | 3576 |
| E04 |  | 512 | 257 | 11664 | 0 | 14 | 257 | 11650 | 11921 |  |  | 3908 |
| F04 | PPCa6 | 314 | 166 | 12345 | 15 | 151 | 2808 | 9537 | 12511 | 0.052 | 5 | 3576 |

TABLE 15-continued

FAM signals (methylated SERPINE1 DNA fragments) and HEX signals (unmethylated SERPINE1 DNA fragments) in serum samples from healthy subjects (GF1-GF20), serum samples from female breast cancer patients (MF1-MF20) and non-template control (NTC, no DNA or genomic DNA, without bisulphite conversion) after 15 BBPA cycles using the SERPINE1 123 bp primers (SEQ ID: 16 and 17) at an $MgCl_2$ concentration of 3.5 mM and a temperature of 52.0° C., and subsequent dPCR. Cut-off value: <25.9%; raw data for FIG. 57.

| Pos. | Sample | Copies/ 20 µl | Positive | Negative | Ch1+ Ch2+ | Ch1+ Ch2- | Ch1- Ch2+ | Ch1- Ch2- | Number of droplets | Ratio | Fractional abundance | Threshold |
|---|---|---|---|---|---|---|---|---|---|---|---|---|
| F04 |  | 6020 | 2823 | 9688 | 15 | 151 | 2808 | 9537 | 12511 |  |  | 3908 |
| G04 | PPCa7 | 1560 | 859 | 12602 | 38 | 821 | 1295 | 11307 | 13461 | 0.63 | 38.7 | 3576 |
| G04 |  | 2460 | 1333 | 12128 | 38 | 821 | 1295 | 11307 | 13461 |  |  | 3908 |
| H04 | PPCa8 | 2060 | 1070 | 11694 | 131 | 939 | 2340 | 9354 | 12764 | 0.407 | 28.9 | 3576 |
| H04 |  | 5060 | 2471 | 10293 | 131 | 939 | 2340 | 9354 | 12764 |  |  | 3908 |
| A05 | PPCa9 | 44 | 25 | 13399 | 1 | 24 | 1095 | 12304 | 13424 | 0.022 | 2.1 | 3576 |
| A05 |  | 2000 | 1096 | 12328 | 1 | 24 | 1095 | 12304 | 13424 |  |  | 3908 |
| B05 | PPCa10 | 9.8 | 5 | 12050 | 0 | 5 | 406 | 11644 | 12055 | 0.012 | 1.2 | 3576 |
| B05 |  | 806 | 406 | 11649 | 0 | 5 | 406 | 11644 | 12055 |  |  | 3908 |
| C05 | PPCa11 | 4320 | 2523 | 12518 | 642 | 1881 | 3607 | 8911 | 15041 | 0.553 | 35.6 | 3576 |
| C05 |  | 7820 | 4249 | 10792 | 642 | 1881 | 3607 | 8911 | 15041 |  |  | 3908 |
| D05 | PPCa12 | 758 | 509 | 15556 | 10 | 499 | 1073 | 14483 | 16065 | 0.461 | 31.6 | 3576 |
| D05 |  | 1642 | 1083 | 14982 | 10 | 499 | 1073 | 14483 | 16065 |  |  | 3908 |
| E05 | PPCa13 | 256 | 155 | 14213 | 3 | 152 | 559 | 13654 | 14368 | 0.272 | 21.4 | 3576 |
| E05 |  | 938 | 562 | 13806 | 3 | 152 | 559 | 13654 | 14368 |  |  | 3908 |
| F05 | PPCa14 | 624 | 394 | 14667 | 21 | 373 | 2408 | 12259 | 15061 | 0.151 | 13.1 | 3576 |
| F05 |  | 4140 | 2429 | 12632 | 21 | 373 | 2408 | 12259 | 15061 |  |  | 3908 |
| G05 | PPCa15 | 50 | 29 | 13505 | 1 | 28 | 313 | 13192 | 13534 | 0.091 | 8.4 | 3576 |
| G05 |  | 552 | 314 | 13220 | 1 | 28 | 313 | 13192 | 13534 |  |  | 3908 |
| H05 | PPCa16 | 8.6 | 5 | 13566 | 0 | 5 | 1356 | 12210 | 13571 | 0.0035 | 0.35 | 3576 |
| H05 |  | 2480 | 1356 | 12215 | 0 | 5 | 1356 | 12210 | 13571 |  |  | 3908 |
| A06 | PPCa17 | 68 | 39 | 13523 | 0 | 39 | 135 | 13388 | 13562 | 0.29 | 22 | 3576 |
| A06 |  | 236 | 135 | 13427 | 0 | 39 | 135 | 13388 | 13562 |  |  | 3908 |
| B06 | PPCa18 | 0 | 0 | 12779 | 0 | 0 | 782 | 11997 | 12779 | 0 | 0 | 3576 |
| B06 |  | 1480 | 782 | 11997 | 0 | 0 | 782 | 11997 | 12779 |  |  | 3908 |
| C06 | PPCa19 | 0 | 0 | 14452 | 0 | 0 | 350 | 14102 | 14452 | 0 | 0 | 3576 |
| C06 |  | 576 | 350 | 14102 | 0 | 0 | 350 | 14102 | 14452 |  |  | 3908 |
| D06 | PPCa20 | 24 | 14 | 13202 | 0 | 14 | 226 | 12976 | 13216 | 0.061 | 5.8 | 3576 |
| D06 |  | 406 | 226 | 12990 | 0 | 14 | 226 | 12976 | 13216 |  |  | 3908 |
| E03 | 15 gNTC | 3.4 | 2 | 13554 | 0 | 2 | 16 | 13538 | 13556 | 0.12 | 11 | 3576 |
| E03 |  | 28 | 16 | 13540 | 0 | 2 | 16 | 13538 | 13556 |  |  | 3908 |
| F03 | 15 NTC | 8.8 | 6 | 16114 | 1 | 5 | 35 | 16079 | 16120 | 0.17 | 14 | 3576 |
| F03 |  | 52 | 36 | 16084 | 1 | 5 | 35 | 16079 | 16120 |  |  | 3908 |

TABLE 16

FAM signals (methylated SERPINE1 DNA fragments) and HEX signals (unmethylated SERPINE1 DNA fragments) in serum samples from healthy subjects (GF1-GF20), serum samples from female breast cancer patients (MF1-MF20) and non-template control (NTC, no DNA or genomic DNA, without bisulphite conversion) after 50 BBPA cycles using the SERPINE1 123 bp primers (SEQ ID: 16 and 17) at an $MgCl_2$ concentration of 3.5 mM and a temperature of 52.0° C., and subsequent dPCR. Cut-off value: <0.0012%; n.d. = no data due to the proportion of unmethylated DNA fragments being too low. Raw data for FIG. 58.

| Pos. | Sample | Copies/ 20 µl | Positive | Negative | Ch1+ Ch2+ | Ch1+ Ch2- | Ch1- Ch2+ | Ch1- Ch2- | Number of droplets | Ratio | Fractional abundance | Threshold |
|---|---|---|---|---|---|---|---|---|---|---|---|---|
| A07 | GM1 | 0 | 0 | 11322 | 0 | 0 | 11002 | 320 | 11322 | 0 | 0 | 3508 |
| A07 |  | 84000 | 11002 | 320 | 0 | 0 | 11002 | 320 | 11322 |  |  | 3780 |
| B07 | GM2 | 0 | 0 | 11951 | 0 | 0 | 9517 | 2434 | 11951 | 0 | 0 | 3508 |
| B07 |  | 37440 | 9517 | 2434 | 0 | 0 | 9517 | 2434 | 11951 |  |  | 3780 |
| C07 | GM3 | 0 | 0 | 14343 | 0 | 0 | 11625 | 2718 | 14343 | 0 | 0 | 3508 |
| C07 |  | 39140 | 11625 | 2718 | 0 | 0 | 11625 | 2718 | 14343 |  |  | 3780 |
| D07 | GM4 | 0 | 0 | 10890 | 0 | 0 | 9128 | 1762 | 10890 | 0 | 0 | 3508 |
| D07 |  | 42800 | 9128 | 1762 | 0 | 0 | 9128 | 1762 | 10890 |  |  | 3780 |
| E07 | GM5 | 0 | 0 | 14075 | 0 | 0 | 14057 | 18 | 14075 | 0 | 0 | 3508 |
| E07 |  | 156000 | 14057 | 18 | 0 | 0 | 14057 | 18 | 14075 |  |  | 3780 |
| F07 | GM6 | 0 | 0 | 13893 | 0 | 0 | 13305 | 588 | 13893 | 0 | 0 | 3508 |
| F07 |  | 74400 | 13305 | 588 | 0 | 0 | 13305 | 588 | 13893 |  |  | 3780 |
| G07 | GM7 | 0 | 0 | 16335 | 0 | 0 | 13 | 16322 | 16335 |  | n.d. | 3508 |
| G07 |  | 18 | 13 | 16322 | 0 | 0 | 13 | 16322 | 16335 |  |  | 3780 |
| H07 | GM8 | 0 | 0 | 12775 | 0 | 0 | 10756 | 2019 | 12775 | 0 | 0 | 3508 |
| H07 |  | 43400 | 10756 | 2019 | 0 | 0 | 10756 | 2019 | 12775 |  |  | 3780 |
| A08 | GM9 | 0 | 0 | 13185 | 0 | 0 | 92 | 13093 | 13185 |  | n.d. | 3508 |
| A08 |  | 164 | 92 | 13093 | 0 | 0 | 92 | 13093 | 13185 |  |  | 3780 |
| B08 | GM10 | 0 | 0 | 14823 | 0 | 0 | 14755 | 68 | 14823 | 0 | 0 | 3508 |
| B08 |  | 126600 | 14755 | 68 | 0 | 0 | 14755 | 68 | 14823 |  |  | 3780 |
| C08 | GM11 | 1.6 | 1 | 14258 | 1 | 0 | 14206 | 52 | 14259 | 1.2E-05 | 0.0012 | 3508 |
| C08 |  | 132000 | 14207 | 52 | 1 | 0 | 14206 | 52 | 14259 |  |  | 3780 |

TABLE 16-continued

FAM signals (methylated SERPINE1 DNA fragments) and HEX signals (unmethylated SERPINE1 DNA fragments)
in serum samples from healthy subjects (GF1-GF20), serum samples from female breast cancer patients (MF1-MF20)
and non-template control (NTC, no DNA or genomic DNA, without bisulphite conversion) after 50 BBPA cycles using
the SERPINE1 123 bp primers (SEQ ID: 16 and 17) at an MgCl$_2$ concentration of 3.5 mM and a temperature of 52.0° C.,
and subsequent dPCR. Cut-off value: <0.0012%; n.d. = no data due to the proportion of unmethylated DNA fragments
being too low. Raw data for FIG. 58.

| Pos. | Sample | Copies/ 20 μl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| D08 | GM12 | 1.6 | 1 | 14402 | 1 | 0 | 110 | 14292 | 14403 | | n.d. | 3508 |
| D08 | | 182 | 111 | 14292 | 1 | 0 | 110 | 14292 | 14403 | | | 3780 |
| E08 | GM13 | 0 | 0 | 15072 | 0 | 0 | 15067 | 5 | 15072 | 0 | 0 | 3508 |
| E08 | | 188000 | 15067 | 5 | 0 | 0 | 15067 | 5 | 15072 | | | 3780 |
| F08 | GM14 | 0 | 0 | 12834 | 0 | 0 | 12596 | 238 | 12834 | 0 | 0 | 3508 |
| F08 | | 93800 | 12596 | 238 | 0 | 0 | 12596 | 238 | 12834 | | | 3780 |
| G08 | GM15 | 0 | 0 | 15407 | 0 | 0 | 14642 | 765 | 15407 | 0 | 0 | 3508 |
| G08 | | 70600 | 14642 | 765 | 0 | 0 | 14642 | 765 | 15407 | | | 3780 |
| H08 | GM16 | 0 | 0 | 14278 | 0 | 0 | 12857 | 1421 | 14278 | 0 | 0 | 3508 |
| H08 | | 54200 | 12857 | 1421 | 0 | 0 | 12857 | 1421 | 14278 | | | 3780 |
| A09 | GM17 | 0 | 0 | 12396 | 0 | 0 | 1546 | 10850 | 12396 | 0 | 0 | 3508 |
| A09 | | 3140 | 1546 | 10850 | 0 | 0 | 1546 | 10850 | 12396 | | | 3780 |
| B09 | GM18 | 0 | 0 | 16490 | 0 | 0 | 9336 | 7154 | 16490 | 0 | 0 | 3508 |
| B09 | | 19640 | 9336 | 7154 | 0 | 0 | 9336 | 7154 | 16490 | | | 3780 |
| C09 | GM19 | 0 | 0 | 16559 | 0 | 0 | 12271 | 4288 | 16559 | 0 | 0 | 3508 |
| C09 | | 31800 | 12271 | 4288 | 0 | 0 | 12271 | 4288 | 16559 | | | 3780 |
| D09 | GM20 | 0 | 0 | 15035 | 0 | 0 | 12902 | 2133 | 15035 | 0 | 0 | 3508 |
| D09 | | 45940 | 12902 | 2133 | 0 | 0 | 12902 | 2133 | 15035 | | | 3780 |
| A10 | PPCa1 | 0 | 0 | 13235 | 0 | 0 | 9609 | 3626 | 13235 | 0 | 0 | 3508 |
| A10 | | 30460 | 9609 | 3626 | 0 | 0 | 9609 | 3626 | 13235 | | | 3780 |
| B10 | PPCa2 | 1.6 | 1 | 13988 | 1 | 0 | 13495 | 493 | 13989 | 2.1E−05 | 0.0021 | 3508 |
| B10 | | 78800 | 13496 | 493 | 1 | 0 | 13495 | 493 | 13989 | | | 3780 |
| C10 | PPCa3 | 20000000 | 14683 | 0 | 4147 | 10536 | 0 | 0 | 14683 | 2600 | 99.961 | 3508 |
| C10 | | 7800 | 4147 | 10536 | 4147 | 10536 | 0 | 0 | 14683 | | | 3780 |
| D10 | PPCa4 | 20000000 | 15104 | 0 | 19 | 15085 | 0 | 0 | 15104 | 680000 | 100 | 3508 |
| D10 | | 30 | 19 | 15085 | 19 | 15085 | 0 | 0 | 15104 | | | 3780 |
| E10 | PPCa5 | 30 | 18 | 14361 | 18 | 0 | 14335 | 26 | 14379 | 0.0002 | 0.02 | 3508 |
| E10 | | 148600 | 14353 | 26 | 18 | 0 | 14335 | 26 | 14379 | | | 3780 |
| F10 | PPCa6 | 1.6 | 1 | 14999 | 1 | 0 | 14951 | 48 | 15000 | 1.2E−05 | 0.0012 | 3508 |
| F10 | | 135200 | 14952 | 48 | 1 | 0 | 14951 | 48 | 15000 | | | 3780 |
| G10 | PPCa7 | 135400 | 14833 | 47 | 11752 | 3081 | 1 | 46 | 14880 | 3.69 | 78.7 | 3508 |
| G10 | | 36700 | 11753 | 3127 | 11752 | 3081 | 1 | 46 | 14880 | | | 3780 |
| H10 | PPCa8 | 56980 | 12597 | 1227 | 12556 | 41 | 1115 | 112 | 13824 | 0.538 | 35 | 3508 |
| H10 | | 106000 | 13671 | 153 | 12556 | 41 | 1115 | 112 | 13824 | | | 3780 |
| A11 | PPCa9 | 0 | 0 | 16071 | 0 | 0 | 15879 | 192 | 16071 | 0 | 0 | 3508 |
| A11 | | 104200 | 15879 | 192 | 0 | 0 | 15879 | 192 | 16071 | | | 3780 |
| B11 | PPCa10 | 0 | 0 | 15132 | 0 | 0 | 14281 | 851 | 15132 | 0 | 0 | 3508 |
| B11 | | 67800 | 14281 | 851 | 0 | 0 | 14281 | 851 | 15132 | | | 3780 |
| C11 | PPCa11 | 766 | 376 | 11348 | 376 | 0 | 10945 | 403 | 11724 | 0.0097 | 0.96 | 3508 |
| C11 | | 79400 | 11321 | 403 | 376 | 0 | 10945 | 403 | 11724 | | | 3780 |
| D11 | PPCa12 | 384 | 219 | 13304 | 63 | 156 | 918 | 12386 | 13523 | 0.217 | 17.8 | 3508 |
| D11 | | 1780 | 981 | 12542 | 63 | 156 | 918 | 12386 | 13523 | | | 3780 |
| E11 | PPCa13 | 70 | 42 | 13912 | 41 | 1 | 12039 | 1873 | 13954 | 0.0015 | 0.15 | 3508 |
| E11 | | 47240 | 12080 | 1874 | 41 | 1 | 12039 | 1873 | 13954 | | | 3780 |
| F11 | PPCa14 | 3.4 | 2 | 14113 | 2 | 0 | 14049 | 64 | 14115 | 2.6E−05 | 0.0026 | 3508 |
| F11 | | 127000 | 14051 | 64 | 2 | 0 | 14049 | 64 | 14115 | | | 3780 |
| G11 | PPCa15 | 0 | 0 | 15448 | 0 | 0 | 15138 | 310 | 15448 | 0 | 0 | 3508 |
| G11 | | 92000 | 15138 | 310 | 0 | 0 | 15138 | 310 | 15448 | | | 3780 |
| H11 | PPCa16 | 0 | 0 | 13649 | 0 | 0 | 13583 | 66 | 13649 | 0 | 0 | 3508 |
| H11 | | 125400 | 13583 | 66 | 0 | 0 | 13583 | 66 | 13649 | | | 3780 |
| E09 | PPCa17 | 18.8 | 13 | 16318 | 8 | 5 | 1868 | 14450 | 16331 | 0.0065 | 0.65 | 3508 |
| E09 | | 2880 | 1876 | 14455 | 8 | 5 | 1868 | 14450 | 16331 | | | 3780 |
| F09 | PPCa18 | 0 | 0 | 16149 | 0 | 0 | 15886 | 263 | 16149 | 0 | 0 | 3508 |
| F09 | | 96800 | 15886 | 263 | 0 | 0 | 15886 | 263 | 16149 | | | 3780 |
| G09 | PPCa19 | 0 | 0 | 14312 | 0 | 0 | 10027 | 4285 | 14312 | 0 | 0 | 3508 |
| G09 | | 28380 | 10027 | 4285 | 0 | 0 | 10027 | 4285 | 14312 | | | 3780 |
| H09 | PPCa20 | 0 | 0 | 15428 | 0 | 0 | 14086 | 1342 | 15428 | 0 | 0 | 3508 |
| H09 | | 57400 | 14086 | 1342 | 0 | 0 | 14086 | 1342 | 15428 | | | 3780 |
| G06 | 50 gDNA | 0 | 0 | 14576 | 0 | 0 | 3 | 14573 | 14576 | 0 | 0 | 3508 |
| G06 | | 4.8 | 3 | 14573 | 0 | 0 | 3 | 14573 | 14576 | | | 3780 |
| H06 | 50 NTC | 0 | 0 | 14603 | 0 | 0 | 3 | 14600 | 14603 | 0 | 0 | 3508 |
| H06 | | 4.8 | 3 | 14600 | 0 | 0 | 3 | 14600 | 14603 | | | 3780 |

TABLE 17

FAM signals (methylated AOX1 DNA fragments) and HEX signals (unmethylated AOX1 DNA fragments) in serum samples from healthy subjects (GF1-GF20), serum samples from female breast cancer patients (MF1-MF20) and non-template control (NTC, no DNA or genomic DNA, without bisulphite conversion) after 15 BBPA cycles using the AOX1 138 bp primers (SEQ ID: 18 and 19) at an MgCl$_2$ concentration of 2.5 mM and a temperature of 50.0° C., and subsequent dPCR. Cut-off value: <3.2% Raw data for FIG. 59.

| Pos. | Sample | Copies/ 20 µl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| A01 | GM1 | 0 | 0 | 12775 | 0 | 0 | 6165 | 6610 | 12775 | 0 | 0 | 2946 |
| A01 |  | 15500 | 6165 | 6610 | 0 | 0 | 6165 | 6610 | 12775 |  |  | 4102 |
| B01 | GM2 | 0 | 0 | 12119 | 0 | 0 | 2097 | 10022 | 12119 | 0 | 0 | 2946 |
| B01 |  | 4480 | 2097 | 10022 | 0 | 0 | 2097 | 10022 | 12119 |  |  | 4102 |
| C01 | GM3 | 0 | 0 | 12749 | 0 | 0 | 4875 | 7874 | 12749 | 0 | 0 | 2946 |
| C01 |  | 11340 | 4875 | 7874 | 0 | 0 | 4875 | 7874 | 12749 |  |  | 4102 |
| D01 | GM4 | 0 | 0 | 13129 | 0 | 0 | 10076 | 3053 | 13129 | 0 | 0 | 2946 |
| D01 |  | 34320 | 10076 | 3053 | 0 | 0 | 10076 | 3053 | 13129 |  |  | 4102 |
| E01 | GM5 | 0 | 0 | 13716 | 0 | 0 | 10633 | 3083 | 13716 | 0 | 0 | 2946 |
| E01 |  | 35120 | 10633 | 3083 | 0 | 0 | 10633 | 3083 | 13716 |  |  | 4102 |
| F01 | GM6 | 0 | 0 | 14337 | 0 | 0 | 8638 | 5699 | 14337 | 0 | 0 | 2946 |
| F01 |  | 21700 | 8638 | 5699 | 0 | 0 | 8638 | 5699 | 14337 |  |  | 4102 |
| G01 | GM7 | 1.6 | 1 | 15201 | 1 | 0 | 4846 | 10355 | 15202 | 0.00017 | 0.017 | 2946 |
| G01 |  | 9040 | 4847 | 10355 | 1 | 0 | 4846 | 10355 | 15202 |  |  | 4102 |
| H01 | GM8 | 0 | 0 | 13459 | 0 | 0 | 4734 | 8725 | 13459 | 0 | 0 | 2946 |
| H01 |  | 10200 | 4734 | 8725 | 0 | 0 | 4734 | 8725 | 13459 |  |  | 4102 |
| A02 | GM9 | 84 | 36 | 10028 | 12 | 24 | 6311 | 3717 | 10064 | 0.0036 | 0.36 | 2946 |
| A02 |  | 23280 | 6323 | 3741 | 12 | 24 | 6311 | 3717 | 10064 |  |  | 4102 |
| B02 | GM10 | 0 | 0 | 10929 | 0 | 0 | 9009 | 1920 | 10929 | 0 | 0 | 2946 |
| B02 |  | 40920 | 9009 | 1920 | 0 | 0 | 9009 | 1920 | 10929 |  |  | 4102 |
| C02 | GM11 | 1.6 | 1 | 14000 | 0 | 1 | 6620 | 7380 | 14001 | 0.00011 | 0.011 | 2946 |
| C02 |  | 15060 | 6620 | 7381 | 0 | 1 | 6620 | 7380 | 14001 |  |  | 4102 |
| D02 | GM12 | 282 | 136 | 11314 | 24 | 112 | 3455 | 7859 | 11450 | 0.033 | 3.2 | 2946 |
| D02 |  | 8520 | 3479 | 7971 | 24 | 112 | 3455 | 7859 | 11450 |  |  | 4102 |
| E02 | GM13 | 0 | 0 | 12943 | 0 | 0 | 8381 | 4562 | 12943 | 0 | 0 | 2946 |
| E02 |  | 24540 | 8381 | 4562 | 0 | 0 | 8381 | 4562 | 12943 |  |  | 4102 |
| F02 | GM14 | 8 | 4 | 11691 | 0 | 4 | 3261 | 8430 | 11695 | 0.001 | 0.1 | 2946 |
| F02 |  | 7700 | 3261 | 8434 | 0 | 4 | 3261 | 8430 | 11695 |  |  | 4102 |
| G02 | GM15 | 0 | 0 | 12712 | 0 | 0 | 3386 | 9326 | 12712 | 0 | 0 | 2946 |
| G02 |  | 7280 | 3386 | 9326 | 0 | 0 | 3386 | 9326 | 12712 |  |  | 4102 |
| H02 | GM16 | 274 | 123 | 10496 | 26 | 97 | 4435 | 6061 | 10619 | 0.0214 | 2.09 | 2946 |
| H02 |  | 12820 | 4461 | 6158 | 26 | 97 | 4435 | 6061 | 10619 |  |  | 4102 |
| A03 | GM17 | 0 | 0 | 12345 | 0 | 0 | 2934 | 9411 | 12345 | 0 | 0 | 2946 |
| A03 |  | 6380 | 2934 | 9411 | 0 | 0 | 2934 | 9411 | 12345 |  |  | 4102 |
| B03 | GM18 | 0 | 0 | 12222 | 0 | 0 | 3388 | 8834 | 12222 | 0 | 0 | 2946 |
| B03 |  | 7640 | 3388 | 8834 | 0 | 0 | 3388 | 8834 | 12222 |  |  | 4102 |
| C03 | GM19 | 0 | 0 | 11851 | 0 | 0 | 5087 | 6764 | 11851 | 0 | 0 | 2946 |
| C03 |  | 13200 | 5087 | 6764 | 0 | 0 | 5087 | 6764 | 11851 |  |  | 4102 |
| C03 | GM20 | 0 | 0 | 10021 | 0 | 0 | 97 | 9924 | 10021 | 0 | 0 | 2946 |
| C03 |  | 228 | 97 | 9924 | 0 | 0 | 97 | 9924 | 10021 |  |  | 4102 |
| A04 | PPCa1 | 0 | 0 | 11521 | 0 | 0 | 921 | 10600 | 11521 | 0 | 0 | 2946 |
| A04 |  | 1960 | 921 | 10600 | 0 | 0 | 921 | 10600 | 11521 |  |  | 4102 |
| B04 | PPCa2 | 34 | 18 | 12312 | 3 | 15 | 2476 | 9836 | 12330 | 0.0065 | 0.65 | 2946 |
| B04 |  | 5280 | 2479 | 9851 | 3 | 15 | 2476 | 9836 | 12330 |  |  | 4102 |
| C04 | PPCa3 | 50080 | 10976 | 1483 | 114 | 10862 | 216 | 1267 | 12459 | 79 | 98.75 | 2946 |
| C04 |  | 632 | 330 | 12129 | 114 | 10862 | 216 | 1267 | 12459 |  |  | 4102 |
| C04 | PPCa4 | 670 | 341 | 11814 | 1 | 340 | 487 | 11327 | 12155 | 0.69 | 41 | 2946 |
| C04 |  | 964 | 488 | 11667 | 1 | 340 | 487 | 11327 | 12155 |  |  | 4102 |
| E04 | PPCa5 | 0 | 0 | 11024 | 0 | 0 | 445 | 10579 | 11024 | 0 | 0 | 2946 |
| E04 |  | 970 | 445 | 10579 | 0 | 0 | 445 | 10579 | 11024 |  |  | 4102 |
| F04 | PPCa6 | 188 | 96 | 11922 | 26 | 70 | 9738 | 2184 | 12018 | 0.0048 | 0.48 | 2946 |
| F04 |  | 39380 | 9764 | 2254 | 26 | 70 | 9738 | 2184 | 12018 |  |  | 4102 |
| G04 | PPCa7 | 3760 | 1605 | 9243 | 38 | 1567 | 2960 | 6283 | 10848 | 0.495 | 33.1 | 2946 |
| G04 |  | 7620 | 2998 | 7850 | 38 | 1567 | 2960 | 6283 | 10848 |  |  | 4102 |
| H04 | PPCa8 | 27180 | 8330 | 3833 | 640 | 7690 | 1347 | 2486 | 12163 | 6.47 | 86.6 | 2946 |
| H04 |  | 4200 | 1987 | 10176 | 640 | 7690 | 1347 | 2486 | 12163 |  |  | 4102 |
| A05 | PPCa9 | 0 | 0 | 12275 | 0 | 0 | 4339 | 7936 | 12275 | 0 | 0 | 2946 |
| A05 |  | 10260 | 4339 | 7936 | 0 | 0 | 4339 | 7936 | 12275 |  |  | 4102 |
| B05 | PPCa10 | 0 | 0 | 12250 | 0 | 0 | 3684 | 8566 | 12250 | 0 | 0 | 2946 |
| B05 |  | 8420 | 3684 | 8566 | 0 | 0 | 3684 | 8566 | 12250 |  |  | 4102 |
| C05 | PPCa11 | 60800 | 13449 | 1094 | 894 | 12555 | 172 | 922 | 14543 | 34 | 97.14 | 2946 |
| C05 |  | 1800 | 1066 | 13477 | 894 | 12555 | 172 | 922 | 14543 |  |  | 4102 |
| D05 | PPCa12 | 1750 | 1018 | 13185 | 41 | 977 | 2474 | 10711 | 14203 | 0.382 | 27.6 | 2946 |
| D05 |  | 4580 | 2515 | 11688 | 41 | 977 | 2474 | 10711 | 14203 |  |  | 4102 |
| E05 | PPCa13 | 0 | 0 | 11674 | 0 | 0 | 710 | 10964 | 11674 | 0 | 0 | 2946 |
| E05 |  | 1480 | 710 | 10964 | 0 | 0 | 710 | 10964 | 11674 |  |  | 4102 |
| F05 | PPCa14 | 714 | 403 | 13078 | 74 | 329 | 5960 | 7118 | 13481 | 0.051 | 4.87 | 2946 |
| F05 |  | 13960 | 6034 | 7447 | 74 | 329 | 5960 | 7118 | 13481 |  |  | 4102 |
| G05 | PPCa15 | 0 | 0 | 13606 | 0 | 0 | 382 | 13224 | 13606 | 0 | 0 | 2946 |
| G05 |  | 670 | 382 | 13224 | 0 | 0 | 382 | 13224 | 13606 |  |  | 4102 |
| H05 | PPCa16 | 0 | 0 | 13111 | 0 | 0 | 4457 | 8654 | 13111 | 0 | 0 | 2946 |

TABLE 17-continued

FAM signals (methylated AOX1 DNA fragments) and HEX signals (unmethylated AOX1 DNA fragments) in
serum samples from healthy subjects (GF1-GF20), serum samples from female breast cancer patients (MF1-MF20)
and non-template control (NTC, no DNA or genomic DNA, without bisulphite conversion) after 15 BBPA cycles
using the AOX1 138 bp primers (SEQ ID: 18 and 19) at an $MgCl_2$ concentration of 2.5 mM and a temperature
of 50.0° C., and subsequent dPCR. Cut-off value: <3.2% Raw data for FIG. 59.

| Pos. | Sample | Copies/ 20 μl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| H05 | | 9780 | 4457 | 8654 | 0 | 0 | 4457 | 8654 | 13111 | | | 4102 |
| A06 | PPCa17 | 2440 | 1261 | 11550 | 34 | 1227 | 1063 | 10487 | 12811 | 1.16 | 53.7 | 2946 |
| A06 | | 2100 | 1097 | 11714 | 34 | 1227 | 1063 | 10487 | 12811 | | | 4102 |
| B06 | PPCa18 | 0 | 0 | 12831 | 0 | 0 | 3704 | 9127 | 12831 | 0 | 0 | 2946 |
| B06 | | 8020 | 3704 | 9127 | 0 | 0 | 3704 | 9127 | 12831 | | | 4102 |
| C06 | PPCa19 | 1.6 | 1 | 14781 | 0 | 1 | 4803 | 9978 | 14782 | 0.00017 | 0.017 | 2946 |
| C06 | | 9240 | 4803 | 9979 | 0 | 1 | 4803 | 9978 | 14782 | | | 4102 |
| D06 | PPCa20 | 0 | 0 | 14244 | 0 | 0 | 1678 | 12566 | 14244 | 0 | 0 | 2946 |
| D06 | | 2940 | 1678 | 12566 | 0 | 0 | 1678 | 12566 | 14244 | | | 4102 |
| E03 | 15 gDNA | 0 | 0 | 13787 | 0 | 0 | 63 | 13724 | 13787 | 0 | 0 | 2946 |
| E03 | | 108 | 63 | 13724 | 0 | 0 | 63 | 13724 | 13787 | | | 4102 |
| F03 | 15 NTC | 0 | 0 | 14654 | 0 | 0 | 84 | 14570 | 14654 | 0 | 0 | 2946 |
| F03 | | 136 | 84 | 14570 | 0 | 0 | 84 | 14570 | 14654 | | | 4102 |

TABLE 18

FAM signals (methylated AOX1 DNA fragments) and HEX signals (unmethylated AOX1 DNA fragments) in serum
samples from healthy subjects (GF1-GF20), serum samples from female breast cancer patients (MF1-MF20) and non-
template control (NTC, no DNA or genomic DNA, without bisulphite conversion) after 30 BBPA cycles using the
AOX1 138 bp primers (SEQ ID: 18 and 19) at an $MgCl_2$ concentration of 2.5 mM and a temperature of 50.0° C., and
subsequent dPCR. Cut-off value: <0.008%. Raw data for FIG. 60.

| Pos. | Sample | Copies/ 20 μl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| A07 | GM1 | 0 | 0 | 13363 | 0 | 0 | 12829 | 534 | 13363 | 0 | 0 | 2522 |
| A07 | | 75800 | 12829 | 534 | 0 | 0 | 12829 | 534 | 13363 | | | 4026 |
| B07 | GM2 | 1.8 | 1 | 13210 | 0 | 1 | 7853 | 5357 | 13211 | 8.00E−05 | 0.008 | 2522 |
| B07 | | 21240 | 7853 | 5358 | 0 | 1 | 7853 | 5357 | 13211 | | | 4026 |
| C07 | GM3 | 0 | 0 | 13321 | 0 | 0 | 11436 | 1885 | 13321 | 0 | 0 | 2522 |
| C07 | | 46000 | 11436 | 1885 | 0 | 0 | 11436 | 1885 | 13321 | | | 4026 |
| D07 | GM4 | 0 | 0 | 13023 | 0 | 0 | 12677 | 346 | 13023 | 0 | 0 | 2522 |
| D07 | | 85400 | 12677 | 346 | 0 | 0 | 12677 | 346 | 13023 | | | 4026 |
| E07 | GM5 | 0 | 0 | 13143 | 0 | 0 | 12216 | 927 | 13143 | 0 | 0 | 2522 |
| E07 | | 62400 | 12216 | 927 | 0 | 0 | 12216 | 927 | 13143 | | | 4026 |
| F07 | GM6 | 0 | 0 | 12889 | 0 | 0 | 7603 | 5286 | 12889 | 0 | 0 | 2522 |
| F07 | | 20980 | 7603 | 5286 | 0 | 0 | 7603 | 5286 | 12889 | | | 4026 |
| G07 | GM7 | 0 | 0 | 12650 | 0 | 0 | 12048 | 602 | 12650 | 0 | 0 | 2522 |
| G07 | | 71600 | 12048 | 602 | 0 | 0 | 12048 | 602 | 12650 | | | 4026 |
| H07 | GM8 | 0 | 0 | 12586 | 0 | 0 | 12099 | 487 | 12588 | 0 | 0 | 2522 |
| H07 | | 76600 | 12099 | 487 | 0 | 0 | 12099 | 487 | 12586 | | | 4026 |
| A08 | GM9 | 0 | 0 | 12154 | 0 | 0 | 11019 | 1135 | 12154 | 0 | 0 | 2522 |
| A08 | | 55800 | 11019 | 1135 | 0 | 0 | 11019 | 1135 | 12154 | | | 4026 |
| B08 | GM10 | 0 | 0 | 13926 | 0 | 0 | 13704 | 222 | 13926 | 0 | 0 | 2522 |
| B08 | | 97400 | 13704 | 222 | 0 | 0 | 13704 | 222 | 13926 | | | 4026 |
| C08 | GM11 | 0 | 0 | 13333 | 0 | 0 | 8498 | 4835 | 13333 | 0 | 0 | 2522 |
| C08 | | 23860 | 8498 | 4835 | 0 | 0 | 8498 | 4835 | 13333 | | | 4026 |
| D08 | GM12 | 1.6 | 1 | 14130 | 1 | 0 | 13577 | 553 | 14131 | 2.2E−05 | 0.0022 | 2522 |
| D08 | | 76200 | 13578 | 553 | 1 | 0 | 13577 | 553 | 14131 | | | 4026 |
| E08 | GM13 | 0 | 0 | 12767 | 0 | 0 | 12491 | 276 | 12767 | 0 | 0 | 2522 |
| E08 | | 90200 | 12491 | 276 | 0 | 0 | 12491 | 276 | 12767 | | | 4026 |
| F08 | GM14 | 0 | 0 | 12841 | 0 | 0 | 5483 | 7358 | 12841 | 0 | 0 | 2522 |
| F08 | | 13100 | 5483 | 7358 | 0 | 0 | 5483 | 7358 | 12841 | | | 4026 |
| G08 | GM15 | 0 | 0 | 13297 | 0 | 0 | 12877 | 420 | 13297 | 0 | 0 | 2522 |
| G08 | | 81200 | 12877 | 420 | 0 | 0 | 12877 | 420 | 13297 | | | 4026 |
| H08 | GM16 | 1.6 | 1 | 13873 | 0 | 1 | 13246 | 627 | 13874 | 2.3E−05 | 0.0023 | 2522 |
| H08 | | 72800 | 13246 | 628 | 0 | 1 | 13246 | 627 | 13874 | | | 4026 |
| A09 | GM17 | 0 | 0 | 13562 | 0 | 0 | 831 | 12731 | 13562 | 0 | 0 | 2522 |
| A09 | | 1480 | 831 | 12731 | 0 | 0 | 831 | 12731 | 13562 | | | 4026 |
| B09 | GM18 | 0 | 0 | 14121 | 0 | 0 | 13408 | 713 | 14121 | 0 | 0 | 2522 |
| B09 | | 70200 | 13408 | 713 | 0 | 0 | 13408 | 713 | 14121 | | | 4026 |
| C09 | GM19 | 0 | 0 | 14979 | 0 | 0 | 14395 | 584 | 14979 | 0 | 0 | 2522 |
| C09 | | 76400 | 14395 | 584 | 0 | 0 | 14395 | 584 | 14979 | | | 4026 |
| D09 | GM20 | 0 | 0 | 13243 | 0 | 0 | 18 | 13225 | 13243 | 0 | 0 | 2522 |
| D09 | | 32 | 18 | 13225 | 0 | 0 | 18 | 13225 | 13243 | | | 4026 |
| E09 | PPCa1 | 0 | 0 | 13470 | 0 | 0 | 4 | 13466 | 13470 | 0 | 0 | 2522 |
| E09 | | 7 | 4 | 13466 | 0 | 0 | 4 | 13466 | 13470 | | | 4026 |
| F09 | PPCa2 | 1.6 | 1 | 14957 | 0 | 1 | 10789 | 4168 | 14958 | 5.00E−05 | 0.005 | 2522 |

TABLE 18-continued

FAM signals (methylated AOX1 DNA fragments) and HEX signals (unmethylated AOX1 DNA fragments) in serum samples from healthy subjects (GF1-GF20), serum samples from female breast cancer patients (MF1-MF20) and non-template control (NTC, no DNA or genomic DNA, without bisulphite conversion) after 30 BBPA cycles using the AOX1 138 bp primers (SEQ ID: 18 and 19) at an MgCl$_2$ concentration of 2.5 mM and a temperature of 50.0° C., and subsequent dPCR. Cut-off value: <0.008%. Raw data for FIG. 60.

| Pos. | Sample | Copies/ 20 µl | Positive | Negative | Ch1+ Ch2+ | Ch1+ Ch2− | Ch1− Ch2+ | Ch1− Ch2− | Number of droplets | Ratio | Fractional abundance | Threshold |
|---|---|---|---|---|---|---|---|---|---|---|---|---|
| F09 | | 30060 | 10789 | 4169 | 0 | 1 | 10789 | 4168 | 14958 | | | 4026 |
| G09 | PPCa3 | 20000000 | 14287 | 0 | 2 | 14285 | 0 | 0 | 14287 | 1000000 | 100 | 2522 |
| G09 | | 3.2 | 2 | 14285 | 2 | 14285 | 0 | 0 | 14287 | | | 4026 |
| H09 | PPCa4 | 74200 | 13824 | 619 | 4240 | 9584 | 0 | 619 | 14443 | 9.06 | 90.06 | 2522 |
| H09 | | 8180 | 4240 | 10203 | 4240 | 9584 | 0 | 619 | 14443 | | | 4026 |
| E10 | PPCa5 | 0 | 0 | 13312 | 0 | 0 | 5568 | 7744 | 13312 | 0 | 0 | 2522 |
| E10 | | 12740 | 5568 | 7744 | 0 | 0 | 5568 | 7744 | 13312 | | | 4026 |
| F10 | PPCa6 | 1.6 | 1 | 15410 | 0 | 1 | 15331 | 79 | 15411 | 1.2E−05 | 0.0012 | 2522 |
| F10 | | 123800 | 15331 | 80 | 0 | 1 | 15331 | 79 | 15411 | | | 4026 |
| G10 | PPCa7 | 79200 | 14676 | 523 | 13689 | 987 | 124 | 399 | 15199 | 1.407 | 58.5 | 2522 |
| G10 | | 56400 | 13813 | 1386 | 13689 | 987 | 124 | 399 | 15199 | | | 4026 |
| H10 | PPCa8 | 145600 | 14096 | 29 | 183 | 13913 | 0 | 29 | 14125 | 470 | 99.79 | 2522 |
| H10 | | 306 | 183 | 13942 | 183 | 13913 | 0 | 29 | 14125 | | | 4026 |
| A11 | PPCa9 | 0 | 0 | 14180 | 0 | 0 | 12203 | 1977 | 14180 | 0 | 0 | 2522 |
| A11 | | 46360 | 12203 | 1977 | 0 | 0 | 12203 | 1977 | 14180 | | | 4026 |
| B11 | PPCa10 | 0 | 0 | 15288 | 0 | 0 | 13636 | 1652 | 15288 | 0 | 0 | 2522 |
| B11 | | 52400 | 13636 | 1652 | 0 | 0 | 13636 | 1652 | 15288 | | | 4026 |
| C11 | PPCa11 | 228000 | 15823 | 1 | 24 | 15799 | 0 | 1 | 15824 | 6400 | 99.984 | 2522 |
| C11 | | 36 | 24 | 15800 | 24 | 15799 | 0 | 1 | 15824 | | | 4026 |
| D11 | PPCa02 | 62280 | 15829 | 1207 | 11567 | 4262 | 95 | 1112 | 17036 | 229 | 69.6 | 2522 |
| D11 | | 27140 | 11662 | 5374 | 11567 | 4262 | 95 | 1112 | 17036 | | | 4026 |
| E11 | PPCa03 | 1.4 | 1 | 16189 | 0 | 1 | 1474 | 14715 | 16190 | 0.0006 | 0.06 | 2522 |
| E11 | | 2240 | 1474 | 14716 | 0 | 1 | 1474 | 14715 | 16190 | | | 4026 |
| F11 | PPCa04 | 0 | 0 | 16641 | 0 | 0 | 16278 | 363 | 16641 | 0 | 0 | 2522 |
| F11 | | 90000 | 16278 | 363 | 0 | 0 | 16278 | 363 | 16641 | | | 4026 |
| G11 | PPCa05 | 0 | 0 | 16513 | 0 | 0 | 12586 | 3927 | 16513 | 0 | 0 | 2522 |
| G11 | | 33800 | 12586 | 3927 | 0 | 0 | 12586 | 3927 | 16513 | | | 4026 |
| H11 | PPCa06 | 0 | 0 | 14607 | 0 | 0 | 8223 | 6384 | 14607 | 0 | 0 | 2522 |
| H11 | | 19480 | 8223 | 6384 | 0 | 0 | 8223 | 6384 | 14607 | | | 4026 |
| A10 | PPCa17 | 11640 | 5373 | 8388 | 6 | 5367 | 1 | 8387 | 13761 | 1000 | 99.9 | 2522 |
| A10 | | 12 | 7 | 13754 | 6 | 5367 | 1 | 8387 | 13761 | | | 4026 |
| B10 | PPCa18 | 0 | 0 | 14246 | 0 | 0 | 11148 | 3098 | 14246 | 0 | 0 | 2522 |
| B10 | | 35900 | 11148 | 3098 | 0 | 0 | 11148 | 3098 | 14246 | | | 4026 |
| C10 | PPCa19 | 0 | 0 | 14141 | 0 | 0 | 13102 | 1039 | 14141 | 0 | 0 | 2522 |
| C10 | | 61400 | 13102 | 1039 | 0 | 0 | 13102 | 1039 | 14141 | | | 4026 |
| D10 | PPCa20 | 0 | 0 | 15013 | 0 | 0 | 13431 | 1582 | 15013 | 0 | 0 | 2522 |
| D10 | | 53000 | 13431 | 1582 | 0 | 0 | 13431 | 1582 | 15013 | | | 4026 |
| G06 | 30 gDNA | 0 | 0 | 15273 | 0 | 0 | 5 | 15268 | 15273 | 0 | 0 | 2522 |
| G06 | | 7.8 | 5 | 15268 | 0 | 0 | 5 | 15268 | 15273 | | | 4026 |
| H06 | 30 NTC | 0 | 0 | 14501 | 0 | 0 | 2 | 14499 | 14501 | 0 | 0 | 2522 |
| H06 | | 3.2 | 2 | 14499 | 0 | 0 | 2 | 14499 | 14501 | | | 4026 |

Embodiment 11: Distinguishing Between Benign Prostatic Hyperplasia and Prostate Cancer Since a basic prerequisite for screening and associated precautionary examinations for tumour diseases is being able to reliably distinguish between benign and malignant diseases, i.e. analytical and diagnostic specificity has to be almost 100%, the benign prostatic hyperplasia cell line BPH-1 was analysed using various PLA2R1 primer pairs alongside normal PrEC cells and malignant prostate cell lines (LNCaP, PC-3 and DU-145). After 50 pre-amplification cycles using an MgCl$_2$ concentration of 2.5 mM and the PLA2R1 primer pair 168 bp, it was found that the level of the FAM and HEX signals according to the annealing temperature remained constant, i.e. there was no bias (FIG. 46). This correlates with the results obtained when 50% standard DNA samples were tested (FIG. 34). By contrast, a clear bias in favour of methylated sequences, noticeable on the basis of increasing FAM signals for the PC-3 cell line, occurred from a temperature of 58.2° C. when the PLA2R1 primer pair 161 bp was used and from a temperature of 50.8° C. when the PLA2R1 primer pair 150 bp was used (FIGS. 47 and 48). Particularly strong bias was already noted for the PLA2R1 primer pair 133 bp at an annealing temperature of 50.0° C. (FIG. 49). In this case, however, increasing numbers of artefacts occurred (i.e. false-positive signals) once the temperature passed 52.6° C. since elevated FAM signals were measured for the normal PrEC and BPH-1 cell lines and the values could not be distinguished from those of malignant prostate cell lines (FIG. 49). It can thus be concluded that a maximum annealing temperature of 52.6° C. should be selected for an MgCl$_2$ concentration of 2.5 mM and this primer pair. At higher annealing temperatures, e.g. 63.0° C., an alternative would be to increase the MgCl$_2$ concentration to 6.0 mM, since this can prevent false-positive signals from occurring (see Tables 28 and 30 and FIGS. 38-45).

A similar phenomenon was noted for the primer pair GSTP1 120 bp, whereby greater numbers of false-positive signals were produced as the annealing temperature was increased with an MgCl$_2$ concentration of 2.5 mM (FIG. 50). In this case, artefacts, i.e. false-positive values, also occurred above an annealing temperature of 60.8° C. Here too, the occurrence of false-positive signals as the annealing temperature increased can be prevented by increasing the MgCl$_2$ concentration and thus significantly higher diagnostic specificities can be achieved.

The observation that the signals approached 0% in healthy samples and 100% in tumour patient samples as the number of pre-amplification cycles was increased, resulting in a reliable distinction between healthy and diseased subjects, was also noted in the example of GSTP1 methylation in samples having 0% and 50% methylated standard DNA (FIGS. 51 and 52). Whereas non-specific signals from the 0% standard DNA sample occurred at 20 cycles when the GSTP1 120 bp primer pair was used, these completely disappeared after 50 cycles (FIG. 51). By contrast, the intensity of the specific FAM signals in the 50% sample increased as the cycle number rose at MgCl$_2$ concentrations of 1.5-2.5 mM (FIG. 51). The fact that this phenomenon is highly dependent on the primer design and MgCl$_2$ concentration was also apparent from the example of the GSTP1 116 bp primer pair. In this case, the FAM signal intensity dropped after more than 20 cycles when the MgCl$_2$ concentration was greater than 2.5 mM (FIG. 52). For this reason, the number of pre-amplification cycles for this primer pair should be limited to 20 if an MgCl$_2$ concentration of between 2.5 and 6.0 mM is used. Alternatively, the MgCl$_2$ concentration can be reduced to 1.5 mM and the cycle number increased accordingly (FIG. 52).

Additionally, in the case of the GSTP1 116 bp primer pair in serum samples from female breast cancer patients, it was found that the diagnostic sensitivity and specificity rose considerably when the MgCl$_2$ concentration was increased to 4.5 mM in the BBPA instead of 1.5 mM (FIGS. 53 and 54). Whereas 4 out of 20 female breast cancer patients were correctly identified at an MgCl$_2$ concentration of 1.5 mM, this number rose to 6 when 4.5 mM MgCl$_2$ was used; however, the proportion of unmethylated DNA fragments also rose at the higher MgCl$_2$ concentration. The latter case can be used as an ideal internal control under these conditions, which was not the case at an MgCl$_2$ concentration of 1.5 mM.

In another test carried out on serum samples from PCa patients, improved diagnostic sensitivity and specificity was found when, under optimum conditions (4.5 mM MgCl$_2$ and an annealing temperature of 53.8° C.), the GSTP1 116 bp primer pair was compared with the GSTP1 120 bp primer pair (2.5 mM MgCl$_2$ and an annealing temperature of 50.7° C.). In this case, 13 out of the group of 20 PCa patients were correctly identified using the GSTP1 116 bp primer pair, without any of the 20 healthy subjects being erroneously identified as being diseased, whereas 8 were correctly identified as suffering from PCa using the GSTP1 120 bp primer pair (FIGS. 55 and 56; Tables 13 and 14). At the same time, when using the GSTP1 120 bp primer pair, positive signals that were negative in the tests using the GSTP1 116 bp primer pair were noted in the serum samples from patients PPCa13 and 20, and so the diagnostic sensitivity of the test can be increased by using the two primer pairs, either separately in two different BBPA-dPCR batches or simultaneously in one batch.

When using the BBPA-dPCR technique for the targets of interest SERPINE1 and AOX1, it was noted that, as already described at the beginning for the RASSF1A 117 bp primer pair, using 50 BBPA cycles (in the case of the SERPINE1 primer pair in particular) and 30 cycles (in the case of the AOX1 primer pair) instead of 15 led to significantly improved identification of PCa patients against healthy subjects in the subsequent dPCR. In the process, no redundant results were produced by the two numbers of cycles, but rather complementary results were produced (FIG. 57-60; Tables 15-18). This means that the sensitivity and specificity of the method can also be further increased by simultaneously using different numbers of BBPA cycles, e.g. 15 and 30, or 15 and 50 cycles. For example, some of the sample material can be removed after e.g. 15 BBPA cycles and the remaining sample material can be pre-amplified in the BBPA for an additional 35 cycles (a total of 50 cycles). If there is sufficient test material available, the patient samples can also be pre-amplified separately in the BBPA for 15 and 30 or 15 and 50 cycles in order to minimise the samples potentially being contaminated.

To verify whether the novel BBPA-dPCR technique is capable of distinguishing between healthy subjects, BPH and PCa for the purposes of differential diagnosis by determining methylated DNA fragments in PLA2R1, RASSF1A, GSTP1 and PAI1 genes, and thus of supporting the question of whether to indicate a tissue biopsy, 20 serum samples each from healthy subjects, BPH patients and PCa patients were analysed. Patient samples for the two groups that did not significantly differ in terms of the PSA serum concentrations were analysed, the PSA values being within the critical range between 2 and 15 ng/ml (p<0.552; FIG. 61). A differential diagnosis between BPH and PCa was also not possible on the basis of the quotient of free PSA to total PSA (reference value >20%) in patients (Table 19).

In 20 serum samples from healthy subjects, i.e. without BPH or PCa diseases, there were only small proportions of methylated DNA fragments; these proportions were then used as cut-off values (PLA2R1<0.11%; RASSF1A<0.11%; GSTP1<0.05% and SERPINE1<0.13%). On the basis of these values, no elevated values could be detected in 11 patients out of the group of 20 BPH patients. Up to today, i.e. two years after the blood was taken and tissue biopsy carried out, these 11 patients do not have PCa (Table 19; as at 15 Dec. 2016). By contrast, methylated tumour DNA for at least one of the four genes tested was detected in 13 serum samples, and all these patients did indeed have PCa (Table 19).

In 9 out of the 20 serum samples from the BPH group, methylated tumour DNA was also identified for at least one of the four genes tested. In four of these BPH patients (patients BPH14, BPH15, BPH17 and BPH18), a PCa developed in the time after the blood was taken and subsequent tests.

For example, a PCa was detected in patient BPH14 in October 2016, despite no malignant cells having been found in two prostate biopsies in 2014 and August 2016. In the BBPA-dPCR analysis, tumour DNA for RASSF1A and GSTP1 was found in the serum sample as early as in October 2014 (Table 19).

In two other BPH patients (BPH15 and BPH17), prostate cancers in stage IIa were found in November 2014 after TURP and biopsy, respectively. Tumour DNA for GSTP1 and SERPINE1 could already be detected in the serum samples two and four months previously, respectively. In patient BPH17, the quotient of free PSA to total PSA was 40.2% and was thus clearly above the cut-off value of 20%; nonetheless, the patient developed a PCa, which was reliably suggested three months earlier by significantly elevated proportions of methylated GSTP1 and SERPINE1 DNA fragments of 9% (normal <0.05%) and 31.7% (normal <0.13%), respectively.

In patient BPH18, blood was taken and a tissue biopsy carried out in August 2014 as a result of an increase in PSA. In the material provided, the histology showed no indication of intraepithelial neoplasia/dysplasia or malignancy. The QfPSA/PSA was above the cut-off value at 22.5%. Since the PSA had doubled within a year to 13.9 ng/ml, a further biopsy was carried out in September 2015, with malignancy again being ruled out on the basis of a repeat needle biopsy. In July 2016, the patient given emergency treatment for acute urinary retention and prostatic hyperplasia requiring an indwelling catheter, and a PCa was finally discovered following a TURP carried out in September 2016. Interestingly, the blood sample from August 2014, i.e. two years earlier, already showed a significant proportion of methylated SERPINE1 DNA fragments (11.4% against a cut-off value of 0.13%) (Table 19).

In the case of the patient BPH16, from whom blood was taken and on whom a biopsy was also carried out in 2014, the histology did not give any indication of intraepithelial neoplasia/dysplasia or malignancy. At 12.9%, the QfPSA/PSA was nonetheless below the cut-off value of 20%. In March 2016, another biopsy was carried out; the biopsy needle showed small foci of high-grade prostatic intraepithelial neoplasia (HGPIN) and so another tissue biopsy was recommended in six months. This is yet to take place. For this patient too, the BBPA-dPCR technique already showed elevated values for all four genes tested in the September 2014 serum sample (Table 19).

Elevated values for all four genes were also found in the October 2014 serum sample for patient BPH12, for whom a TURP was carried out at the same time and atypical adenomatous hyperplasia (AAH) was detected in the test material provided (chips), though no cancer.

For patient BPH13, whose October 2014 serum sample showed significantly elevated numbers of methylated GSTP1 gene fragments, a prostate biopsy also carried out in October 2014 found isolated glandular proliferations of unknown malignancy status. In the subsequent tests, no racemase overexpression could be detected, and so neither could PCa. In February 2016, this patient underwent a TURP owing to a prostatic hyperplasia requiring an indwelling catheter. Isolated glandular proliferations of unknown malignancy status were also identified in this case too, although subsequent tests did not identify any PCa (Table 19).

In patients BPH19 and BPH20, for whom elevated numbers of methylated DNA fragments for all four genes could be identified in the serum, the histology reports showed suspicious findings following the TURP and prostate biopsy, respectively, even though no PCa had been unambiguously detectable previously in both cases (Table 19).

In summary, the values obtained in all 20 healthy subjects using the BBPA-dPCR technique were below the set cut-off values and so no false-positive signals were obtained in any of the cases (100% diagnostic specificity). In the group of 20 PCa patients, 13 were correctly identified as positive (65% diagnostic sensitivity). In the group of 20 BPH patients, 11 patients were given negative results, i.e. these patients were deemed healthy (no PCa). More than two years on from the blood tests (as at 15 Dec. 2016), none of these patients has actually developed PCa. In 9 of the 20 BPH patients tested, positive signals were identified for at least one target of interest tested in the BBPA-dPCR. In four cases among these patients, a PCa developed within four months to two years after the blood tests. In the other five patients, the histology showed suspicious findings in the time following the blood tests, despite no malignant changes having been unambiguously identified previously (Table 19). Only future tests will show how many of these patients also subsequently develop a PCa.

In light of the above, it has been shown that the novel BBPA-dPCR technique produces significantly higher diagnostic specificity and a considerably higher positive predicative value compared with PSA determinations, in particular in the PSA concentration range of from 2-15 ng/ml, in which there were no significant differences between the BPH and PCa groups (FIG. 61).

The importance of establishing new biomarkers and providing corresponding commercial test kits for diagnosing PCa was already discussed at the outset. In this respect, the newly developed BBPA-dPCR method can make a significant contribution to reduce unnecessary biopsies or to ensure biopsies are carried out at the right time, thereby potentially lessening unnecessary burdens and side effects and also considerably reducing the costs for these treatments. In Germany alone, between 250,000 and 350,000 biopsies are carried out each year on the basis of PSA determinations and up to 75% of these are unnecessary.

Moreover, the diagnostic sensitivity of the novel method is significantly better than PSA, in particular when we consider that at most 1 ml serum was available for the tests being described and that the serum did not have to undergo any special pre-treatment in terms of specific pre-analysis such as DNase inhibition. Therefore, the presence of at least one tumour DNA copy is the basic requirement for detecting tumour DNA, and so the probability of such a copy existing naturally rises as the quantity of sample material being tested increases, in particular when the tumour disease is to be diagnosed as early as possible, i.e. at an early tumour development stage, in order to prevent any metastasis that may have already occurred.

In addition, there was no further sample material available for the tests in order to use further primer pairs such as the GSTP1 116 bp primer pair or to test other targets of interest such as AOX1, thrombomodulin and/or septin-9, meaning that the diagnostic sensitivity could be further increased.

In particular when diagnosing PCa, renal cancer and bladder cancer, urine samples are also advantageous in addition to blood sample tests (serum or plasma) since they are non-invasive and large volumes can be obtained and easily made available for the tests.

A high analytical and diagnostic sensitivity at almost 100% specificity is provided in particular for diagnosing minimal residual diseases (MRD), e.g. following a surgical operation when the question of subsequent chemotherapy/radiotherapy is being discussed, and a diagnostic sensitivity and specificity of almost 100% is also vital for patient after-care so as to detect recurrences as early as possible. In patient PCa1, for example, the histology following the surgical removal of the tumour showed infiltration of the resection edge, and so the question here how much cf-tumour DNA can be detected in the bloodstream or urinary excretion and whether this could form the basis for intensive after-care, e.g. involving an early second surgical intervention.

TABLE 19

Test results for differentiating between healthy subjects, benign prostatic hyperplasia (BPH) patients and prostate cancer patients (PCa) on the basis of PSA concentrations in serum, the quotient of free PSA to total PSA (QfPSA/PSA), the quantity of methylated PLA2R1, RASSF1A (RASS), GSTP1 and SERPINE1 (PAI1) DNA fragments compared with unmethylated fragments, and the clinical data. The cut-off values are given in the first row.

| | Date | Age/ years | PSA <4.0 ng/ml | QfPSA/ TPSA >20% | PLA2R1 <0.11% | RASS <0.4% | GSTP1 <0.05% | PAI1 <0.13% | Clinical data |
|---|---|---|---|---|---|---|---|---|---|
| GM1 | May 2015 | 22 | | | 0.009 | 0 | 0 | 0.056 | |
| GM2 | May 2015 | 28 | | | 0 | 0 | 0 | 0 | |
| GM3 | May 2015 | 22 | | | 0 | 0.4 | 0 | 0.003 | |
| GM4 | May 2015 | 32 | | | 0.023 | 0 | 0 | 0 | |
| GM5 | May 2015 | 35 | | | 0 | 0 | 0 | 0 | |
| GM6 | May 2015 | 23 | | | 0 | 0.007 | 0 | 0 | |
| GM7 | May 2015 | 30 | | | 0 | 0 | 0 | 0 | |
| GM8 | May 2015 | 28 | | | 0 | 0 | 0.007 | 0.018 | |
| GM9 | May 2015 | 44 | | | 0.019 | 0 | 0.046 | 0.03 | |
| GM10 | May 2015 | 50 | | | 0 | 0 | 0 | 0 | |
| GM11 | May 2015 | 49 | | | 0 | 0 | 0 | 0.017 | |
| GM12 | May 2015 | 63 | | | 0.0025 | 0.025 | 0 | 0 | |
| GM13 | May 2015 | 21 | | | 0 | 0 | 0 | 0.008 | |
| GM14 | May 2015 | 23 | | | 0.0026 | 0 | 0 | 0.0029 | |
| GM15 | May 2015 | 23 | | | 0 | 0 | 0 | 0 | |
| GM16 | May 2015 | 28 | | | 0 | 0.007 | 0.005 | 0.015 | |
| GM17 | May 2015 | 62 | | | 0 | 0 | 0 | 0.0027 | |
| GM18 | May 2015 | 29 | | | 0 | 0 | 0 | 0.044 | |
| GM19 | May 2015 | 23 | | | 0 | 0 | 0 | 0.007 | |
| GM20 | May 2015 | 46 | | | 0.104 | 0.012 | 0 | 0.13 | |
| BPH-1 | September 2014 | 60 | 8.6 | | 0 | 0.029 | 0 | 0.06 | no PCa to date |
| BPH-2 | September 2014 | 73 | 6.27 | 18.50 | 0 | 0.05 | 0 | 0 | no PCa to date |
| BPH-3 | August 2014 | 76 | 7.92 | | 0.032 | 0.003 | 0 | 0 | no PCa to date |
| BPH-4 | August 2014 | 59 | 8.56 | | 0.052 | 0 | 0 | 0.009 | no PCa to date |
| BPH-5 | August 2014 | 83 | 5.2 | | 0.051 | 0 | 0.117 | 0.004 | no PCa to date |
| BPH-6 | August 2014 | 73 | 4.19 | 15.27 | 0.18 | 0 | 0.062 | 0.168 | no PCa to date |
| BPH-7 | August 2014 | 64 | 6.56 | 13.72 | 0.104 | 0.42 | 0.066 | 0 | no PCa to date |
| BPH-8 | August 2014 | 66 | 6.44 | 15.06 | 0 | 0.005 | 0.04 | 0.003 | no PCa to date |
| BPH-9 | July 2014 | 65 | 4.84 | | 0 | 0.017 | 0.008 | 1.88 | no PCa to date |
| BPH-10 | July 2014 | 58 | 13.2 | | 0 | 0.028 | 0.051 | 0.028 | no PCa to date |
| BPH-11 | July 2014 | 74 | 2 | | 0 | 0 | 0 | 0.17 | no PCa to date |
| BPH-12 | October 2014 | 75 | 0.33 | | 5.2 | 2.62 | 3.24 | 4.2 | October 2014 TURP (12 g) owing to obstructive prostatic hyperplasia; histology: atypical adenomatous hyperplasia (AAH) [1] |
| BPH-13 | October 2014 | 71 | 14.23 | | 0 | 0.009 | 14.49 | 0.005 | Prostate biopsy (Pb) 2007 and 2011 negative, October 2014 negative [2]; February 2016 patient refuses Pb, but TURP owing to prostatic hyperplasia requiring an indwelling catheter: histology [3] |
| BPH-14 | October 2014 | 67 | 6.39 | 23.63 | 0 | 0.83 | 1.41 | 0.012 | Pb 2010, 2011, 2014 and August 2016 negative [4]; October 2016 PCa detected |
| BPH-15 | September 2014 | 66 | 4.12 | | 0.12 | 0.061 | 3.39 | 0 | November 2014 TURP due to prostate cancer, pT1a, pNx, L0, V0, Rx, Gleason score 3 + 3 = 6, stage IIa with symptomatic prostatic hyperplasia |
| BPH-16 | September 2014 | 47 | 6.53 | 12.86 | 1.45 | 0.75 | 7.42 | 1.99 | Pb 2012 and 2014 negative, Pb March 2016 HGPIN detected in one biopsy needle [5]; repeat biopsy recommended in 6 months, not yet carried out. |
| BPH-17 | August 2014 | 66 | 4.75 | 40.21 | 0 | 0.12 | 9 | 31.7 | Pb 2011 and July 2014 negative, although repeat Pb recommended in 3-6 months due to atypical small acinar proliferation with PSA of 4.75 ng/ml; Q = 40.2%; November 2014: PCa detected (Gleason score 3 + 4 = 7, stage IIa) in Pb [6]; February 2015: PCa operated |
| BPH-18 | August 2014 | 72 | 6.31 | 22.50 | 0.018 | 0.1 | 0 | 11.4 | Pb 2013 negative, August 2014 PSA increase to 6.31 ng/ml, Q = 22.5% and Pb [7]; September 2015 repeat Pb due to PSA increase to 13.9 ng/ml [8]; July 2016 emergency presentation due to acute urinary retention; prostatic hyperplasia requiring an indwelling catheters; September 2016: TURP with post-operative tumour classification T1a; Rx, Gleason score 3 + 3 = 6 [9]. |
| BPH-19 | August 2014 | 75 | 9.31 | 21.27 | 1.27 | 2.26 | 0.21 | 0.019 | Pb 2006, 2008, 2012 and 2014 negative; March 2016 treatment by TURP (50 g) due to persistently elevated PSA of 9.28 ng/ml; histology [10]; |
| BPH-20 | July 2014 | 73 | 4.75 | | 1.52 | 2.16 | 0 | 1.6 | Pb 2012 and 2013 negative; August 2014: Pb due to PSA of 4.75 ng/ml; histology [11]; |

TABLE 19-continued

Test results for differentiating between healthy subjects, benign prostatic hyperplasia (BPH) patients and prostate cancer patients (PCa) on the basis of PSA concentrations in serum, the quotient of free PSA to total PSA (QfPSA/PSA), the quantity of methylated PLA2R1, RASSF1A (RASS), GSTP1 and SERPINE1 (PAI1) DNA fragments compared with unmethylated fragments, and the clinical data. The cut-off values are given in the first row.

| | Date | Age/ years | PSA <4.0 ng/ml | QfPSA/ TPSA >20% | PLA2R1 <0.11% | RASS <0.4% | GSTP1 <0.05% | PAI1 <0.13% | Clinical data |
|---|---|---|---|---|---|---|---|---|---|
| PCa1 | | 59 | 6.35 | | 2.86 | 0 | 0 | 0.08 | October 2014: PCa operated; pT2c, cN0, cM0, L0, V0, Pn1, Rx (infiltration of resection edge traced in left apex), Gleason score 3 + 4 = 7, stage IIb [12] |
| PCa2 | | 60 | 9.42 | | 0 | 0.19 | 0 | 0.14 | October 2014 PCa operated; pT2c, pN0 (0/10 LK), L0, V0, Pn1, R0 (local), Gleason score; 3 + 3 = 6, stage IIa Pb April 2014: 3/12 cylinders positive |
| PCa3 | | 72 | 8.4 | | 0 | 0.88 | 0 | 0 | October 2014 PCa operated; pT2c, pN0 (0/18 LK), cM0, L0, V0, Pn1, R0 (local), Gleason score: 4 + 3 = 7, tertiary differentiation pattern Gleason 5, stage IIIb August 2014 Pb: 1/12 cylinders positive, left side |
| PCa4 | | 60 | 3.53 | | 0 | 6.5 | 11.5 | 0.27 | October 2014 PCa operated; pT2c, pN0 (0/19 LK), cM0, L0, V0, Pn1, R0 (local), Gleason score: 3 + 4 = 7, stage IIa August 2014 Pb: cT1c (8/12 cylinder positive, both sides) |
| PCa5 | | 67 | 13.16 | | 0.012 | 0.28 | 1.2 | 0 | September 2014 PCa operated; pT2c, pN0 (0/28 LK), L0, V0, Pn0, R0 (local), Gleason score: 3 + 4 = 7, stage IIa |
| PCa6 | | 62 | 3.6 | | 0 | 21.6 | 7.4 | 0.07 | September 2014 PCa operated; pT2c, pN0 (0/11 LK), cM0, L0, V0, Pn1, R0 (local), Gleason score: 3 + 4 = 7, stage IIa; May 2014: Pb: 1/12 cylinders positive, left side (5%) |
| PCa7 | | 68 | 4.25 | | 1.02 | 1.28 | 0 | 0.011 | September 2014 PCa operated; pT2c pN0 (0/20 LK) cM0 L0 V0 Pn1 R1 (dorsal both sides), Gleason score: 3 + 4 = 7, tertiary differentiation pattern Gleason 5, stage IIIb July 2014 Pb: 2/12 cylinders positive, right side |
| PCa8 | | 60 | 6.45 | | 0.019 | 0.4 | 0.85 | 0.014 | September 2014 MR fusion transperineal (6 cylinders) and TRUS transrectal (12 cylinders) Pb: 1/18 cylinders positive, right side; Gleason score: 3 + 3 = 6 |
| PCa9 | | 44 | 8.73 | | 0.79 | 0.015 | 0.52 | 0.045 | September 2014 PCa operated; pT2c, pN0 (0/17 LK), cM0, L0, V0, Pn1, R0 (local), Gleason score: 3 + 4 = 7, stage IIa June 2014 Pb 1/6 right-side and 3/6 left-side cylinders positive |
| PCa10 | | 60 | 10.86 | | 0.11 | 0.037 | 1.36 | 0.42 | September 2014 PCa operated; pT2c, pN0 (0/11 LK), cM0, L0, V0, Pn1, R0 (local), Gleason score 3 + 4 = 7, stage IIa |
| PCa11 | | 67 | 15.05 | | 0 | 0 | 0.51 | 0.077 | August 2014 PCa operated; pT2c, pN0 (0/16 LK), cM0, L0, V0, Pn0, R0 (local), Gleason score: 3 + 4 = 7, stage IIa December 2013 Pb: 3/20 cylinders both sides, Gleason 3 + 3 = 6 |
| PCa12 | | 70 | 14.19 | | 0 | 0.67 | 0 | 0.043 | August 2014 PCa operated; pT3b, pN0 (0/13 LK), cM0, L0, V0, Pn1, R0 (local), Gleason score 4 + 3 = 7, stage IIb |
| PCa13 | | 73 | 7.2 | | 0.59 | 0.6 | 0 | 0.0026 | August 2014 PCa operated; pT2c, pN0 (0/10 LK), cM0, L0, V0, Pn1, R0 (local), Gleason score 3 + 4 = 7, stage IIa |
| PCa14 | | 64 | 2.22 | | 0 | 0.06 | 0 | 0 | October 2014 PCa operated; pT2c, pN0 (0/14 LK), cM0, L0, V0, Pn1, R0 (local), Gleason score; 3 + 4 = 7, stage IIa June 2014: TURP Gleason 3 + 3 = 6 |
| PCa15 | | 75 | 10.34 | | 0.005 | 0.004 | 0 | 0.017 | September 2014 PCa operated; pT2c, pN0 (0/16 LK), cM0, L0, V0, Pn1, R1 (multifocal dorso-peripheral, right), Gleason score 4 + 3 = 7, stage IIb |
| PCa16 | | 69 | 5.72 | | 0.044 | 0.011 | 0.033 | 0.133 | September 2014 PCa operated; pT2c, pN0 (0/24 LK), cM0, L0, V0, Pn1, R0 (local), Gleason score 3 + 4 = 7, stage IIb July 2014 Pb (5/7 cylinders positive, left side) |
| PCa17 | | 59 | 8.52 | | 0 | 0.054 | 0 | 0 | September 2014 Pb with 2/20 cylinders positive, Gleason score 3 + 3 = 6; stage IIa |
| PCa18 | | 71 | 0.12 | | 0 | 0.059 | 0.096 | 0.025 | August 2014 PCa operated; pT2a, pN0 (0/13 LK), cM0, L0, V0, Pn1, R0 (local), Gleason score: 4 + 3 = 7; third differentiation pattern Gleason 5, stage IIIa February 2014 Pb: 1/6 cylinders positive, right side, Gleason score, 3 + 3 = 6 |
| PCa19 | | 79 | 4.48 | | 0 | 0 | 0 | 0.01 | August 2014 PCa operated; pT2c, pN0 (0/10 LK), cM0, L0, V0, Pn1, R0 (local), Gleason score: 3 + 4 = 7, stage IIb July 2014 Pb: 6/12 cylinders positive, both sides, Gleason 3 + 4 = 7 |

TABLE 19-continued

Test results for differentiating between healthy subjects, benign prostatic hyperplasia (BPH) patients and prostate cancer patients (PCa) on the basis of PSA concentrations in serum, the quotient of free PSA to total PSA (QfPSA/PSA), the quantity of methylated PLA2R1, RASSF1A (RASS), GSTP1 and SERPINE1 (PAI1) DNA fragments compared with unmethylated fragments, and the clinical data. The cut-off values are given in the first row.

| | Date | Age/ years | PSA <4.0 ng/ml | QfPSA/ TPSA >20% | PLA2R1 <0.11% | RASS <0.4% | GSTP1 <0.05% | PAI1 <0.13% | Clinical data |
|---|---|---|---|---|---|---|---|---|---|
| PCa20 | | 60 | 10.88 | | 0.062 | 0 | 0 | 0.009 | August 2014 PCa operated; pT3a, pN0 (0/25 LK), cM0, L0, V0, Pn1, R0 (local), Gleason score: 3 + 4 = 7, stage IIb |

[1] October 2014: TURP (12 g) owing to prostatic hyperplasia; histology: due to isolated glandular proliferations of unknown malignancy status, further immunohistochemical tests were carried out (using anti-CK4/14 and anti-racemase antibodies). The results showed glands having incomplete loss of basal cytokeratins with no substantial racemase overexpression, so the diagnosis was atypical adenomatous hyperplasia (AAH); to date, this has not been able to support the existence of an invasive carcinoma in the material available.
[2] October 2014: TRUS saturation biopsy (25 biopsy cylinders) due to PSA incease to 14.23 ng/ml. Prostate needle cylinder material 1 to 13 showed isolated hyperplastic glands, some in small groups, and largely diffuse hyperplasia of the fibromuscular stroma, also with regressive changes in some foci showing prostate gland atrophy and postatrophic hyperplasia, as well as locally moderate basal cell hyperplasia and moderate chronic active prostatitis elsewhere, minor in some foci; further immunohistochemical tests carried out on samples 2 and 7 due to isolated glandular proliferations of unknown malignancy status. In the area around the aforementioned glandular proliferation, the subsequent tests predominantly showed sustained expression of basal cytokeratins (with expression of CK5/14 but no detection of racemase overexpression), so the diagnosis was atrophic prostate glands. No indication of malignancy in the material available.
[3] February 2016: TURP (94 g) due to prostatic hyperplasia requiring an indwelling catheter with further PSA increase to 20.5 ng/ml. Due to isolated glandular proliferations of unknown malignancy status, immunohistochemical tests were carried out (using antibodies against CK5/14, racemase, calretinin, pan-cytokeratin, CK7, cadherin 17, p63, PAX8, CD34, 34βE12, androgen receptor, EMA, PSA and WT1). Within the aforementioned abnormal glandular proliferations, these tests detected expression of pan-cytokeratin and, in some cases, CK7 and EMA, and androgen receptor at nuclear level, with no expression of WT1, PSA, racemase, cadherin 17, 34βE12 and p63, and largely no expression of CD34, PAX8 or calretinin. Since the Ki67 proliferation index was low (around 1%), taking account of the immunohistology and the PAS-positive intraluminal containments and secretions detectable in the PAS, the overall diagnosis is of a nephrogenic adenoma. No indication of malignancy in the material available.
[4] August 2016: MR fusion transperineal (4 biopsy cylinders) and TRUS transrectal (12 biopsy cylinders) prostate biopsy. Prostate needle cylinders 1-16 showing fibromuscular nodular stromal hyperplasia, with prostate gland atrophy and hypertrophic prostate glands, some foci showing chronic uncharacteristic inflammation reaction and some showing squamous epithelial metaplasia in the larger excretory ducts; detection of urothelial metaplasia in larger excretory ducts. No indication of intraepithelial neoplasia/dysplasia or malignancy in material provided. PSA 10.94 ng/ml. However, October 2016: PCa detected.
[5] March 2016; Prostate needle cylinders 1-17 showing benign adenomatous parenchymal hyperplasia, fibromyomatous in some parts, and some sites with pronounced basal cell hyperplasia of the glandular epithelium and gland atrophy, some sites showing minor secretion retention, isolated corpora amylacea detected in gland lumens; sample 7 showing small foci of high-grade prostatic intraepithelial neoplasia (HGPIN) and in some parts non-recent to moderately chronic and florid non-specific prostatitis.
[6] November 2014: Prostate needle cylinder material 1 of 17 (right, apical, peripheral) showing small foci of infiltration due to largely minor glandular, isolated, confluent prostate adenocarcinoma with moderate nuclear pleomorphism, taking up around 5% of the original cylinder surface area; largest coherent carcinoma lesion measuring 1.2 mm. Gleason score: 3 + 4 = 7 (of which Gleason 3 90%, Gleason 4 10%). Stage IIa.
[7] August 2014: MRT fusion, ultrasound guided transperineal prostate biopsy (6 biopsy cylinders) and TRUS prostate biopsy: Prostate needle cylinders 1-18 showing nodular stromal hyperplasia, prostate gland hyperplasia and, in parts, atrophic prostate glands, with numerous corpora amylacea in slightly dilated glands. No indication of intraepithelial neoplasia/dysplasia or malignancy in the material provided.
[8] September 2015: MRT fusion transperineal prostate biopsy (8 cylinders) and transrectal prostate biopsy (12 cylinders); MRT showed PI-RADS 4 basal lesions to the left in the transitional region and to the right in the central prostate third in the transitional region; the digital rectal examination produced no suspicious tactile findings. A total of 20 cylinders were taken, and malignancy was ruled out on the basis of the needle biopsy with PSA re-measured at 14.2 ng/ml.
[9] September 2016: Histology showed small acinar adenocarcinoma with moderate nuclear pleomorphism in individual chips, though carcinoma occupied less than 5% of the surface area tested. Recommended treatment: active surveillance with monitoring biopsy in 3-6 months, or watchful waiting.
[10] March 2016: Prostate resection chips showing nodular, muscular and glandular (adenomyomatous) prostatic hyperplasia, focally with basal cell hyperplasia, cystically expanded glands with secretion retention and inflammation reaction, in some cases of unknown and in others resorptive; corpora amylacea also detected, focally with calcium carbonate stroma encrustation, including portions of the pars prostatica urethrae with largely regular urothelium. No indication of intraepithelial neoplasia/dysplasia or malignancy in this material.
[11] August 2014: MR fusion, ultrasound-guided transperineal (8 cylinders) prostate biopsy and transrectal ultrasound-guided prostate biopsy (12 cylinders). Prostate needle cylinders 1-20 showing nodular stromal hyperplasia and prostate gland atrophy and, in parts, hypertrophic prostate glands, focally chronic uncharacteristic inflammation reaction; cylinders 9 and 12 each showing abnormal small acinar proliferation of unknown malignancy status (formerly ASAP). For material 9 and 12, further immunohistological tests showed small acinar proliferation with intermittent CK5/14-positive basal cell layer. Negative racemase reaction, so no indication of prostate cancer.
[12] November 2014 Histopathological findings (Rx resection) lead to recommendation of PSA-based after-care with salvage radiotherapy in the event of PSA recurrence; otherwise adjuvant RTx. Additionally PSA monitoring (PSA = 0.12 ng/ml) to confirm post-operative PSA normalisation.

Embodiment 12: Testing Serum Samples from Healthy Patients and Breast and Ovarian Cancer Patients The tests showed that very low methylation rates (≤0.05%) could be detected in all the serum samples from healthy subjects, especially when using the GSTP1 116 bp primer pair, whereas the serum samples from female subjects with breast and ovarian cancer showed clearly distinct elevated values (Table 31). While 18 out of 23 samples were positive when using the primer pair GSTP1 116 bp primer pair, 5 out of 23 samples showed positive signals when the GSTP1 120 bp primer pair was used and 12 out of 23 were positive with the RASSF1A 117 bp primer pair. What was interesting was that, when the GSTP1 120 bp primer pair was used, positive signals that had been negative with the GSTP1 116 bp primer pair were measured once again in two patient samples; this means that the combination of the two primer pairs can lead to increased diagnostic sensitivity, whether they are used separately or simultaneously in one batch. 100% diagnostic sensitivity with a diagnostic specificity of 100% was achieved when the data obtained when using the GSTP1 primers was combined with that obtained from the RASSF1A primers (Table 31).

The data from a patient suffering from primary osseous and hepatic metastatic breast-CA prior to (P8a) and after eight weeks of chemotherapy (P8b) was also noteworthy. In addition to the CA 15-3 value dropping from 941.4 U/ml to 133.0 U/ml, drops were also noted in the methylation values for GSTP1 116 bp (0.9% to 0%) and RASSF1A 117 bp (18.9% to 2%). This result points to a good response to treatment. Following the completion of treatment, the GSTP1 and RASSF1A methylation values were already in the normal range, while the CA 15-3 values was still elevated; this can be explained by the longer biological half-life. These results illustrate the potential offered by BBPA-dPCR tests for direct treatment and progress monitoring, and the detection of MRD, since the concentration of fcT-DNA drops significantly faster than conventional tumour markers such as CA 15-3 when the treatment is successful. Therefore, this method can also be used as an aid for treatment decisions, such as the issue of the need to undergo subsequent direct chemo and/or radiotherapy following a successful tumour operation, depending on whether the initially elevated fcT-DNA concentrations drop to the normal range or, ideally, are no longer detectable, thus ruling out an MRD.

The sample P24 came from a 32-year-old female who had a pathological mutation in the BRCA-1 gene with an associated family risk for breast and ovarian cancer. The patient's mother had developed breast cancer at just 33, the patient's grandmother at 56. The patient underwent a prophylactic subcutaneous mastectomy at her own wish. The histological tests carried out on the surgical specimens did not show any indication of intraepithelial neoplasia/dysplasia or malignancy, and the tumour marker CA 15-3 was also normal. Surprisingly, though, elevated values were already noted when the GSTP1 116 bp primer pair was used in the BBPA-dPCR (Table 31). This leads us to conclude that this technique can indicate early pathological changes, e.g. by means of a blood test (liquid biopsy), in patients having a higher family risk of breast and ovarian cancer, and that this method can be used as a decision aid in relation to a prophylactic mastectomy or ovariectomy, in particular when the patients affected are still planning a family.

In principle, the novel BBPA-dPCR being described can be used for all potential target gene sequences in which the methylation level differs between healthy and diseased subjects. After designing the primers and probes in accordance with the above-described principles, the bias towards methylated and unmethylated target sequences and the optimum number of BBPA cycles can be empirically determined using a sample having a known methylation level according to the annealing temperature and the $MgCl_2$ concentration, e.g. for septin-9 (SEPT9, HGNC:HGNC: 7323 Ensembl: ENSG00000184640, SEQ ID No 140-144, 159-164 and 179-184). On the basis of the data obtained, the conditions for each primer pair are set such that the target sequence to be analysed (methylated or unmethylated) can be copied to the maximum possible extent while the control target sequences (unmethylated or methylated wild-type sequences) can still be copied to a sufficient extent. In this way, the values determined for the target sequences can be correlated with those for the wild-type DNA sequences acting as the internal control and the quantity of the bisulphite-converted DNA introduced into the BBPA-dPCR can thus be taken into account. Additionally, this process makes it possible to obtain high analytical sensitivities similar to those in the MS-PCR technique (using methyl-specific (MS) primers), without increased numbers of false-positive signals occurring, as is the case with the MS-PCR technique [4]. Compared with the MS-HRM technique (using methyl-independent (MIP) primers), in which fewer false-positive signals occur than in MS-PCR, the BBPA-dPCR technique has a much higher analytical and thus diagnostic sensitivity. If diagnostic specificities of almost 100% can also be achieved in this manner for new target sequences using the BBPA-dPCR, these target sequences can be added to the above-described panel of targets of interest (PLA2R1, RASSF1A, GSTP1, SERPINE1, AOX1, TM and/or septin-9) in order to further increase the diagnostic sensitivity for detecting malignant diseases such as prostate, breast, ovarian and renal cell cancers, as well as other solid tumours such as colorectal cancer.

TABLE 20

Number of copies of methylated (met) and unmethylated (unm) PLA2R1 sequences without BBPA and after 50 BBPA cycles at 63.0° C. and an $MgCl_2$ concentration of 2.5 mmol/l in normal prostate epithelial cells (PrEC), the benign prostatic hyperplasia cell line (BPH-1) and malignant prostate cancer cell lines (LNCaP, PC-3 and DU-145). Following BBPA, 1 μl of the, 25 μl PCR, batches was added to the dPCR and so the values following BBPA were multiplied by 25 for comparison. The terms PrEC 0x, BPH-1 0x, LNCaP 0x, PC-3 0x and DU-124 0x in the first column show the data without BBPA, and the terms PrEC 50x, BPH-1 50x, LNCaP 50x, PC-3 50x and DU-145 50x show the data after 50 BBPA cycles.

| Sample | Target | Copies/ 20 μl well | 1:25 | Positive | Negative | Ch1+ Ch2+ | Ch1+ Ch2− | Ch1− Ch2+ | Ch1− Ch2− | Accepted droplets | Fractional abundance | Poisson fractional abundance min. | Poisson fractional abundance max. |
|---|---|---|---|---|---|---|---|---|---|---|---|---|---|
| PrEC 0x | PLA2R1 met | 34 | 34 | 18 | 12233 | 0 | 18 | 813 | 11420 | 12251 | 2.1 | 1.1 | 3.1 |
| PrEC 0x | PLA2R1 unm | 1620 | 1620 | 813 | 11438 | | | | | | | | |
| BPH-1 0x | PLA2R1 Met | 270 | 270 | 157 | 13568 | 16 | 141 | 1632 | 11936 | 13725 | 8.3 | 7 | 9.5 |
| BPH-1 0x | PLA2R1 unm | 3000 | 3000 | 1648 | 12077 | | | | | | | | |
| LNCaP 0x | PLA2R1 met | 1660 | 1660 | 961 | 13172 | 9 | 952 | 116 | 13056 | 14133 | 88.8 | 86.9 | 90.7 |
| LNCaP 0x | PLA2R1 unm | 210 | 210 | 125 | 14008 | | | | | | | | |
| PC-3 0x | PLA2R1 Met | 1178 | 1178 | 623 | 12131 | 38 | 585 | 872 | 11259 | 12754 | 40.4 | 37.9 | 42.8 |
| PC-3 0x | PLA2R1 unm | 1740 | 1740 | 910 | 11844 | | | | | | | | |
| DU-145 0x | PLA2R1 met | 3280 | 3280 | 1363 | 9117 | 0 | 1363 | 6 | 9111 | 10480 | 99.59 | 99.25 | 99.93 |
| DU-145 0x | PLA2R1 unm | 14 | 14 | 6 | 10474 | | | | | | | | |
| PrEC 50x | PLA2R1 met | 0 | 0 | 0 | 12402 | 0 | 0 | 12269 | 133 | 12402 | 0 | 0 | 0 |
| PrEC 50x | PLA2R1 unm | 106800 | 2670000 | 12269 | 133 | | | | | | | | |
| BPH-1 50x | PLA2R1 Met | 0 | 0 | 0 | 11839 | 0 | 0 | 11690 | 149 | 11839 | 0 | 0 | 0 |
| BPH-1 50x | PLA2R1 unm | 103000 | 2575000 | 11690 | 149 | | | | | | | | |
| LNCaP 50x | PLA2R1 Met | 115400 | 2885000 | 11674 | 87 | 140 | 11534 | 0 | 87 | 11761 | 99.757 | 99.715 | 99.798 |
| LNCaP 50x | PLA2R1 unm | 282 | 7050 | 140 | 11621 | | | | | | | | |
| PC-3 50x | PLA2R1 met | 72600 | 1815000 | 11867 | 566 | 11858 | 9 | 229 | 337 | 12433 | 46.3 | 45.3 | 47.3 |
| PC-3 50x | PLA2R1 unm | 84200 | 2105000 | 12087 | 346 | | | | | | | | |

TABLE 20-continued

Number of copies of methylated (met) and unmethylated (unm) PLA2R1 sequences without BBPA and after 50 BBPA cycles at 63.0° C. and an MgCl₂ concentration of 2.5 mmol/l in normal prostate epithelial cells (PrEC), the benign prostatic hyperplasia cell line (BPH-1) and malignant prostate cancer cell lines (LNCaP, PC-3 and DU-145). Following BBPA, 1 µl of the, 25 µl PCR, batches was added to the dPCR and so the values following BBPA were multiplied by 25 for comparison. The terms PrEC 0x, BPH-1 0x, LNCaP 0x, PC-3 0x and DU-124 0x in the first column show the data without BBPA, and the terms PrEC 50x, BPH-1 50x, LNCaP 50x, PC-3 50x and DU-145 50x show the data after 50 BBPA cycles.

| Sample | Target | Copies/ 20 µl well | 1:25 | Positive | Negative | Ch1+ Ch2+ | Ch1+ Ch2− | Ch1− Ch2+ | Ch1− Ch2− | Accepted droplets | Fractional abundance | Poisson fractional abundance min. | Poisson fractional abundance max. |
|---|---|---|---|---|---|---|---|---|---|---|---|---|---|
| DU-145 50× | PLA2R1 met | 186000 | 4650000 | 13181 | 5 | 0 | 13181 | 0 | 5 | 13186 | 100 | 100 | 100 |
| DU-145 50 × 5 | PLA2R1 unm | 0 | 0 | 0 | 13186 | | | | | | | | |

TABLE 21

Number of copies of methylated (M) and unmethylated (U) RASSF1A DNA fragments following 15 pre-amplification cycles at rising annealing temperatures (50-60° C.) as a function of MgCl₂ concentrations (1.5 mM-8.0 mM) using the RASSF1A 117 bp primer pair (SEQ ID: 3 and 4) and RASSF1A 124 bp primer pair (SEQ ID: 61 and 62) and subsequent dPCR.

| R-117 | | | | | | | | | | | | |
|---|---|---|---|---|---|---|---|---|---|---|---|---|
| Tm in ° C. | M | U | M | U | M | U | M | U | M | U | M | U |
| 60 | 44 | 0 | 1580 | 0 | 868 | 454 | 3800 | 402 | 2520 | 270 | 6060 | 300 |
| 59.2 | 130 | 3.2 | 1960 | 0 | 942 | 310 | 4460 | 5 | 3520 | 26 | 5340 | 38 |
| 58 | 664 | 104 | 3020 | 118 | 456 | 272 | 3360 | 92 | 2680 | 184 | 8080 | 134 |
| 56.1 | 2800 | 1.8 | 1016 | 46 | 476 | 224 | 1978 | 532 | 1352 | 788 | 4780 | 1920 |
| 53.8 | 1724 | 40 | 392 | 920 | 90 | 194 | 628 | 860 | 980 | 1258 | 1892 | 1960 |
| 51.9 | 1142 | 706 | 184 | 572 | 34 | 48 | 78 | 366 | 158 | 258 | 566 | 680 |
| 50.7 | 1082 | 776 | 70 | 344 | 9.6 | 28 | 19.4 | 64 | 52 | 78 | 56 | 280 |
| 50 | 1014 | 1336 | 74 | 154 | 2.6 | 9.2 | 10.4 | 44 | 22.8 | 30 | 76 | 126 |
| MgCl₂ | 1.5 mM | | 2.5 mM | | 3.5 mM | | 4.5 mM | | 6.0 mM | | 8.0 mM | |

| R-124 | | | | | | | | | | | | |
|---|---|---|---|---|---|---|---|---|---|---|---|---|
| Tm in ° C. | M | U | M | U | M | U | M | U | M | U | M | U |
| 60 | 292 | 0 | 2240 | 168 | 4040 | 122 | 6600 | 0 | 9460 | 0 | 4640 | 0 |
| 59.2 | 1232 | 0 | 7580 | 120 | 5060 | 8.4 | 4840 | 0 | 11720 | 0 | 4760 | 0 |
| 58 | 2230 | 1.6 | 5380 | 8 | 5380 | 0 | 8240 | 0 | 8340 | 20 | 7600 | 9 |
| 56.1 | 4840 | 0 | 5920 | 244 | 5220 | 10.6 | 1466 | 0 | 5480 | 0 | 8100 | 0 |
| 53.8 | 5900 | 14 | 1470 | 514 | 10780 | 0 | 8580 | 720 | 5920 | 3 | 5560 | 474 |
| 51.9 | 5220 | 20 | 470 | 124 | 7500 | 48 | 7620 | 58 | 5460 | 330 | 4200 | 78 |
| 50.7 | 5180 | 30 | 202 | 140 | 4960 | 138 | 2430 | 234 | 3180 | 616 | 3840 | 144 |
| 50 | 3000 | 290 | 136 | 82 | 4720 | 298 | 2880 | 472 | 1906 | 372 | 3760 | 768 |
| MgCl₂ | 1.5 mM | | 2.5 mM | | 3.5 mM | | 4.5 mM | | 6.0 mM | | 8.0 mM | |

TABLE 22

Number of copies of methylated (M) and unmethylated (U) GSTP1 DNA fragments following 15 pre-amplification cycles at rising annealing temperatures (50-60° C.) as a function of MgCl₂ concentrations (1.5 mM-8.0 mM) using the GSTP1 114 bp primer pair (SEQ ID: 91 and 92), the GSTP1 116 bp primer pair (SEQ ID: 93 and 94), the GSTP1 129 bp primer pair (SEQ ID: 95 and 96) and the GSTP1 132 bp primer pair (SEQ ID: 97 and 98) and subsequent dPCR.

| GSTP 114 bp (3 CpG sites) | | | | | | | | | | | | |
|---|---|---|---|---|---|---|---|---|---|---|---|---|
| Tm in ° C. | M | U | M | U | M | U | M | U | M | U | M | U |
| 60 | 764 | 1.8 | 9660 | 0 | 11180 | 26 | 17220 | 124 | 8080 | 12 | 17140 | 130 |
| 59.2 | 726 | 1.6 | 7820 | 14 | 17660 | 30 | 19560 | 44 | 6740 | 12 | 14980 | 36 |
| 58 | 2380 | 12.6 | 10440 | 7.2 | 12640 | 92 | 17640 | 64 | 16180 | 146 | 6480 | 56 |
| 56.1 | 6640 | 0 | 14820 | 30 | 21760 | 198 | 17660 | 624 | 19600 | 896 | 14060 | 1516 |
| 53.8 | 8520 | 13.6 | 15100 | 938 | 11440 | 1068 | 13940 | 2500 | 8680 | 2560 | 7960 | 1960 |
| 51.9 | 9200 | 200 | 12140 | 1580 | 7520 | 2560 | 5460 | 1860 | 2900 | 1780 | 960 | 666 |
| 50.7 | 8680 | 390 | 7140 | 3740 | 4140 | 2500 | 2700 | 1126 | 868 | 824 | 122 | 100 |

TABLE 22-continued

Number of copies of methylated (M) and unmethylated (U) GSTP1 DNA fragments following 15 pre-amplification cycles at rising annealing temperatures (50-60° C.) as a function of MgCl$_2$ concentrations (1.5 mM-8.0 mM) using the GSTP1 114 bp primer pair (SEQ ID: 91 and 92), the GSTP1 116 bp primer pair (SEQ ID: 93 and 94), the GSTP1 129 bp primer pair (SEQ ID: 95 and 96) and the GSTP1 132 bp primer pair (SEQ ID: 97 and 98) and subsequent dPCR.

| 50 | 6780 | 678 | 6740 | 1680 | 2620 | 3160 | 2360 | 926 | 506 | 466 | 460 | 254 |
|---|---|---|---|---|---|---|---|---|---|---|---|---|
| MgCl$_2$ | 1.5 mM | | 2.5 mM | | 3.5 mM | | 4.5 mM | | 6.0 mM | | 8.0 mM | |

GSTP 116 bp (3 CpG sites)

| Tm in ° C. | M | U | M | U | M | U | M | U | M | U | M | U |
|---|---|---|---|---|---|---|---|---|---|---|---|---|
| 60 | 284 | 24 | 5700 | 1.6 | 11260 | 2.8 | 16340 | 1.6 | 14960 | 252 | 7960 | 4.8 |
| 59.2 | 778 | 2.8 | 7760 | 5 | 13700 | 11.4 | 18920 | 14 | 17420 | 10.2 | 8160 | 11.4 |
| 58 | 1544 | 6.8 | 7560 | 5 | 22640 | 16.6 | 16740 | 4.4 | 17560 | 17.2 | 16220 | 6.2 |
| 56.1 | 4260 | 6 | 19880 | 12.8 | 25420 | 100 | 20640 | 390 | 17980 | 376 | 12640 | 134 |
| 53.8 | 9040 | 9.2 | 23020 | 108 | 24540 | 774 | 18480 | 1760 | 23280 | 1014 | 13560 | 582 |
| 51.9 | 10560 | 262 | 11520 | 776 | 16740 | 2400 | 15620 | 5280 | 15600 | 4560 | 8740 | 2100 |
| 50.7 | 5400 | 46 | 16120 | 1028 | 12960 | 4800 | 10520 | 5680 | 13500 | 4060 | 6200 | 2460 |
| 50 | 9200 | 86 | 14800 | 2300 | 14900 | 5100 | 14720 | 4800 | 8480 | 3660 | 4760 | 1800 |
| MgCl$_2$ | 1.5 mM | | 2.5 mM | | 3.5 mM | | 4.5 mM | | 6.0 mM | | 8.0 mM | |

GSTP 129 bp 4 CpG sites)

| Tm in ° C. | M | U | M | U | M | U | M | U | M | U |
|---|---|---|---|---|---|---|---|---|---|---|
| 60 | 578 | 14 | 8940 | 16 | 15220 | 0 | 19040 | 5.4 | 15140 | 24 |
| 59.2 | 450 | 4.6 | 7420 | 22 | 15900 | 204 | 26660 | 46 | 18400 | 15.4 |
| 58 | 1462 | 9.4 | 10660 | 14 | 22880 | 10 | 35400 | 4.4 | 15620 | 34 |
| 56.1 | 5480 | 10.8 | 24640 | 6 | 21860 | 16 | 25800 | 44 | 24880 | 30 |
| 53.8 | 12020 | 11.4 | 17060 | 22 | 15820 | 170 | 27780 | 350 | 16460 | 216 |
| 51.9 | 8740 | 22 | 20160 | 254 | 20480 | 370 | 21740 | 1068 | 18740 | 234 |
| 50.7 | 8720 | 7.8 | 15960 | 208 | 19100 | 544 | 22980 | 1144 | 16060 | 474 |
| 50 | 9220 | 110 | 19480 | 312 | 19520 | 892 | 16900 | 962 | 10440 | 516 |
| MgCl$_2$ | 1.5 mM | | 2.5 mM | | 3.5 mM | | 4.5 mM | | 6.0 mM | |

GSTP 132 bp (3 CpG sites, one CPG directly at 3' end)

| Tm in ° C. | M | U | M | U | M | U | M | U | M | U |
|---|---|---|---|---|---|---|---|---|---|---|
| 60 | 98 | 6 | 5420 | 1.6 | 8640 | 3 | 15740 | 380 | 11080 | 8.4 |
| 59.2 | 264 | 4.8 | 4860 | 10.2 | 13100 | 0 | 12120 | 0 | 9260 | 9.6 |
| 58 | 988 | 3.2 | 8520 | 282 | 19520 | 4.8 | 17740 | 14 | 19060 | 20 |
| 56.1 | 4160 | 24 | 14040 | 7.8 | 13580 | 14 | 22340 | 4.2 | 12020 | 40 |
| 53.8 | 4920 | 2.8 | 20460 | 94 | 19300 | 66 | 18540 | 174 | 11700 | 422 |
| 51.9 | 6820 | 16 | 11360 | 100 | 18440 | 360 | 13400 | 718 | 8260 | 1100 |
| 50.7 | 6580 | 18 | 11820 | 314 | 12920 | 808 | 14760 | 1002 | 6820 | 756 |
| 50 | 5020 | 82 | 10820 | 230 | 14660 | 1182 | 7380 | 334 | 5520 | 1000 |
| MgCl$_2$ | 1.5 mM | | 2.5 mM | | 3.5 mM | | 4.5 mM | | 6.0 mM | |

TABLE 23

Number of copies of methylated (M) and unmethylated (U) PLA2R1 DNA fragments (copies/20 μl well), proportion M/M + U (ratio) and relative proportion M/M + U (fractional abundance) in samples having 3,000 (trace 1), 20 (trace 2), 10 (trace 3) 5 (trace 4) and no copies (trace 5) of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 168 bp (SEQ ID: 1 and 2) without pre-amplification. NTC: non-template negative control.

| Sample | Target | Copies/ 20 μl well | Positive | Negative | Ch1+ Ch2+ | Ch1+ Ch2− | Ch1− Ch2+ | Ch1− Ch2− | Accepted droplets | Ratio | Fractional abundance |
|---|---|---|---|---|---|---|---|---|---|---|---|
| 70K/0 | M | 0 | 0 | 14071 | 0 | 0 | 13369 | 702 | 14071 | 0 | 0 |
| | U | 70600 | 13369 | 702 | | | | | | | |
| 70K/5 | M | 5.4 | 3 | 13198 | 3 | 0 | 12584 | 614 | 13201 | 7.00E−05 | 0.007 |
| | U | 72200 | 12587 | 614 | | | | | | | |
| 70K/10 | M | 10 | 6 | 14086 | 4 | 2 | 13438 | 648 | 14092 | 0.00014 | 0.014 |
| | U | 72400 | 13442 | 650 | | | | | | | |
| 70K/20 | M | 28 | 13 | 11255 | 12 | 1 | 10718 | 537 | 11268 | 0.00038 | 0.038 |
| | U | 71600 | 10730 | 538 | | | | | | | |
| 70K/3000 | M | 2780 | 1640 | 13103 | 1479 | 161 | 12415 | 688 | 14743 | 0.0413 | 3.97 |
| | U | 67200 | 13894 | 849 | | | | | | | |
| 175K/0 | M | 0 | 0 | 13938 | 0 | 0 | 13926 | 12 | 13938 | 0 | 0 |
| | U | 166000 | 13926 | 12 | | | | | | | |

TABLE 23-continued

Number of copies of methylated (M) and unmethylated (U) PLA2R1 DNA fragments (copies/20 µl well), proportion M/U (ratio) and relative proportion M/M + U (fractional abundance) in samples having 3,000 (trace 1), 20 (trace 2), 10 (trace 3) 5 (trace 4) and no copies (trace 5) of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 168 bp (SEQ ID: 1 and 2) without pre-amplification. NTC: non-template negative control.

| Sample | Target | Copies/ 20 µl well | Positive | Negative | Ch1+ Ch2+ | Ch1+ Ch2− | Ch1− Ch2+ | Ch1− Ch2− | Accepted droplets | Ratio | Fractional abundance |
|---|---|---|---|---|---|---|---|---|---|---|---|
| 175K/5 | M | 3.8 | 2 | 12554 | 2 | 0 | 12548 | 6 | 12556 | 2.1E−05 | 0.0021 |
|  | U | 180000 | 12550 | 6 |  |  |  |  |  |  |  |
| 175K/10 | M | 9.4 | 5 | 12592 | 5 | 0 | 12585 | 7 | 12597 | 5.3E−05 | 0.0053 |
|  | U | 176000 | 12590 | 7 |  |  |  |  |  |  |  |
| 175K/20 | M | 16 | 9 | 13287 | 9 | 0 | 13286 | 1 | 13296 | 7.00E−05 | 0.007 |
|  | U | 224000 | 13295 | 1 |  |  |  |  |  |  |  |
| 175K/3000 | M | 1968 | 891 | 10215 | 887 | 4 | 10210 | 5 | 11106 | 0.0117 | 1.16 |
|  | U | 168000 | 11097 | 9 |  |  |  |  |  |  |  |
| 350K/0 | M | 0 | 0 | 14661 | 0 | 0 | 14661 | 0 | 14661 | 0 | 0 |
|  | U | 20000000 | 14661 | 0 |  |  |  |  |  |  |  |
| 360K/5 | M | 2 | 1 | 12059 | 1 | 0 | 12059 | 0 | 12060 | 1.00E−07 | 1.00E−05 |
|  | U | 20000000 | 12060 | 0 |  |  |  |  |  |  |  |
| 350K/10 | M | 0 | 0 | 12984 | 0 | 0 | 12981 | 3 | 12984 | 0 | 0 |
|  | U | 198000 | 12981 | 3 |  |  |  |  |  |  |  |
| 350K/20 | M | 6.4 | 3 | 10969 | 3 | 0 | 10967 | 2 | 10972 | 3.2E−05 | 0.0032 |
|  | U | 202000 | 10970 | 2 |  |  |  |  |  |  |  |
| 350K/3000 | M | 560 | 283 | 11757 | 283 | 0 | 11756 | 1 | 12040 | 0.0025 | 0.25 |
|  | U | 222000 | 12039 | 1 |  |  |  |  |  |  |  |
| 700K/0 | M | 0 | 0 | 11327 | 0 | 0 | 11327 | 0 | 11327 | 0 | 0 |
|  | U | 20000000 | 11327 | 0 |  |  |  |  |  |  |  |
| 700K/5 | M | 0 | 0 | 10189 | 0 | 0 | 10189 | 0 | 10189 | 0 | 0 |
|  | U | 20000000 | 10189 | 0 |  |  |  |  |  |  |  |
| 700K/10 | M | 0 | 0 | 9889 | 0 | 0 | 9872 | 17 | 9889 | 0 | 0 |
|  | U | 150000 | 9872 | 17 |  |  |  |  |  |  |  |
| 700K/20 | M | 0 | 0 | 11500 | 0 | 0 | 11499 | 1 | 11500 | 0 | 0 |
|  | U | 220000 | 11499 | 1 |  |  |  |  |  |  |  |
| 700K/3000 | M | 114 | 50 | 10332 | 50 | 0 | 10328 | 4 | 10382 | 0.00061 | 0.061 |
|  | U | 184000 | 10378 | 4 |  |  |  |  |  |  |  |
| NTC | M | 0 | 0 | 12186 | 0 | 0 | 1 | 12185 | 12186 | 0 | 0 |
|  | U | 2 | 1 | 12185 |  |  |  |  |  |  |  |

TABLE 24

Number of copies of methylated (M) and unmethylated (U) PLA2R1 DNA fragments (copies/20 µl well), proportion M/U (ratio) and relative proportion M/M + U (fractional abundance) in samples having 3,000 (trace 1), 20 (trace 2), 10 (trace 3) 5 (trace 4) and no copies (trace 5) of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) without pre-amplification. NTC: non-template negative control.

| Sample | Target | Copies/ 20 µl well | Positive | Negative | Ch1+ Ch2+ | Ch1+ Ch2− | Ch1− Ch2+ | Ch1− Ch2− | Accepted droplets | Ratio | Fractional abundance |
|---|---|---|---|---|---|---|---|---|---|---|---|
| 70K/0 | M | 0 | 0 | 15481 | 0 | 0 | 2 | 15479 | 15481 | 0 | 0 |
|  | U | 3 | 2 | 15479 |  |  |  |  |  |  |  |
| 70K/5 | M | 1.8 | 1 | 13718 | 0 | 1 | 6 | 13712 | 13719 | 0.17 | 14 |
|  | U | 10.2 | 6 | 13713 |  |  |  |  |  |  |  |
| 70K/10 | M | 13 | 8 | 14504 | 0 | 8 | 7 | 14497 | 14512 | 1.1 | 53 |
|  | U | 11.4 | 7 | 14505 |  |  |  |  |  |  |  |
| 70K/20 | M | 24 | 13 | 12954 | 0 | 13 | 8 | 12946 | 12967 | 1.6 | 62 |
|  | U | 14 | 8 | 12959 |  |  |  |  |  |  |  |
| 70K/3000 | M | 3320 | 1585 | 10455 | 0 | 1585 | 9 | 10446 | 12040 | 190 | 99.47 |
|  | U | 18 | 9 | 12031 |  |  |  |  |  |  |  |
| 175K/0 | M | 2.6 | 2 | 17436 | 0 | 2 | 27 | 17409 | 17438 | 0.07 | 7 |
|  | U | 36 | 27 | 17411 |  |  |  |  |  |  |  |
| 175K/5 | M | 1.4 | 1 | 17244 | 0 | 1 | 1 | 17243 | 17245 | 1 | 50 |
|  | U | 1.4 | 1 | 17244 |  |  |  |  |  |  |  |
| 175K/10 | M | 8 | 5 | 14708 | 0 | 5 | 26 | 14682 | 14713 | 0.19 | 16 |
|  | U | 42 | 26 | 14687 |  |  |  |  |  |  |  |
| 175K/20 | M | 22 | 12 | 12577 | 0 | 12 | 14 | 12563 | 12589 | 0.9 | 46 |
|  | U | 26 | 14 | 12575 |  |  |  |  |  |  |  |
| 175K/3000 | M | 3020 | 1749 | 12789 | 1 | 1748 | 21 | 12768 | 14538 | 85 | 98.83 |
|  | U | 36 | 22 | 14516 |  |  |  |  |  |  |  |
| 350K/0 | M | 32 | 20 | 14348 | 0 | 20 | 19 | 14329 | 14368 | 1.1 | 51 |
|  | U | 32 | 19 | 14349 |  |  |  |  |  |  |  |

TABLE 24-continued

Number of copies of methylated (M) and unmethylated (U) PLA2R1 DNA fragments (copies/20 μl well), proportion M/U (ratio) and relative proportion M/M + U (fractional abundance) in samples having 3,000 (trace 1), 20 (trace 2), 10 (trace 3) 5 (trace 4) and no copies (trace 5) of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) without pre-amplification. NTC: non-template negative control.

| Sample | Target | Copies/20 μl well | Positive | Negative | Ch1+ Ch2+ | Ch1+ Ch2− | Ch1− Ch2+ | Ch1− Ch2− | Accepted droplets | Ratio | Fractional abundance |
|---|---|---|---|---|---|---|---|---|---|---|---|
| 350K/5 | M | 142 | 71 | 11757 | 0 | 71 | 28 | 11729 | 11828 | 2.5 | 72 |
| | U | 56 | 28 | 11800 | | | | | | | |
| 350K/10 | M | 16 | 8 | 11558 | 0 | 8 | 38 | 11520 | 11566 | 0.21 | 17 |
| | U | 78 | 38 | 11528 | | | | | | | |
| 350K/20 | M | 20 | 11 | 13597 | 0 | 11 | 50 | 13547 | 13608 | 0.22 | 18 |
| | U | 86 | 50 | 13558 | | | | | | | |
| 350K/3000 | M | 3160 | 1553 | 10816 | 0 | 1553 | 40 | 10776 | 12369 | 41 | 97.6 |
| | U | 76 | 40 | 12329 | | | | | | | |
| 700K/0 | M | 0 | 0 | 12883 | 0 | 0 | 62 | 12821 | 12883 | 0 | 0 |
| | U | 114 | 62 | 12821 | | | | | | | |
| 700K/5 | M | 0 | 0 | 11231 | 0 | 0 | 66 | 11165 | 11231 | 0 | 0 |
| | U | 138 | 66 | 11165 | | | | | | | |
| 700K/10 | M | 6 | 3 | 11863 | 0 | 3 | 40 | 11823 | 11866 | 0.07 | 7 |
| | U | 80 | 40 | 11826 | | | | | | | |
| 700K/20 | M | 8 | 4 | 11745 | 0 | 4 | 75 | 11670 | 11749 | 0.05 | 5 |
| | U | 150 | 75 | 11674 | 0 | | | | | | |
| 700K/3000 | M | 3140 | 1360 | 9515 | 1 | 1359 | 84 | 9431 | 10875 | 17 | 94.5 |
| | U | 184 | 85 | 10790 | | | | | | | |
| NTC | M | 0 | 0 | 16702 | 0 | 0 | 1 | 16701 | 16702 | 0 | 0 |
| | U | 1.4 | 1 | 16701 | 0 | 0 | 1 | 16701 | 16702 | | |

TABLE 25

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 168 bp (SEQ ID: 1 and 2, shown in the right-hand column), the primer pair 161 bp (SEQ ID: 53 and 10) and the primer pair 150 bp (SEQ ID: 53 and 9) after 15 pre-amplification cycles at an MgCl$_2$ concentration of 2.5 mM and an annealing temperature of 63° C. and subsequent dPCR. NTC: non-template negative control.

| Sample | Target | Copies/20 μl well | Positive | Negative | Ch1+ Ch2+ | Ch1+ Ch2− | Ch1− Ch2+ | Ch1− Ch2− | Accepted droplets | Ratio | Fractional abundance | PLA2R1 |
|---|---|---|---|---|---|---|---|---|---|---|---|---|
| 70K/0 | M | 0 | 0 | 13332 | 0 | 0 | 13331 | 1 | 13332 | 0 | 0 | 168 bp |
| | U | 224000 | 13331 | 1 | | | | | | | | |
| 70K/5 | M | 0 | 0 | 10775 | 0 | 0 | 10775 | 0 | 10775 | 0 | 0 | |
| | U | 20000000 | 10775 | 0 | | | | | | | | |
| 70K/10 | M | 0 | 0 | 11431 | 0 | 0 | 11431 | 0 | 11431 | 0 | 0 | |
| | U | 20000000 | 11431 | 0 | | | | | | | | |
| 70K/20 | M | 1.8 | 1 | 13839 | 1 | 0 | 13824 | 15 | 13840 | 1.1E−05 | 0.0011 | |
| | U | 160000 | 13825 | 15 | | | | | | | | |
| 70K/3000 | M | 5880 | 2845 | 10030 | 2845 | 0 | 10030 | 0 | 12875 | 0.00029 | 0.029 | |
| | U | 20000000 | 12875 | 0 | | | | | | | | |
| 175K/0 | M | 0 | 0 | 12634 | 0 | 0 | 12632 | 2 | 12634 | 0 | 0 | |
| | U | 206000 | 12632 | 2 | | | | | | | | |
| 175K/5 | M | 0 | 0 | 12656 | 0 | 0 | 12656 | 0 | 12656 | 0 | 0 | |
| | U | 20000000 | 12656 | 0 | | | | | | | | |
| 175K/10 | M | 0 | 0 | 12889 | 0 | 0 | 12888 | 1 | 12889 | 0 | 0 | |
| | U | 222000 | 12888 | 1 | | | | | | | | |
| 175K/20 | M | 0 | 0 | 12562 | 0 | 0 | 12560 | | 12562 | 0 | 0 | |
| | U | 20000000 | 12562 | 0 | | | | | | | | |
| 175K/3000 | M | 11.2 | 6 | 12622 | 6 | 0 | 12622 | 0 | 12628 | 6.00E−07 | 6.00E−05 | |
| | U | 20000000 | 12628 | 0 | | | | | | | | |
| 350K/0 | M | 0 | 0 | 13868 | 0 | 0 | 13868 | 0 | 13868 | 0 | 0 | |
| | U | 20000000 | 13868 | 0 | | | | | | | | |
| 350K/5 | M | 0 | 0 | 13080 | 0 | 0 | 13077 | | 13080 | 0 | 0 | |
| | U | 198000 | 13077 | 3 | | | | | | | | |
| 350K/10 | M | 0 | 0 | 14193 | 0 | 0 | 14188 | 5 | 14193 | 0 | 0 | |
| | U | 188000 | 14188 | 5 | | | | | | | | |
| 350K/20 | M | 0 | 0 | 14508 | 0 | 0 | 14503 | 5 | 14508 | 0 | 0 | |
| | U | 188000 | 14503 | 5 | | | | | | | | |
| 350K/3000 | M | 0 | 0 | 13295 | 0 | 0 | 13295 | 0 | 13295 | 0 | 0 | |
| | U | 20000000 | 13295 | 0 | | | | | | | | |
| 700K/0 | M | 0 | 0 | 14732 | 0 | 0 | 14729 | 3 | 14732 | 0 | 0 | |
| | U | 200000 | 14729 | 3 | | | | | | | | |

TABLE 25-continued

Number of copies of methylated (M) and unmethylated (U) PLA2R1 DNA fragments (copies/20 µl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 168 bp (SEQ ID: 1 and 2, shown in the right-hand column), the primer pair 161 bp (SEQ ID: 53 and 10) and the primer pair 150 bp (SEQ ID: 53 and 9) after 15 pre-amplification cycles at an MgCl₂ concentration of 2.5 mM and an annealing temperature of 63° C. and subsequent dPCR. NTC: non-template negative control.

| Sample | Target | Copies/20 µl well | Positive | Negative | Ch1+ Ch2+ | Ch1+ Ch2− | Ch1− Ch2+ | Ch1− Ch2− | Accepted droplets | Ratio | Fractional abundance | PLA2R1 |
|---|---|---|---|---|---|---|---|---|---|---|---|---|
| 700K/5 | M | 0 | 0 | 13799 | 0 | 0 | 13799 | 0 | 13799 | 0 | 0 | |
| | U | 20000000 | 13799 | 0 | | | | | | | | |
| 700K/10 | M | 0 | 0 | 13579 | 0 | 0 | 13579 | 0 | 13579 | 0 | 0 | |
| | U | 20000000 | 13579 | 0 | | | | | | | | |
| 700K/20 | M | 0 | 0 | 10322 | 0 | 0 | 10321 | | 10322 | 0 | 0 | |
| | U | 218000 | 10321 | 1 | | | | | | | | |
| 700K/3000 | M | 0 | 0 | 12072 | 0 | 0 | 12071 | 1 | 12072 | 0 | 0 | |
| | U | 222000 | 12071 | 1 | | | | | | | | |
| 70K/0 | M | 252 | 144 | 13392 | 17 | 127 | 1400 | 11992 | 13536 | 0.097 | 8.8 | 161 bp |
| | U | 2600 | 1417 | 12119 | | | | | | | | |
| 70K/5 | M | 264 | 142 | 12622 | 62 | 80 | 5878 | 6744 | 12764 | 0.0179 | 1.76 | |
| | U | 14740 | 5940 | 6824 | | | | | | | | |
| 70K/10 | M | 174 | 99 | 13355 | 36 | 63 | 4202 | 9153 | 13454 | 0.0195 | 1.91 | |
| | U | 8900 | 4238 | 9216 | | | | | | | | |
| 70K/20 | M | 1180 | 668 | 12992 | 262 | 406 | 7252 | 5740 | 13660 | 0.0628 | 5.91 | |
| | U | 18800 | 7514 | 6146 | | | | | | | | |
| 70K/3000 | M | 95000 | 14721 | 265 | 17 | 14704 | 0 | 265 | 14986 | 3600 | 99.972 | |
| | U | 26 | 17 | 14969 | | | | | | | | |
| 175K/0 | M | 38 | 23 | 14359 | 5 | 18 | 1270 | 13089 | 14382 | 0.017 | 1.7 | |
| | U | 2180 | 1275 | 13107 | | | | | | | | |
| 175K/5 | M | 344 | 187 | 12734 | 96 | 91 | 5027 | 7707 | 12921 | 0.0289 | 2.81 | |
| | U | 11880 | 5123 | 7798 | | | | | | | | |
| 175K/10 | M | 476 | 263 | 12886 | 196 | 67 | 9772 | 3114 | 13149 | 0.0142 | 1.4 | |
| | U | 33400 | 9968 | 3181 | | | | | | | | |
| 175K/20 | M | 1382 | 873 | 14429 | 535 | 338 | 8245 | 6184 | 15302 | 0.0689 | 6.44 | |
| | U | 20060 | 8780 | 6522 | | | | | | | | |
| 175K/3000 | M | 132800 | 13824 | 49 | 743 | 13081 | 2 | 47 | 13873 | 102 | 99.03 | |
| | U | 1298 | 745 | 13128 | | | | | | | | |
| 350K/0 | M | 0 | 0 | 14731 | 0 | 0 | 2731 | 12000 | 14731 | 0 | 0 | |
| | U | 4820 | 2731 | 12000 | | | | | | | | |
| 350K/5 | M | 48 | 32 | 15565 | 18 | 14 | 5530 | 10035 | 15597 | 0.0047 | 0.47 | |
| | U | 10340 | 5548 | 10049 | | | | | | | | |
| 350K/10 | M | 172 | 116 | 15774 | 75 | 41 | 7280 | 8494 | 15890 | 0.0118 | 1.17 | |
| | U | 14620 | 7355 | 8535 | | | | | | | | |
| 350K/20 | M | 994 | 578 | 13382 | 552 | 26 | 13193 | 189 | 13960 | 0.0101 | 1 | |
| | U | 98200 | 13745 | 215 | | | | | | | | |
| 350K/3000 | M | 104800 | 15203 | 179 | 2323 | 12880 | 11 | 168 | 15382 | 27.1 | 96.44 | |
| | U | 3880 | 2334 | 13048 | | | | | | | | |
| 700K/0 | M | 50 | 28 | 13360 | 23 | 5 | 8016 | 5344 | 13388 | 0.0023 | 0.23 | |
| | U | 21580 | 8039 | 5349 | | | | | | | | |
| 700K/5 | M | 0 | 0 | 13344 | 0 | 0 | 14 | 13330 | 13344 | 0 | 0 | |
| | U | 24 | 14 | 13330 | | | | | | | | |
| 700K/10 | M | 312 | 155 | 11614 | 154 | 1 | 14760 | 850 | 11769 | 0.005 | 0.5 | |
| | U | 61800 | 10918 | 851 | | | | | | | | |
| 700K/20 | M | 680 | 417 | 14213 | 417 | 0 | 133783 | 430 | 14630 | 0.0082 | 0.81 | |
| | U | 83000 | 14200 | 430 | | | | | | | | |
| 700K/3000 | M | 121600 | 13316 | 76 | 9932 | 3384 | 49 | 27 | 13392 | 3.78 | 79.1 | |
| | U | 32180 | 9981 | 3411 | | | | | | | | |
| 70K/0 | M | 1.8 | 1 | 13056 | 0 | 1 | 2201 | 10855 | 13057 | 0.0004 | 0.04 | 150 bp |
| | U | 4340 | 2201 | 10856 | | | | | | | | |
| 70K/5 | M | 1126 | 597 | 12181 | 84 | 513 | 2285 | 9896 | 12778 | 0.233 | 18.9 | |
| | U | 4820 | 2369 | 10409 | | | | | | | | |
| 70K/10 | M | 2214 | 1176 | 11914 | 238 | 938 | 2937 | 8977 | 13090 | 0.339 | 25.3 | |
| | U | 6540 | 3175 | 9915 | | | | | | | | |
| 70K/20 | M | 1954 | 917 | 10593 | 83 | 834 | 1273 | 9320 | 11510 | 0.66 | 39.8 | |
| | U | 2940 | 1356 | 10154 | | | | | | | | |
| 70K/3000 | M | 208000 | 13610 | 2 | 5 | 13605 | 0 | 2 | 13612 | 24000 | 100 | |
| | U | 8.6 | 5 | 13607 | | | | | | | | |
| 175K/0 | M | 336 | 208 | 14436 | 78 | 130 | 7291 | 7145 | 14644 | 0.0204 | 2 | |
| | U | 16460 | 7369 | 7275 | | | | | | | | |
| 175K/5 | M | 26 | 15 | 13524 | 0 | 15 | 7 | 13517 | 13539 | 2.1 | 68 | |
| | U | 12.2 | 7 | 13532 | | | | | | | | |
| 175K/10 | M | 3140 | 1872 | 13111 | 740 | 1132 | 6118 | 6993 | 14983 | 0.218 | 17.9 | |
| | U | 14400 | 6858 | 8125 | | | | | | | | |
| 175K/20 | M | 4360 | 2416 | 11841 | 445 | 1971 | 3608 | 8233 | 14257 | 0.555 | 35.7 | |
| | U | 7860 | 4053 | 10204 | | | | | | | | |
| 175K/3000 | M | 196000 | 12343 | 3 | 29 | 12314 | 0 | 3 | 12346 | 3500 | 99.972 | |
| | U | 56 | 29 | 12317 | | | | | | | | |
| 350K/0 | M | 13.8 | 8 | 13569 | 3 | 5 | 8570 | 4999 | 13577 | 0.05009 | 0.059 | |
| | U | 23480 | 8573 | 5004 | | | | | | | | |

TABLE 25-continued

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 168 bp (SEQ ID: 1 and 2, shown in the right-hand column), the primer pair 161 bp (SEQ ID: 53 and 10) and the primer pair 150 bp (SEQ ID: 53 and 9) after 15 pre-amplification cycles at an MgCl$_2$ concentration of 2.5 mM and an annealing temperature of 63° C. and subsequent dPCR. NTC: non-template negative control.

| Sample | Target | Copies/20 μl well | Positive | Negative | Ch1+ Ch2+ | Ch1+ Ch2− | Ch1− Ch2+ | Ch1− Ch2− | Accepted droplets | Ratio | Fractional abundance | PLA2R1 |
|---|---|---|---|---|---|---|---|---|---|---|---|---|
| 350K/5 | M | 740 | 398 | 12472 | 221 | 177 | 7918 | 4554 | 12870 | 0.0314 | 3.04 | |
| | U | 23540 | 8139 | 4731 | | | | | | | | |
| 350K/10 | M | 1278 | 578 | 10354 | 293 | 285 | 5884 | 4470 | 10932 | 0.065 | 6.13 | |
| | U | 19580 | 6177 | 4755 | | | | | | | | |
| 350K/20 | M | 4300 | 2065 | 10286 | 1093 | 972 | 6630 | 3656 | 12351 | 0.186 | 15.7 | |
| | U | 23100 | 7723 | 4628 | | | | | | | | |
| 350K/3000 | M | 222000 | 12675 | 1 | 0 | 12675 | 0 | 1 | 12676 | 100 | 100 | |
| | U | 0 | 0 | 12676 | | | | | | | | |
| 700K/0 | M | 6.6 | 4 | 14339 | 3 | 1 | 11469 | 2870 | 14343 | 0.0001 | 0.017 | |
| | U | 37840 | 11472 | 2871 | | | | | | | | |
| 700K/5 | M | 458 | 281 | 14297 | 202 | 79 | 12338 | 1959 | 14578 | 0.0099 | 0.98 | |
| | U | 46300 | 12540 | 2038 | | | | | | | | |
| 700K/10 | M | 1396 | 801 | 13102 | 617 | 184 | 11285 | 1817 | 13903 | 0.0306 | 2.97 | |
| | U | 45620 | 11902 | 2001 | | | | | | | | |
| 700K/20 | M | 5300 | 2600 | 10289 | 1756 | 844 | 8252 | 2037 | 12889 | 0.15 | 13.1 | |
| | U | 35260 | 10008 | 2881 | | | | | | | | |
| 700K/3000 | M | 196000 | 12054 | 3 | 271 | 11783 | 0 | 3 | 12057 | 370 | 99.73 | |
| | U | 534 | 271 | 11786 | | | | | | | | |
| NTC | M | 0 | 0 | 11564 | 0 | 0 | 1 | 11563 | 11564 | 0 | 0 | |
| | U | 2 | 1 | 11563 | | | | | | | | |

TABLE 26

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 168 bp (SEQ ID: 1 and 2, shown in the right-hand column), the primer pair 161 bp (SEQ ID: 53 and 10) and the primer pair 150 bp (SEQ ID: 53 and 9) after 50 pre-amplification cycles at an MgCl$_2$ concentration of 2.5 mM and an annealing temperature of 63° C. and subsequent dPCR. NTC: non-template negative control.

| Sample | Target | Copies/ 20 μl well | Positive | Negative | Ch1+ Ch2+ | Ch1+ Ch2− | Ch1− Ch2+ | Ch1− Ch2− | Accepted droplets | Ratio | Fractional abudance | PLA2R1 |
|---|---|---|---|---|---|---|---|---|---|---|---|---|
| 70K/0 | M | 0 | 0 | 12316 | 0 | 0 | 12315 | 1 | 12316 | 0 | 0 | 168 bp |
| | U | 222000 | 12315 | 1 | | | | | | | | |
| 70K/5 | M | 1.8 | 1 | 12779 | 1 | 0 | 12779 | 0 | 12780 | 9.00E−08 | 9.00E−06 | |
| | U | 20000000 | 12780 | 0 | | | | | | | | |
| 70K/10 | M | 0 | 0 | 13964 | 0 | 0 | 13964 | 0 | 13964 | 0 | 0 | |
| | U | 20000000 | 13964 | 0 | | | | | | | | |
| 70K/20 | M | 0 | 0 | 11379 | 0 | 0 | 11379 | 0 | 11379 | 0 | 0 | |
| | U | 20000000 | 11379 | 0 | | | | | | | | |
| 70K/3000 | M | 66400 | 10448 | 662 | 10448 | 0 | 661 | 1 | 11110 | 0.3 | 23.2 | |
| | U | 220000 | 11109 | 1 | | | | | | | | |
| 175K/0 | M | 0 | 0 | 12717 | 0 | 0 | 12711 | 6 | 12717 | 0 | 0 | |
| | U | 180000 | 12711 | 6 | | | | | | | | |
| 175K/5 | M | 0 | 0 | 13886 | 0 | 0 | 13883 | 3 | 13886 | 0 | 0 | |
| | U | 198000 | 13883 | 3 | | | | | | | | |
| 175K/10 | M | 0 | 0 | 13828 | 0 | 0 | 13827 | 1 | 13828 | 0 | 0 | |
| | U | 224000 | 13827 | 1 | | | | | | | | |
| 175K/20 | M | 0 | 0 | 13782 | 0 | 0 | 13781 | 1 | 13782 | 0 | 0 | |
| | U | 224000 | 13781 | 1 | | | | | | | | |
| 175K/3000 | M | 1010 | 560 | 12764 | 560 | 0 | 12764 | 0 | 13324 | 5.1E−05 | 0.0051 | |
| | U | 20000000 | 13324 | 0 | | | | | | | | |
| 350K/0 | M | 2 | 1 | 11827 | 1 | 0 | 11827 | 0 | 11828 | 1.00E−07 | 1.00E−05 | |
| | U | 20000000 | 11828 | 0 | | | | | | | | |
| 350K/5 | M | 3.8 | 2 | 12441 | 2 | 0 | 12441 | 0 | 12443 | 1.9E−07 | 1.9E−05 | |
| | U | 20000000 | 12443 | 0 | | | | | | | | |
| 350K/10 | M | 0 | 0 | 12247 | 0 | 0 | 12247 | 0 | 12247 | 0 | 0 | |
| | U | 20000000 | 12247 | 0 | | | | | | | | |
| 350K/20 | M | 0 | 0 | 12760 | 0 | 0 | 12759 | 1 | 12760 | 0 | 0 | |
| | U | 222000 | 12759 | 1 | | | | | | | | |
| 350K/3000 | M | 6.2 | 3 | 11393 | 3 | 0 | 11393 | 0 | 11396 | 3.1E−07 | 3.1E−05 | |
| | U | 20000000 | 11396 | 0 | | | | | | | | |
| 700K/0 | M | 10.6 | 6 | 13199 | 6 | 0 | 13199 | 0 | 13205 | 5.00E−07 | 5.00E−05 | |
| | U | 20000000 | 13205 | 0 | | | | | | | | |

TABLE 26-continued

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 168 bp (SEQ ID: 1 and 2, shown in the right-hand column), the primer pair 161 bp (SEQ ID: 53 and 10) and the primer pair 150 bp (SEQ ID: 53 and 9) after 50 pre-amplification cycles at an $MgCl_2$ concentration of 2.5 mM and an annealing temperature of 63° C. and subsequent dPCR. NTC: non-template negative control.

| Sample | Target | Copies/ 20 μl well | Positive | Negative | Ch1+ Ch2+ | Ch1+ Ch2− | Ch1− Ch2+ | Ch1− Ch2− | Accepted droplets | Ratio | Fractional abudance | PLA2R1 |
|---|---|---|---|---|---|---|---|---|---|---|---|---|
| 700K/5 | M | 0 | 0 | 11011 | 0 | 0 | 11011 | 0 | 11011 | 0 | 0 | |
| | U | 20000000 | 11011 | 0 | | | | | | | | |
| 700K/10 | M | 0 | 0 | 10392 | 0 | 0 | 10392 | 0 | 10392 | 0 | 0 | |
| | U | 20000000 | 10392 | 0 | | | | | | | | |
| 700K/20 | M | 2.4 | 1 | 9789 | 1 | 0 | 9789 | 0 | 9790 | 1.2E−07 | 1.2E−05 | |
| | U | 20000000 | 9790 | 0 | | | | | | | | |
| 700K/3000 | M | 2 | 1 | 11840 | 1 | 0 | 11839 | 1 | 11841 | 9.00E−06 | 0.0009 | |
| | U | 220000 | 11840 | 1 | | | | | | | | |
| 70K/0 | M | 0 | 0 | 16276 | 0 | 0 | 1169 | 15107 | 16276 | 0 | 0 | 161 bp |
| | U | 1760 | 1169 | 15107 | | | | | | | | |
| 70K/5 | M | 1.8 | 1 | 12665 | 1 | 0 | 12642 | 23 | 12666 | 1.3E−05 | 0.0013 | |
| | U | 148400 | 12643 | 23 | | | | | | | | |
| 70K/10 | M | 1.4 | 1 | 16320 | 1 | 0 | 16191 | 129 | 16321 | 1.3E−05 | 0.0013 | |
| | U | 113800 | 16192 | 129 | | | | | | | | |
| 70K/20 | M | 542 | 315 | 13509 | 315 | 0 | 13509 | 0 | 13824 | 2.7E−05 | 0.0027 | |
| | U | 20000000 | 13824 | 0 | | | | | | | | |
| 70K/3000 | M | 20000000 | 13433 | 0 | 0 | 13433 | 0 | 0 | 13433 | | 100 | |
| | U | 0 | 0 | 13433 | | | | | | | | |
| 175K/0 | M | 4 | 2 | 12059 | 2 | 0 | 11282 | 777 | 12061 | 6.00E−05 | 0.006 | |
| | U | 64600 | 11284 | 777 | | | | | | | | |
| 175K/5 | M | 1.8 | 1 | 12715 | 1 | 0 | 12706 | 9 | 12716 | 1.1E−05 | 0.0011 | |
| | U | 170000 | 12707 | 9 | | | | | | | | |
| 175K/10 | M | 0 | 0 | 12541 | 0 | 0 | 12537 | 4 | 12541 | 0 | 0 | |
| | U | 190000 | 12537 | 4 | | | | | | | | |
| 175K/20 | M | 17.6 | 10 | 13290 | 10 | 0 | 13288 | 2 | 13300 | 9.00E−05 | 0.009 | |
| | U | 208000 | 13298 | 2 | | | | | | | | |
| 175K/3000 | M | 226000 | 14492 | 1 | 362 | 14130 | 0 | 1 | 14493 | 380 | 99.74 | |
| | U | 596 | 362 | 14131 | | | | | | | | |
| 350K/0 | M | 0 | 0 | 14659 | 0 | 0 | 14574 | 85 | 14659 | 0 | 0 | |
| | U | 121200 | 14574 | 85 | | | | | | | | |
| 350K/5 | M | 0 | 0 | 15066 | 0 | 0 | 15055 | 11 | 15066 | 0 | 0 | |
| | U | 170000 | 15055 | 11 | | | | | | | | |
| 350K/10 | M | 1.8 | 1 | 13384 | 1 | 0 | 13383 | 1 | 13385 | 8.00E−06 | 0.0008 | |
| | U | 224000 | 13384 | 1 | | | | | | | | |
| 350K/20 | M | 100 | 59 | 13894 | 59 | 0 | 13892 | 2 | 13953 | 0.00048 | 0.048 | |
| | U | 208000 | 13951 | 2 | | | | | | | | |
| 350K/3000 | M | 206000 | 12365 | 2 | 1741 | 10624 | 0 | 2 | 12367 | 58 | 98.29 | |
| | U | 3580 | 1741 | 10626 | | | | | | | | |
| 700K/0 | M | 9.8 | 5 | 12126 | 5 | 0 | 12119 | 7 | 12131 | 6.00E−05 | 0.006 | |
| | U | 176000 | 12124 | 7 | | | | | | | | |
| 700K/5 | M | 0 | 0 | 13123 | 0 | 0 | 233 | 12890 | 13123 | 0 | 0 | |
| | U | 422 | 233 | 12890 | | | | | | | | |
| 700K/10 | M | 0 | 0 | 14715 | 0 | 0 | 14712 | 3 | 14715 | 0 | 0 | |
| | U | 200000 | 14712 | 3 | | | | | | | | |
| 700K/20 | M | 7 | 4 | 13428 | 4 | 0 | 13427 | 1 | 13432 | 3.1E−05 | 0.0031 | |
| | U | 224000 | 13431 | 1 | | | | | | | | |
| 700K/3000 | M | 20000000 | 14850 | 0 | 14847 | 3 | 0 | 0 | 14850 | 100 | 99 | |
| | U | 200000 | 14847 | 3 | | | | | | | | |
| 70K/0 | M | 1.4 | 1 | 16313 | 1 | 0 | 16313 | 0 | 16314 | 7.00E−08 | 7.00E−06 | 150 bp |
| | U | 20000000 | 16314 | 0 | | | | | | | | |
| 70K/5 | M | 136000 | 12892 | 40 | 12838 | 54 | 40 | 0 | 12932 | 1.05 | 51.3 | |
| | U | 129000 | 12878 | 54 | | | | | | | | |
| 70K/10 | M | 104600 | 13330 | 158 | 13209 | 121 | 149 | 9 | 13488 | 0.958 | 48.9 | |
| | U | 109200 | 13358 | 130 | | | | | | | | |
| 70K/20 | M | 172000 | 12971 | 9 | 1311 | 11660 | 0 | 9 | 12980 | 68 | 98.56 | |
| | U | 2500 | 1311 | 11669 | | | | | | | | |
| 70K/3000 | M | 20000000 | 13448 | 0 | 0 | 13448 | 0 | 0 | 13448 | 100 | | |
| | U | 0 | 0 | 13448 | | | | | | | | |
| 175K/0 | M | 4.4 | 3 | 15894 | 3 | 0 | 15893 | 1 | 15897 | 2.00E−05 | 0.002 | |
| | U | 228000 | 15896 | 1 | | | | | | | | |
| 175K/5 | M | 19.2 | 11 | 13482 | 0 | 11 | 0 | 13482 | 13493 | 0 | 0 | |
| | U | 0 | 0 | 13493 | | | | | | | | |
| 175K/10 | M | 20000000 | 14399 | 0 | 14399 | 0 | 0 | 0 | 14399 | 1 | 50 | |
| | U | 20000000 | 14399 | 0 | | | | | | | | |
| 175K/20 | M | 20000000 | 14118 | 0 | 13754 | 364 | 0 | 0 | 14118 | 230 | 99.57 | |
| | U | 86000 | 13754 | 364 | | | | | | | | |
| 175K/3000 | M | 206000 | 12998 | 2 | 0 | 12998 | 0 | 2 | 13000 | 100 | | |
| | U | 0 | 0 | 13000 | | | | | | | | |

TABLE 26-continued

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 168 bp (SEQ ID: 1 and 2, shown in the right-hand column), the primer pair 161 bp (SEQ ID: 53 and 10) and the primer pair 150 bp (SEQ ID: 53 and 9) after 50 pre-amplification cycles at an MgCl$_2$ concentration of 2.5 mM and an annealing temperature of 63° C. and subsequent dPCR. NTC: non-template negative control.

| Sample | Target | Copies/ 20 μl well | Posi- tive | Nega- tive | Ch1+ Ch2+ | Ch1+ Ch2− | Ch1− Ch2+ | Ch1− Ch2− | Accepted droplets | Ratio | Fractional abudance | PLA2R1 |
|---|---|---|---|---|---|---|---|---|---|---|---|---|
| 350K/0 | M | 0 | 0 | 13480 | 0 | 0 | 13479 | 1 | 13480 | 0 | 0 | |
| | U | 224000 | 13479 | 1 | | | | | | | | |
| 350K/5 | M | 892 | 536 | 13866 | 536 | 0 | 13866 | 0 | 14402 | 4.5E−05 | 0.0045 | |
| | U | 20000000 | 14402 | 0 | | | | | | | | |
| 350K/10 | M | 17580 | 8007 | 7211 | 8007 | 0 | 7199 | 12 | 15218 | 0.105 | 9.5 | |
| | U | 168000 | 15206 | 12 | | | | | | | | |
| 350K/20 | M | 184000 | 14938 | 6 | 14938 | 0 | 2 | 4 | 14944 | 0.95 | 48.7 | |
| | U | 194000 | 14940 | 4 | | | | | | | | |
| 350K/3000 | M | 20000000 | 14921 | 0 | 0 | 14921 | 0 | 0 | 14921 | | 100 | |
| | U | 0 | 0 | 14921 | | | | | | | | |
| 700K/0 | M | 6.8 | 4 | 13729 | 4 | 0 | 13729 | 0 | 13733 | 3.4E−07 | 3.4E−05 | |
| | U | 20000000 | 13733 | 0 | | | | | | | | |
| 700K/5 | M | 8.4 | 5 | 13937 | 5 | 0 | 13937 | 0 | 13942 | 4.2E−07 | 4.2E−05 | |
| | U | 20000000 | 13942 | 0 | | | | | | | | |
| 700K/10 | M | 142 | 74 | 12298 | 74 | 0 | 12297 | 1 | 12372 | 0.00064 | 0.064 | |
| | U | 222000 | 12371 | 1 | | | | | | | | |
| 700K/20 | M | 54220 | 12087 | 1340 | 12087 | 0 | 1340 | 0 | 13427 | 0.0027 | 0.27 | |
| | U | 20000000 | 13427 | 0 | | | | | | | | |
| 700K/3000 | M | 220000 | 11331 | 1 | 7 | 11324 | 0 | 1 | 11332 | 15000 | 99.993 | |
| | U | 14 | 7 | 11325 | | | | | | | | |
| NTC | M | 0 | 0 | 15130 | 0 | 0 | 0 | 15130 | 15130 | 0 | 0 | |
| | U | 0 | 0 | 15130 | | | | | | | | |

TABLE 27

Number of copies of methylated (M) and unmethylated (U) PLA2R1 DNA fragments (copies/20 μl well), proportion M/U (ratio) and relative proportion M/M + U (fractional abundance) in samples having 0, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) after 15 pre-amplification cycles at an MgCl$_2$ concentration of 1.5 mM or 6.0 mM and an annealing temperature of 50° C. and subsequent dPCR. NTC: non-template negative control.

| Sample | Target | Copies/ 20 μl | Posi- tive | Nega- tive | Ch1+ Ch2+ | Ch1+ Ch2− | Ch1− Ch2+ | Ch1− Ch2− | Accepted droplets | Ratio | Fractional abundance | MgCl$_2$ |
|---|---|---|---|---|---|---|---|---|---|---|---|---|
| 70K/0 | M | 7.4 | 4 | 12620 | 1 | 3 | 8774 | 3846 | 12624 | 0.00027 | 0.027 | 1.5 mM |
| | U | 27940 | 8775 | 3849 | | | | | | | | |
| 70K/5 | M | 1938 | 1081 | 12592 | 893 | 188 | 10688 | 1904 | 13673 | 0.0439 | 4.2 | |
| | U | 44180 | 11581 | 2092 | | | | | | | | |
| 70K/10 | M | 2642 | 1585 | 13335 | 1280 | 305 | 11016 | 2319 | 14920 | 0.0646 | 6.07 | |
| | U | 40900 | 12296 | 2624 | | | | | | | | |
| 70K/20 | M | 4980 | 2716 | 11547 | 1991 | 725 | 8731 | 2816 | 14263 | 0.152 | 13.17 | |
| | U | 32780 | 10722 | 3541 | | | | | | | | |
| 70K/3000 | M | 228000 | 16143 | 1 | 13 | 16130 | 0 | 1 | 16144 | 12.7 | 99.992 | |
| | U | 18 | 13 | 16131 | | | | | | | | |
| 175K/0 | M | 3 | 2 | 15991 | 0 | 2 | 15267 | 724 | 15993 | 4.00E−05 | 0.004 | |
| | U | 72800 | 15267 | 726 | | | | | | | | |
| 175K/5 | M | 1374 | 827 | 13748 | 820 | 7 | 13599 | 149 | 14575 | 0.0129 | 1.27 | |
| | U | 106800 | 14419 | 156 | | | | | | | | |
| 175K/10 | M | 2920 | 1518 | 11463 | 1504 | 14 | 11337 | 126 | 12981 | 0.0275 | 2.67 | |
| | U | 106600 | 12841 | 140 | | | | | | | | |
| 175K/20 | M | 4340 | 2534 | 12520 | 2443 | 91 | 12217 | 303 | 15054 | 0.0506 | 4.82 | |
| | U | 85800 | 14660 | 394 | | | | | | | | |
| 175K/3000 | M | 200000 | 15362 | 3 | 1274 | 14088 | 0 | 3 | 15365 | 99 | 99 | |
| | U | 2040 | 1274 | 14091 | | | | | | | | |
| 350K/0 | M | 394 | 249 | 14709 | 247 | 2 | 14670 | 39 | 14958 | 0.00285 | 0.284 | |
| | U | 138800 | 14917 | 41 | | | | | | | | |
| 350K/5 | M | 1980 | 1101 | 12543 | 1095 | 6 | 12514 | 29 | 13644 | 0.0141 | 1.39 | |
| | U | 140400 | 13609 | 35 | | | | | | | | |
| 350K/10 | M | 2660 | 1420 | 11905 | 1403 | 17 | 11765 | 140 | 13325 | 0.0254 | 2.47 | |
| | U | 104400 | 13168 | 157 | | | | | | | | |
| 350K/20 | M | 6660 | 3064 | 9355 | 3061 | 3 | 9340 | 15 | 12419 | 0.0433 | 4.15 | |
| | U | 154000 | 12401 | 18 | | | | | | | | |
| 350K/3000 | M | 20000000 | 13089 | 0 | 5406 | 7683 | 0 | 0 | 13089 | 1600 | 99.937 | |
| | U | 12540 | 5406 | 7683 | | | | | | | | |

TABLE 27-continued

Number of copies of methylated (M) and unmethylated (U) PLA2R1 DNA fragments (copies/20 μl well), proportion M/U (ratio) and relative proportion M/M + U (fractional abundance) in samples having 0, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) after 15 pre-amplification cycles at an MgCl$_2$ concentration of 1.5 mM or 6.0 mM and an annealing temperature of 50° C. and subsequent dPCR. NTC: non-template negative control.

| Sample | Target | Copies/20 μl | Positive | Negative | Ch1+ Ch2+ | Ch1+ Ch2− | Ch1− Ch2+ | Ch1− Ch2− | Accepted droplets | Ratio | Fractional abundance | MgCl$_2$ |
|---|---|---|---|---|---|---|---|---|---|---|---|---|
| 700K/0 | M | 4.6 | 2 | 10144 | 2 | 0 | 10139 | 5 | 10146 | 2.6E−05 | 0.0026 | |
|  | U | 180000 | 10141 | 5 | | | | | | | | |
| 700K/5 | M | 1206 | 512 | 9729 | 512 | 0 | 9721 | 8 | 10241 | 0.0072 | 0.71 | |
|  | U | 168000 | 10233 | 8 | | | | | | | | |
| 700K/10 | M | 1914 | 954 | 11254 | 954 | 0 | 11247 | 7 | 12208 | 0.0109 | 1.08 | |
|  | U | 176000 | 12201 | 7 | | | | | | | | |
| 700K/20 | M | 5820 | 3030 | 10810 | 3030 | 0 | 10805 | 5 | 13840 | 0.0312 | 3.02 | |
|  | U | 186000 | 13835 | 5 | | | | | | | | |
| 700K/3000 | M | 148800 | 15035 | 27 | 10868 | 4167 | 0 | 27 | 15062 | 4.95 | 83.2 | |
|  | U | 30080 | 10868 | 4194 | | | | | | | | |
| 70K/0 | M | 384 | 166 | 10081 | 166 | 0 | 10081 | 0 | 10247 | 1.9E−05 | 0.0019 | 6 mM |
|  | U | 20000000 | 10247 | 0 | | | | | | | | |
| 70K/5 | M | 4.4 | 2 | 10676 | 2 | 0 | 10676 | 0 | 10678 | 2.2E−07 | 2.2E−05 | |
|  | U | 20000000 | 10678 | 0 | | | | | | | | |
| 70K/10 | M | 11.2 | 6 | 12627 | 6 | 0 | 12594 | 33 | 12633 | 8.00E−05 | 0.008 | |
|  | U | 140000 | 12600 | 33 | | | | | | | | |
| 70K/20 | M | 8 | 4 | 11819 | 4 | 0 | 11819 | 0 | 11823 | 4.00E−07 | 4.00E−05 | |
|  | U | 20000000 | 11823 | 0 | | | | | | | | |
| 70K/3000 | M | 20000000 | 12141 | 0 | 12140 | 1 | 0 | 0 | 12141 | 90 | 98.9 | |
|  | U | 222000 | 12140 | 1 | | | | | | | | |
| 175K/0 | M | 0 | 0 | 13218 | 0 | 0 | 13218 | 0 | 13218 | 0 | 0 | |
|  | U | 20000000 | 13218 | 0 | | | | | | | | |
| 175K/5 | M | 0 | 0 | 11762 | 0 | 0 | 11762 | 0 | 11762 | 0 | 0 | |
|  | U | 20000000 | 11762 | 0 | | | | | | | | |
| 175K/10 | M | 2 | 1 | 11472 | 1 | 0 | 11472 | 0 | 11473 | 1.00E−07 | 1.00E−05 | |
|  | U | 20000000 | 11473 | 0 | | | | | | | | |
| 175K/20 | M | 6.2 | 3 | 11227 | 3 | 0 | 11213 | 14 | 11230 | 4.00E−05 | 0.004 | |
|  | U | 158000 | 11216 | 14 | | | | | | | | |
| 175K/3000 | M | 180000 | 14518 | 7 | 14516 | 2 | 2 | 5 | 14525 | 1 | 50 | |
|  | U | 180000 | 14518 | 7 | | | | | | | | |
| 350K/0 | M | 3.2 | 2 | 14917 | 2 | 0 | 14915 | 2 | 14919 | 1.5E−05 | 0.0015 | |
|  | U | 210000 | 14917 | 2 | | | | | | | | |
| 350K/5 | M | 0 | 0 | 16205 | 0 | 0 | 16205 | 0 | 16205 | 0 | 0 | |
|  | U | 20000000 | 16205 | 0 | | | | | | | | |
| 350K/10 | M | 0 | 0 | 15567 | 0 | 0 | 15567 | 0 | 15567 | 0 | 0 | |
|  | U | 20000000 | 15567 | 0 | | | | | | | | |
| 350K/20 | M | 1.4 | 1 | 15904 | 1 | 0 | 15904 | 0 | 15905 | 7.00E−08 | 7.00E−06 | |
|  | U | 20000000 | 15905 | 0 | | | | | | | | |
| 350K/3000 | M | 98400 | 13487 | 209 | 13487 | 0 | 209 | 0 | 13696 | 0.0049 | 0.49 | |
|  | U | 20000000 | 13696 | 0 | | | | | | | | |
| 700K/0 | M | 0 | 0 | 12117 | 0 | 0 | 12117 | 0 | 12117 | 0 | 0 | |
|  | U | 20000000 | 12117 | 0 | | | | | | | | |
| 700K/5 | M | 0 | 0 | 15213 | 0 | 0 | 15213 | 0 | 15213 | 0 | 0 | |
|  | U | 20000000 | 15213 | 0 | | | | | | | | |
| 700K/10 | M | 3 | 2 | 15564 | 2 | 0 | 15563 | 1 | 15566 | 1.3E−05 | 0.0013 | |
|  | U | 228000 | 15565 | 1 | | | | | | | | |
| 700K/20 | M | 18.2 | 11 | 14274 | 11 | 0 | 14272 | 2 | 14285 | 9.00E−05 | 0.009 | |
|  | U | 208000 | 14283 | 2 | | | | | | | | |
| 700K/3000 | M | 16840 | 8103 | 7752 | 8103 | 0 | 7750 | 2 | 15855 | 0.08 | 7.4 | |
|  | U | 212000 | 15853 | 2 | | | | | | | | |
| NTC | M | 0 | 0 | 16573 | 0 | 0 | 0 | 16573 | 16573 | 0 | 0 | |
|  | U | 0 | 0 | 16573 | | | | | | | | |

TABLE 28

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) after 15 pre-amplification cycles at an MgCl$_2$ concentration of 1.5 mM or 6.0 mM and an annealing temperature of 63° C. and subsequent dPCR. NTC: non-template negative control.

| Well | Sample | Target | Copies/20 μl well | Positive | Negative | Ch1+ Ch2+ | Ch1+ Ch2− | Ch1− Ch2+ | Ch1− Ch2− | Accepted droplets | Ratio | Fractional abundance | MgCl$_2$ |
|---|---|---|---|---|---|---|---|---|---|---|---|---|---|
| D03 | 70K/0 | M | 0 | 0 | 15574 | 0 | 0 | 64 | 15510 | 15574 | 0 | 0 | 1.5 mM |
|  |  | U | 96 | 64 | 15510 | | | | | | | | |

TABLE 28-continued

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) after 15 pre-amplification cycles at an MgCl₂ concentration of 1.5 mM or 6.0 mM and an annealing temperature of 63° C. and subsequent dPCR. NTC: non-template negative control.

| Well | Sample | Target | Copies/20 μl well | Positive | Negative | Ch1+ Ch2+ | Ch1+ Ch2− | Ch1− Ch2+ | Ch1− Ch2− | Accepted droplets | Ratio | Fractional abundance | MgCl₂ |
|---|---|---|---|---|---|---|---|---|---|---|---|---|---|
| C03 | 70K/5 | M | 14 | 9 | 15186 | 0 | 9 | 54 | 15132 | 15195 | 0.17 | 14 | |
| | | U | 84 | 54 | 15141 | | | | | | | | |
| B03 | 70K/10 | M | 42 | 26 | 14512 | 0 | 26 | 64 | 14448 | 14538 | 0.41 | 29 | |
| | | U | 104 | 64 | 14474 | | | | | | | | |
| A03 | 70K/20 | M | 42 | 26 | 14816 | 0 | 26 | 55 | 14761 | 14842 | 0.47 | 32 | |
| | | U | 88 | 55 | 14787 | | | | | | | | |
| H02 | 70K/3000 | M | 3032 | 2179 | 15843 | 2 | 2177 | 91 | 15752 | 18022 | 25 | 96.1 | |
| | | U | 122 | 93 | 17929 | | | | | | | | |
| G02 | 175K/0 | M | 0 | 0 | 14398 | 0 | 0 | 188 | 14210 | 14398 | 0 | 0 | |
| | | U | 310 | 188 | 14210 | | | | | | | | |
| F02 | 175K/5 | M | 7.4 | 5 | 15993 | 0 | 5 | 223 | 15770 | 15998 | 0.022 | 2.2 | |
| | | U | 330 | 223 | 15775 | | | | | | | | |
| E02 | 175K/10 | M | 32 | 22 | 15991 | 0 | 22 | 260 | 15731 | 16013 | 0.084 | 7.7 | |
| | | U | 386 | 260 | 15753 | | | | | | | | |
| D02 | 175K/20 | M | 36 | 24 | 15674 | 0 | 24 | 237 | 15437 | 15698 | 0.101 | 9.1 | |
| | | U | 358 | 237 | 15461 | | | | | | | | |
| C02 | 175K/3000 | M | 6660 | 3889 | 11890 | 5 | 3884 | 143 | 11747 | 15779 | 30 | 96.8 | |
| | | U | 222 | 148 | 15631 | | | | | | | | |
| B02 | 350K/0 | M | 0 | 0 | 13714 | 0 | 0 | 294 | 13420 | 13714 | 0 | 0 | |
| | | U | 510 | 294 | 13420 | | | | | | | | |
| A02 | 350K/5 | M | 1.4 | 1 | 15766 | 0 | 1 | 387 | 15379 | 15767 | 0.0026 | 0.25 | |
| | | U | 584 | 387 | 15380 | | | | | | | | |
| H01 | 350K/10 | M | 7 | 4 | 13299 | 0 | 4 | 373 | 12926 | 13303 | 0.011 | 1 | |
| | | U | 670 | 373 | 12930 | | | | | | | | |
| G01 | 350K/20 | M | 16.2 | 10 | 14489 | 0 | 10 | 493 | 13996 | 14499 | 0.02 | 2 | |
| | | U | 814 | 493 | 14006 | | | | | | | | |
| F01 | 350K/3000 | M | 4260 | 1456 | 7323 | 5 | 1451 | 286 | 7037 | 8779 | 5.4 | 84.3 | |
| | | U | 794 | 291 | 8488 | | | | | | | | |
| E01 | 700K/0 | M | 1.8 | 1 | 13385 | 0 | 1 | 616 | 12769 | 13386 | 0.0016 | 0.16 | |
| | | U | 1108 | 616 | 12770 | | | | | | | | |
| D01 | 700K/5 | M | 1.6 | 1 | 13958 | 0 | 1 | 909 | 13049 | 13959 | 0.0011 | 0.11 | |
| | | U | 1580 | 909 | 13050 | | | | | | | | |
| C01 | 700K/10 | M | 54 | 27 | 11833 | 0 | 27 | 765 | 11068 | 11860 | 0.034 | 3.3 | |
| | | U | 1560 | 765 | 11095 | | | | | | | | |
| B01 | 700K/20 | M | 2.2 | 1 | 10432 | 0 | 1 | 709 | 9723 | 10433 | 0.0014 | 0.14 | |
| | | U | 1660 | 709 | 9724 | | | | | | | | |
| A01 | 700K/3000 | M | 2780 | 1400 | 11205 | 7 | 1393 | 876 | 10329 | 12605 | 1.62 | 61.8 | |
| | | U | 1700 | 883 | 11722 | | | | | | | | |
| H05 | 70K/0 | M | 0 | 0 | 8874 | 0 | 0 | 42 | 8832 | 8874 | 0 | 0 | 6 mM |
| | | U | 112 | 42 | 8832 | | | | | | | | |
| G05 | 70K/5 | M | 1990 | 1039 | 11769 | 3 | 1036 | 47 | 11722 | 12808 | 22 | 95.6 | |
| | | U | 92 | 50 | 12758 | | | | | | | | |
| F05 | 70K/10 | M | 1866 | 1039 | 12595 | 0 | 1039 | 66 | 12529 | 13634 | 16.3 | 94.2 | |
| | | U | 114 | 66 | 13568 | | | | | | | | |
| E05 | 70K/20 | M | 6060 | 2669 | 9102 | 1 | 2668 | 54 | 9048 | 11771 | 55 | 98.21 | |
| | | U | 110 | 55 | 11716 | | | | | | | | |
| D05 | 70K/3000 | M | 224000 | 13388 | 1 | 3 | 13385 | 0 | 1 | 13389 | 42000 | 100 | |
| | | U | 5.2 | 3 | 13386 | | | | | | | | |
| C05 | 175K/0 | M | 5.6 | 3 | 12577 | 1 | 2 | 123 | 12454 | 12580 | 0.024 | 2.4 | |
| | | U | 234 | 124 | 12456 | | | | | | | | |
| B05 | 175K/5 | M | 770 | 432 | 12989 | 1 | 431 | 189 | 12800 | 13421 | 2.29 | 69.6 | |
| | | U | 336 | 190 | 13231 | | | | | | | | |
| A05 | 175K/10 | M | 3820 | 1801 | 10204 | 2 | 1799 | 134 | 10070 | 12005 | 14.3 | 93.4 | |
| | | U | 268 | 136 | 11869 | | | | | | | | |
| H04 | 175K/20 | M | 4980 | 2559 | 10837 | 2 | 2557 | 153 | 10684 | 13396 | 18.2 | 94.8 | |
| | | U | 274 | 155 | 13241 | | | | | | | | |
| G04 | 175K/3000 | M | 20000000 | 15139 | 0 | 0 | 15139 | 0 | 0 | 15139 | | 100 | |
| | | U | 0 | 0 | 15139 | | | | | | | | |
| F04 | 350K/0 | M | 9.4 | 6 | 14969 | 0 | 6 | 289 | 14680 | 14975 | 0.021 | 2 | |
| | | U | 458 | 289 | 14686 | | | | | | | | |
| E04 | 350K/5 | M | 976 | 588 | 13876 | 7 | 581 | 429 | 13447 | 14464 | 1.36 | 57.6 | |
| | | U | 720 | 436 | 14028 | | | | | | | | |
| D04 | 350K/10 | M | 1270 | 711 | 12815 | 2 | 709 | 344 | 12471 | 13526 | 2.08 | 67.6 | |
| | | U | 610 | 346 | 13180 | | | | | | | | |
| C04 | 350K/20 | M | 4700 | 2644 | 11951 | 15 | 2629 | 312 | 11639 | 14595 | 8.8 | 89.8 | |
| | | U | 534 | 327 | 14268 | | | | | | | | |
| B04 | 350K/3000 | M | 20000000 | 15336 | 0 | 2 | 15334 | 0 | 0 | 15336 | | 100 | |
| | | U | 3 | 2 | 15334 | | | | | | | | |
| A04 | 700K/0 | M | 1.6 | 1 | 14278 | 0 | 1 | 538 | 13740 | 14279 | 0.0018 | 0.18 | |
| | | U | 904 | 538 | 13741 | | | | | | | | |

TABLE 28-continued

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) after 15 pre-amplification cycles at an MgCl$_2$ concentration of 1.5 mM or 6.0 mM and an annealing temperature of 63° C. and subsequent dPCR. NTC: non-template negative control.

| Well | Sample | Target | Copies/20 μl well | Positive | Negative | Ch1+ Ch2+ | Ch1+ Ch2− | Ch1− Ch2+ | Ch1− Ch2− | Accepted droplets | Ratio | Fractional abundance | MgCl$_2$ |
|---|---|---|---|---|---|---|---|---|---|---|---|---|---|
| H03 | 700K/5 | M | 584 | 337 | 13425 | 12 | 325 | 976 | 12449 | 13762 | 0.333 | 25 | |
|  |  | U | 1760 | 988 | 12774 |  |  |  |  |  |  |  | |
| G03 | 700K/10 | M | 1536 | 1093 | 16213 | 22 | 1071 | 1076 | 15137 | 17306 | 1 | 49.9 | |
|  |  | U | 1542 | 1098 | 16208 |  |  |  |  |  |  |  | |
| F03 | 700K/20 | M | 4760 | 2541 | 11344 | 28 | 2513 | 496 | 10848 | 13885 | 5.25 | 84 | |
|  |  | U | 906 | 524 | 13361 |  |  |  |  |  |  |  | |
| E03 | 700K/3000 | M | 20000000 | 14373 | 0 | 0 | 14373 | 0 | 0 | 14373 |  | 100 | |
|  |  | U | 0 | 0 | 14373 |  |  |  |  |  |  |  | |
| H11 | NTC | M | 0 | 0 | 12407 | 0 | 0 | 0 | 12407 | 12407 | 0 | 0 | |
|  |  | U | 0 | 0 | 12407 |  |  |  |  |  |  |  | |

TABLE 29

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) after 50 pre-amplification cycles at an MgCl$_2$ concentration of 1.5 mM or 6.0 mM and an annealing temperature of 50° C. and subsequent dPCR. NTC: non-template negative control.

| Well | Sample | Target | Copies/20 μl well | Positive | Negative | Ch1+ Ch2+ | Ch1+ Ch2− | Ch1− Ch2+ | Ch1− Ch2− | Accepted droplets | Ratio | Fractional abundance | MgCl$_2$ |
|---|---|---|---|---|---|---|---|---|---|---|---|---|---|
| D08 | 70K/0 | M | 1.6 | 1 | 14934 | 1 | 0 | 14933 | 1 | 14935 | 7.00E−06 | 0.0007 | 1.5 mM |
|  |  | U | 226000 | 14934 | 1 |  |  |  |  |  |  |  | |
| C08 | 70K/5 | M | 2800 | 1611 | 12708 | 1611 | 0 | 12708 | 0 | 14319 | 0.00014 | 0.014 | |
|  |  | U | 20000000 | 14319 | 0 |  |  |  |  |  |  |  | |
| B08 | 70K/10 | M | 101800 | 16700 | 223 | 16700 | 0 | 223 | 0 | 16923 | 0.0051 | 0.51 | |
|  |  | U | 20000000 | 16923 | 0 |  |  |  |  |  |  |  | |
| A08 | 70K/20 | M | 176000 | 14400 | 8 | 14400 | 0 | 6 | 2 | 14408 | 0.84 | 45.8 | |
|  |  | U | 208000 | 14406 | 2 |  |  |  |  |  |  |  | |
| H07 | 70K/3000 | M | 20000000 | 14647 | 0 | 0 | 14647 | 0 | 0 | 14647 |  | 100 | |
|  |  | U | 0 | 0 | 14647 |  |  |  |  |  |  |  | |
| G07 | 175K/0 | M | 0 | 0 | 15079 | 0 | 0 | 15079 | 0 | 15079 | 0 | 0 | |
|  |  | U | 20000000 | 15079 | 0 |  |  |  |  |  |  |  | |
| F07 | 175K/5 | M | 1.4 | 1 | 15751 | 1 | 0 | 15751 | 0 | 15752 | 7.00E−08 | 7.00E−06 | |
|  |  | U | 20000000 | 15752 | 0 |  |  |  |  |  |  |  | |
| E07 | 175K/10 | M | 1458 | 847 | 13258 | 847 | 0 | 13258 | 0 | 14105 | 7.3E−05 | 0.0073 | |
|  |  | U | 20000000 | 14105 | 0 |  |  |  |  |  |  |  | |
| D07 | 175K/20 | M | 2192 | 1482 | 15175 | 1482 | 0 | 15174 | 1 | 16657 | 0.0096 | 0.95 | |
|  |  | U | 228000 | 16656 | 1 |  |  |  |  |  |  |  | |
| C07 | 175K/3000 | M | 20000000 | 14743 | 0 | 4 | 14739 | 0 | 0 | 14743 |  | 100 | |
|  |  | U | 6.4 | 4 | 14739 |  |  |  |  |  |  |  | |
| B07 | 350K/0 | M | 0 | 0 | 15783 | 0 | 0 | 15779 | 4 | 15783 | 0 | 0 | |
|  |  | U | 194000 | 15779 | 4 |  |  |  |  |  |  |  | |
| A07 | 350K/5 | M | 430 | 318 | 17265 | 318 | 0 | 17239 | 26 | 17583 | 0.0028 | 0.279 | |
|  |  | U | 153400 | 17557 | 26 |  |  |  |  |  |  |  | |
| H06 | 350K/10 | M | 286 | 119 | 9764 | 119 | 0 | 9763 | 1 | 9883 | 0.00132 | 0.132 | |
|  |  | U | 216000 | 9882 | 1 |  |  |  |  |  |  |  | |
| G06 | 350K/20 | M | 33680 | 9971 | 3131 | 9971 | 0 | 3131 | 0 | 13102 | 0.0017 | 0.17 | |
|  |  | U | 20000000 | 13102 | 0 |  |  |  |  |  |  |  | |
| F06 | 350K/3000 | M | 20000000 | 11525 | 0 | 367 | 11158 | 0 | 0 | 11525 | 26000 | 100 | |
|  |  | U | 762 | 367 | 11158 |  |  |  |  |  |  |  | |
| E06 | 700K/0 | M | 0 | 0 | 13798 | 0 | 0 | 13798 | 0 | 13798 | 0 | 0 | |
|  |  | U | 20000000 | 13798 | 0 |  |  |  |  |  |  |  | |
| D06 | 700K/5 | M | 22 | 11 | 12214 | 11 | 0 | 12212 | 2 | 12225 | 0.0001 | 0.01 | |
|  |  | U | 206000 | 12223 | 2 |  |  |  |  |  |  |  | |
| C06 | 700K/10 | M | 5.8 | 3 | 12099 | 3 | 0 | 12098 | 1 | 12102 | 2.6E−05 | 0.0026 | |
|  |  | U | 222000 | 12101 | 1 |  |  |  |  |  |  |  | |
| B06 | 700K/20 | M | 856 | 470 | 12694 | 470 | 0 | 12694 | 0 | 13164 | 4.3E−05 | 0.0043 | |
|  |  | U | 20000000 | 13164 | 0 |  |  |  |  |  |  |  | |
| A06 | 700K/3000 | M | 20000000 | 11920 | 0 | 7202 | 4718 | 0 | 0 | 11920 | 920 | 99.89 | |
|  |  | U | 21800 | 7202 | 4718 |  |  |  |  |  |  |  | |
| H10 | 70K/0 | M | 0 | 0 | 16220 | 0 | 0 | 16216 | 4 | 16220 | 0 | 0 | 6 mM |
|  |  | U | 196000 | 16216 | 4 |  |  |  |  |  |  |  | |
| G10 | 70K/5 | M | 0 | 0 | 15609 | 0 | 0 | 15609 | 0 | 15609 | 0 | 0 | |
|  |  | U | 20000000 | 15609 | 0 |  |  |  |  |  |  |  | |

TABLE 29-continued

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) after 50 pre-amplification cycles at an MgCl$_2$ concentration of 1.5 mM or 6.0 mM and an annealing temperature of 50° C. and subsequent dPCR. NTC: non-template negative control.

| Well | Sample | Target | Copies/20 μl well | Positive | Negative | Ch1+ Ch2+ | Ch1+ Ch2− | Ch1− Ch2+ | Ch1− Ch2− | Accepted droplets | Ratio | Fractional abundance | MgCl$_2$ |
|---|---|---|---|---|---|---|---|---|---|---|---|---|---|
| F10 | 70K/10 | M | 1.6 | 1 | 15284 | 1 | 0 | 15284 | 0 | 15285 | 8.00E−08 | 8.00E−06 | |
|  |  | U | 20000000 | 15285 | 0 |  |  |  |  |  |  |  |  |
| E10 | 70K/20 | M | 0 | 0 | 16842 | 0 | 0 | 16841 | 1 | 16842 | 0 | 0 | |
|  |  | U | 228000 | 16841 | 1 |  |  |  |  |  |  |  |  |
| D10 | 70K/3000 | M | 20000000 | 15099 | 0 | 15089 | 10 | 0 | 0 | 15099 | 120 | 99.15 | |
|  |  | U | 172000 | 15089 | 10 |  |  |  |  |  |  |  |  |
| C10 | 175K/0 | M | 1.6 | 1 | 14131 | 1 | 0 | 14127 | 4 | 14132 | 9.00E−06 | 0.0009 | |
|  |  | U | 192000 | 14128 | 4 |  |  |  |  |  |  |  |  |
| B10 | 175K/5 | M | 0 | 0 | 14404 | 0 | 0 | 14400 | 4 | 14404 | 0 | 0 | |
|  |  | U | 192000 | 14400 | 4 |  |  |  |  |  |  |  |  |
| A10 | 175K/10 | M | 0 | 0 | 14134 | 0 | 0 | 14129 | 5 | 14134 | 0 | 0 | |
|  |  | U | 186000 | 14129 | 5 |  |  |  |  |  |  |  |  |
| H09 | 175K/20 | M | 0 | 0 | 12685 | 0 | 0 | 12684 | 1 | 12685 | 0 | 0 | |
|  |  | U | 222000 | 12684 | 1 |  |  |  |  |  |  |  |  |
| G09 | 175K/3000 | M | 116000 | 13858 | 101 | 13847 | 11 | 79 | 22 | 13959 | 0.82 | 44.9 | |
|  |  | U | 142200 | 13926 | 33 |  |  |  |  |  |  |  |  |
| F09 | 350K/0 | M | 0 | 0 | 13733 | 0 | 0 | 13733 | 0 | 13733 | 0 | 0 | |
|  |  | U | 20000000 | 13733 | 0 |  |  |  |  |  |  |  |  |
| E09 | 350K/5 | M | 1.6 | 1 | 14852 | 1 | 0 | 14851 | 1 | 14853 | 7.00E−06 | 0.0007 | |
|  |  | U | 226000 | 14852 | 1 |  |  |  |  |  |  |  |  |
| D09 | 350K/10 | M | 3.2 | 2 | 14367 | 2 | 0 | 14367 | 0 | 14369 | 1.6E−07 | 1.6E−05 | |
|  |  | U | 20000000 | 14369 | 0 |  |  |  |  |  |  |  |  |
| C09 | 350K/20 | M | 0 | 0 | 13833 | 0 | 0 | 13833 | 0 | 13833 | 0 | 0 | |
|  |  | U | 20000000 | 13833 | 0 |  |  |  |  |  |  |  |  |
| B09 | 350K/3000 | M | 137200 | 13956 | 41 | 13956 | 0 | 41 | 0 | 13997 | 0.0069 | 0.68 | |
|  |  | U | 20000000 | 13997 | 0 |  |  |  |  |  |  |  |  |
| A09 | 700K/0 | M | 1.6 | 1 | 13937 | 1 | 0 | 13937 | 0 | 13938 | 8.00E−08 | 8.00E−06 | |
|  |  | U | 20000000 | 13938 | 0 |  |  |  |  |  |  |  |  |
| H08 | 700K/5 | M | 1.4 | 1 | 16530 | 1 | 0 | 16528 | 2 | 16531 | 7.00E−06 | 0.0007 | |
|  |  | U | 212000 | 16529 | 2 |  |  |  |  |  |  |  |  |
| G08 | 700K/10 | M | 7.4 | 5 | 16058 | 5 | 0 | 16053 | 5 | 16063 | 3.9E−05 | 0.0039 | |
|  |  | U | 190000 | 16058 | 5 |  |  |  |  |  |  |  |  |
| F08 | 700K/20 | M | 0 | 0 | 16236 | 0 | 0 | 16221 | 15 | 16236 | 0 | 0 | |
|  |  | U | 164000 | 16221 | 15 |  |  |  |  |  |  |  |  |
| E08 | 700K/3000 | M | 7760 | 4538 | 11614 | 4538 | 0 | 11614 | 0 | 16152 | 0.00039 | 0.039 | |
|  |  | U | 20000000 | 16152 | 0 |  |  |  |  |  |  |  |  |
| G11 | NTC | M | 0 | 0 | 16573 | 0 | 0 | 0 | 16573 | 16573 | 0 | 0 | |
|  |  | U | 0 | 0 | 16573 |  |  |  |  |  |  |  |  |

TABLE 30

Number of copies of methylated (M) and unmethylated (U) PLA2R1 DNA fragments (copies/20 μl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) after 50 pre-amplification cycles at an MgCl$_2$ concentration of 1.5 mM or 6.0 mM and an annealing temperature of 63° C. and subsequent dPCR. NTC: non-template negative control.

| Well | Sample | Target | Copies/20 μl well | Positive | Negative | Ch1+ Ch2+ | Ch1+ Ch2− | Ch1− Ch2+ | Ch1− Ch2− | Accepted droplets | Ratio | Fractional abundance | MgCl$_2$ |
|---|---|---|---|---|---|---|---|---|---|---|---|---|---|
| D08 | 70K/0 | M | 0 | 0 | 12948 | 0 | 0 | 12947 | 1 | 12948 | 0 | 0 | 1.5 mM |
|  |  | U | 222000 | 12947 | 1 |  |  |  |  |  |  |  |  |
| C08 | 70K/5 | M | 20000000 | 12682 | 0 | 2227 | 10455 | 0 | 0 | 12682 | 4400 | 99.977 | |
|  |  | U | 4540 | 2227 | 10455 |  |  |  |  |  |  |  |  |
| B08 | 70K/10 | M | 20000000 | 14665 | 0 | 5625 | 9040 | 0 | 0 | 14665 | 1800 | 99.943 | |
|  |  | U | 11380 | 5625 | 9040 |  |  |  |  |  |  |  |  |
| A08 | 70K/20 | M | 190000 | 12963 | 4 | 568 | 12395 | 0 | 4 | 12967 | 180 | 99.45 | |
|  |  | U | 1054 | 568 | 12399 |  |  |  |  |  |  |  |  |
| H07 | 70K/3000 | M | 20000000 | 14373 | 0 | 0 | 14373 | 0 | 0 | 14373 |  | 100 | |
|  |  | U | 0 | 0 | 14373 |  |  |  |  |  |  |  |  |
| G07 | 175K/0 | M | 7.4 | 5 | 15986 | 5 | 0 | 15978 | 8 | 15991 | 4.1E−05 | 0.0041 | |
|  |  | U | 178000 | 15983 | 8 |  |  |  |  |  |  |  |  |
| F07 | 175K/5 | M | 224000 | 13736 | 1 | 13735 | 1 | 1 | 0 | 13737 | 1 | 50 | |
|  |  | U | 224000 | 13736 | 1 |  |  |  |  |  |  |  |  |
| E07 | 175K/10 | M | 20000000 | 13236 | 0 | 3441 | 9795 | 0 | 0 | 13236 | 2800 | 99.965 | |
|  |  | U | 7080 | 3441 | 9795 |  |  |  |  |  |  |  |  |

TABLE 30-continued

Number of copies of methylated (M) and unmethylated (U) PLA2R1 DNA fragments (copies/20 µl well), proportion M/U (ratio) and relative proportion M/M + U (fractional abundance) in samples having 0, 5, 10, 20 and 3,000 copies of methylated PLA2R1 DNA fragments, and for each case a proportion of 70,000 (70K/0-3000), 175,000 (170K/0-3000), 350,000 (350K/0-3000) and 700,000 (700K/0-3000) copies of unmethylated PLA2R1 DNA fragments using the primer pair 133 bp (SEQ ID: 7 and 8) after 50 pre-amplification cycles at an MgCl$_2$ concentration of 1.5 mM or 6.0 mM and an annealing temperature of 63° C. and subsequent dPCR. NTC: non-template negative control.

| Well | Sample | Target | Copies/20 µl well | Positive | Negative | Ch1+ Ch2+ | Ch1+ Ch2− | Ch1− Ch2+ | Ch1− Ch2− | Accepted droplets | Ratio | Fractional abundance | MgCl$_2$ |
|---|---|---|---|---|---|---|---|---|---|---|---|---|---|
| D07 | 175K/20 | M | 20000000 | 13433 | 0 | 4918 | 8515 | 0 | 0 | 13433 | 1900 | 99.946 | |
|  |  | U | 10720 | 4918 | 8515 |  |  |  |  |  |  |  |  |
| C07 | 175K/3000 | M | 226000 | 14414 | 1 | 1 | 14413 | 0 | 1 | 14415 | 140000 | 99.993 | |
|  |  | U | 1.6 | 1 | 14414 |  |  |  |  |  |  |  |  |
| B07 | 350K/0 | M | 0 | 0 | 14207 | 0 | 0 | 14207 | 0 | 14207 | 0 | 0 | |
|  |  | U | 20000000 | 14207 | 0 |  |  |  |  |  |  |  |  |
| A07 | 350K/5 | M | 58600 | 12525 | 1133 | 12525 | 0 | 996 | 137 | 13658 | 0.541 | 35.1 | |
|  |  | U | 108200 | 13521 | 137 |  |  |  |  |  |  |  |  |
| H06 | 350K/10 | M | 20000000 | 13957 | 0 | 13957 | 0 | 0 | 0 | 13957 | 1 | 50 | |
|  |  | U | 20000000 | 13957 | 0 |  |  |  |  |  |  |  |  |
| G06 | 350K/20 | M | 20000000 | 13838 | 0 | 13838 | 0 | 0 | 0 | 13838 | 1 | 50 | |
|  |  | U | 20000000 | 13838 | 0 |  |  |  |  |  |  |  |  |
| F06 | 350K/3000 | M | 20000000 | 13946 | 0 | 0 | 13946 | 0 | 0 | 13946 |  | 100 | |
|  |  | U | 0 | 0 | 13946 |  |  |  |  |  |  |  |  |
| E06 | 700K/0 | M | 0 | 0 | 13541 | 0 | 0 | 13538 | 3 | 13541 | 0 | 0 | |
|  |  | U | 198000 | 13538 | 3 |  |  |  |  |  |  |  |  |
| D06 | 700K/5 | M | 0 | 0 | 13368 | 0 | 0 | 13368 | 0 | 13368 | 0 | 0 | |
|  |  | U | 20000000 | 13368 | 0 |  |  |  |  |  |  |  |  |
| C06 | 700K/10 | M | 20000000 | 11725 | 0 | 11724 | 1 | 0 | 0 | 11725 | 90 | 98.9 | |
|  |  | U | 220000 | 11724 | 1 |  |  |  |  |  |  |  |  |
| B06 | 700K/20 | M | 224000 | 13323 | 1 | 13323 | 0 | 1 | 0 | 13324 | 0.011 | 1.1 | |
|  |  | U | 20000000 | 13324 | 0 |  |  |  |  |  |  |  |  |
| A06 | 700K/3000 | M | 224000 | 13197 | 1 | 0 | 13197 | 0 | 1 | 13198 |  | 100 | |
|  |  | U | 0 | 0 | 13198 |  |  |  |  |  |  |  |  |
| H10 | 70K/0 | M | 0 | 0 | 13306 | 0 | 0 | 13306 | 0 | 13306 | 0 | 0 | 6 mM |
|  |  | U | 20000000 | 13306 | 0 |  |  |  |  |  |  |  |  |
| G10 | 70K/5 | M | 20000000 | 16759 | 0 | 1 | 16758 | 0 | 0 | 16759 | 1000000 | 100 | |
|  |  | U | 1.4 | 1 | 16758 |  |  |  |  |  |  |  |  |
| F10 | 70K/10 | M | 226000 | 14386 | 1 | 0 | 14386 | 0 | 1 | 14387 |  | 100 | |
|  |  | U | 0 | 0 | 14387 |  |  |  |  |  |  |  |  |
| E10 | 70K/20 | M | 228000 | 15578 | 1 | 2 | 15576 | 0 | 1 | 15579 | 80000 | 100 | |
|  |  | U | 3 | 2 | 15577 |  |  |  |  |  |  |  |  |
| D10 | 70K/3000 | M | 20000000 | 14384 | 0 | 11 | 14373 | 0 | 0 | 14384 | 1000000 | 100 | |
|  |  | U | 18 | 11 | 14373 |  |  |  |  |  |  |  |  |
| C10 | 175K/0 | M | 0 | 0 | 14344 | 0 | 0 | 14288 | 56 | 14344 | 0 | 0 | |
|  |  | U | 130400 | 14288 | 56 |  |  |  |  |  |  |  |  |
| B10 | 175K/5 | M | 20000000 | 16380 | 0 | 10788 | 5592 | 0 | 0 | 16380 | 790 | 99.87 | |
|  |  | U | 25280 | 10788 | 5592 |  |  |  |  |  |  |  |  |
| A10 | 175K/10 | M | 20000000 | 14283 | 0 | 0 | 14283 | 0 | 0 | 14283 |  | 100 | |
|  |  | U | 0 | 0 | 14283 |  |  |  |  |  |  |  |  |
| H09 | 175K/20 | M | 20000000 | 12692 | 0 | 0 | 12692 | 0 | 0 | 12692 |  | 100 | |
|  |  | U | 0 | 0 | 12692 |  |  |  |  |  |  |  |  |
| G09 | 175K/3000 | M | 20000000 | 15891 | 0 | 2 | 15889 | 0 | 0 | 15891 | 1000000 | 100 | |
|  |  | U | 3 | 2 | 15889 |  |  |  |  |  |  |  |  |
| F09 | 350K/0 | M | 1.4 | 1 | 16234 | 1 | 0 | 16220 | 14 | 16235 | 9.00E−06 | 0.0009 | |
|  |  | U | 166000 | 16221 | 14 |  |  |  |  |  |  |  |  |
| E09 | 350K/5 | M | 20000000 | 14935 | 0 | 11316 | 3619 | 0 | 0 | 14935 | 600 | 99.83 | |
|  |  | U | 33360 | 11316 | 3619 |  |  |  |  |  |  |  |  |
| D09 | 350K/10 | M | 20000000 | 15498 | 0 | 682 | 14816 | 0 | 0 | 15498 | 19000 | 100 | |
|  |  | U | 1058 | 682 | 14816 |  |  |  |  |  |  |  |  |
| C09 | 350K/20 | M | 20000000 | 11865 | 0 | 21 | 11844 | 0 | 0 | 11865 | 480000 | 100 | |
|  |  | U | 42 | 21 | 11844 |  |  |  |  |  |  |  |  |
| B09 | 350K/3000 | M | 20000000 | 13551 | 0 | 0 | 13551 | 0 | 0 | 13551 |  | 100 | |
|  |  | U | 0 | 0 | 13551 |  |  |  |  |  |  |  |  |
| A09 | 700K/0 | M | 0 | 0 | 14046 | 0 | 0 | 14046 | 0 | 14046 | 0 | 0 | |
|  |  | U | 20000000 | 14046 | 0 |  |  |  |  |  |  |  |  |
| H08 | 700K/5 | M | 20000000 | 13431 | 0 | 13427 | 4 | 0 | 0 | 13431 | 100 | 99.05 | |
|  |  | U | 192000 | 13427 | 4 |  |  |  |  |  |  |  |  |
| G08 | 700K/10 | M | 20000000 | 12296 | 0 | 1472 | 10824 | 0 | 0 | 12296 | 6700 | 99.985 | |
|  |  | U | 3000 | 1472 | 10824 |  |  |  |  |  |  |  |  |
| F08 | 700K/20 | M | 188000 | 14635 | 5 | 8 | 14627 | 0 | 5 | 14640 | 15000 | 100 | |
|  |  | U | 12.8 | 8 | 14632 |  |  |  |  |  |  |  |  |
| E08 | 700K/3000 | M | 20000000 | 14344 | 0 | 0 | 14344 | 0 | 0 | 14344 |  | 100 | |
|  |  | U | 0 | 0 | 14344 |  |  |  |  |  |  |  |  |
| H11 | NTC | M | 0 | 0 | 12407 | 0 | 0 | 0 | 12407 | 12407 | 0 | 0 | |
|  |  | U | 0 | 0 | 12407 |  |  |  |  |  |  |  |  |

TABLE 31

Determination of GSTP1 and RASSF1A methylation by means of the BBPA-dPCR method and using the GSTP1 116 bp primer (SEQ ID No: 93 and 94; 4.5 mM MgCl$_2$ concentration; 53.7° C. annealing temperature and 15× BBPA cycles), GSTP1 120 bp primer (SEQ ID No: 5 and 6; 2.5 mM MgCl$_2$ concentration; 50.7° C. annealing temperature and 15× BBPA cycles) and RASSF1A 117 bp primer (SEQ ID No: 3 and 4; 2.5 mM MgCl$_2$ concentration; 55.7° C. annealing temperature and 15× BBPA cycles) in serum samples from healthy women (K1-K25) and patients with breast-CA (P1-P16) and ovarian CA (P17-P23), one serum sample from patient P8a after eight weeks of chemotherapy (P8b) and one patient (P24) with pathogenic BRCA1 mutation. Pathological methylation values are in bold. The cut-off values for each gene are given in the first row.

| ID | Age | CA 15-3 or CA125 in U/ml | GSTP1 116 bp <0.05% | GSTP1 120 bp <0.067% | RASSF1A 117 bp <3.0% | Clinical findings |
|---|---|---|---|---|---|---|
| K1  | 21 |       | 0     | 0      | 1.1  | |
| K2  | 21 |       | 0     | 0      | 1    | |
| K3  | 29 |       | 0     | 0      | 0.94 | |
| K4  | 23 |       | 0     | 0      | 0.9  | |
| K5  | 20 |       | 0     | 0.0022 | 0.63 | |
| K6  | 18 |       | 0     | 0      | 0.4  | |
| K7  | 26 |       | 0     | 0      | 1.5  | |
| K8  | 20 |       | 0     | 0      | 2.7  | |
| K9  | 31 |       | 0.029 | 0      | 1.26 | |
| K10 | 45 |       | 0     | 0      | 1.6  | |
| K11 | 48 |       | 0     | 0      | 0.7  | |
| K12 | 34 |       | 0     | 0      | 0.8  | |
| K13 | 16 |       | 0     | 0      | 0.8  | |
| K14 | 23 |       | 0     | 0      | 1.6  | |
| K15 | 20 |       | 0     | 0      | 0.9  | |
| K16 | 43 |       | 0.05  | 0      | 1.1  | |
| K17 | 41 |       | 0     | 0.017  | 0    | |
| K18 | 22 |       | 0     | 0      | 1    | |
| K19 | 71 |       | 0     | 0.014  | 3    | |
| K20 | 36 |       | 0     | 0.055  | 0.4  | |
| K21 | 25 |       | 0     | 0      | 1.3  | |
| K22 | 34 |       | 0     | 0.067  | 0.6  | |
| K23 | 46 |       | 0.03  | 0      | 1.4  | |
| K24 | 19 |       | 0     | 0      | 0.9  | |
| K25 | 49 |       | 0     | 0      | 0    | |
|     |    | CA 15-3 |     |        |      | |
| P1  | 57 | 28.5  | 0.19 | 0      | 3.4  | bifocal invasive breast-CA |
| P2  | 67 | 27.8  | 0.54 | 0      | 0.88 | invasive breast-CA, left |
| P3  | 42 | 25.4  | 7.9  | 0      | 1    | lymphogenic, osseous, pulmonary and hepatic metastatic breast-CA, right |
| P4  | 71 | 99.7  | 0.65 | 0      | 5.7 | breast-CA with known BRCA1 mutation |
| P5  | 75 | 59.0  | 27.6 | 0      | 1.4  | secondary osseous, lymphogenic, pleural and pulmonary metastatic breast-CA |
| P6  | 76 | 73.0  | 1.9  | 0      | 7.6 | secondary cutaneous, osseous and stomach metastatic invasive lobular breast-CA |
| P7  | 47 | 504.3 | 37.7 | 0.15 | 10.0 | secondary osseous metastatic breast-CA with tumour progression |
| P8a | 63 | 941.3 | 0.9  | 0      | 18.0 | primary osseous and hepatic metastatic breast-CA |
| P9  | 58 | 120.5 | 0.04     | 0      | 6.2 | osseous, lymphogenic, pleural and pulmonary metastatic breast-CA |
| P10 | 87 | 1098  | 3.6  | 0.12 | 1.5 | secondary osseous metastatic breast-CA with tumour progression |
| P11 | 73 | 106.8 | 0        | 0.011  | 6.7 | secondary osseous, lymphogenic, pleural and pulmonary metastatic breast-CA |
| P12 | 64 | 130.7 | 11.6 | 0      | 0.69 | secondary osseous and hepatic metastatic breast-CA |
| P13 | 60 | 157.5 | 5.3  | 0      | 3.4 | secondary pulmonary, pleural and osseous metastatic breast-CA |
| P14 | 76 | 145.2 | 8.8  | 0      | 0.32 | secondary lymphogenic, pleural and adrenal metastatic breast-CA |
| P15 | 30 | 178.5 | 18.4 | 0.005  | 50.1 | secondary osseous, lymphogenic, pleural, hepatic and meningeal metastatic breast-CA |
| P16 | 56 | 650   | 1.39 | 0      | 2.3  | secondary pleural and hepatic metastatic breast-CA |

TABLE 31-continued

Determination of GSTP1 and RASSF1A methylation by means of the BBPA-dPCR method and using the GSTP1 116 bp primer (SEQ ID No: 93 and 94; 4.5 mM MgCl$_2$ concentration; 53.7° C. annealing temperature and 15× BBPA cycles), GSTP1 120 bp primer (SEQ ID No: 5 and 6; 2.5 mM MgCl$_2$ concentration; 50.7° C. annealing temperature and 15× BBPA cycles) and RASSF1A 117 bp primer (SEQ ID No: 3 and 4; 2.5 mM MgCl$_2$ concentration; 55.7° C. annealing temperature and 15× BBPA cycles) in serum samples from healthy women (K1-K25) and patients with breast-CA (P1-P16) and ovarian CA (P17-P23), one serum sample from patient P8a after eight weeks of chemotherapy (P8b) and one patient (P24) with pathogenic BRCA1 mutation. Pathological methylation values are in bold. The cut-off values for each gene are given in the first row.

| ID | Age | CA 15-3 or CA125 in U/ml | GSTP1 116 bp <0.05% | GSTP1 120 bp <0.067% | RASSF1A 117 bp <3.0% | Clinical findings |
|---|---|---|---|---|---|---|
| | | CA 125 | | | | |
| P17 | 70 | 57.2 | 1.12 | 0 | 1.02 | serous high-grade ovarian-CA |
| P18 | 76 | 1871 | 2.7 | 0 | 1.1 | lymphogenic and hepatic metastatic ovarian cancer |
| P19 | 57 | 23.8 | 0 | 6.1 | 9.0 | malignant mesodermal mixed tumour in ovary area |
| P20 | 51 | 188.6 | 0 | 0 | 6.0 | late-recurrent ovarian cancer with hepatic and lymphogenic metastasis |
| P21 | 54 | 903.2 | 0 | 1.3 | 7.0 | lymphogenic and peritoneal metastatic ovarian cancer |
| P22 | 73 | 56.2 | 0.12 | 0.005 | 2.5 | early-recurring ovarian cancer with liver metastasis |
| P23 | 49 | 196.7 | 1.1 | 5.8 | 0 | late-recurrent ovarian cancer |
| | | CA 15-3 | | | | |
| P8b | 63 | 133 | 0 | 0 | 2 | serum sample from patient P8a after 8 weeks of chemotherapy |
| P24 | 32 | 9.8 | 0.54 | 0 | 1.1 | pathogenic BRCA1 mutation, prophylactic mastectomy |

BIBLIOGRAPHY

[1] Mikeska T, Candiloro I L, Dobrovic A. Epigenomics. 2010; 2: 561-73.
[2] Kristensen L S and Hansen L L. Clin Chem. 2009; 8: 1471-83.
[3] Shen L and Waterland R A. Curr Opin Clin Nutr Metab Care 2007; 5: 576-81.
[4] Hernández H G, Tse M Y, Pang S C, et al. BioTechniques. 2013; 4: 181-97.
[5] Herman J G, Graff J R, Myöhänen S, et al. Proc Nat Acad Sci USA. 1996; 18: 9821-26.
[6] Kristensen L S, Wojdacz T K, Thestrup B B, et al. BMC Cancer 2009; 9: 453.
[7] Candiloro I L, Mikeska T, Hokland P, et al. Epigenetics Chromatin. 2008; 1: 7.
[8] Kraytsberg Y and Khrapko K. Expert Review of Molecular Diagnostics. 2005; 5: 809-15.
[9] Applications Guide dPCR, Biorad. http://www.bio-rad.com/webroot/web/pdf/lsr/literature/Bulletin_6407. pdf
[10] Grützmann R, Molnar B, Pilarsky C, et al. PLoS One. 2008; 3: e3759.
[11] How Kit A, Nielsen H M, Tost J. Biochimie. 2012 November; 94(11): 2314-37.
[12] Stewart G D, Van Neste L, Delvenne P, et al. J Urol. 2013; 189: 110-1116.
[13] Tombal B. EurUrol. 2012; 62: 997-8.
[14] Tombal B. Eur Urology Suppl. 2006; 5: 511-513.
[15] Castellanos-Rizaldos E, Milbury C A, Karatza E, et al., PLoS One. 2014; 9(4): e94103.
[16] Warnecke P M, Stirzaker C, Melki J R, Miliar O S, Paul C L, Clark S J. Nucleic Acids Res. 1997 Nov. 1; 25(21): 4422-6.
[17] Wojdacz T K, Dobrovic A, Hansen L L. Nat Protoc. 2008; 3(12): 1903-8. DOI: 10.1038/nprot.2008.191.
[18] Wojdacz T K, Hansen L L, Dobrovic A. BMC Res Notes. 2008 Jul. 28; 1: 54. DOI: 10.1186/1756-0500-1-54.
[19] Wojdacz T K, Hansen L L: BioTechnique. 2006; 41: 274-8.
[20] Hubbard R A. Annals of Internal Medicine. 2011; 155: 481-92.

The invention claimed is:

1. Method for amplifying and quantifying DNA in an isolated sample, comprising the steps of:
 a) bisulphite conversion of the DNA in the sample,
 b) pre-amplifying methylated and unmethylated DNA sequences by means of PCR, wherein the methylated DNA sequences are amplified to a different extent than the unmethylated DNA sequences,
 c) quantifying the methylated and unmethylated DNA obtained in step b) by means of digital PCR, wherein the average number of DNA molecules per compartment used in the digital PCR is at least 8.

2. Method according to claim 1, wherein the isolated sample is a bodily fluid.

3. Method according to claim 1, wherein methylated and unmethylated DNA sequences in PLA2R1, RASSF1A and GSTP1 genes are pre-amplified in step b).

4. Method according to claim 1, wherein step b) for pre-amplification, multiple primer pairs are simultaneously used in the PCR.

5. Method according to claim 1, wherein the methylated and unmethylated DNA sequences are quantified in step c) using probes, the probes for the methylated DNA sequences comprising a total of at least three 5'-CG-3' dinucleotides for each DNA sequence and/or the probes for the unmethylated DNA sequences comprising a total of at least three 5'-CA-3' dinucleotides or at least three 5'-TG-3' dinucleotides for each DNA sequence, the probes wherein the probes comprise sequences selected from the group consisting of SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: and SEQ ID NO: 60.

6. The method according to claim 1, wherein the average number of DNA molecules per compartment used in the digital PCR is at least 10.

7. The method according to claim 3, wherein at least one forward primer and at least one reverse primer is used in step b) for pre-amplifying methylated and unmethylated PLA2R1 sequences, the at least one forward primer comprises a sequence corresponding to SEQ ID NO: 1, SEQ ID NO: 7, or SEQ ID NO:
 53, and the at least one reverse primer comprises a sequence corresponding to SEQ ID NO: 2, SEQ ID NO: 8, SEQ ID NO: 9, SEQ ID NO: 10, or SEQ ID NO: 11.

8. The method according to claim 7, wherein the at least one forward primer comprises a sequence corresponding to SEQ ID NO: 1 or SEQ ID NO: 7 and the at least one reverse primer comprises a sequence corresponding to SEQ ID NO: 2 or SEQ ID NO: 8.

9. The method according to claim 3, wherein at least one forward primer and at least one reverse primer is used in step b) for pre-amplifying methylated and unmethylated RASSF1A sequences, the at least one forward primer comprises a sequence corresponding to SEQ ID NO: 3, SEQ ID NO: 61, SEQ ID NO: 104, SEQ ID NO: 106, SEQ ID NO: 108, or SEQ ID NO: 110, and the at least one reverse primer comprises a sequence corresponding to SEQ ID NO: 4, SEQ ID NO: 62, SEQ ID NO: 105, SEQ ID NO: 107, SEQ ID NO: 109, or SEQ ID NO: 111.

10. The method according to claim 9, wherein the at least one forward primer comprises a sequence corresponding to SEQ ID NO: 3, SEQ ID NO: 106, or SEQ ID NO: 108, and the at least one reverse primer comprises a sequence corresponding to SEQ ID NO: 4, SEQ ID NO: 107, or SEQ ID NO: 109.

11. The method according to claim 3, wherein at least one forward primer and at least one reverse primer is used in step b) for pre-amplifying methylated and unmethylated GSTP1 sequences, the at least one forward primer comprises a sequence corresponding to SEQ ID NO: 5, SEQ ID NO: 12, SEQ ID NO: 91, SEQ ID NO: 93, SEQ ID NO: 95, or SEQ ID NO: 97, and the at least one reverse primer comprises a sequence corresponding to SEQ ID NO: 6, SEQ ID NO: 13, SEQ ID NO: 92, SEQ ID NO: 94, SEQ ID NO: 96, or SEQ ID NO: 98.

12. The method according to claim 11, wherein the at least one forward primer comprises a sequence corresponding to SEQ ID NO: 5 or SEQ ID NO: 93 and the at least one reverse primer comprises a sequence corresponding to SEQ ID NO: 6 or SEQ ID NO: 94.

13. Method according to claim 1, wherein the methylated and unmethylated DNA sequences are quantified in step c) using probes, the probes for the methylated DNA sequences comprising a total of at least three 5'-CG-3' dinucleotides for each DNA sequence and/or the probes for the unmethylated DNA sequences comprising a total of at least three 5'-CA-3' dinucleotides or at least three 5'-TG-3' dinucleotides for each DNA sequence, the probes wherein the probes comprise sequences selected from the group consisting of SEQ ID NO: 24, SEQ ID NO: 25, SEQ ID NO: 29, SEQ ID NO: 30, SEQ ID NO: 31, SEQ ID NO: 32, SEQ ID NO: 54, SEQ ID NO: 55, SEQ ID NO: 115, SEQ ID NO: 116, SEQ ID NO: 117, SEQ ID NO: 118, SEQ ID NO: 122, SEQ ID NO: 123, SEQ ID NO: 124, and SEQ ID NO: 125.

14. Method according to claim 1, wherein the methylated and unmethylated DNA sequences are quantified in step c) using probes, the probes for the methylated DNA sequences comprising a total of at least three 5'-CG-3' dinucleotides for each DNA sequence and/or the probes for the unmethylated DNA sequences comprising a total of at least three 5'-CA-3' dinucleotides or at least three 5'-TG-3' dinucleotides for each DNA sequence, the probes wherein the probes comprise sequences selected from the group consisting of SEQ ID NO: 33, SEQ ID NO: 34, SEQ ID NO: 35, SEQ ID NO: 36, SEQ ID NO: 45, SEQ ID NO: 46, SEQ ID NO: 47, SEQ ID NO: 48, SEQ ID NO: 49, SEQ ID NO:
50, SEQ ID NO: 51, SEQ ID NO: 52, SEQ ID NO: 56, SEQ ID NO: 57, SEQ ID NO: 58, and SEQ ID NO: 59.

15. Method according to claim 1, wherein the methylated and unmethylated DNA sequences are quantified in step c) using probes, the probes for the methylated DNA sequences comprising a total of at least three 5'-CG-3' dinucleotides for each DNA sequence and/or the probes for the unmethylated DNA sequences comprising a total of at least three 5'-CA-3' dinucleotides or at least three 5'-TG-3' dinucleotides for each DNA sequence, the probes wherein the probes comprise sequences selected from the group consisting of SEQ ID NO: 39, SEQ ID NO: 40, SEQ ID NO: 41, SEQ ID NO: 42, SEQ ID NO: 77, SEQ ID NO: 78, SEQ ID NO: 79, SEQ ID NO: 84, SEQ ID NO: 85, SEQ ID NO:
86, SEQ ID NO: 112, SEQ ID NO: 113, SEQ ID NO: 114, SEQ ID NO: 119, SEQ ID NO: 120, and SEQ ID NO: 121.

16. Method according to claim 1, wherein the methylated and unmethylated DNA sequences are quantified in step c) using probes, the probes for the methylated DNA sequences comprising a total of at least three 5'-CG-3' dinucleotides for each DNA sequence and/or the probes for the unmethylated DNA sequences comprising a total of at least three 5'-CA-3' dinucleotides or at least three 5'-TG-3' dinucleotides for each DNA sequence, the probes wherein the probes comprise sequences selected from the group consisting of SEQ ID NO: 80, SEQ ID NO: 81, SEQ ID NO: 82, SEQ ID NO: 83, SEQ ID NO: 87, SEQ ID NO: 88, SEQ ID NO: 89, SEQ ID NO: 90, SEQ ID NO: 155, SEQ ID NO: 156, SEQ ID NO: 157, SEQ ID NO: 158, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, and SEQ ID NO: 178.

17. Method according to claim 1, wherein the methylated and unmethylated DNA sequences are quantified in step c) using probes, the probes for the methylated DNA sequences comprising a total of at least three 5'-CG-3' dinucleotides for each DNA sequence and/or the probes for the unmethylated DNA sequences comprising a total of at least three 5'-CA-3' dinucleotides or at least three 5'-TG-3' dinucleotides for each DNA sequence, the probes wherein the probes comprise sequences selected from the group consisting of SEQ ID NO: 159, SEQ ID NO: 160, SEQ ID NO: 161, SEQ ID NO: 162, SEQ ID NO: 163, SEQ ID NO: 164, SEQ ID NO: 179, SEQ ID NO: 180, SEQ ID NO:
181, SEQ ID NO: 182, SEQ ID NO: 183, and SEQ ID NO: 184.

18. Method according to claim 1, wherein the methylated and unmethylated DNA sequences are quantified in step c) using probes, the probes for the methylated DNA sequences comprising a total of at least three 5'-CG-3' dinucleotides for each DNA sequence and/or the probes for the unmethylated DNA sequences comprising a total of at least three 5'-CA-3' dinucleotides or at least three 5'-TG-3' dinucleotides for each DNA sequence, the probes wherein the probes comprise sequences selected from the group consisting of SEQ ID NO: 43 and SEQ ID NO: 44.

19. The method according to claim 1, wherein the average number of DNA molecules per compartment used in the digital PCR is at least 20.

20. The method according to claim 1, wherein the average number of DNA molecules per compartment used in the digital PCR is at least 50.

* * * * *

SEQUENCE LISTING

<160> NUMBER OF SEQ ID NOS: 184

<210> SEQ ID NO 1
<211> LENGTH: 20
<212> TYPE: DNA
<213> ORGANISM: Artificial Sequence
<220> FEATURE:
<223> OTHER INFORMATION: Forward Primer for PLA2R1 (168 bp amplificate)

<400> SEQUENCE: 1

-continued ggggtaagga aggtggagat                                           20

<210> SEQ ID NO 2
<211> LENGTH: 27
<212> TYPE: DNA
<213> ORGANISM: Artificial Sequence
<220> FEATURE:
<223> OTHER INFORMATION: Reverse Primer for PLA2R1 (168 bp amplificate)

<400> SEQUENCE: 2
acaaaccacc taaattctaa taaacac                                   27

<210> SEQ ID NO 3
<211> LENGTH: 22
<212> TYPE: DNA
<213> ORGANISM: Artificial Sequence
<220> FEATURE:
<223> OTHER INFORMATION: Forward Primer for RASSF1A (117 bp amplificate)

<400> SEQUENCE: 3
gtttgttagc gtttaaagtt ag                                        22

<210> SEQ ID NO 4
<211> LENGTH: 18
<212> TYPE: DNA
<213> ORGANISM: Artificial Sequence
<220> FEATURE:
<223> OTHER INFORMATION: Reverse Primer for RASSF1A (117 bp amplificate)

<400> SEQUENCE: 4
aatacgaccc ttcccaac                                             18

<210> SEQ ID NO 5
<211> LENGTH: 21
<212> TYPE: DNA
<213> ORGANISM: Artificial Sequence
<220> FEATURE:
<223> OTHER INFORMATION: Forward Primer for GSTP1 (120 bp amplificate)

<400> SEQUENCE: 5
gtgaagcggg tgtgtaagtt t                                         21

<210> SEQ ID NO 6
<211> LENGTH: 23
<212> TYPE: DNA
<213> ORGANISM: Artificial Sequence
<220> FEATURE:
<223> OTHER INFORMATION: Reverse Primer for GSTP1 (120 bp amplificate)

<400> SEQUENCE: 6
taaacaaaca caaaaaaaa aac                                        23

<210> SEQ ID NO 7
<211> LENGTH: 18
<212> TYPE: DNA
<213> ORGANISM: Artificial Sequence
<220> FEATURE:
<223> OTHER INFORMATION: Forward Primer for PLA2R1 (133 bp amplificate)

<400> SEQUENCE: 7
ggaaggtgga gattacgg                                             18

<210> SEQ ID NO 8
<211> LENGTH: 20
<212> TYPE: DNA

```
<213> ORGANISM: Artificial Sequence
<220> FEATURE:
<223> OTHER INFORMATION: Reverse Primer for PLA2R1 (133 bp amplificate)

<400> SEQUENCE: 8
gcgaatttac aacgaacaac                                               20

<210> SEQ ID NO 9
<211> LENGTH: 23
<212> TYPE: DNA
<213> ORGANISM: Artificial Sequence
<220> FEATURE:
<223> OTHER INFORMATION: Reverse Primer for PLA2R1 (150 bp amplificate)

<400> SEQUENCE: 9
aataaacacc gcgaatttac aac                                           23

<210> SEQ ID NO 10
<211> LENGTH: 23
<212> TYPE: DNA
<213> ORGANISM: Artificial Sequence
<220> FEATURE:
<223> OTHER INFORMATION: Reverse Primer for PLA2R1 (161 bp amplificate)

<400> SEQUENCE: 10
acctaaattc taataaacac cgc                                           23

<210> SEQ ID NO 11
<211> LENGTH: 22
<212> TYPE: DNA
<213> ORGANISM: Artificial Sequence
<220> FEATURE:
<223> OTHER INFORMATION: Reverse Primer for PLA2R1 (160 bp amplificate)

<400> SEQUENCE: 11
cctaaattct aataaacacc gc                                            22

<210> SEQ ID NO 12
<211> LENGTH: 19
<212> TYPE: DNA
<213> ORGANISM: Artificial Sequence
<220> FEATURE:
<223> OTHER INFORMATION: Forward Primer for GSTP1 (171 bp amplificate)

<400> SEQUENCE: 12
gttcggttaa tatggtgaa                                                19

<210> SEQ ID NO 13
<211> LENGTH: 22
<212> TYPE: DNA
<213> ORGANISM: Artificial Sequence
<220> FEATURE:
<223> OTHER INFORMATION: Reverse Primer for GSTP1 (171 bp amplificate)

<400> SEQUENCE: 13
acccaaacta aaatacaata ac                                            22

<210> SEQ ID NO 14
<211> LENGTH: 22
<212> TYPE: DNA
<213> ORGANISM: Artificial Sequence
<220> FEATURE:
<223> OTHER INFORMATION: Forward Primer for AOX1 (180 bp amplificate)

<400> SEQUENCE: 14
tgggttggat tttaggtttt ag                                            22
```

```
<210> SEQ ID NO 15
<211> LENGTH: 18
<212> TYPE: DNA
<213> ORGANISM: Artificial Sequence
<220> FEATURE:
<223> OTHER INFORMATION: Reverse Primer for AOX1 (180 bp amplificate)

<400> SEQUENCE: 15
ctcaccttac gaccgttc                                                 18

<210> SEQ ID NO 16
<211> LENGTH: 18
<212> TYPE: DNA
<213> ORGANISM: Artificial Sequence
<220> FEATURE:
<223> OTHER INFORMATION: Forward Primer for SERPINE1 (123 bp
      amplificate)

<400> SEQUENCE: 16
agagcgttgt taagaaga                                                 18

<210> SEQ ID NO 17
<211> LENGTH: 22
<212> TYPE: DNA
<213> ORGANISM: Artificial Sequence
<220> FEATURE:
<223> OTHER INFORMATION: Reverse Primer for SERPINE1 (123 bp
      amplificate)

<400> SEQUENCE: 17
ctcctaccta aaattctcaa aa                                            22

<210> SEQ ID NO 18
<211> LENGTH: 23
<212> TYPE: DNA
<213> ORGANISM: Artificial Sequence
<220> FEATURE:
<223> OTHER INFORMATION: Forward Primer for AOX1 (138 bp amplificate)

<400> SEQUENCE: 18
gttggatttt aggttttagt aag                                           23

<210> SEQ ID NO 19
<211> LENGTH: 20
<212> TYPE: DNA
<213> ORGANISM: Artificial Sequence
<220> FEATURE:
<223> OTHER INFORMATION: Reverse Primer for AOX1 (138 bp amplificate)

<400> SEQUENCE: 19
gcccgatcca ttataatatc                                               20

<210> SEQ ID NO 20
<211> LENGTH: 21
<212> TYPE: DNA
<213> ORGANISM: Artificial Sequence
<220> FEATURE:
<223> OTHER INFORMATION: Probe for PLA2R1 (3 CpG) methylated

<400> SEQUENCE: 20
cccaactact ccgcgacgca a                                             21

<210> SEQ ID NO 21
<211> LENGTH: 24
<212> TYPE: DNA
```

```
<213> ORGANISM: Artificial Sequence
<220> FEATURE:
<223> OTHER INFORMATION: Probe for PLA2R1 (3 CpG) non-methylated

<400> SEQUENCE: 21
aacccaacta ctccacaaca caaa                                          24

<210> SEQ ID NO 22
<211> LENGTH: 22
<212> TYPE: DNA
<213> ORGANISM: Artificial Sequence
<220> FEATURE:
<223> OTHER INFORMATION: Probe for PLA2R1 (4 CpG) methylated

<400> SEQUENCE: 22
caactactcc gcgacgcaaa cg                                            22

<210> SEQ ID NO 23
<211> LENGTH: 26
<212> TYPE: DNA
<213> ORGANISM: Artificial Sequence
<220> FEATURE:
<223> OTHER INFORMATION: Probe for PLA2R1 (4 CpG) non-methylated

<400> SEQUENCE: 23
aacccaacta ctccacaaca caaaca                                        26

<210> SEQ ID NO 24
<211> LENGTH: 23
<212> TYPE: DNA
<213> ORGANISM: Artificial Sequence
<220> FEATURE:
<223> OTHER INFORMATION: Probe for RASSF1A (3 CpG) methylated

<400> SEQUENCE: 24
cgcccaacga ataccaactc ccg                                           23

<210> SEQ ID NO 25
<211> LENGTH: 26
<212> TYPE: DNA
<213> ORGANISM: Artificial Sequence
<220> FEATURE:
<223> OTHER INFORMATION: Probe for RASSF1A (3 CpG) non-methylated

<400> SEQUENCE: 25
cacccaacaa ataccaactc ccacaa                                        26

<210> SEQ ID NO 26
<211> LENGTH: 24
<212> TYPE: DNA
<213> ORGANISM: Artificial Sequence
<220> FEATURE:
<223> OTHER INFORMATION: Probe for PLA2R1 (3 CpG) non-methylated

<400> SEQUENCE: 26
tttgtgttgt ggagtagttg ggtt                                          24

<210> SEQ ID NO 27
<211> LENGTH: 22
<212> TYPE: DNA
<213> ORGANISM: Artificial Sequence
<220> FEATURE:
<223> OTHER INFORMATION: Probe for PLA2R1 (4 CpG) methylated

<400> SEQUENCE: 27
cgtttgcgtc gcggagtagt tg                                            22
```

<210> SEQ ID NO 28
<211> LENGTH: 26
<212> TYPE: DNA
<213> ORGANISM: Artificial Sequence
<220> FEATURE:
<223> OTHER INFORMATION: Probe for PLA2R1 (4 CpG) non-methylated

<400> SEQUENCE: 28
tgtttgtgtt gtggagtagt tgggtt                                26

<210> SEQ ID NO 29
<211> LENGTH: 23
<212> TYPE: DNA
<213> ORGANISM: Artificial Sequence
<220> FEATURE:
<223> OTHER INFORMATION: Probe for RASSF1A (3 CpG) methylated

<400> SEQUENCE: 29
cgggagttgg tattcgttgg gcg                                   23

<210> SEQ ID NO 30
<211> LENGTH: 26
<212> TYPE: DNA
<213> ORGANISM: Artificial Sequence
<220> FEATURE:
<223> OTHER INFORMATION: Probe for RASSF1A (3 CpG) non-methylated

<400> SEQUENCE: 30
ttgtgggagt tggtatttgt tgggtg                                26

<210> SEQ ID NO 31
<211> LENGTH: 25
<212> TYPE: DNA
<213> ORGANISM: Artificial Sequence
<220> FEATURE:
<223> OTHER INFORMATION: Probe for RASSF1A (4 CpG) methylated

<400> SEQUENCE: 31
cgcgggagtt ggtattcgtt gggcg                                 25

<210> SEQ ID NO 32
<211> LENGTH: 29
<212> TYPE: DNA
<213> ORGANISM: Artificial Sequence
<220> FEATURE:
<223> OTHER INFORMATION: Probe for RASSF1A (4 CpG) non-methylated

<400> SEQUENCE: 32
gagttgtggg agttggtatt tgttgggtg                             29

<210> SEQ ID NO 33
<211> LENGTH: 20
<212> TYPE: DNA
<213> ORGANISM: Artificial Sequence
<220> FEATURE:
<223> OTHER INFORMATION: Probe for GSTP1 (3 CpG) methylated

<400> SEQUENCE: 33
gttgcgtata tttcgttgcg                                       20

<210> SEQ ID NO 34
<211> LENGTH: 20
<212> TYPE: DNA
<213> ORGANISM: Artificial Sequence
<220> FEATURE:

<223> OTHER INFORMATION: Probe for GSTP1 (3 CpG) non-methylated

<400> SEQUENCE: 34
gttgtgtata ttttgttgtg                                          20

<210> SEQ ID NO 35
<211> LENGTH: 20
<212> TYPE: DNA
<213> ORGANISM: Artificial Sequence
<220> FEATURE:
<223> OTHER INFORMATION: Probe for GSTP1 (4 CpG) methylated

<400> SEQUENCE: 35
gtttcggcgc gttagttcgt                                          20

<210> SEQ ID NO 36
<211> LENGTH: 20
<212> TYPE: DNA
<213> ORGANISM: Artificial Sequence
<220> FEATURE:
<223> OTHER INFORMATION: Probe for GSTP1 (4 CpG) non-methylated

<400> SEQUENCE: 36
gttttggtgt gttagtttgt                                          20

<210> SEQ ID NO 37
<211> LENGTH: 24
<212> TYPE: DNA
<213> ORGANISM: Artificial Sequence
<220> FEATURE:
<223> OTHER INFORMATION: Probe for AOX1 (3 CpG) methylated

<400> SEQUENCE: 37
actcgaacgc ccgatccatt ataa                                     24

<210> SEQ ID NO 38
<211> LENGTH: 27
<212> TYPE: DNA
<213> ORGANISM: Artificial Sequence
<220> FEATURE:
<223> OTHER INFORMATION: Probe for AOX1 (3 CpG) non-methylated

<400> SEQUENCE: 38
acaactcaaa cacccaatcc attataa                                  27

<210> SEQ ID NO 39
<211> LENGTH: 24
<212> TYPE: DNA
<213> ORGANISM: Artificial Sequence
<220> FEATURE:
<223> OTHER INFORMATION: Probe for AOX1 (4 CpG) methylated

<400> SEQUENCE: 39
cgctaattcg aaacccgaa acga                                      24

<210> SEQ ID NO 40
<211> LENGTH: 24
<212> TYPE: DNA
<213> ORGANISM: Artificial Sequence
<220> FEATURE:
<223> OTHER INFORMATION: Probe for AOX1 (4 CpG) non-methylated

<400> SEQUENCE: 40
cactaattca aaaccccaaa acaa                                     24

```
<210> SEQ ID NO 41
<211> LENGTH: 26
<212> TYPE: DNA
<213> ORGANISM: Artificial Sequence
<220> FEATURE:
<223> OTHER INFORMATION: Probe for AOX1 (5 CpG) methylated

<400> SEQUENCE: 41
cgcgctaatt cgaaaacccg aaacga                                        26

<210> SEQ ID NO 42
<211> LENGTH: 26
<212> TYPE: DNA
<213> ORGANISM: Artificial Sequence
<220> FEATURE:
<223> OTHER INFORMATION: Probe for AOX1 (5 CpG) non-methylated

<400> SEQUENCE: 42
cacactaatt caaaaaccca aaacaa                                        26

<210> SEQ ID NO 43
<211> LENGTH: 27
<212> TYPE: DNA
<213> ORGANISM: Artificial Sequence
<220> FEATURE:
<223> OTHER INFORMATION: Probe for SERPINE1 (4 CpG) methylated

<400> SEQUENCE: 43
cgattaacga ttcgtcctac tctaacg                                       27

<210> SEQ ID NO 44
<211> LENGTH: 27
<212> TYPE: DNA
<213> ORGANISM: Artificial Sequence
<220> FEATURE:
<223> OTHER INFORMATION: Probe for SERPINE1 (4 CpG) non-methylated

<400> SEQUENCE: 44
caattaacaa ttcatcctac tctaaca                                       27

<210> SEQ ID NO 45
<211> LENGTH: 24
<212> TYPE: DNA
<213> ORGANISM: Artificial Sequence
<220> FEATURE:
<223> OTHER INFORMATION: Probe for GSTP1 (3 CpG) methylated

<400> SEQUENCE: 45
cgatctcgac gactcactac aacc                                          24

<210> SEQ ID NO 46
<211> LENGTH: 26
<212> TYPE: DNA
<213> ORGANISM: Artificial Sequence
<220> FEATURE:
<223> OTHER INFORMATION: Probe for GSTP1 (3 CpG) non-methylated

<400> SEQUENCE: 46
caatctcaac aactcactac aacctc                                        26

<210> SEQ ID NO 47
<211> LENGTH: 24
<212> TYPE: DNA
<213> ORGANISM: Artificial Sequence
<220> FEATURE:
<223> OTHER INFORMATION: Probe for GSTP1 (4 CpG) methylated
```

```
<400> SEQUENCE: 47
cgcgatctcg acgactcact acaa                                          24

<210> SEQ ID NO 48
<211> LENGTH: 27
<212> TYPE: DNA
<213> ORGANISM: Artificial Sequence
<220> FEATURE:
<223> OTHER INFORMATION: Probe for GSTP1 (4 CpG) non-methylated

<400> SEQUENCE: 48
cacaatctca acaactcact acaacct                                       27

<210> SEQ ID NO 49
<211> LENGTH: 24
<212> TYPE: DNA
<213> ORGANISM: Artificial Sequence
<220> FEATURE:
<223> OTHER INFORMATION: Probe for GSTP1 (3 CpG) methylated

<400> SEQUENCE: 49
ggttgtagtg agtcgtcgag atcg                                          24

<210> SEQ ID NO 50
<211> LENGTH: 26
<212> TYPE: DNA
<213> ORGANISM: Artificial Sequence
<220> FEATURE:
<223> OTHER INFORMATION: Probe for GSTP1 (3 CpG) non-methylated

<400> SEQUENCE: 50
gaggttgtag tgagtcgtcg agatcg                                        26

<210> SEQ ID NO 51
<211> LENGTH: 24
<212> TYPE: DNA
<213> ORGANISM: Artificial Sequence
<220> FEATURE:
<223> OTHER INFORMATION: Probe for GSTP1 (4 CpG) methylated

<400> SEQUENCE: 51
ttgtagtgag tcgtcgagat cgcg                                          24

<210> SEQ ID NO 52
<211> LENGTH: 27
<212> TYPE: DNA
<213> ORGANISM: Artificial Sequence
<220> FEATURE:
<223> OTHER INFORMATION: Probe for GSTP1 (4 CpG) non-methylated

<400> SEQUENCE: 52
aggttgtagt gagtcgtcga gatcgcg                                       27

<210> SEQ ID NO 53
<211> LENGTH: 20
<212> TYPE: DNA
<213> ORGANISM: Artificial Sequence
<220> FEATURE:
<223> OTHER INFORMATION: Forward-Primer for PLA2R1 (150bp amplificate)

<400> SEQUENCE: 53
ggggtaagga aggtggagat                                               20

<210> SEQ ID NO 54
<211> LENGTH: 25
```

```
<212> TYPE: DNA
<213> ORGANISM: Artificial Sequence
<220> FEATURE:
<223> OTHER INFORMATION: Probe for RASSF1A (4 CpG) methylated

<400> SEQUENCE: 54
cgcccaacga ataccaactc ccgcg                                       25

<210> SEQ ID NO 55
<211> LENGTH: 29
<212> TYPE: DNA
<213> ORGANISM: Artificial Sequence
<220> FEATURE:
<223> OTHER INFORMATION: Probe for RASSF1A (4 CpG) non-methylated

<400> SEQUENCE: 55
cacccaacaa ataccaactc ccacaactc                                   29

<210> SEQ ID NO 56
<211> LENGTH: 20
<212> TYPE: DNA
<213> ORGANISM: Artificial Sequence
<220> FEATURE:
<223> OTHER INFORMATION: Probe for GSTP1 (3 CpG) methylated

<400> SEQUENCE: 56
cgcaacgaaa tatacgcaac                                             20

<210> SEQ ID NO 57
<211> LENGTH: 20
<212> TYPE: DNA
<213> ORGANISM: Artificial Sequence
<220> FEATURE:
<223> OTHER INFORMATION: Probe for GSTP1 (3 CpG) non-methylated

<400> SEQUENCE: 57
cacaacaaaa tatacacaac                                             20

<210> SEQ ID NO 58
<211> LENGTH: 20
<212> TYPE: DNA
<213> ORGANISM: Artificial Sequence
<220> FEATURE:
<223> OTHER INFORMATION: Probe for GSTP1 (4 CpG) methylated

<400> SEQUENCE: 58
acgaactaac gcgccgaaac                                             20

<210> SEQ ID NO 59
<211> LENGTH: 20
<212> TYPE: DNA
<213> ORGANISM: Artificial Sequence
<220> FEATURE:
<223> OTHER INFORMATION: Probe for GSTP1 (4 CpG) non-methylated

<400> SEQUENCE: 59
acaaactaac acaccaaaac                                             20

<210> SEQ ID NO 60
<211> LENGTH: 21
<212> TYPE: DNA
<213> ORGANISM: Artificial Sequence
<220> FEATURE:
<223> OTHER INFORMATION: Probe for GSTP1 (3 CpG) methylated

<400> SEQUENCE: 60
```

```
ttgcgtcgcg gagtagttgg g                                              21
```

<210> SEQ ID NO 61
<211> LENGTH: 20
<212> TYPE: DNA
<213> ORGANISM: Artificial Sequence
<220> FEATURE:
<223> OTHER INFORMATION: Forward Primer for RASSF1A (124 bp amplificate)

<400> SEQUENCE: 61

```
gcgtttgtta gcgtttaaag                                                20
```

<210> SEQ ID NO 62
<211> LENGTH: 18
<212> TYPE: DNA
<213> ORGANISM: Artificial Sequence
<220> FEATURE:
<223> OTHER INFORMATION: Reverse Primer for RASSF1A (124 bp amplificate)

<400> SEQUENCE: 62

```
aaccgaatac gacccttc                                                  18
```

<210> SEQ ID NO 63
<211> LENGTH: 23
<212> TYPE: DNA
<213> ORGANISM: Artificial Sequence
<220> FEATURE:
<223> OTHER INFORMATION: Forward Primer for AOX1 (138 bp amplificate)

<400> SEQUENCE: 63

```
gttggatttt aggttttagt aag                                            23
```

<210> SEQ ID NO 64
<211> LENGTH: 20
<212> TYPE: DNA
<213> ORGANISM: Artificial Sequence
<220> FEATURE:
<223> OTHER INFORMATION: Reverse Primer for AOX1 (138 bp amplificate)

<400> SEQUENCE: 64

```
gcccgatcca ttataatatc                                                20
```

<210> SEQ ID NO 65
<211> LENGTH: 24
<212> TYPE: DNA
<213> ORGANISM: Artificial Sequence
<220> FEATURE:
<223> OTHER INFORMATION: Forward Primer for AOX1 (135 bp amplificate)

<400> SEQUENCE: 65

```
ggattttagg ttttagtaag tttc                                           24
```

<210> SEQ ID NO 66
<211> LENGTH: 22
<212> TYPE: DNA
<213> ORGANISM: Artificial Sequence
<220> FEATURE:
<223> OTHER INFORMATION: Reverse Primer for AOX1 (135 bp amplificate)

<400> SEQUENCE: 66

```
gcccgatcca ttataatatc cg                                             22
```

<210> SEQ ID NO 67
<211> LENGTH: 24
<212> TYPE: DNA
<213> ORGANISM: Artificial Sequence

```
<220> FEATURE:
<223> OTHER INFORMATION: Forward Primer for AOX1 (134 bp amplificate)

<400> SEQUENCE: 67
gattttaggt tttagtaagt ttcg                                          24

<210> SEQ ID NO 68
<211> LENGTH: 21
<212> TYPE: DNA
<213> ORGANISM: Artificial Sequence
<220> FEATURE:
<223> OTHER INFORMATION: Forward Primer for SERPINE1 (119 bp
      amplificate)

<400> SEQUENCE: 68
cgttgttaag aagatttata c                                             21

<210> SEQ ID NO 69
<211> LENGTH: 23
<212> TYPE: DNA
<213> ORGANISM: Artificial Sequence
<220> FEATURE:
<223> OTHER INFORMATION: Reverse Primer for SERPINE1 (119 bp
      amplificate)

<400> SEQUENCE: 69
taaacccgaa ataaaaaatt aaa                                           23

<210> SEQ ID NO 70
<211> LENGTH: 19
<212> TYPE: DNA
<213> ORGANISM: Artificial Sequence
<220> FEATURE:
<223> OTHER INFORMATION: Forward Primer for Thrombomodulin (125 bp
      amplificate)

<400> SEQUENCE: 70
ggtcgattcg tatgttaga                                                19

<210> SEQ ID NO 71
<211> LENGTH: 18
<212> TYPE: DNA
<213> ORGANISM: Artificial Sequence
<220> FEATURE:
<223> OTHER INFORMATION: Reverse Primer for Thrombomodulin (125 bp
      amplificate)

<400> SEQUENCE: 71
aaccgtaccg aaacaaaa                                                 18

<210> SEQ ID NO 72
<211> LENGTH: 19
<212> TYPE: DNA
<213> ORGANISM: Artificial Sequence
<220> FEATURE:
<223> OTHER INFORMATION: Forward Primer for Thrombomodulin (144 bp
      amplificate)

<400> SEQUENCE: 72 gtttggttg ggacggata                                                 19

<210> SEQ ID NO 73
<211> LENGTH: 20
<212> TYPE: DNA
<213> ORGANISM: Artificial Sequence
<220> FEATURE:
<223> OTHER INFORMATION: Reverse Primer for Thrombomodulin (144 bp
``` amplificate)

<400> SEQUENCE: 73
aaaaaccaaa accccaaaca                                               20

<210> SEQ ID NO 74
<211> LENGTH: 20
<212> TYPE: DNA
<213> ORGANISM: Artificial Sequence
<220> FEATURE:
<223> OTHER INFORMATION: Forward Primer for Thrombomodulin (166 bp
      amplificate)

<400> SEQUENCE: 74
gtttggggtt ttggtttttg                                               20

<210> SEQ ID NO 75
<211> LENGTH: 20
<212> TYPE: DNA
<213> ORGANISM: Artificial Sequence
<220> FEATURE:
<223> OTHER INFORMATION: Reverse Primer for Thrombomodulin (166 bp
      amplificate)

<400> SEQUENCE: 75
gcaatccgtc gcaaatctaa                                               20

<210> SEQ ID NO 76
<211> LENGTH: 20
<212> TYPE: DNA
<213> ORGANISM: Artificial Sequence
<220> FEATURE:
<223> OTHER INFORMATION: Reverse Primer for Thrombomodulin (165 bp
      amplificate)

<400> SEQUENCE: 76
caatccgtcg caaatctaac                                               20

<210> SEQ ID NO 77
<211> LENGTH: 24
<212> TYPE: DNA
<213> ORGANISM: Artificial Sequence
<220> FEATURE:
<223> OTHER INFORMATION: Probe for AOX1 (4 CpG) methylated

<400> SEQUENCE: 77
cgctaattcg aaacccgaa acga                                           24

<210> SEQ ID NO 78
<211> LENGTH: 24
<212> TYPE: DNA
<213> ORGANISM: Artificial Sequence
<220> FEATURE:
<223> OTHER INFORMATION: Probe for AOX1 (4 CpG) non-methylated

<400> SEQUENCE: 78
cactaattca aaacccaaa acaa                                           24

<210> SEQ ID NO 79
<211> LENGTH: 27
<212> TYPE: DNA
<213> ORGANISM: Artificial Sequence
<220> FEATURE:
<223> OTHER INFORMATION: Probe for AOX1 (4 CpG) non-methylated

<400> SEQUENCE: 79

```
cactaattca aaaacccaaa acaaaaa                                        27
```

<210> SEQ ID NO 80
<211> LENGTH: 21
<212> TYPE: DNA
<213> ORGANISM: Artificial Sequence
<220> FEATURE:
<223> OTHER INFORMATION: Probe for Thrombomodulin (3CpG) methylated

<400> SEQUENCE: 80

```
acgccgataa cgacaacctc t                                              21
```

<210> SEQ ID NO 81
<211> LENGTH: 24
<212> TYPE: DNA
<213> ORGANISM: Artificial Sequence
<220> FEATURE:
<223> OTHER INFORMATION: Probe for Thrombomodulin (3CpG) non-methylated

<400> SEQUENCE: 81

```
aaaaagcaga taaagacaac ctct                                           24
```

<210> SEQ ID NO 82
<211> LENGTH: 25
<212> TYPE: DNA
<213> ORGANISM: Artificial Sequence
<220> FEATURE:
<223> OTHER INFORMATION: Probe for Thrombomodulin (4CpG) methylated

<400> SEQUENCE: 82

```
ccgactacga ctctacgaat acgaa                                          25
```

<210> SEQ ID NO 83
<211> LENGTH: 29
<212> TYPE: DNA
<213> ORGANISM: Artificial Sequence
<220> FEATURE:
<223> OTHER INFORMATION: Probe for Thrombomodulin (4CpG) non-methylated

<400> SEQUENCE: 83

```
cagactaaga ctctaagaat aagaaaaac                                      29
```

<210> SEQ ID NO 84
<211> LENGTH: 24
<212> TYPE: DNA
<213> ORGANISM: Artificial Sequence
<220> FEATURE:
<223> OTHER INFORMATION: Probe for AOX1 (4 CpG) methylated

<400> SEQUENCE: 84

```
tcgtttcggg ttttcgaatt agcg                                           24
```

<210> SEQ ID NO 85
<211> LENGTH: 24
<212> TYPE: DNA
<213> ORGANISM: Artificial Sequence
<220> FEATURE:
<223> OTHER INFORMATION: Probe for AOX1 (4 CpG) non-methylated

<400> SEQUENCE: 85

```
ttgttttggg tttttgaatt agtg                                           24
```

<210> SEQ ID NO 86
<211> LENGTH: 27
<212> TYPE: DNA
<213> ORGANISM: Artificial Sequence

```
<220> FEATURE:
<223> OTHER INFORMATION: Probe for AOX1 (4 CpG) non-methylated

<400> SEQUENCE: 86
tttttgtttt gggttttga attagtg                                          27

<210> SEQ ID NO 87
<211> LENGTH: 21
<212> TYPE: DNA
<213> ORGANISM: Artificial Sequence
<220> FEATURE:
<223> OTHER INFORMATION: Probe for Thrombomodulin (3CpG) methylated

<400> SEQUENCE: 87
agaggttgtc gttatcggcg t                                               21

<210> SEQ ID NO 88
<211> LENGTH: 21
<212> TYPE: DNA
<213> ORGANISM: Artificial Sequence
<220> FEATURE:
<223> OTHER INFORMATION: Probe for Thrombomodulin (3CpG) non-methylated

<400> SEQUENCE: 88
agaggttgtt gttattggtg t                                               21

<210> SEQ ID NO 89
<211> LENGTH: 25
<212> TYPE: DNA
<213> ORGANISM: Artificial Sequence
<220> FEATURE:
<223> OTHER INFORMATION: Probe for Thrombomodulin (4CpG) methylated

<400> SEQUENCE: 89
ttcgtattcg tagagtcgta gtcgg                                           25

<210> SEQ ID NO 90
<211> LENGTH: 25
<212> TYPE: DNA
<213> ORGANISM: Artificial Sequence
<220> FEATURE:
<223> OTHER INFORMATION: Probe for Thrombomodulin (4CpG) non-methylated

<400> SEQUENCE: 90
tttgtatttg tagagttgta gttgg                                           25

<210> SEQ ID NO 91
<211> LENGTH: 21
<212> TYPE: DNA
<213> ORGANISM: Artificial Sequence
<220> FEATURE:
<223> OTHER INFORMATION: Forward Primer for GSTP1 (114 bp amplificate)

<400> SEQUENCE: 91
cgtagcggtt ttagggaatt t                                               21

<210> SEQ ID NO 92
<211> LENGTH: 20
<212> TYPE: DNA
<213> ORGANISM: Artificial Sequence
<220> FEATURE:
<223> OTHER INFORMATION: Reverse Primer for GSTP1 (114 bp amplificate)

<400> SEQUENCE: 92
tccccaacga aacctaaaaa                                                 20
```

<210> SEQ ID NO 93
<211> LENGTH: 20
<212> TYPE: DNA
<213> ORGANISM: Artificial Sequence
<220> FEATURE:
<223> OTHER INFORMATION: Forward Primer for GSTP1 (116 bp amplificate)

<400> SEQUENCE: 93
atcgtagcgg ttttagggaa                                        20

<210> SEQ ID NO 94
<211> LENGTH: 20
<212> TYPE: DNA
<213> ORGANISM: Artificial Sequence
<220> FEATURE:
<223> OTHER INFORMATION: Reverse Primer for GSTP1 (116 bp amplificate)

<400> SEQUENCE: 94
tccccaacga aacctaaaaa                                        20

<210> SEQ ID NO 95
<211> LENGTH: 21
<212> TYPE: DNA
<213> ORGANISM: Artificial Sequence
<220> FEATURE:
<223> OTHER INFORMATION: Forward Primer for GSTP1 (129 bp amplificate)

<400> SEQUENCE: 95
tgtaagtttc gggatcgtag c                                      21

<210> SEQ ID NO 96
<211> LENGTH: 20
<212> TYPE: DNA
<213> ORGANISM: Artificial Sequence
<220> FEATURE:
<223> OTHER INFORMATION: Reverse Primer for GSTP1 (129 bp amplificate)

<400> SEQUENCE: 96
tccccaacga aacctaaaaa                                        20

<210> SEQ ID NO 97
<211> LENGTH: 20
<212> TYPE: DNA
<213> ORGANISM: Artificial Sequence
<220> FEATURE:
<223> OTHER INFORMATION: Forward Primer for GSTP1 (132 bp amplificate)

<400> SEQUENCE: 97
gtgtgtaagt ttcgggatcg                                        20

<210> SEQ ID NO 98
<211> LENGTH: 20
<212> TYPE: DNA
<213> ORGANISM: Artificial Sequence
<220> FEATURE:
<223> OTHER INFORMATION: Reverse Primer for GSTP1 (132 bp amplificate)

<400> SEQUENCE: 98
tccccaacga aacctaaaaa                                        20

<210> SEQ ID NO 99
<211> LENGTH: 24
<212> TYPE: DNA
<213> ORGANISM: Artificial Sequence
<220> FEATURE:
<223> OTHER INFORMATION: Forward Primer for AOX1 (171 bp amplificate)

```
<400> SEQUENCE: 99
ttttaattaa ggttttttc gtcg                                          24

<210> SEQ ID NO 100
<211> LENGTH: 21
<212> TYPE: DNA
<213> ORGANISM: Artificial Sequence
<220> FEATURE:
<223> OTHER INFORMATION: Reverse Primer for AOX1 (171 bp amplificate)

<400> SEQUENCE: 100
cccgatccat tataatatcc g                                            21

<210> SEQ ID NO 101
<211> LENGTH: 23
<212> TYPE: DNA
<213> ORGANISM: Artificial Sequence
<220> FEATURE:
<223> OTHER INFORMATION: Forward Primer for Thrombomodulin (160 bp
      amplificate)

<400> SEQUENCE: 101
tttgtgtttt tttgtttcgg tac                                          23

<210> SEQ ID NO 102
<211> LENGTH: 20
<212> TYPE: DNA
<213> ORGANISM: Artificial Sequence
<220> FEATURE:
<223> OTHER INFORMATION: Reverse Primer for Thrombomodulin (160 bp
      amplificate)

<400> SEQUENCE: 102
cacccgacta cgactctacg                                              20

<210> SEQ ID NO 103
<211> LENGTH: 20
<212> TYPE: DNA
<213> ORGANISM: Artificial Sequence
<220> FEATURE:
<223> OTHER INFORMATION: Reverse Primer for Thrombomodulin (159 bp
      amplificate)

<400> SEQUENCE: 103
acccgactac gactctacga                                              20

<210> SEQ ID NO 104
<211> LENGTH: 21
<212> TYPE: DNA
<213> ORGANISM: Artificial Sequence
<220> FEATURE:
<223> OTHER INFORMATION: Forward Primer for RASSF1A (86 bp amplificate)

<400> SEQUENCE: 104
tttagtttgg attttggggg a                                            21

<210> SEQ ID NO 105
<211> LENGTH: 21
<212> TYPE: DNA
<213> ORGANISM: Artificial Sequence
<220> FEATURE:
<223> OTHER INFORMATION: Reverse Primer for RASSF1A (86 bp amplificate)

<400> SEQUENCE: 105 ctaacttaa acgctaacaa a                                             21
```

<210> SEQ ID NO 106
<211> LENGTH: 19
<212> TYPE: DNA
<213> ORGANISM: Artificial Sequence
<220> FEATURE:
<223> OTHER INFORMATION: Forward Primer for RASSF1A (82 bp amplificate)

<400> SEQUENCE: 106
gtttggattt tgggggagc                                                19

<210> SEQ ID NO 107
<211> LENGTH: 20
<212> TYPE: DNA
<213> ORGANISM: Artificial Sequence
<220> FEATURE:
<223> OTHER INFORMATION: Reverse Primer for RASSF1A (82 bp amplificate)

<400> SEQUENCE: 107
actttaaacg ctaacaaacg                                               20

<210> SEQ ID NO 108
<211> LENGTH: 19
<212> TYPE: DNA
<213> ORGANISM: Artificial Sequence
<220> FEATURE:
<223> OTHER INFORMATION: Forward Primer for RASSF1A (82 bp amplificate)

<400> SEQUENCE: 108
tttggatttt gggggagcg                                                19

<210> SEQ ID NO 109
<211> LENGTH: 20
<212> TYPE: DNA
<213> ORGANISM: Artificial Sequence
<220> FEATURE:
<223> OTHER INFORMATION: Reverse Primer for RASSF1A (82 bp amplificate)

<400> SEQUENCE: 109
cgctaacttt aaacgctaac                                               20

<210> SEQ ID NO 110
<211> LENGTH: 22
<212> TYPE: DNA
<213> ORGANISM: Artificial Sequence
<220> FEATURE:
<223> OTHER INFORMATION: Forward Primer for RASSF1A (86 bp amplificate)

<400> SEQUENCE: 110
tttagtttgg attttggggg ag                                            22

<210> SEQ ID NO 111
<211> LENGTH: 23
<212> TYPE: DNA
<213> ORGANISM: Artificial Sequence
<220> FEATURE:
<223> OTHER INFORMATION: Reverse Primer for RASSF1A (86 bp amplificate)

<400> SEQUENCE: 111
cgctaacttt aaacgctaac aaa                                           23

<210> SEQ ID NO 112
<211> LENGTH: 26
<212> TYPE: DNA
<213> ORGANISM: Artificial Sequence
<220> FEATURE:

```
<223> OTHER INFORMATION: Probe for AOX1 (5 CpG) methylated

<400> SEQUENCE: 112
cgcgctaatt cgaaaacccg aaacga                                          26

<210> SEQ ID NO 113
<211> LENGTH: 26
<212> TYPE: DNA
<213> ORGANISM: Artificial Sequence
<220> FEATURE:
<223> OTHER INFORMATION: Probe for AOX1 (5 CpG) non-methylated

<400> SEQUENCE: 113
cacactaatt caaaaaccca aaacaa                                          26

<210> SEQ ID NO 114
<211> LENGTH: 29
<212> TYPE: DNA
<213> ORGANISM: Artificial Sequence
<220> FEATURE:
<223> OTHER INFORMATION: Probe for AOX1 (5 CpG) non-methylated

<400> SEQUENCE: 114
cacactaatt caaaaaccca aacaaaaa                                        29

<210> SEQ ID NO 115
<211> LENGTH: 20
<212> TYPE: DNA
<213> ORGANISM: Artificial Sequence
<220> FEATURE:
<223> OTHER INFORMATION: Probe for RASSF1A (4 CpG) methylated

<400> SEQUENCE: 115
cgcgaaccga acgaaaccac                                                 20

<210> SEQ ID NO 116
<211> LENGTH: 20
<212> TYPE: DNA
<213> ORGANISM: Artificial Sequence
<220> FEATURE:
<223> OTHER INFORMATION: Probe for RASSF1A (4 CpG) non-methylated

<400> SEQUENCE: 116
cacaaaccaa acaaaaccac                                                 20

<210> SEQ ID NO 117
<211> LENGTH: 23
<212> TYPE: DNA
<213> ORGANISM: Artificial Sequence
<220> FEATURE:
<223> OTHER INFORMATION: Probe for RASSF1A (4 CpG) non-methylated

<400> SEQUENCE: 117
cacaaaccaa acaaaaccac aaa                                             23

<210> SEQ ID NO 118
<211> LENGTH: 26
<212> TYPE: DNA
<213> ORGANISM: Artificial Sequence
<220> FEATURE:
<223> OTHER INFORMATION: Probe for RASSF1A (4 CpG) non-methylated

<400> SEQUENCE: 118
aaacacaaac caaacaaaac cacaaa                                          26
```

-continued

```
<210> SEQ ID NO 119
<211> LENGTH: 26
<212> TYPE: DNA
<213> ORGANISM: Artificial Sequence
<220> FEATURE:
<223> OTHER INFORMATION: Probe for AOX1 (5CpG) methylated

<400> SEQUENCE: 119
tcgtttcggg ttttcgaatt agcgcg                                        26

<210> SEQ ID NO 120
<211> LENGTH: 26
<212> TYPE: DNA
<213> ORGANISM: Artificial Sequence
<220> FEATURE:
<223> OTHER INFORMATION: Probe for AOX1 (5CpG) non-methylated

<400> SEQUENCE: 120
ttgttttggg tttttgaatt agtgtg                                        26

<210> SEQ ID NO 121
<211> LENGTH: 29
<212> TYPE: DNA
<213> ORGANISM: Artificial Sequence
<220> FEATURE:
<223> OTHER INFORMATION: Probe for AOX1 (5CpG) non-methylated

<400> SEQUENCE: 121
tttttgtttt gggtttttga attagtgtg                                     29

<210> SEQ ID NO 122
<211> LENGTH: 20
<212> TYPE: DNA
<213> ORGANISM: Artificial Sequence
<220> FEATURE:
<223> OTHER INFORMATION: Probe for RASSF1A (4CpG) methylated

<400> SEQUENCE: 122
gtggtttcgt tcggttcgcg                                               20

<210> SEQ ID NO 123
<211> LENGTH: 20
<212> TYPE: DNA
<213> ORGANISM: Artificial Sequence
<220> FEATURE:
<223> OTHER INFORMATION: Probe for RASSF1A (4CpG) non-methylated

<400> SEQUENCE: 123
gtggttttgt ttggtttgtg                                               20

<210> SEQ ID NO 124
<211> LENGTH: 23
<212> TYPE: DNA
<213> ORGANISM: Artificial Sequence
<220> FEATURE:
<223> OTHER INFORMATION: Probe for RASSF1A (4CpG) non-methylated

<400> SEQUENCE: 124
tttgtggttt tgtttggttt gtg                                           23

<210> SEQ ID NO 125
<211> LENGTH: 26
<212> TYPE: DNA
<213> ORGANISM: Artificial Sequence
<220> FEATURE:
<223> OTHER INFORMATION: Probe for RASSF1A (4CpG) non-methylated
```

```
<400> SEQUENCE: 125
tttgtggttt tgtttggttt gtgttt                                          26

<210> SEQ ID NO 126
<211> LENGTH: 19
<212> TYPE: DNA
<213> ORGANISM: Artificial Sequence
<220> FEATURE:
<223> OTHER INFORMATION: Forward Primer for Thrombomodulin (125 bp
      amplificate)

<400> SEQUENCE: 126
ggtcgattcg tatgttaga                                                  19

<210> SEQ ID NO 127
<211> LENGTH: 18
<212> TYPE: DNA
<213> ORGANISM: Artificial Sequence
<220> FEATURE:
<223> OTHER INFORMATION: Reverse Primer for Thrombomodulin(125 bp
      amplificate)

<400> SEQUENCE: 127
aaccgtaccg aaacaaaa                                                   18

<210> SEQ ID NO 128
<211> LENGTH: 19
<212> TYPE: DNA
<213> ORGANISM: Artificial Sequence
<220> FEATURE:
<223> OTHER INFORMATION: Forward Primer for Thrombomodulin (83 bp
      amplificate)

<400> SEQUENCE: 128
tagcggtaag aagtgtttg                                                  19

<210> SEQ ID NO 129
<211> LENGTH: 18
<212> TYPE: DNA
<213> ORGANISM: Artificial Sequence
<220> FEATURE:
<223> OTHER INFORMATION: Forward Primer for Thrombomodulin (70 bp
      amplificate)

<400> SEQUENCE: 129
tacggttttg tcgtagtg                                                   18

<210> SEQ ID NO 130
<211> LENGTH: 20
<212> TYPE: DNA
<213> ORGANISM: Artificial Sequence
<220> FEATURE:
<223> OTHER INFORMATION: Reverse Primer for Thrombomodulin (70 bp
      amplificate)

<400> SEQUENCE: 130
cccaaacata ttacccaaac                                                 20

<210> SEQ ID NO 131
<211> LENGTH: 18
<212> TYPE: DNA
<213> ORGANISM: Artificial Sequence
<220> FEATURE:
<223> OTHER INFORMATION: Forward Primer for Thrombomodulin (113 bp
      amplificate)

<400> SEQUENCE: 131
```
ggagaggttg tcgttatc                                                    18

<210> SEQ ID NO 132
<211> LENGTH: 20
<212> TYPE: DNA
<213> ORGANISM: Artificial Sequence
<220> FEATURE:
<223> OTHER INFORMATION: Reverse Primer for Thrombomodulin (113 bp
      amplificate)

<400> SEQUENCE: 132
cccaaacata ttacccaaac                                                  20

<210> SEQ ID NO 133
<211> LENGTH: 18
<212> TYPE: DNA
<213> ORGANISM: Artificial Sequence
<220> FEATURE:
<223> OTHER INFORMATION: Reverse Primer for Thrombomodulin (115 bp
      amplificate)

<400> SEQUENCE: 133
accccaaaca tattaccc                                                    18

<210> SEQ ID NO 134
<211> LENGTH: 18
<212> TYPE: DNA
<213> ORGANISM: Artificial Sequence
<220> FEATURE:
<223> OTHER INFORMATION: Forward Primer for Thrombomodulin (99 bp
      amplificate)

<400> SEQUENCE: 134
gtcgagtacg attgtttc                                                    18

<210> SEQ ID NO 135
<211> LENGTH: 21
<212> TYPE: DNA
<213> ORGANISM: Artificial Sequence
<220> FEATURE:
<223> OTHER INFORMATION: Reverse Primer for Thrombomodulin (99 bp
      amplificate)

<400> SEQUENCE: 135
acgcactatc attaaataac c                                                21

<210> SEQ ID NO 136
<211> LENGTH: 18
<212> TYPE: DNA
<213> ORGANISM: Artificial Sequence
<220> FEATURE:
<223> OTHER INFORMATION: Forward Primer for Thrombomodulin (97 bp
      amplificate)

<400> SEQUENCE: 136
cggtggttgt cgatgtta                                                    18

<210> SEQ ID NO 137
<211> LENGTH: 18
<212> TYPE: DNA
<213> ORGANISM: Artificial Sequence
<220> FEATURE:
<223> OTHER INFORMATION: Reverse Primer for Thrombomodulin (97 bp
      amplificate)

<400> SEQUENCE: 137
ccgcaaccga ataacaac                                          18

<210> SEQ ID NO 138
<211> LENGTH: 18
<212> TYPE: DNA
<213> ORGANISM: Artificial Sequence
<220> FEATURE:
<223> OTHER INFORMATION: Forward Primer for Thrombomodulin (125 bp
      amplificate)

<400> SEQUENCE: 138
ttgcggggtt atttaatg                                          18

<210> SEQ ID NO 139
<211> LENGTH: 19
<212> TYPE: DNA
<213> ORGANISM: Artificial Sequence
<220> FEATURE:
<223> OTHER INFORMATION: Reverse Primer for Thrombomodulin (125 bp
      amplificate)

<400> SEQUENCE: 139
caaccgaata acaactaca                                         19

<210> SEQ ID NO 140
<211> LENGTH: 19
<212> TYPE: DNA
<213> ORGANISM: Artificial Sequence
<220> FEATURE:
<223> OTHER INFORMATION: Forward Primer for Septin-9 (72 bp amplificate)

<400> SEQUENCE: 140
gcgattcgtt gtttattag                                         19

<210> SEQ ID NO 141
<211> LENGTH: 18
<212> TYPE: DNA
<213> ORGANISM: Artificial Sequence
<220> FEATURE:
<223> OTHER INFORMATION: Reverse Primer for Septin-9 (72 bp amplificate)

<400> SEQUENCE: 141
atccgaaata atcccatc                                          18

<210> SEQ ID NO 142
<211> LENGTH: 20
<212> TYPE: DNA
<213> ORGANISM: Artificial Sequence
<220> FEATURE:
<223> OTHER INFORMATION: Forward Primer for Septin-9 (169 bp
      amplificate)

<400> SEQUENCE: 142
cggttagttt tgtattgtag                                        20

<210> SEQ ID NO 143
<211> LENGTH: 19
<212> TYPE: DNA
<213> ORGANISM: Artificial Sequence
<220> FEATURE:
<223> OTHER INFORMATION: Forward Primer for Septin-9 (94 bp amplificate)

<400> SEQUENCE: 143
cggggttgtt ttgtttaag                                         19

<210> SEQ ID NO 144

```
<211> LENGTH: 18
<212> TYPE: DNA
<213> ORGANISM: Artificial Sequence
<220> FEATURE:
<223> OTHER INFORMATION: Reverse Primer for Septin-9 (94 bp amplificate)

<400> SEQUENCE: 144
ccaacaccga caatcaaa                                                 18

<210> SEQ ID NO 145
<211> LENGTH: 21
<212> TYPE: DNA
<213> ORGANISM: Artificial Sequence
<220> FEATURE:
<223> OTHER INFORMATION: Probe for Thrombomodulin (3CpG) methylated

<400> SEQUENCE: 145
acgccgataa cgacaacctc t                                             21

<210> SEQ ID NO 146
<211> LENGTH: 21
<212> TYPE: DNA
<213> ORGANISM: Artificial Sequence
<220> FEATURE:
<223> OTHER INFORMATION: Probe for Thrombomodulin (3CpG) non-methylated

<400> SEQUENCE: 146
aagcagataa agacaacctc t                                             21

<210> SEQ ID NO 147
<211> LENGTH: 20
<212> TYPE: DNA
<213> ORGANISM: Artificial Sequence
<220> FEATURE:
<223> OTHER INFORMATION: Probe for Thrombomodulin (5CpG) methylated

<400> SEQUENCE: 147
cgccgcgtac aaacgccgaa                                               20

<210> SEQ ID NO 148
<211> LENGTH: 20
<212> TYPE: DNA
<213> ORGANISM: Artificial Sequence
<220> FEATURE:
<223> OTHER INFORMATION: Probe for Thrombomodulin (5CpG) non-methylated

<400> SEQUENCE: 148
agcagagtac aaaagcagaa                                               20

<210> SEQ ID NO 149
<211> LENGTH: 20
<212> TYPE: DNA
<213> ORGANISM: Artificial Sequence
<220> FEATURE:
<223> OTHER INFORMATION: Probe for Thrombomodulin (5CpG) methylated

<400> SEQUENCE: 149
aacgcgccgc gtacaaacgc                                               20

<210> SEQ ID NO 150
<211> LENGTH: 20
<212> TYPE: DNA
<213> ORGANISM: Artificial Sequence
<220> FEATURE:
<223> OTHER INFORMATION: Probe for Thrombomodulin (5CpG) non-methylated

<400> SEQUENCE: 150
```
aaagagcaga gtacaaaagc 20

<210> SEQ ID NO 151
<211> LENGTH: 23
<212> TYPE: DNA
<213> ORGANISM: Artificial Sequence
<220> FEATURE:
<223> OTHER INFORMATION: Probe for Thrombomodulin (3CpG) methylated

<400> SEQUENCE: 151
cgcaatccgt cgcaaatcta act 23

<210> SEQ ID NO 152
<211> LENGTH: 23
<212> TYPE: DNA
<213> ORGANISM: Artificial Sequence
<220> FEATURE:
<223> OTHER INFORMATION: Probe for Thrombomodulin (3CpG) non-methylated

<400> SEQUENCE: 152
agcaatcagt agcaaatcta act 23

<210> SEQ ID NO 153
<211> LENGTH: 20
<212> TYPE: DNA
<213> ORGANISM: Artificial Sequence
<220> FEATURE:
<223> OTHER INFORMATION: Probe for Thrombomodulin (5CpG) methylated

<400> SEQUENCE: 153
aacgccgacg accaacgccg 20

<210> SEQ ID NO 154
<211> LENGTH: 20
<212> TYPE: DNA
<213> ORGANISM: Artificial Sequence
<220> FEATURE:
<223> OTHER INFORMATION: Probe for Thrombomodulin (5CpG) non-methylated

<400> SEQUENCE: 154
aaagcagaag accaaagcag 20

<210> SEQ ID NO 155
<211> LENGTH: 20
<212> TYPE: DNA
<213> ORGANISM: Artificial Sequence
<220> FEATURE:
<223> OTHER INFORMATION: Probe for Thrombomodulin (4CpG) methylated

<400> SEQUENCE: 155
aaaacgccga cgaccaacgc 20

<210> SEQ ID NO 156
<211> LENGTH: 20
<212> TYPE: DNA
<213> ORGANISM: Artificial Sequence
<220> FEATURE:
<223> OTHER INFORMATION: Probe for Thrombomodulin (4CpG) non-methylated

<400> SEQUENCE: 156
aaaaagcaga agaccaaagc 20

<210> SEQ ID NO 157
<211> LENGTH: 21
<212> TYPE: DNA

```
<213> ORGANISM: Artificial Sequence
<220> FEATURE:
<223> OTHER INFORMATION: Probe for Thrombomodulin (4CpG) methylated

<400> SEQUENCE: 157
aaaacgccga cgaccaacgc c                                              21

<210> SEQ ID NO 158
<211> LENGTH: 21
<212> TYPE: DNA
<213> ORGANISM: Artificial Sequence
<220> FEATURE:
<223> OTHER INFORMATION: Probe for Thrombomodulin (4CpG) non-methylated

<400> SEQUENCE: 158
aaaaagcaga agaccaaagc c                                              21

<210> SEQ ID NO 159
<211> LENGTH: 25
<212> TYPE: DNA
<213> ORGANISM: Artificial Sequence
<220> FEATURE:
<223> OTHER INFORMATION: Probe for Septin-9 (4CpG) methylated

<400> SEQUENCE: 159
cgttaaccgc gaaatccgac ataat                                          25

<210> SEQ ID NO 160
<211> LENGTH: 25
<212> TYPE: DNA
<213> ORGANISM: Artificial Sequence
<220> FEATURE:
<223> OTHER INFORMATION: Probe for Septin-9 (4CpG) non-methylated

<400> SEQUENCE: 160
agttaacaga gaaatcagac ataat                                          25

<210> SEQ ID NO 161
<211> LENGTH: 27
<212> TYPE: DNA
<213> ORGANISM: Artificial Sequence
<220> FEATURE:
<223> OTHER INFORMATION: Probe for Septin-9 (4CpG) methylated

<400> SEQUENCE: 161
cgttaaccgc gaaatccgac ataataa                                        27

<210> SEQ ID NO 162
<211> LENGTH: 27
<212> TYPE: DNA
<213> ORGANISM: Artificial Sequence
<220> FEATURE:
<223> OTHER INFORMATION: Probe for Septin-9 (4CpG) non-methylated

<400> SEQUENCE: 162
agttaacaga gaaatcagac ataataa                                        27

<210> SEQ ID NO 163
<211> LENGTH: 21
<212> TYPE: DNA
<213> ORGANISM: Artificial Sequence
<220> FEATURE:
<223> OTHER INFORMATION: Probe for Septin-9 (2CpG) methylated

<400> SEQUENCE: 163
aaacgcacgc actcacaaac t                                              21
```

-continued

<210> SEQ ID NO 164
<211> LENGTH: 21
<212> TYPE: DNA
<213> ORGANISM: Artificial Sequence
<220> FEATURE:
<223> OTHER INFORMATION: Probe for Septin-9 (2CpG) non-methylated

<400> SEQUENCE: 164
aaaagcaagc actcacaaac t                                              21

<210> SEQ ID NO 165
<211> LENGTH: 21
<212> TYPE: DNA
<213> ORGANISM: Artificial Sequence
<220> FEATURE:
<223> OTHER INFORMATION: Probe for Thrombomodulin (3CpG) methylated

<400> SEQUENCE: 165
agaggttgtc gttatcggcg t                                              21

<210> SEQ ID NO 166
<211> LENGTH: 21
<212> TYPE: DNA
<213> ORGANISM: Artificial Sequence
<220> FEATURE:
<223> OTHER INFORMATION: Probe for Thrombomodulin (3CpG) non-methylated

<400> SEQUENCE: 166
agaggttgtc tttatctgct t                                              21

<210> SEQ ID NO 167
<211> LENGTH: 20
<212> TYPE: DNA
<213> ORGANISM: Artificial Sequence
<220> FEATURE:
<223> OTHER INFORMATION: Probe for Thrombomodulin (5CpG) methylated

<400> SEQUENCE: 167
ttcggcgttt gtacgcggcg                                                20

<210> SEQ ID NO 168
<211> LENGTH: 20
<212> TYPE: DNA
<213> ORGANISM: Artificial Sequence
<220> FEATURE:
<223> OTHER INFORMATION: Probe for Thrombomodulin (5CpG) non-methylated

<400> SEQUENCE: 168
ttctgctttt gtactctgct                                                20

<210> SEQ ID NO 169
<211> LENGTH: 20
<212> TYPE: DNA
<213> ORGANISM: Artificial Sequence
<220> FEATURE:
<223> OTHER INFORMATION: Probe for Thrombomodulin (5CpG) methylated

<400> SEQUENCE: 169
gcgtttgtac gcggcgcgtt                                                20

<210> SEQ ID NO 170
<211> LENGTH: 20
<212> TYPE: DNA
<213> ORGANISM: Artificial Sequence
<220> FEATURE:

<223> OTHER INFORMATION: Probe for Thrombomodulin (5CpG) non-methylated

<400> SEQUENCE: 170
gcttttgtac tctgctcttt          20

<210> SEQ ID NO 171
<211> LENGTH: 23
<212> TYPE: DNA
<213> ORGANISM: Artificial Sequence
<220> FEATURE:
<223> OTHER INFORMATION: Probe for Thrombomodulin (3CpG) methylated

<400> SEQUENCE: 171
agttagattt gcgacggatt gcg          23

<210> SEQ ID NO 172
<211> LENGTH: 23
<212> TYPE: DNA
<213> ORGANISM: Artificial Sequence
<220> FEATURE:
<223> OTHER INFORMATION: Probe for Thrombomodulin (3CpG) non-methylated

<400> SEQUENCE: 172
agttagattt gctactgatt gct          23

<210> SEQ ID NO 173
<211> LENGTH: 20
<212> TYPE: DNA
<213> ORGANISM: Artificial Sequence
<220> FEATURE:
<223> OTHER INFORMATION: Probe for Thrombomodulin (5CpG) methylated

<400> SEQUENCE: 173
cggcgttggt cgtcggcgtt          20

<210> SEQ ID NO 174
<211> LENGTH: 20
<212> TYPE: DNA
<213> ORGANISM: Artificial Sequence
<220> FEATURE:
<223> OTHER INFORMATION: Probe for Thrombomodulin (5CpG) non-methylated

<400> SEQUENCE: 174
ctgctttggt cttctgcttt          20

<210> SEQ ID NO 175
<211> LENGTH: 20
<212> TYPE: DNA
<213> ORGANISM: Artificial Sequence
<220> FEATURE:
<223> OTHER INFORMATION: Probe for Thrombomodulin (4CpG) methylated

<400> SEQUENCE: 175
gcgttggtcg tcggcgtttt          20

<210> SEQ ID NO 176
<211> LENGTH: 20
<212> TYPE: DNA
<213> ORGANISM: Artificial Sequence
<220> FEATURE:
<223> OTHER INFORMATION: Probe for Thrombomodulin (4CpG) non-methylated

<400> SEQUENCE: 176
gctttggtct tctgcttttt          20

```
<210> SEQ ID NO 177
<211> LENGTH: 21
<212> TYPE: DNA
<213> ORGANISM: Artificial Sequence
<220> FEATURE:
<223> OTHER INFORMATION: Probe for Thrombomodulin (4CpG) methylated

<400> SEQUENCE: 177
ggcgttggtc gtcggcgttt t                                        21

<210> SEQ ID NO 178
<211> LENGTH: 21
<212> TYPE: DNA
<213> ORGANISM: Artificial Sequence
<220> FEATURE:
<223> OTHER INFORMATION: Probe for Thrombomodulin (4CpG) non-methylated

<400> SEQUENCE: 178
ggctttggtc ttctgctttt t                                        21

<210> SEQ ID NO 179
<211> LENGTH: 25
<212> TYPE: DNA
<213> ORGANISM: Artificial Sequence
<220> FEATURE:
<223> OTHER INFORMATION: Probe for Septin-9 (4CpG) methylated

<400> SEQUENCE: 179
attatgtcgg atttcgcggt taacg                                    25

<210> SEQ ID NO 180
<211> LENGTH: 25
<212> TYPE: DNA
<213> ORGANISM: Artificial Sequence
<220> FEATURE:
<223> OTHER INFORMATION: Probe for Septin-9 (4CpG) non-methylated

<400> SEQUENCE: 180
attatgtctg atttctctgt taact                                    25

<210> SEQ ID NO 181
<211> LENGTH: 27
<212> TYPE: DNA
<213> ORGANISM: Artificial Sequence
<220> FEATURE:
<223> OTHER INFORMATION: Probe for Septin-9 (4CpG) methylated

<400> SEQUENCE: 181
ttattatgtc ggatttcgcg gttaacg                                  27

<210> SEQ ID NO 182
<211> LENGTH: 27
<212> TYPE: DNA
<213> ORGANISM: Artificial Sequence
<220> FEATURE:
<223> OTHER INFORMATION: Probe for Septin-9 (4CpG) non-methylated

<400> SEQUENCE: 182
ttattatgtc tgatttctct gttaact                                  27

<210> SEQ ID NO 183
<211> LENGTH: 21
<212> TYPE: DNA
<213> ORGANISM: Artificial Sequence
<220> FEATURE:
<223> OTHER INFORMATION: Probe for Septin-9 (2CpG) methylated
```

```
<400> SEQUENCE: 183
agtttgtgag tgcgtgcgtt t                                           21

<210> SEQ ID NO 184
<211> LENGTH: 20
<212> TYPE: DNA
<213> ORGANISM: Artificial Sequence
<220> FEATURE:
<223> OTHER INFORMATION: Probe for Septin-9 (2CpG) non-methylated

<400> SEQUENCE: 184
agtttgtgag tgctgctttt                                             20
```